United States Patent [19]
Chupp et al.

[11] Patent Number: 5,939,326
[45] Date of Patent: *Aug. 17, 1999

[54] METHOD AND APPARATUS FOR PERFORMING AUTOMATED ANALYSIS

[75] Inventors: Vernon L. Chupp, Los Altos; Peter E. Lobban, Palo Alto; Young Ran Kim, Sunnyvale; Roderick Walton Larue, Sebastopol; John Paul Stuart, Mt. View, all of Calif.

[73] Assignee: Abbott Laboratories, Abbott Park, Ill.

[*] Notice: This patent is subject to a terminal disclaimer.

[21] Appl. No.: 08/816,712

[22] Filed: Mar. 13, 1997

Related U.S. Application Data

[60] Division of application No. 08/482,678, Jun. 7, 1995, Pat. No. 5,656,499, which is a continuation-in-part of application No. 08/283,379, Aug. 1, 1994, abandoned.

[51] Int. Cl.[6] .................................................. G01N 33/533
[52] U.S. Cl. .............................. 436/43; 436/63; 436/172; 436/174; 436/175; 436/180; 436/522; 436/523; 436/805; 422/63; 422/67; 422/73; 422/82.08
[58] Field of Search ..................................... 436/8, 10, 17, 436/18, 522, 519, 523, 49, 54, 164, 165, 172, 174, 175, 179, 180, 63, 805; 422/58.1, 73, 63, 65, 67, 82.01, 82.02, 82.08, 82.09; 435/808, 767, 809, 973, 7.24; 356/39, 73, 335, 336; 364/413.07, 413.08

[56] References Cited

U.S. PATENT DOCUMENTS

| | | |
|---|---|---|
| 3,586,859 | 6/1971 | Katz . |
| 3,770,349 | 11/1973 | Legorreta-Sanchez . |
| 4,053,229 | 10/1977 | McCluney ................................ 356/103 |
| 4,054,151 | 10/1977 | Parker et al. ............................ 137/110 |
| 4,265,538 | 5/1981 | Wertheimer .............................. 356/246 |

(List continued on next page.)

FOREIGN PATENT DOCUMENTS

| | | |
|---|---|---|
| 0299419 | 1/1989 | European Pat. Off. . |
| 0355801 | 2/1990 | European Pat. Off. . |
| 0360487 | 3/1990 | European Pat. Off. . |
| 0370549 | 5/1990 | European Pat. Off. . |
| 0515099 | 11/1992 | European Pat. Off. . |
| 0525398 | 2/1993 | European Pat. Off. . |
| 0545315 | 6/1993 | European Pat. Off. . |
| 0548983 | 6/1993 | European Pat. Off. . |
| 3220879 | 12/1983 | Germany . |
| 9216829 | 10/1992 | WIPO . |
| 9429800 | 12/1994 | WIPO . |
| 9506909 | 3/1995 | WIPO . |

OTHER PUBLICATIONS

European Patent Search Report corresponding to European Patent Application No. 97113064.6.
*Particle Analyzing Apparatus* vol. 9 No. 243(P392)1966 Sep. 30, 1988.
International Search Report PCT/US95/09555 (5588.PC.01).
Robinson, G., et al. Effect of Type of Haematology Analyser on CD4 Count The Lancet, vol. 340 Aug. 22, 1992 p. 485.

(List continued on next page.)

*Primary Examiner*—Long V. Le
*Attorney, Agent, or Firm*—Mark C. Bach

[57] ABSTRACT

A device for analyzing a whole blood sample is provided. The device comprises a conventionl hematology analyzer integrated with a fluorescence cyometry analyzer. A controller is provided for controlling the analyzers, obtaining and utilizing data from both and reporting a quantitative result. Methods are also provided for analyzing a whole blood sample. One such method comprises the steps of performing on a single instrument an analysis of impedance associated with the blood sample, an analysis of light scatter associated with the blood sample, and an analysis of fluorescence associated with the blood sample. Data is collected and utilized. A result is reported.

8 Claims, 61 Drawing Sheets

U.S. PATENT DOCUMENTS

| | | |
|---|---|---|
| 4,284,412 | 8/1981 | Hansen et al. .......................... 23/230 B |
| 4,463,708 | 8/1984 | Gerry .......................................... 123/25 |
| 4,520,110 | 5/1985 | Stryer et al. . |
| 4,542,104 | 9/1985 | Stryer et al. . |
| 4,577,964 | 3/1986 | Hansen, Jr. . |
| 4,599,307 | 7/1986 | Saunder et al. . |
| 4,661,913 | 4/1987 | Wu et al. . |
| 4,710,021 | 12/1987 | von Behrens . |
| 4,727,020 | 2/1988 | Recktenwald . |
| 4,745,285 | 5/1988 | Recktenwald et al. . |
| 4,751,179 | 6/1988 | Ledis et al. . |
| 4,896,961 | 1/1990 | Ito .............................................. 356/73 |
| 4,941,809 | 7/1990 | Pinkerton . |
| 4,943,164 | 7/1990 | Oshishi et al. ........................... 366/149 |
| 4,978,624 | 12/1990 | Cremins et al. ........................... 436/17 |
| 4,986,657 | 1/1991 | Ohe . |
| 4,987,086 | 1/1991 | Brosnan et al. . |
| 4,989,977 | 2/1991 | North, Jr. . |
| 5,015,157 | 5/1991 | Pinkerton et al. . |
| 5,017,497 | 5/1991 | de Grooth et al. ........................ 436/63 |
| 5,032,381 | 7/1991 | Bronstein et al. ........................... 424/9 |
| 5,044,889 | 9/1991 | Pinkerton . |
| 5,047,321 | 9/1991 | Loken et al. ................................ 435/6 |
| 5,073,497 | 12/1991 | Schwartz ..................................... 436/8 |
| 5,135,302 | 8/1992 | Hirako ....................................... 356/73 |
| 5,188,935 | 2/1993 | Leif et al. ................................ 435/7.24 |
| 5,223,398 | 6/1993 | Kortright et al. ....................... 435/7.24 |
| 5,238,812 | 8/1993 | Coulter et al. ............................ 435/7.2 |
| 5,260,192 | 11/1993 | Russell et al. .......................... 435/7.24 |
| 5,260,764 | 11/1993 | Fukuda et al. ............................ 356/73 |
| 5,308,772 | 5/1994 | Sakata et al. .............................. 436/63 |
| 5,320,964 | 6/1994 | Young et al. .............................. 436/10 |
| 5,371,585 | 12/1994 | Morgan et al. .......................... 356/246 |
| 5,378,633 | 1/1995 | von Behrens et al. .................... 436/63 |
| 5,380,663 | 1/1995 | Schwartz et al. .......................... 436/10 |
| 5,385,822 | 1/1995 | Melnicoff et al. ........................... 435/5 |
| 5,408,307 | 4/1995 | Yamamoto et al. ....................... 356/73 |

OTHER PUBLICATIONS

Kessler, H. A. et al. Absolute Number Versus Percentage of T–Helper Lymphocytes in Human Immunodeficiency Virus Infection Journal of Infectious Disease 1990; 161 (Feb. pp. 356–357.

Malone, J.L., et al. Sources of Variability in Repeated T–Helper Lymphocyte Counts From Human Immunodeficiency Virus Type 1–Infected Patients: Total Lymphocyte Count Fluctuations and Diurnal Cycle are Important Journal of Acquired Immune Deficiency Syndromes 3:144–151, 1990.

Cornbleet, MD., J., Spurious Results from Automated Hematology Cell Counters Laboratory Medicine vol. 14, No. 8 Aug. 1983.

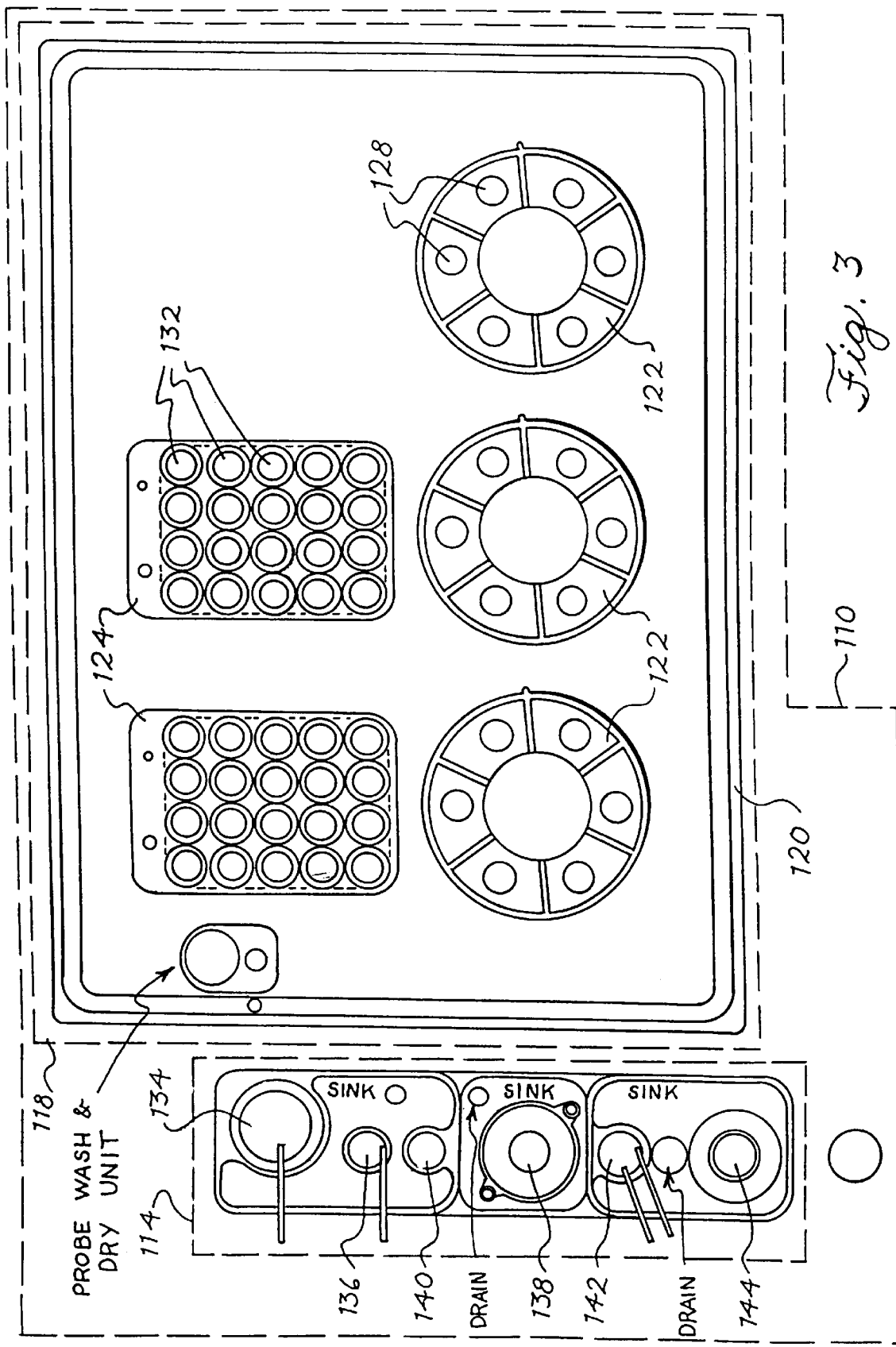

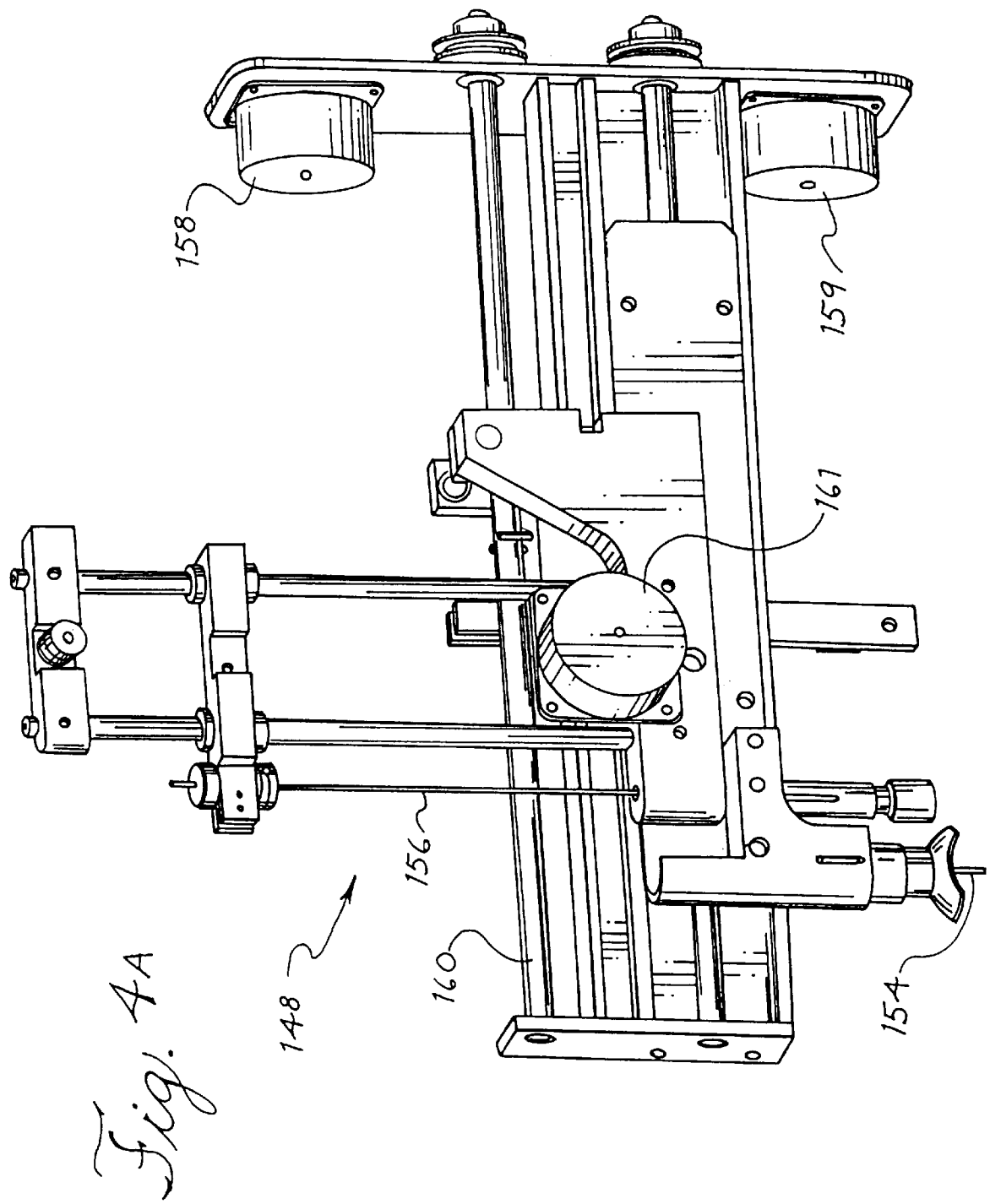

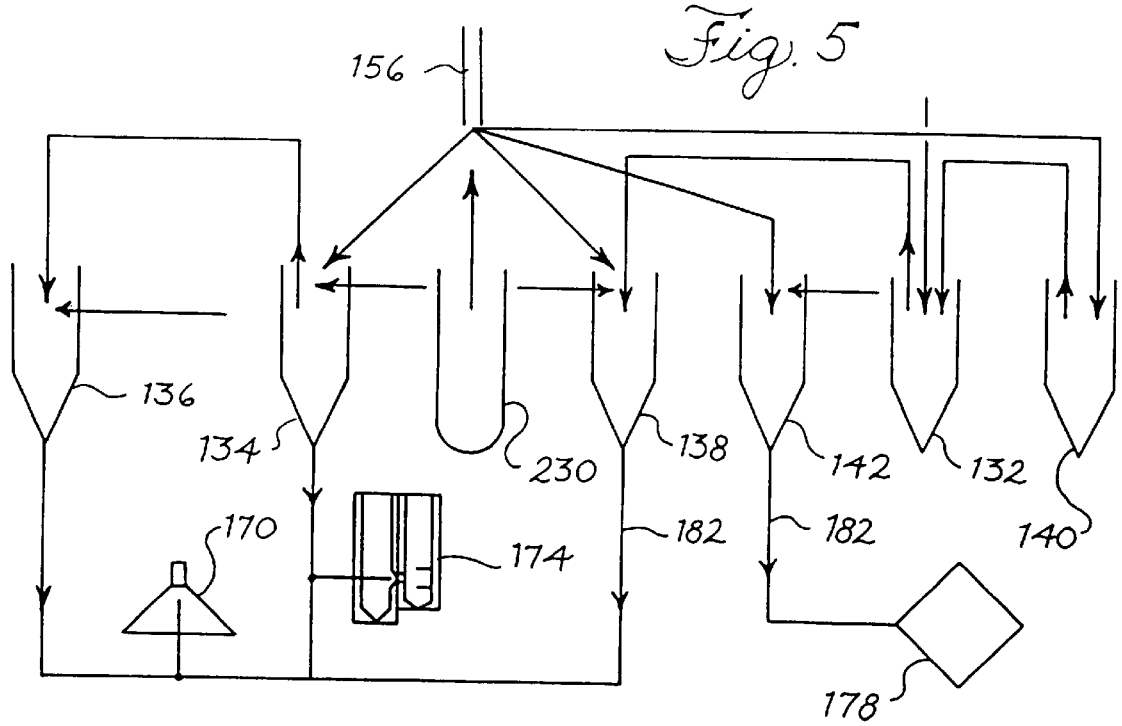
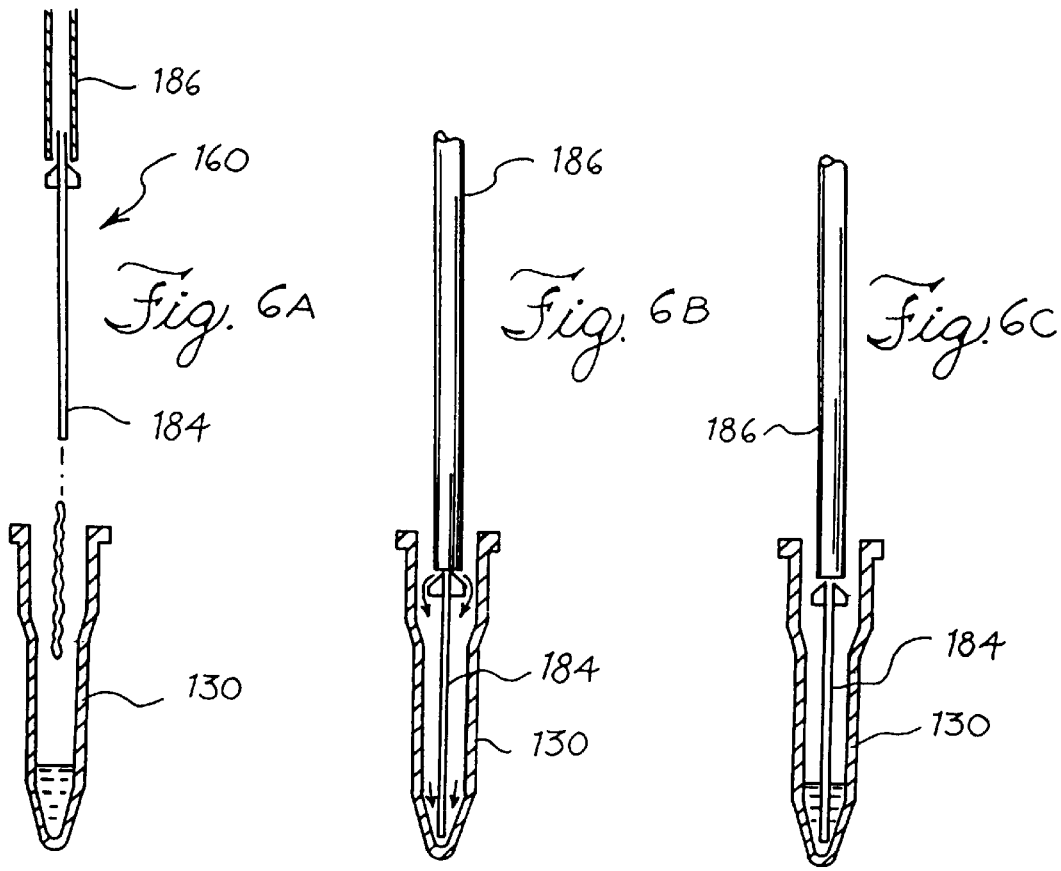

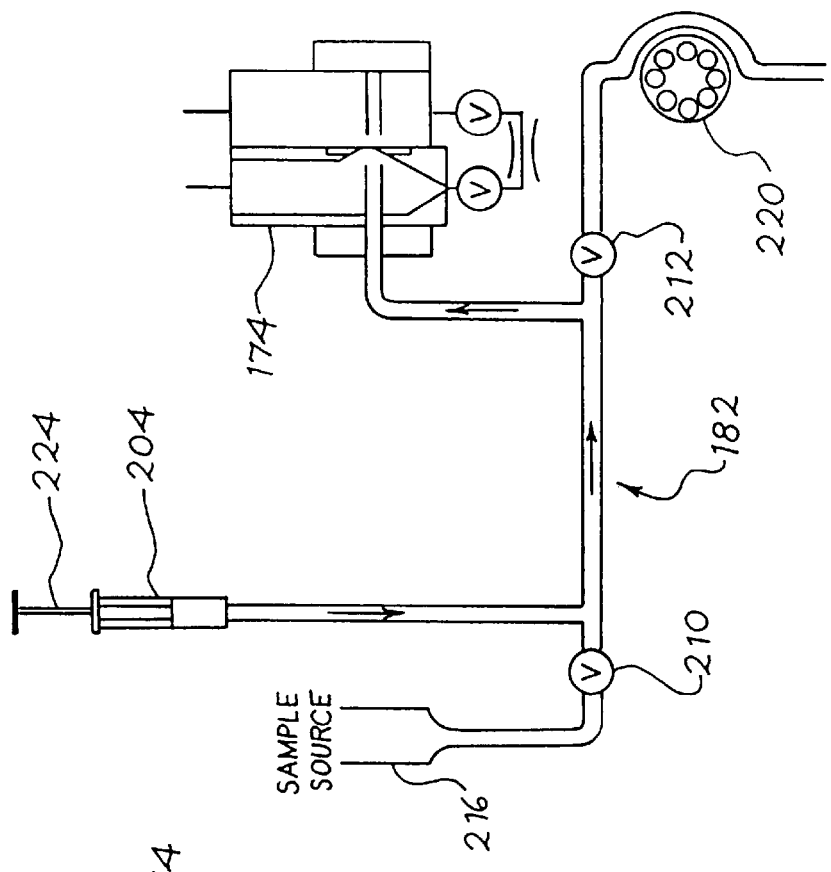
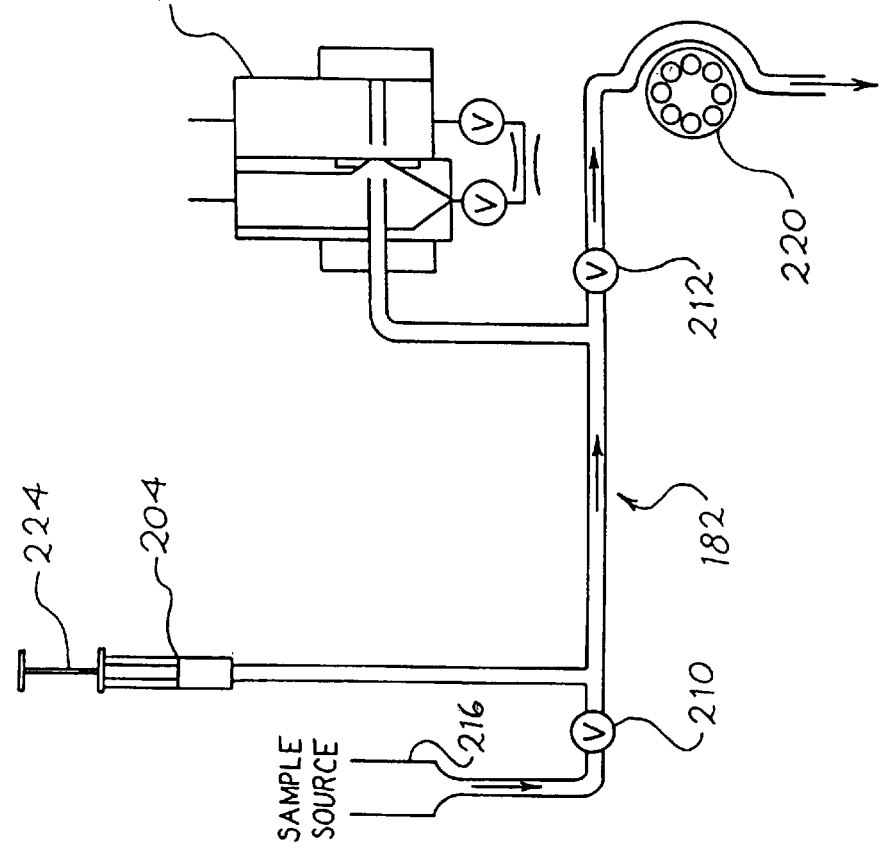

Fig. 13A

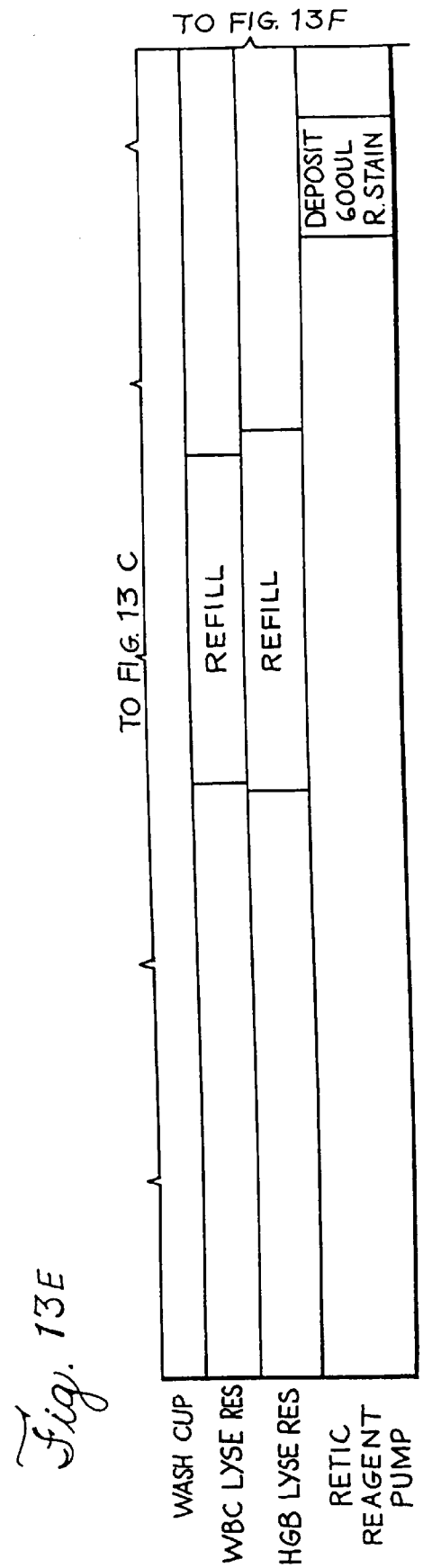

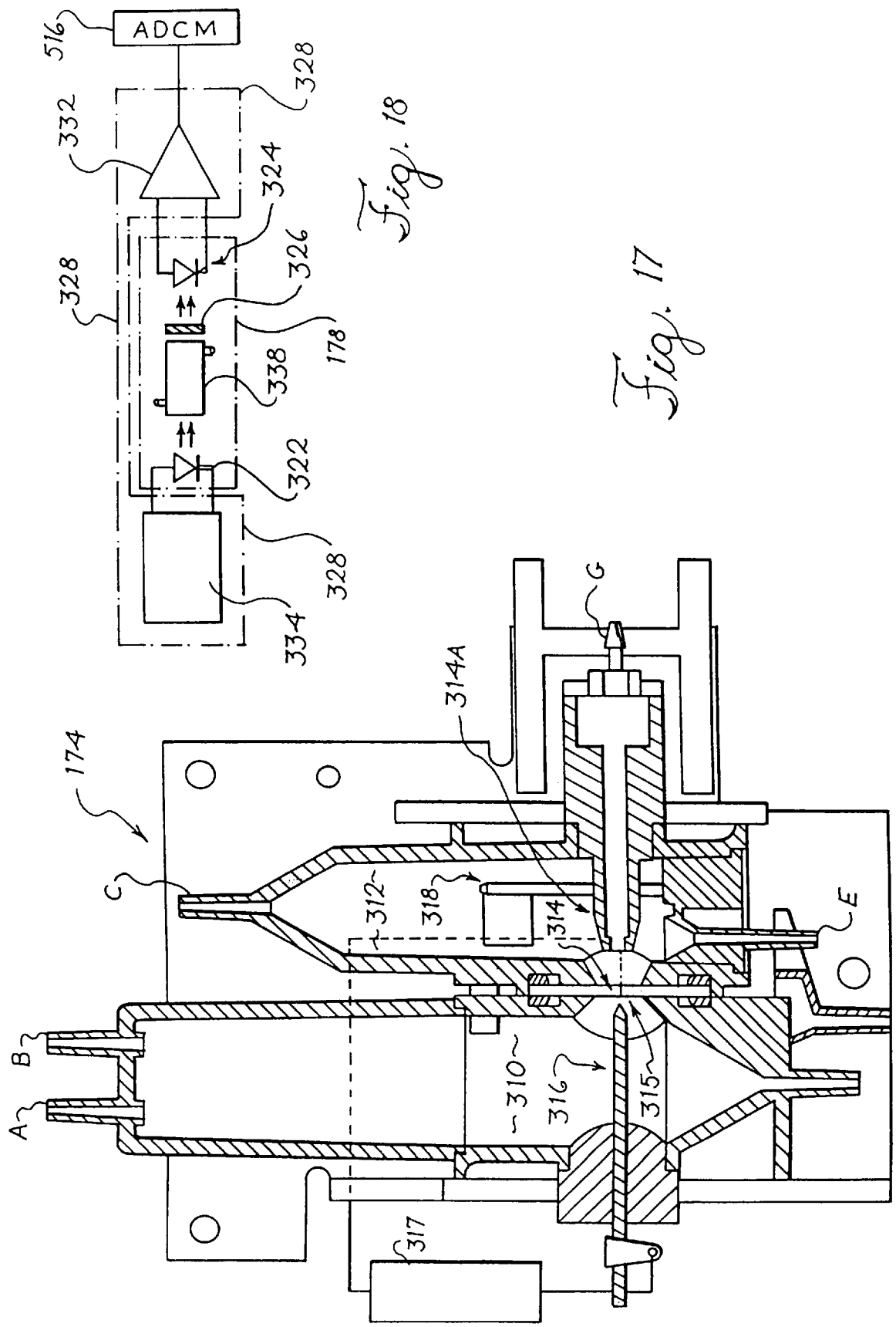

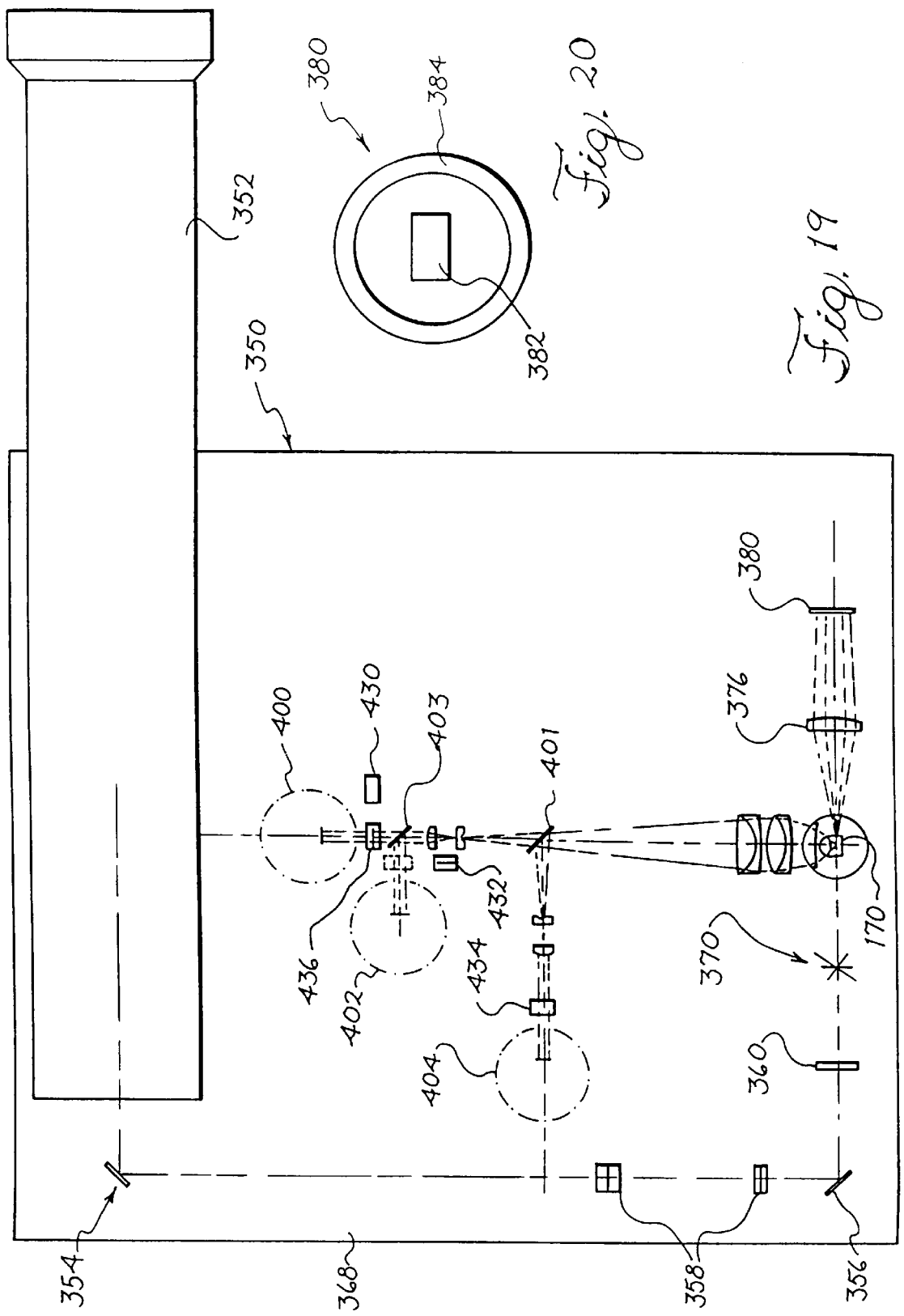

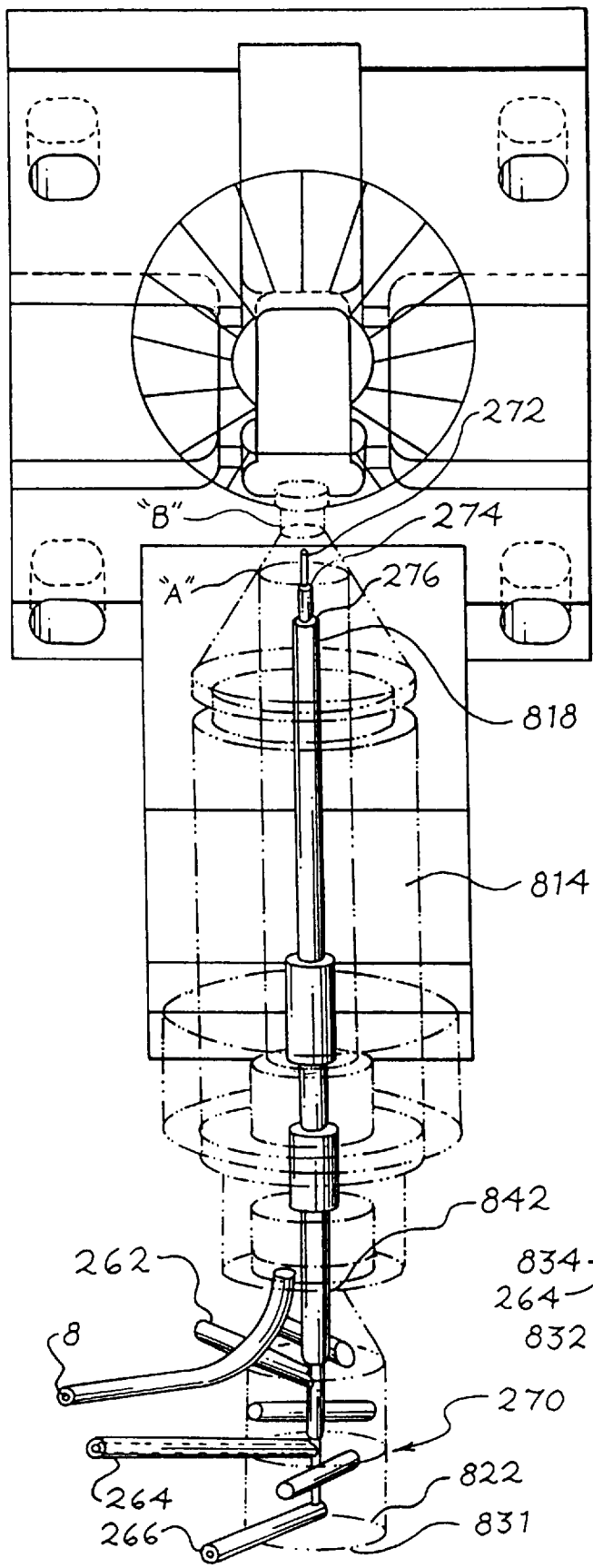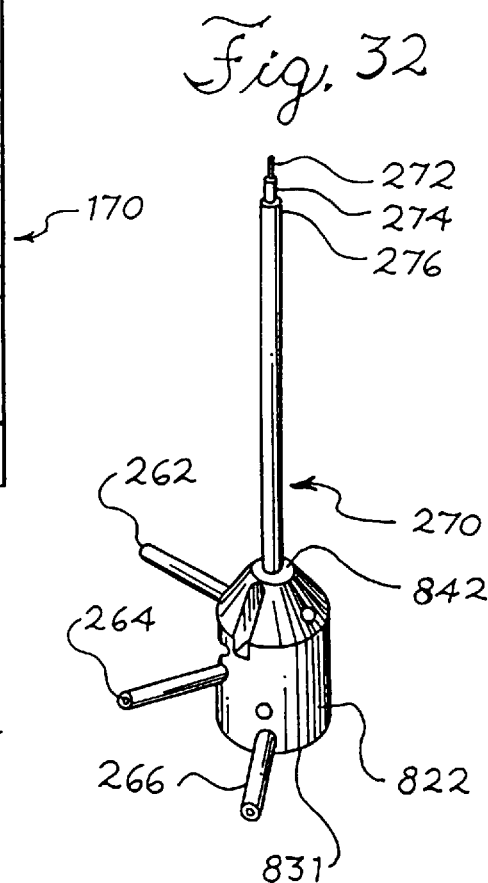
Fig. 31
Fig. 32
Fig. 33

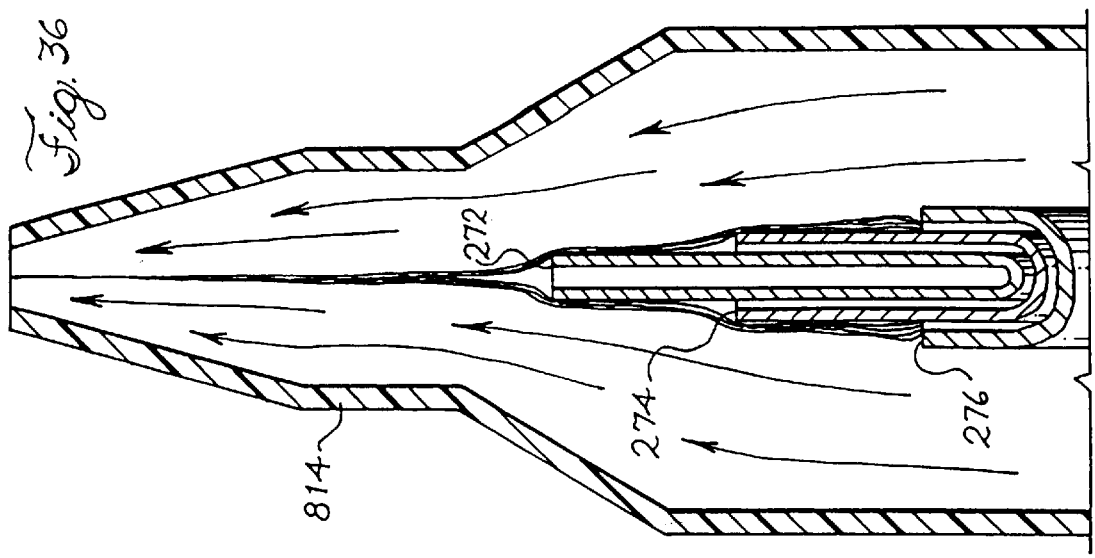
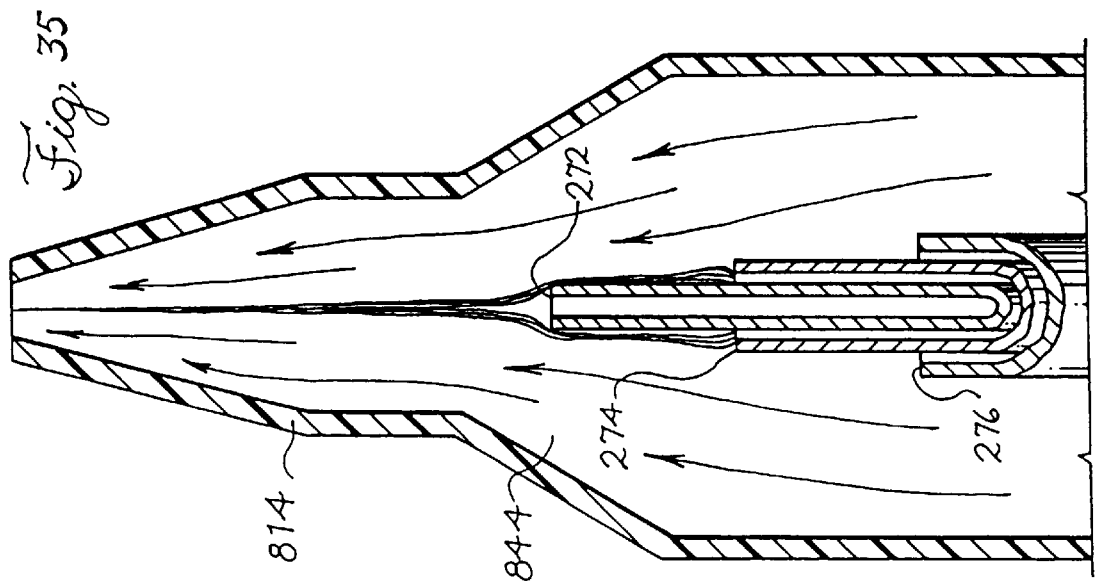
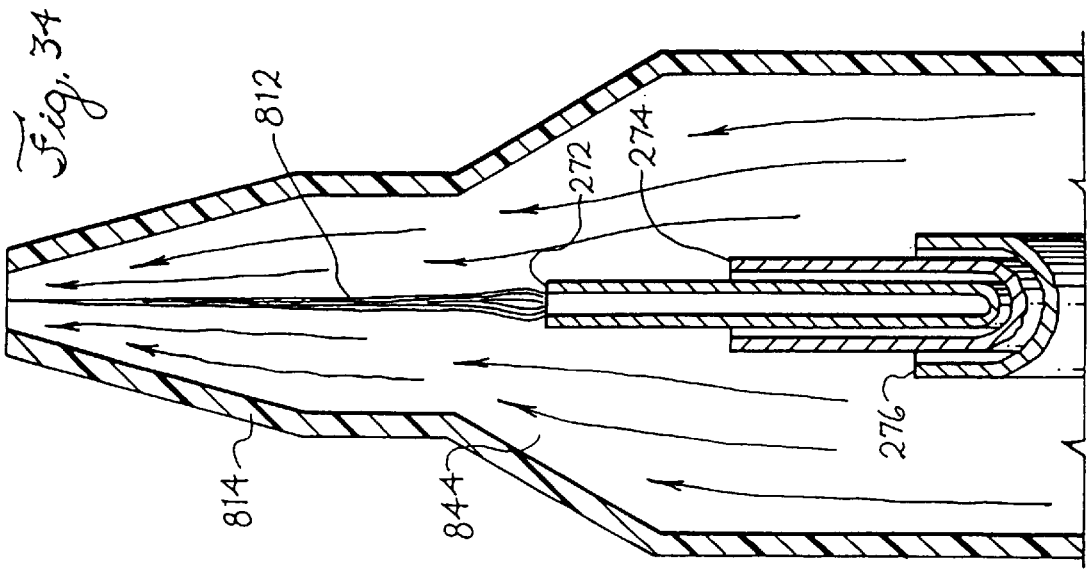

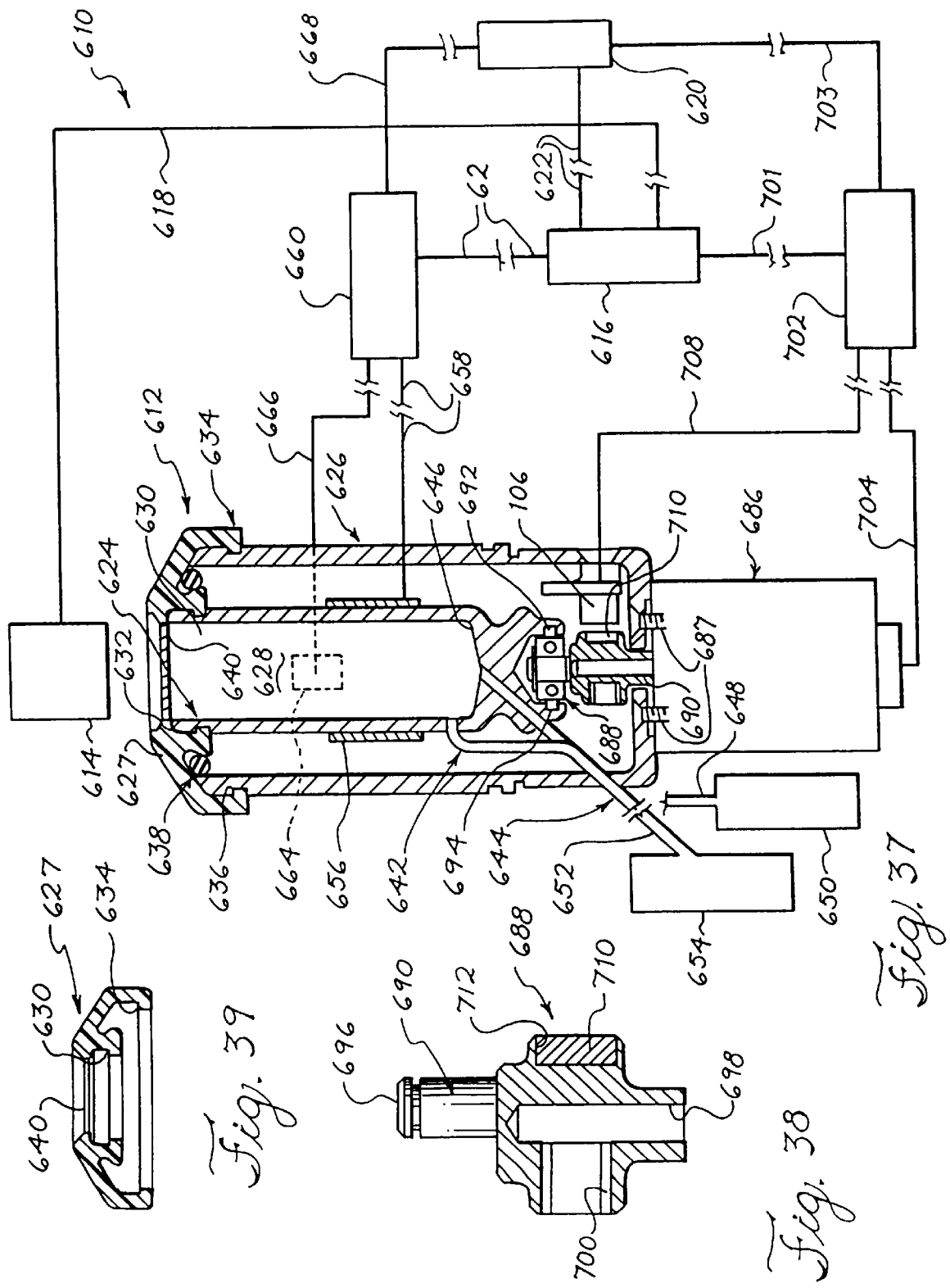

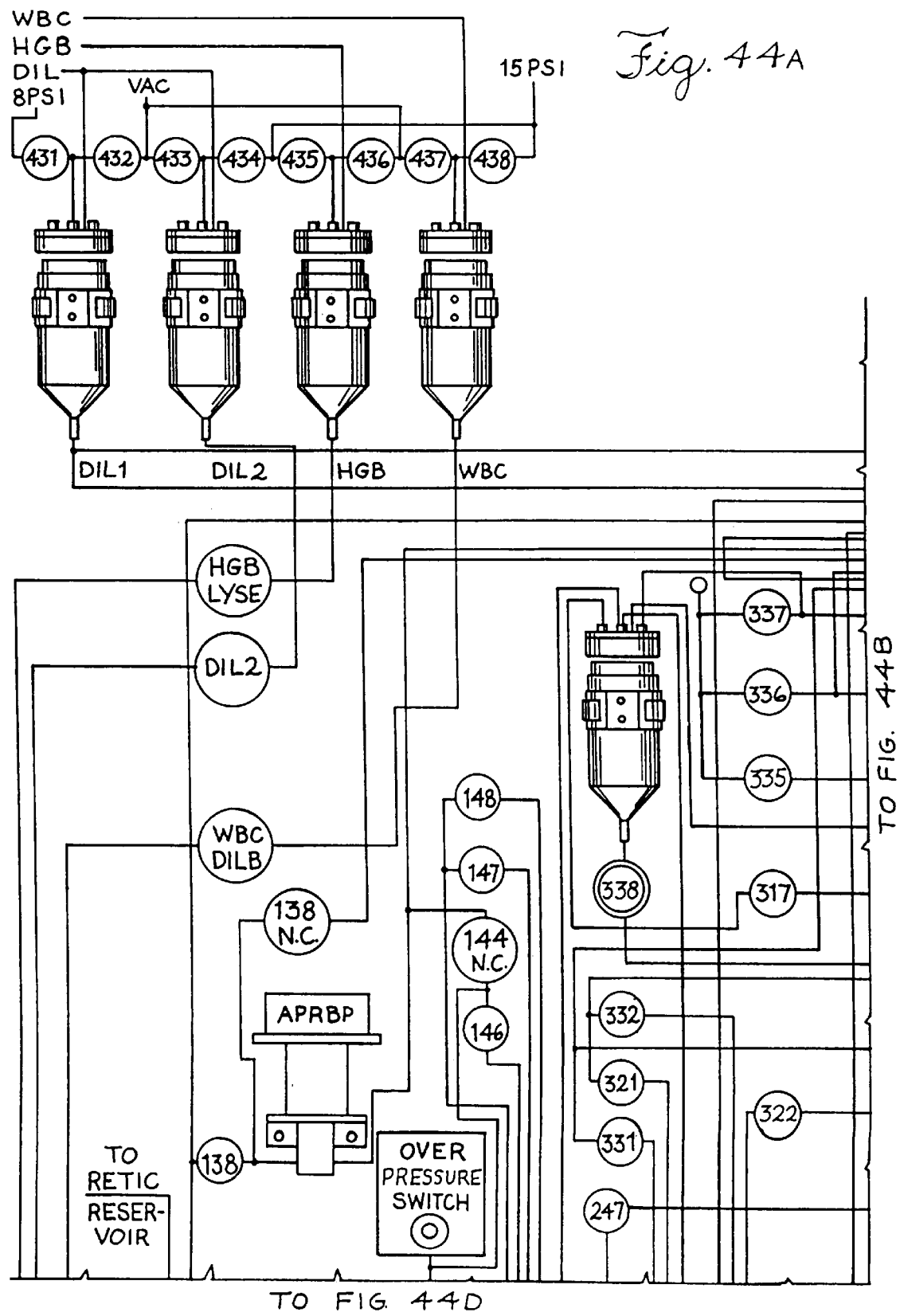

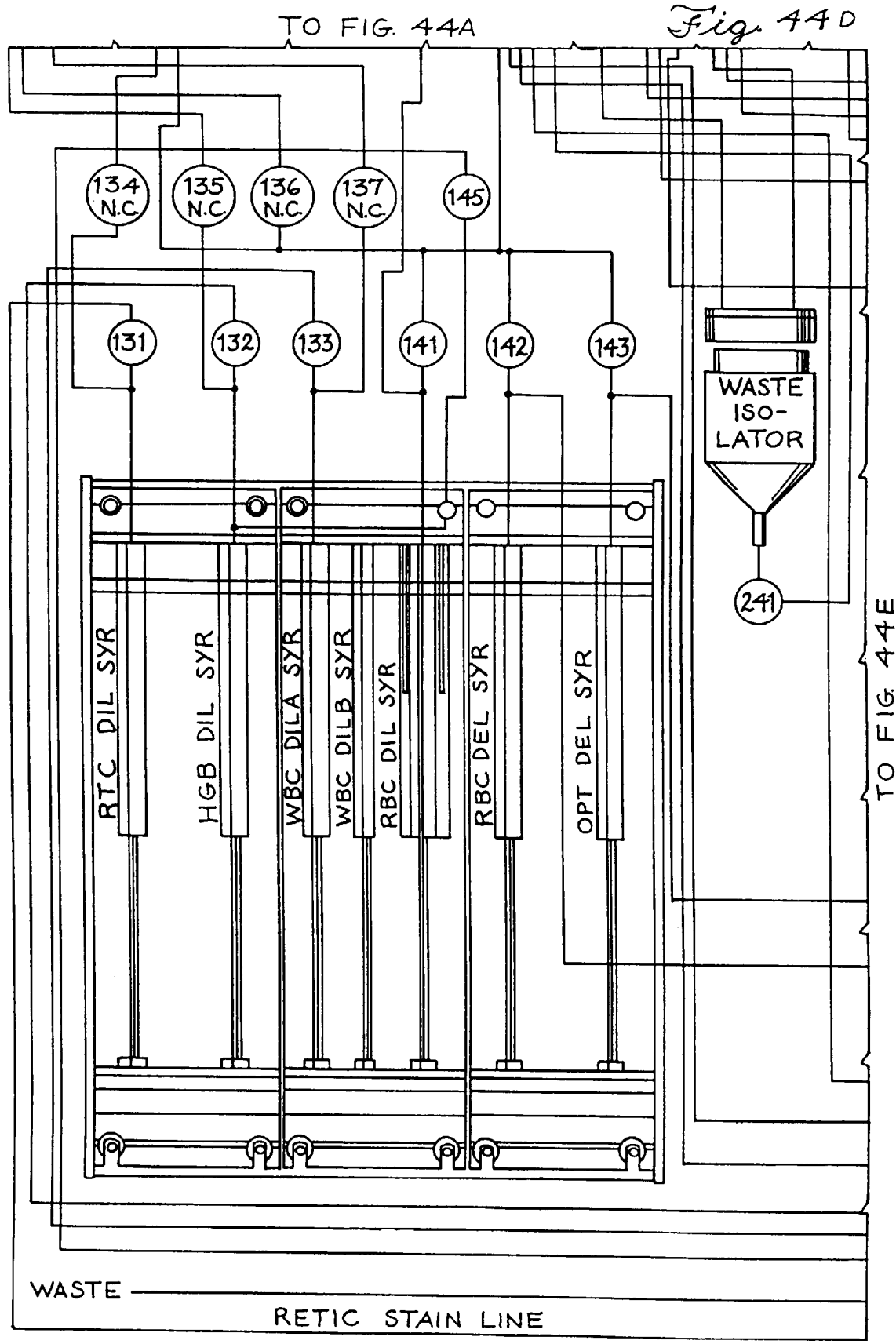

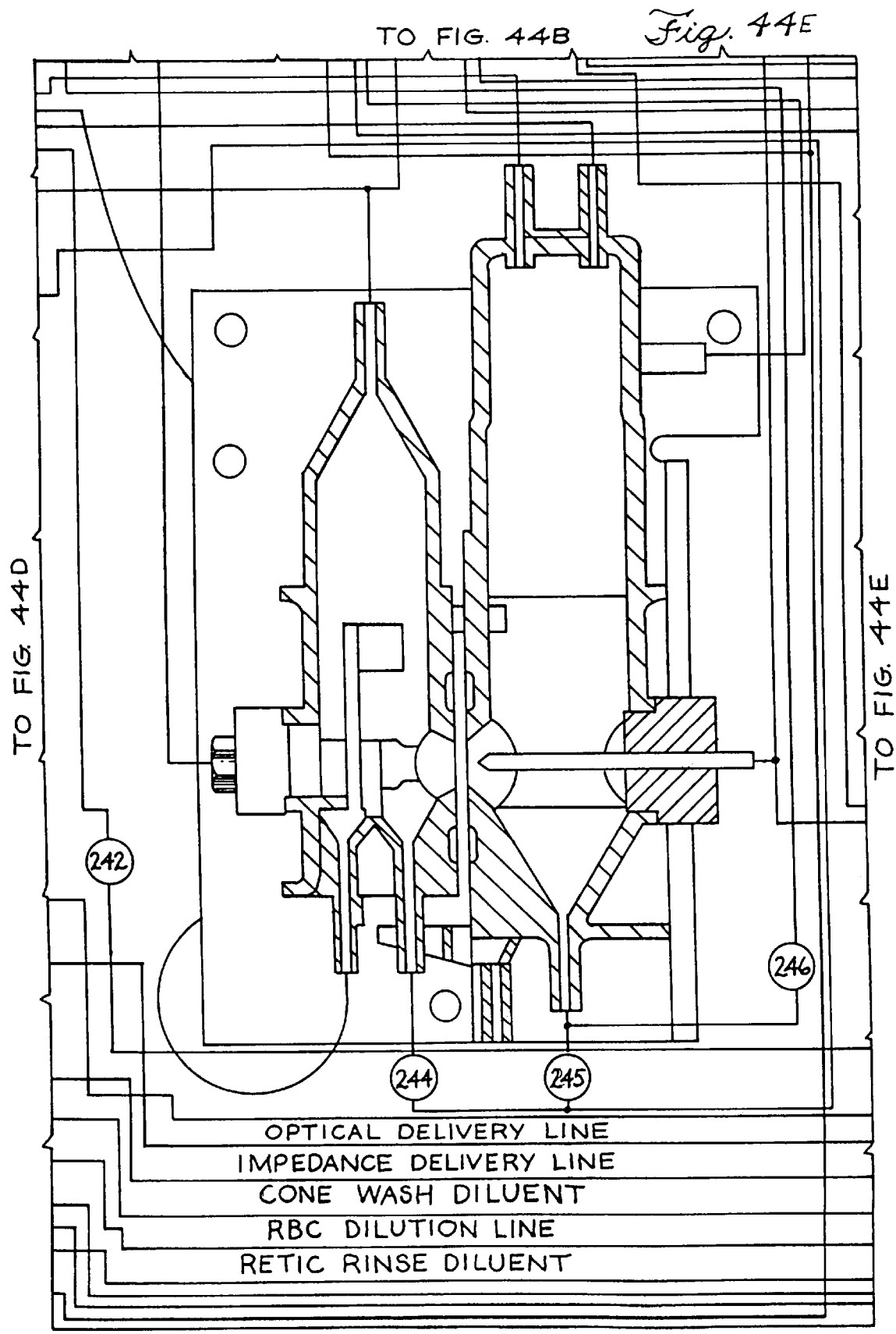

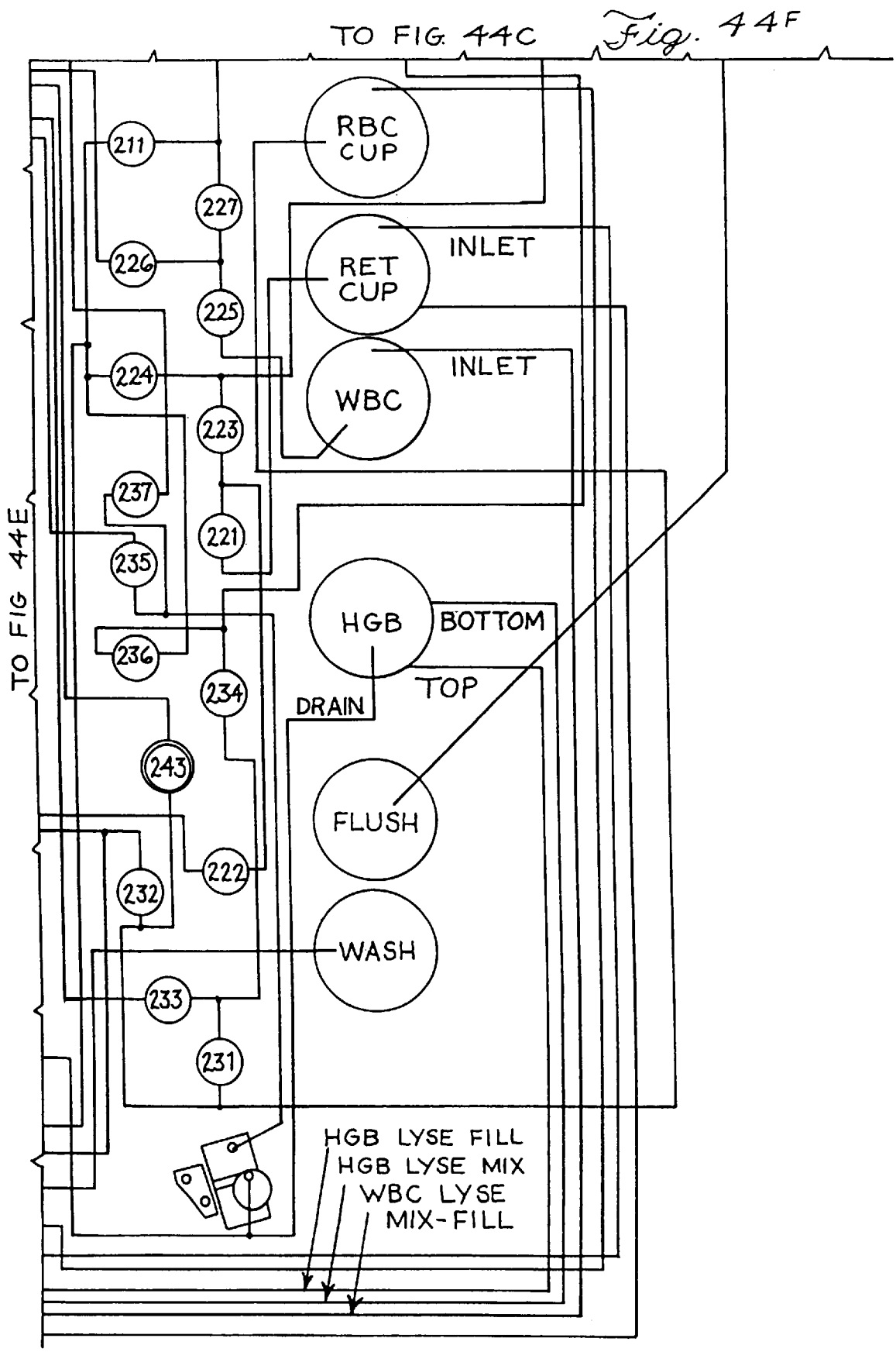

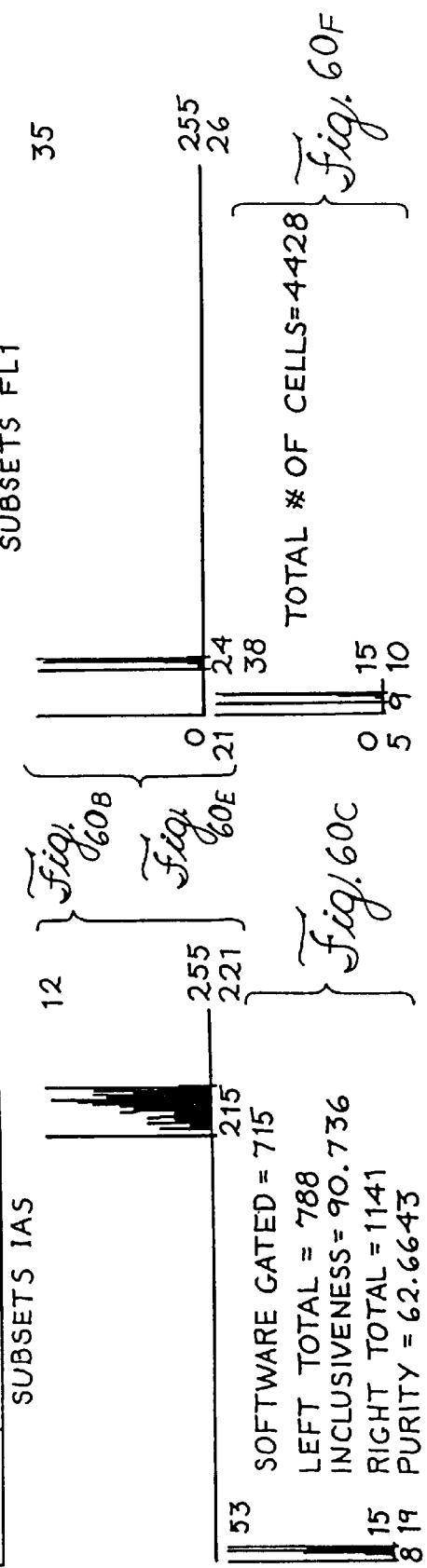
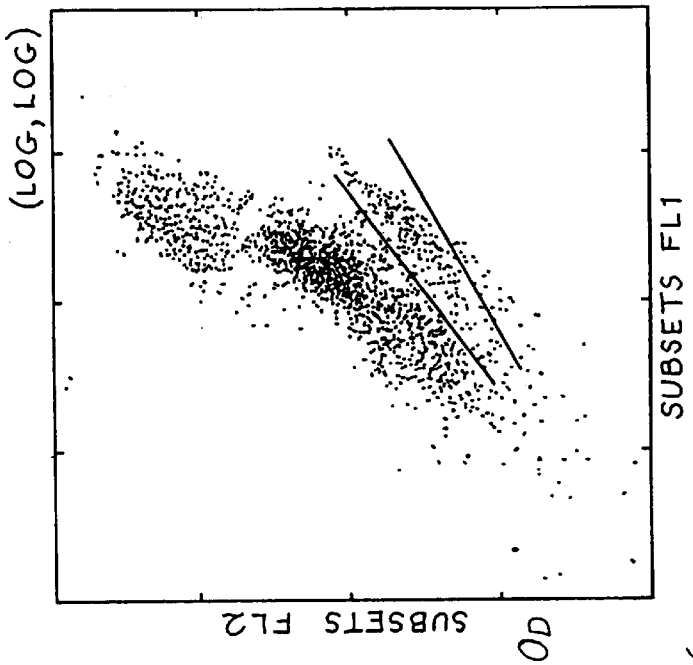
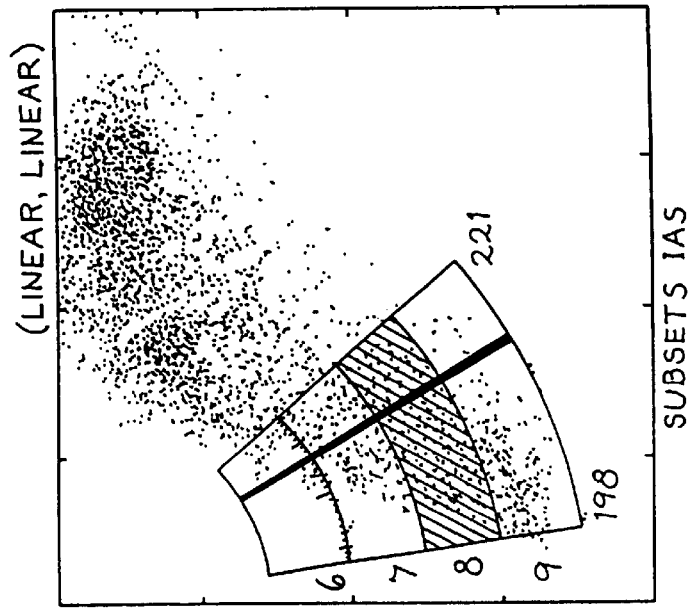

TO FIG. 63B

| n= | 0 | 1 | 2 | 3 | 4 |
|---|---|---|---|---|---|
| 11n= | SAMPLE PROCESSOR | VENT Z UP/DOWN CYLINDER 155 | ASPIRATE PROBE TILT CYLINDER 151 | VENT Z SLIDE LATCH CYLINDER 154 | |
| 12n= | REAGENT & FLOW PANEL | | | | |
| 13n= | REAGENT & FLOW PANEL | RETIC STAIN SYRINGE OUTPUT 64 | HGB CUP HIGH VELOCITY INPUT PORT 12 | WBC LYSE SYRINGE OUTPUT 13 | RETIC STAIN RESERVOIR OUTPUT 14 |
| 14n= | REAGENT & FLOW PANEL | RBC DILUTION SYRINGE DILUENT SUPPLY 21 | RBC DELIVERY SYRINGE DILUENT SUPPLY 22 | OPTICAL DELIVERY SYRINGE DILUENT SUPPLY 23 | RBC DIL SYRINGE TO ASPIRATION PROBE 61 |
| 21n= | REAGENT & FLOW PANEL | OPT DELIV SYRINGE TO WBC OPTICAL DELIV LINE 71 | IMPEDANCE NOZZLE SAMP DELIVERY ISO 72 | WBC OPTICAL NOZZLE SAMP DELIVERY ISO 73 | IMPEDANCE SECONDARY VENT. 74 |
| 22n= | REAGENT & FLOW PANEL | RETIC CUP TO OPTICAL SAMPLE STAGING NODE 51 | RETIC NODE DRAIN (WC #2) 52 | RETIC NODE TO OPTICAL FLOWCELL 53 | OPTICAL DELIVERY SYRINGE TO RETIC DELIVERY LINE 54 |
| 23n= | REAGENT & FLOW PANEL | RBC CUP TO OPTICAL SAMPLE STAGING NODE 41 | RBC CUP TO IMPEDANCE SAMPLE STAGING NODE 42 | OPTICAL PLATELET NODE DRAIN (WC #2) 43 | OPTICAL PLATELET NODE TO OPTICAL FLOWCELL 44 |

| 5 | 6 | 7 | 8 |
|---|---|---|---|
| | | | HOTPOT MOTOR ENABLE  67 |
| | | PMT1 DSS/FL1 FILTER CYLINDER  127 | PMT2 PSS/FL2 FILTER CYLINDER  128 |
| HGB LYSE SYRINGE DILUENT SUPPLY (HGB LYSE RES. OUTLET)  15 | DIL2 (NOISY) DILUENT SYRINGE SUPPLY  16 | WBC LYSE SYRINGE SUPPLY (WBC LYSE RESERVOIR SUPPLY)  24 | ASP PROBE PISTON PUMP INLET PRESS VENT. 1 NO, 1 NC  65 |
| HGB CUP LOW VELOCITY INPUT PORT  11 | RBC CUP DILUTION  26 | RETIC CUP RINSE DILUENT  62 | CONE WASH CUP DILUENT  63 |
| RETIC OPTICAL NOZZLE SAMPLE DELIVERY ISOLATION  75 | WASTE CUP DRAIN (WC #1)  76 | OPTICAL PLATLET NOZZLE SAMPLE DELIVERY ISOLATION  77 | |
| WBC CUP TO OPTICAL WBC NODE  55 | OPTICAL WBC NODE DRAIN LINE (WC #2)  56 | WBC NODE TO OPTICAL FLOW CELL  57 | |
| HGB FLOW CELL SAMPLE STAGING  45 | OPTICAL DELIVERY SYRINGE TO OPTICAL PLATELET DELIVERY  46 | HGB TRANSDUCER DRAIN (WC #2)  47 | |

|  |  | TO FIG. 63A |  |  |
|---|---|---|---|---|
| 24n REAGENT & FLOW PANEL | IMPEDANCE ISOLATOR DRAIN 31 | HGB CUP DRAIN (WC #1) 32 | RBC CUP DRAIN (WC #2) 33 | IMPEDANCE TRANSDUCER SECONDARY DRAIN (WC #1) 34 |
| 31n REAGENT & FLOW PANEL | OPTICAL FLOWCELL DRAIN (WC #3) 101 | PERIPUMP #2 TO WASTE CUP #2 (WC #2) 102 | DILUENT TO OPTICAL FLOWCELL WASTE (FOR BACKFLUSH) 103 | DILUENT TO OPTICAL FLOWCELL SHEATH 104 |
| 32n REAGENT & FLOW PANEL | IMPEDANCE SECONDARY DRAIN PRESSURE 91 | IMPEDANCE PRIMARY DRAIN VENTURE 92 | OPTICAL TRANSDUCER WASTE ISO. DRAIN (WC #3) 93 | WASTE CUP #2 PRESSURE 94 |
| 33n REAGENT & FLOW PANEL | IMPEDANCE SECONDARY DILUENT 81 | IMPEDANCE PRIMARY DRAIN PRESSURE 82 | WASTE CUP #1 DRAIN 83 | INCUBATION PROBE WASH CUP DRAIN 84 |
| 34n REAGENT & FLOW PANEL | ASPIRATION PROBE WASH BLOCK DILUENT 111 | "QUIET" TO "NOISEY" DIL. SUPPLY LINK 112 | INCUBATION CUP FLUSH DILUENT SUPPLY 113 | INCUBATION PROBE WASTE 114 |
| 43n REAGENT & FLOW PANEL | DIL1 (QUIET) RESERVOIR PRESSURE 112 | DIL1 (QUIET) RESERVOIR VACUUM 124 | DIL2 (NOISY) RESERVOIR VACUUM 126 | DIL2 (NOISY) RESERVOIR PRESSURE 132 |
| 44n REAGENT & FLOW PANEL | STATUS ALERT BOARD INDICATORS (TBD) | STATUS ALERT BOARD INDICATORS (TBD) | STATUS ALERT BOARD INDICATORS (TBD) | STATUS ALERT BOARD INDICATORS (TBD) |

| | TO FIG. 63B | | | |
|---|---|---|---|---|
| | IMPEDANCE TRANSDUCER SAMPLE FLOW OUTLET 37 | | | WBC REAGENT RESERVOIR PRESSURE 134 |
| | FLUSH CUP DRAIN (WC #1) 107 | | | |
| | DIL 1 (QUIET) DILUENT SUPPLY INLET 97 | | | |
| | WASTE CUP #1 VACUUM 87 | | | |
| | WBC LYSE SYRINGE TO INCUBATION PROBE 117 | | | |
| | WBC REAGENT RESERVOIR VACUUM 136 | | | |
| | STATUS ALERT BOARD INDICATORS | | | |
| IMPEDANCE TRANSDUCER PRIMARY DRAIN (WC #1) 35 | IMPEDANCE TRANSDUCER PRIMARY DILUENT SUPPLY 36 | | | |
| WASTE CUP #3 DRAIN 105 | OPTICAL FLOWCELL SAMPLE FLOW OUTLET 106 | | | |
| WASTE CUP #1 PRESSURE 95 | WASTE CUP #3 PRESSURE 96 | | | |
| WASTE CUP #2 VACUUM 85 | WASTE CUP #3 VACUUM 86 | | | |
| PIERCER CLEANING WASTE (WC #3) 115 | ASPIRATION PROBE WASH BLOCK WASTE (WC #3) 116 | | | |
| HGB LYSE RESERVOIR PRESSURE 142 | HGB LYSE RESERVOIR VACUUM 138 | | | |
| STATUS ALERT BOARD INDICATORS | STATUS ALERT BOARD INDICATORS | | | |
| TO FIG. 63C | TO FIG. 63F | | | |

| | RACK LOCATE CYLINDER | RACK MARK CYLINDER | CROSS TRANSFER LEFT CYLINDER | CROSS TRANSFER RIGHT CYLINDER |
|---|---|---|---|---|
| 71n AUTO SAMPLER | MIX LIFT CYLINDER | ROTARY MIX CYLINDER | | |
| 72n AUTO SAMPLER | | | | |
| 74n AUTO SAMPLER | INDEX RAIL INTERFACE BOARD (TBD) | INDEX RAIL INTERFACE BOARD (TBD) | INDEX RAIL INTERFACE BOARD (TBD) | INDEX RAIL INTERFACE BOARD (TBD) |
| 80n PNEUMATIC UNIT | 8 PSI CONTROL 161 | VACUUM PRESSURIZE (PURGE ACC.) 162 | 12 PSI DRAIN 163 | 8 PSI DRAIN 164 |
| 81n PNEUMATIC UNIT | 12 PSI CONTROL | 40 PSI SUPPLY | 12 PSI SUPPLY | 8 PSI SUPPLY |

EXCEPTIONS:

| 809 | PRESSURE PUMP VENT |
|---|---|
| 810 | 30 PSI DRAIN |

| REVERSE INDEX CYLINDER | FORWARD INDEX CYLINDER (FRONT) | FORWARD INDEX CYLINDER (REAR) | BAR CODE SPIN LIFT CYLINDER |
|---|---|---|---|
| INDEX RAIL INTERFACE BOARD (TBD) | INDEX RAIL INTERFACE BOARD (TBD) | INDEX RAIL INTERFACE BOARD (TBD) | INDEX RAIL INTERFACE BOARD (TBD) |
| VACUUM CONTROL VACUUM PUMP VENT 165 166 | | N/A 167 | N/A 168 |
| VACUUM SUPPLY N/A | | | |

Fig. 63F

METHOD AND APPARATUS FOR PERFORMING AUTOMATED ANALYSIS

REFERENCE TO RELATED APPLICATIONS

This is a divisional of U.S. patent application Ser. No. 08/482,678, filed Jun. 7, 1995, now U.S. Pat. No. 5,656,499, which is a continuation-in-part application of Ser. No. 08/Ser. No. 08/283,379 filed Aug. 1, 1994, now abandoned, entitled METHOD AND APPARATUS FOR PERFORMING AUTOMATED ANALYSIS. The parent application is assigned to the assignee of this application. The disclosure of the parent application is incorporated herein in its entirety by this reference.

BACKGROUND

This invention relates in general to particle analysis. More particularly, it relates to methods and devices for performing automated blood cell analysis by integrating "impedance," "light scattering," and "fluorescence" analysis and flow cytometric techniques. This invention also relates to a multipurpose reagent system and a method for rapid analysis of a whole blood sample.

Peripheral blood of a human usually contains red blood cells (RBC), platelets (PLT), and white blood cells (WBC), all of which are suspended in a conductive medium commonly known as plasma. Plasma comprises proteins, anions and cations. Plasma also contains components which assist in forming blood clots.

The blood in an adult usually contains about 4.5 to 5 million RBCs or erythrocytes per cubic millimeter. Mature RBCs have no nuclei and are generally shaped as circular biconcave disks with a diameter of about 7.5 to 8 microns ($\mu$), and a thickness of about 1.5 to 1.8 microns. RBCs contain hemoglobin which gives blood its red color. Hemoglobin helps transport oxygen and carbon dioxide and plays a role in maintaining pH in blood.

The blood in an adult usually contains about 200,000 to 400,000 platelets per cubic millimeter. Platelets are small, biconvex cellular particles whose mean volume is about $7\mu$ to $8\mu$. Their general configuration includes a granular central portion embedded in a homogeneous matrix.

Peripheral blood also contains red cells of earlier maturation levels which are important diagnostic indicators. Two of these are reticuldcytes and nucleated red blood cells.

At the earliest stage of development the red cell consists mostly of nucleus, and is referred to as an erythroblast. As the erythroblast matures, the nucleus becomes smaller, anucleolate, and more nearly spherical. Subsequent maturity involves a complete loss of nucleus. The immature red cells that retain a nucleus are referred to as nucleated red blood cells (NRBCs). The NRBC count has been useful in patient monitoring under many disease states. However, NRBCs in peripheral blood often contribute to inaccurate enumeration of the white cell count, due in part to the presence of a nucleus which makes them difficult to distinguish from small white cells.

Reticulocytes are red cells at the maturation level just between NRBCs and mature RBCs. Reticulocytes provide a means of evaluating a patient's anemic state. Anemia usually occurs as a result of an uncompensated increase in the rate of removal of erythrocytes from blood, or a decrease in the rate at which they are formed and released into blood. An increased reticulocyte patient count in an anemic patient indicates rapid erythroicd turnover which suggests acute blood loss or hemolysis.

In normal human blood, the concentration of white cells, referred to as WBCs or leukocytes, is much lower than the concentration of red cells. The normal concentration of WBCS is approximately 7000 per microliter. They vary in size, most of them from about 7.5 to 12.5 microns in diameter. They are more nearly spherical in shape than RBCs and usually somewhat larger in volume. WBCs may be classified generally as either granular or non-granular. The granular WBCs include neutrophils, eosinophils and basophils. The nongranular WBCs include monocytes and lymphocytes. These categories of WBCs are often referred to collectively as a "five-part differential," and, generally, the most significant of these categories are neutrophils and lymphocytes.

Neutrophils usually comprise from about 50 to 60% of all WBCs. Their cytoplasm contains numerous minute granules which can be stained. Under certain conditions neutrophils may leave the blood vessels and disintegrate, thereby releasing granules into the connective tissues. These granules are rich in certain enzymes which become active and take part in the body's defense mechanism.

Lymphocytes comprise about 30% of the WBCs in humans. The nucleus of a normal lymphocyte occupies nearly the entire cell volume, and thus the cytoplasm surrounding the nucleus is a rather thin shell. Lymphocyte cytoplasm may stain with dyes due to the cytoplasm's content of ribonucleic acid.

Lymphocytes may leave the blood vessels and enter the connective tissue where, they also constitute a part of the body's defense mechanism, playing a major role in the body's immunological responses.

There are three major "subsets" of lymphocytes that are currently clinically significant: T lymphocytes, B lymphocytes, and Natural Killer cells, also known as "large granular lymphocytes" or NK cells. Each of these subsets can be distinguished based on the existence of distinctive cell surface markers or antigens. Also, B lymphocytes have a high density of immunoglobulin of their surfaces, whereas T lymphocytes have little or none. T lymphocytes are characterized by various surface markers against which antibodies can be produced.

Categories of T lymphocytes have been identified according to their surface markers and overall function. The "helper" T cells help B cells produce certain classes of antibody molecules, and help other T cells in their immune responses. The "suppressor" T cells are regulatory cells that can suppress the responsiveness of other T or B cells. The suppressor T cells include several subsets which are also recognized by distinct surface markers.

The ability to count, size and classify blood cells is useful when evaluating the health of an individual. For example, the level of circulating CD4 lymphocytes (helper-T cells having a CD4 antigen expressed on the surface of the cell) is currently regarded as the best single predictor of progression of HIV infections. The CD4 level may be used for classifying individuals for enrollment in experimental treatment regimes, determining when anti viral therapy should be initiated, and monitoring treatment responses in clinical trials. Because CD4 lymphocyte levels may be important to some HIV-infected individuals, it is desirable to measure this parameter accurately.

In the current state of the art of cell analysis, there are two technologies used for counting and classifying cells. These are generally known as "flow cytometry" and "image cytometry." The flow cytometry technology, which essentially consists of passing cells one at a time through a sensing zone of a flow cell, is preferred in clinical applications where patient test load is an important metric. This is mainly because it has at least an order of magnitude advantage in the number of cells that can be analyzed per second.

Instrumentation incorporating flow cytometry can be further subdivided into two methods which can be generally classified as "conventional hematology" and "fluorescence cytometry."

A primary distinction between the two methods is that conventional hematology generally distinguish cells by means of size and shape alone using primarily impedance and light scatter technologies, whereas fluorescence cytometry uses cell nucleic acid content and/or surface antigens in addition to size and shape in distinguishing cells. Therefore the fluorescence method may be used to subdivide the cell types into finer classifications.

A second distinction between the two methods is that conventional hematology gives results in absolute terms, whereas fluorescence cytometry results are in relative terms. Hematology analyzers deliver precise volumes and dilutions, and are thus able to measure absolute cell concentrations, or absolute counts of cell types per microliter of human blood. The fluorescence cytometry method gives only relative concentrations, or percentages of the various cell types.

A third distinction is that the hematology method is generally automated, whereas the fluorescence cytometric method as generally practiced today, is at best semiautomated, both in sample preparation, and in sample analysis. The fluorescence cytometry method is therefore significantly more labor intensive than the hematology method.

Both methods use cell by cell analysis. Therefore, due to the high concentration of cells in whole blood, it is necessary to dilute the blood samples prior to analysis so that individual cells can be isolated for sensing within a flowcell.

An example of an instrument for performing automated hematology measurements is the Cell-Dyn® 3000 instrument, which has been sold for several years by Sequoia-Turner, a predecessor in interest of Abbott Laboratories. The Cell-Dyn® 3000 instrument uses "impedance" measurements to count and size RBCs and PLTs, "absorption" measurements to determine the concentration of hemogloiin in RBCs (MCH), and "optical scatter" measurements to count and classify WBCs and the five part differential.

The Cell-Dyn® 3000 instrument automatically prepares blood samples, measures cell parameters and generates test results. The complete automation of sample preparation is such that no substantive operator intervention is required once the patient sample of whole blood has been presented to the analyzer. As mentioned previously, in order to assure accurate "patient counts" for the various cell classes, the Cell-Dyn® 3000 instrument provides precise sample volumes, reagent volumes and dilution volumes. Patient counts are generally defined as the number of "events" per microliter of blood. The events may be RBCS, PLTS, WBCS, and classes or subclasses thereof.

Other commercially available devices for performing hematology measurements include the Coulter® STKR, the Sysmex® NE8000, and the Technicon® H-1. Each of these uses combinations of scatter, impedance, and absorption to distinguish and quantify cells, and can thus be classified as a conventional hematology instrument.

In contrast, the fluorescence flow cytometer incorporates the principles of fluorescence cell analysis with light scatter. In general this requires that the cell be stained with an appropriate color dye, or that a fluorochrome label be attached to an antigen or antibody on the cell's surface thus Indicating the occurrence of a specific antigen-antibody reaction.

In fluorescence flow cytometry, a suspension of previously stained or fluorescently labelled particles, typically cells in a blood or other biological fluid sample, is transported through a flowcell where the individual particles in the sample are illuminated with one or more focused light beams. One or more detectors detect the interaction between the light beam(s) and the labeled particles flowing through the flowcell. Commonly, some of the detectors are designed to measure fluorescent emissions, while other detectors measure scatter intensity or pulse duration. Thus, each particle that passes through the flowcell can be mapped into a feature space whose axes are the emission colors, light intensities, or other properties, i.e. scatter, measured by the detectors. Preferably, the different particles in the sample can be mapped into distinct and non-overlapping regions of the feature space, allowing each particle to be analyzed based on its mapping in the feature space. In this respect, flow cytometry differs from the conventional hematology instruments in that some of the feature space axis includes fluorescence emissions.

As noted above, lymphocyte subclasses are health determinants. Thus, it is desirable that these and other parameters be measured accurately. Although known hematology and fluorescent flow cytometry instruments have made significant advances in the ability to characterize blood cells, a problem still faced in this area is the difficulty in obtaining accurate patient count values for certain classes of cells.

An example of this problem is the CD4 cell patient count. Current analysis methods calculate the CD4 cell patient count from cell parameters measured on a hematology instrument and a separate fluorescence flow cytometry instrument. This calculation can provide up to 100% variability in absolute CD4 patient counts done on a single individual one week apart. See, e.g.: Update, Testing In The Blood Bank, Volume 5, No. 2, pages 1 to 6, published 1991 by Ortho Diagnostics Systems, Inc.

The following articles discuss additional difficulties with developing CD4 patient counts using current methods and devices;

*The Lancet*, Volume 340, Aug. 22, 1992, page 485 describes variation in CD4 count results when different analyzers are used. The variation appears to stem from different lymphocyte count results.

*Journal of Infectious Diseases*, 1990, Volume 161, pages 356 to 357 describes variations in CD4 count due to variability in the reported lymphocyte concentration. The resulting variation in CD4 results has a deleterious effect on the patients, morale.

*Journal of Acquired Immune Deficiency Syndromes*, 1990, Volume 3, No. 2, pages 144 to 181 reports large variations in CD4 counts for both HIV positive and control subjects. The fraction of lymphocytes that are CD4 positive is relatively constant, while the WBC count and the fraction of wBcs that are lymphocytes vary greatly. This variability points to the need for standardized analysis procedures.

*Laboratory Medicine*, August 1983, Volume 14, No. 8, pages 509 to 514 discusses numerous spurious results and their causes in automated hematology analyzers.

The entire disclosure of each of the above-identified references is incorporated herein by reference.

One reason for variability in CD4 patient counts is manual sample preparation that cannot be controlled precisely and depends on operator proficiency. For example, a conventional procedure for determining a CD4 patient count starts with drawing two tubes of blood from a patient. One tube is analyzed on a hematology instrument which generates several measured and/or calculated parameters for the blood sample, including a total lymphocyte patient count, a lymphocyte percentage and a total WBC patient count. The second tube of blood is analyzed on a fluorescence flow cytometry instrument. The sample preparation steps for the flow cytometry tests are labor intensive and operator dependent. These steps do not readily lend themselves to automation and precision.

To prepare the sample for the flow cytometry instrument, the operator manually pipettes a volume of blood from the sample tube into an analysis tube. A volume of the desired fluorochrome labeled monoclonal antibody is added. The sample/antibody mixture is then incubated for a predetermined time at a predetermined temperature to allow antibody/antigen bindings to take place. After incubation, the operator adds a volume of RBC lyse to destroy the RBCs in the sample. Timing is important during the lysing stage. If the operator does not allow the lyse reaction to continue long enough, RBCs may remain in the sample and distort the measurements. If the operator allows the lyse reaction to continue for too long, the lyse may attack the WBCs.

After determining that the lyse reaction is complete, the operator centrifuges and washes the sample to remove any debris left over from lysed RBCs. The centrifuge/wash step may be performed several times until the operator is satisfied that the sample is sufficiently clean. Debris, red cell "stroma" can interfere with the detection processes of the typical flow cytometer. The sample now contains WBCs with antibodies bound to cells bearing the complementary surface antigens. The operator re-suspends the sample in a volume of fixative, and then passes the sample through the fluorescence flow cytometry instrument.

The fluorescence flow cytometry instrument generates only percentage values for lymphocyte subsets. This is at least partially due to the fact that the numerous manual dilutions and volume reductions performed during the sample preparation steps do not allow the isolation of a precise measurement volume. Thus, the fluorescence flow cytometry instrument identifies the CD4 positive helper-T cells as the percentage of lymphocytes which are both positive for CD3 (T cell marker), and positive for CD4 (helper-T marker).

The CD4 patient count is then calculated using the following equations:

(% lymph/100)×(WBC count)=lymph count (% helper-T in lymph/100)×lymph count=CD4 count The lymph count and the WBC patient count are taken from the hematology instrument, while the "% helper-T cells in lymph" value is taken from the fluorescence instrument after a correction factor is applied based on the flow cytometer mapping of scatter and fluorescence.

There are several problems with the current methods of calculating patient count values for lymphocyte subsets. First of all, the calculation is based on values obtained from separate instruments that each have their own calibration and overall separate functions. Additionally, different testing methods may be used on the different instruments.

Not only are hematology instrument measurements different from fluorescence instrument measurements, but also there may be variations in results obtained from different hematology instruments.

Previous attempts to automate sample preparation in fluorescence cytometry testing have only been partially successful. Such systems still require the operator to perform sample preparation steps such as separating lymphocytes from other peripheral blood cells by density gradient centrifugation, and/or lysing red cells, removing red cell ghosts and cell debris by centrifugation, or preserving the morphology of the remaining white cells by suspending the white cells in an isotonic saline solution containing appropriate fixatives. These operations generally require the operator to manually alter the volume of the sample, thus compromising sample volume precision which can be achieved with automated mechanical volume dispensers.

Another problem with the present technique of doing the measurements on separate instruments is that a relatively large volume of patient blood is needed to fill two tubes. This is a problem because of the increased likelihood that the blood will become hemolyzed (red cells destroyed) as larger amounts of blood are drawn. Additionally, it may not be advisable or possible to draw a sufficient amount of blood from certain patients.

In leukocyte analyses, it is desirable that all of the RBCs be lysed. Because RBCs outnumber WBCs by about 700 to 1, a small number of unlysed red cells may significantly distort white cell patient counts. Some reagents used to lyse, red cells require too lengthy an incubation period to be practical in an automated clinical analyzer. For example, the Tris buffered ammonium chloride solution recommended by K. A. Murihead in Clinical Cytometry, Ann.N.Y. Acd. Sci., vol. 468, pp. 113–127 (1986) takes about 5 to 10 minutes to lyse red cells, which may be impractical for automation.

Furthermore, incomplete hemolysis with certain lytic reagents may result in red cell stroma that retain sufficient hemoglobin or particulate matter to generate high background patient counts in automated clinical electro-optical systems. When this occurs, it is usually necessary to remove the WBCs to be analyzed from the red cell stroma by centrifugation, a procedure that is a limiting factor when adapting a reagent system for automation.

Some currently used reagent systems require cytochemical staining of fixed WBCs before differential analysis. These systems require timed addition of multiple reagents and incubation periods and may not be generally adaptable for quantifying nucleated red cells or lymphocyte subsets. Furthermore, each step of reagent addition or other manipulation of a blood sample may decrease the precision of the final patient count obtained.

The earliest stage of RBC, the nucleated red cell, NRBC, when found in the peripheral blood on conventional hematology analyzers can be confused for a small lymphocyte, since the lysis will not destroy the nucleus of the NRBC. Because of the ratio of RBCs to WBCs, even a relatively small percentage of NRBCs can lead to substantial error in the WBC and lymphocyte count. This may be troublesome in neonate or pediatric samples, in which the presence of NRBCs in peripheral blood is a normal condition. For this reason, the laboratory may do manual slide inspections on some of these samples. Conventional hematology analyzers are only able to flag these samples by noting the spreading out of the usual lymphocyte scatter cluster. The manual inspection results in a count of the number of NRBCs per 100 nucleated cells. This percentage is then used to correct the analyzer WBC count as follows:

Corrected WBC count=Analyzer count(1-manual NRBC percentage/100)

Clearly the need exists for an accurate automated count of NRBCs.

Another important class of immature red blood cells are "reticulocytes" which typically contain detectable amounts of RNA. A manual method of identifying and counting reticulocytes involves precipitating the RNA with a stain. A smear is pulled from the slained blood and manually examined under a microscope. The precipitated RNA appears as intracellular dots or filaments. Reticulocyte % is determined by manually counting 1,000 RBCs under a microscope and dividing those qualifying as reticulocytes by 10. The reticulocyte patient count is derived from the RBC patient count according to the following equation:

Reticulocyte count=(RBC count)×(percent reticulocytes)/100

Both the precision and the accuracy of this manual method are less than desirable. There may be considerable variation in identification of reticulocytes as well as variation in counting techniques. Accordingly, there is a need for a cell analysis system that addresses the deficiencies described above.

SUMMARY OF THE INVENTION

A device for analyzing a whole blood sample is provided. The device, an automated instrument system for distinguishing and differentiating cells in a sample, comprises a conventional hematology analyzer fully integrated with a fluorescence cytometry analyzer. Both analyzers are controlled by a controller which utilizes the results obtained from each analyzer to report test results in absolute, or quantitative terms. Methods are also provided for analyzing a whole blood sample. One such method comprises the steps of automatedly performing both conventional hematology and fluorescence cytometry analysis on a sample. Data is collected and utilized and a quantitative result is reported when appropriate.

A further embodiment provides an automated instrument system comprising a sample handler for receiving a sample container and aspirating and dispensing the sample, a sample analyzer that performs both multi-angle light scatter and fluorescence signal detection, and a controller fully integrating the analyzer to enable the instrument system to report quantitative results of both conventional hematological and fluorescence cytometric results. This instrument system is further able to perform these functions, sequentially if necessary, without any intervention from the instrument operator once the operator has selected an array of tests to be performed by the instrument from a menu presented to the operator, and without separating cells from the sample during any phase of the analyses.

BRIEF DESCRIPTION OF THE DRAWINGS

FIG. 3 illustrates one embodiment of a sample processing area of the cell analysis system shown in FIG. 1;

FIG. 4 is a more detailed diagram of the sample processing area shown in FIG. 3;

FIG. 5 is illustrates one embodiment of a fluid distribution system of the cell analysis system shown in FIG. 1;

FIGS. 6a, 6b, and 6c illustrate the incubation probe of the cell analysis system during deposition, cleaning and aspiration;

FIG. 10a is a diagram illustrating one embodiment of an impedance sample delivery system of the cell analysis system shown in FIG. 1. In this view, the valves are open, and the sample is being transferred in bulk to the impedance transducer proximity via the pump 220;

FIG. 10b is a diagram of the impedance sample delivery system shown in FIG. 10a. In this view, the valves are closed, and a volume of the sample is being metered to the impedance transducer;

Figure 13A:
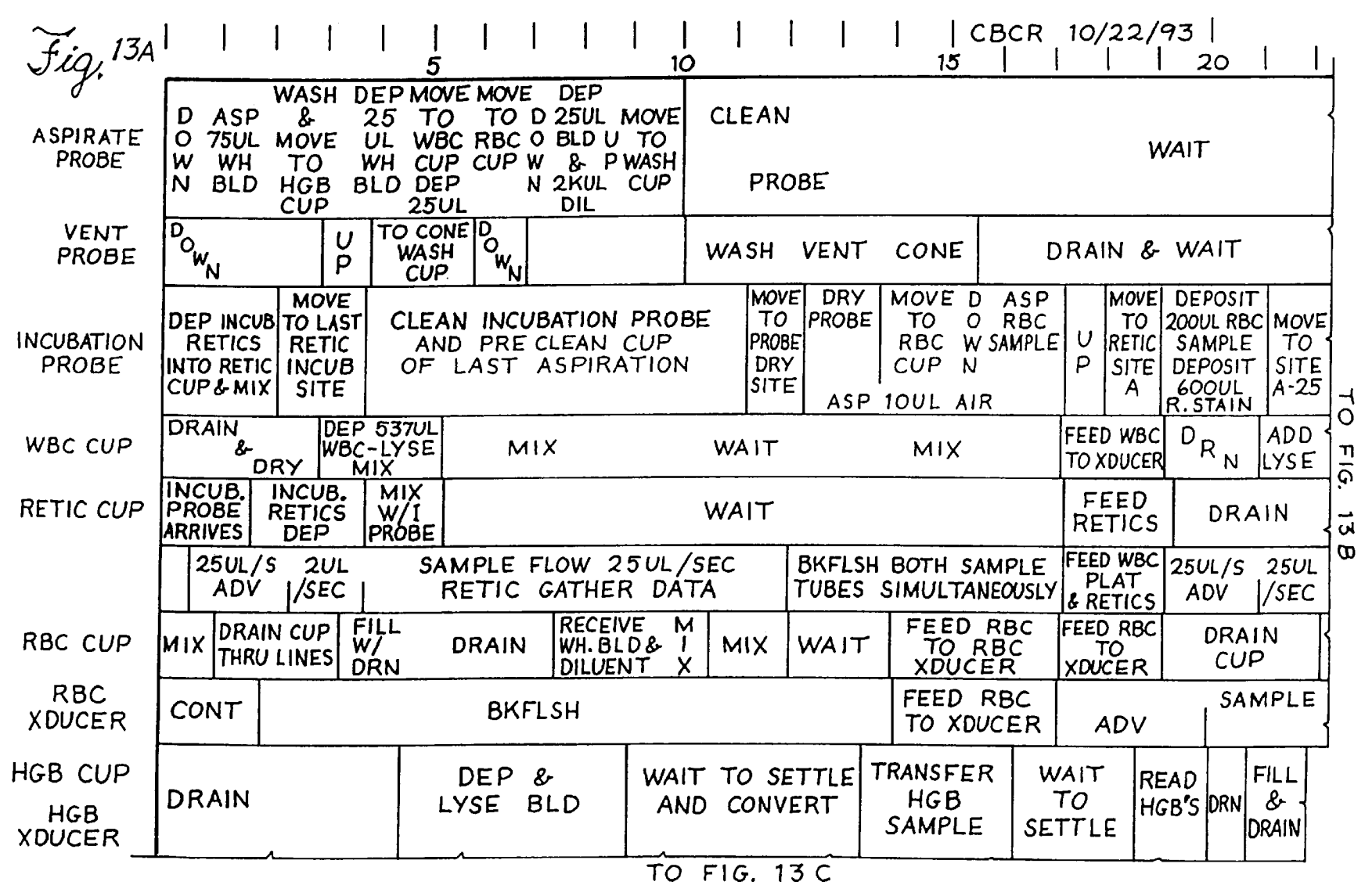

FIGS. 13A–F comprise a timing diagram illustrating one embodiment of an integrated, automated, hematology/immunology sample processing method of the cell analysis system shown in FIG. 1;

FIG. 17 is a diagram illustrating one embodiment of an impedance transducer of the cell analysis system of FIG. 1;

FIG. 18 is a diagram illustrating one embodiment of an HGB transducer of the cell analysis system shown in FIG. 1;

FIG. 19 is a diagram illustrating one embodiment of an optics bench of the cell analysis system shown in FIG. 1;

FIG. 20 is a diagram illustrating the forward path collection system of the optics bench shown in FIG. 19;

FIG. 31 is a generic elevational view of an apparatus containing a nozzle for introducing a fluid;

FIG. 32 is a perspective view of the nozzle of FIG. 31;

FIG. 33 is a sectional view of a portion of the nozzle of FIG. 32 with conduits shown in FIG. 32 being arranged mutually parallelly for clarity;

FIG. 34 is a sectional view of a portion of the nozzle of FIG. 32 illustrating fluid introduction;

FIG. 35 is a sectional view substantially similar to that of FIG. 34 illustrating fluid introduction;

FIG. 36 is a sectional view substantially similar to that of FIG. 35 illustrating fluid introduction;

FIG. 37 is a schematic diagram of a sample preparation apparatus described herein;

FIG. 38 is a partially sectioned view of a portion of the apparatus of FIG. 37;

FIG. 39 is a partially sectioned view of another portion of the apparatus of FIG. 37;

FIGS. 44A–F comprise a side elevational view of a portion of one embodiment of the cell analysis system of FIG. 1;

FIGS. 60A–F illustrate an example of data processing as described in Example 6;

FIGS. 63A–F are tables depicting valves and valve functions as described in section 13. F.

DETAILED DESCRIPTION OF THE PREFERRED EMBODIMENTS

Figure 1:
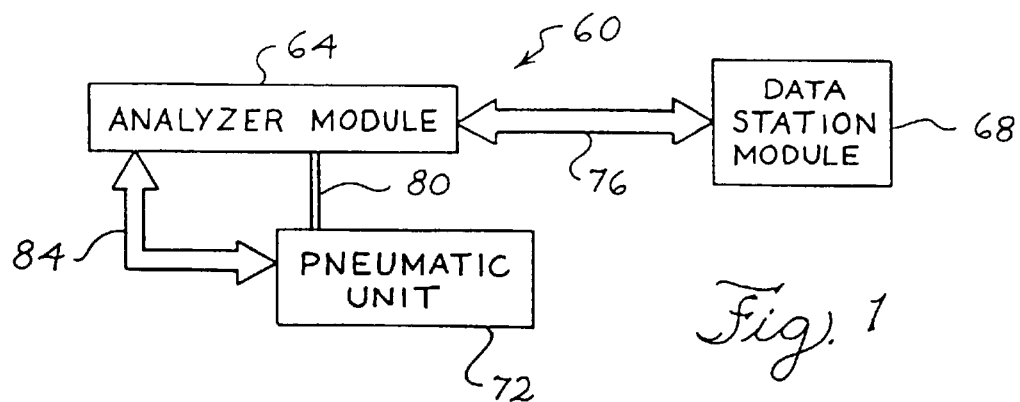
FIG. 1 is a block diagram of a cell analysis system constructed according to teachings of the present invention.

Embodiments of the present invention comprise an analytical instrument system and a method for analyzing fluid samples. Generally, one such automated instrument system includes a conventional hematology analyzer fully integrated with a controller and a fluorescent cytometer. The instrument system is able to distinguish and classify cells, whereby the data collected by the hematology analyzer is automatedly utilized by the fluorescent cytometer to process samples, analyze sample and classify cells within the sample and report quantitative as well as qualitative results.

The automated instrument system herein disclosed combines or integrates conventional hematology with fluorescent cytometry on a single analyzer platform. Heretofore, this approach has not been possible. Both methods benefit by this unique combination. Fluorescence information is improved by total automation and absolute concentrations. The hematology information is enhanced by adding fluorescence cytometry to the technology of colorimetry, impedance, and multi-angle light scatter, thereby enabling superior hematology and total automation of tests which currently are done either manually, or on separate and distinct analyzers.

For the sake of this disclosure, automation is distinguished in that an operator does not need to intervene in the sample preparation process or analysis of the sample, once the sample, i.e., whole blood, urine, saliva etc., is presented to the instrument. Additionally, all sample handling, processing and analyzing steps and functions are carried out automatedly by the instrument based upon the tests selected by the operator. All data and other information pertaining to each initial test sample is monitored, collected, and processed by the instrument controller.

The embodiments of the invention generally comprise an automated hematology analyzer and a flow cytometry analyzer integrated with a controller which monitors and controls the analyzers, collects data from the analyzers and reports a result. Illustrating by example, integration of the analyzers with a controller allows an operator to input data about a whole blood sample into the controller. The operator selects a series of tests to be performed on the sample, generally whole blood, with the aid of the controller. The operator presents the whole blood sample to the integrated analyzers at a centralized sample handling, or processing area. The controller activates the analyzers, allowing the analyzers to automatedly perform analyses on the whole blood sample under the direction of the controller. The controller utilizes data obtained from the analyzers to formulate a result. The controller reports the result to the operator. It is to be noted that no operator action is needed after the whole blood sample is presented to the integrated analyzers. Because the whole blood sample preparation is entirely automated, in a preferred embodiment, conventional hematology tests are done first with the incubated sample tests to follow. Because the analyzers are integrated with the controller, the controller obtains data from both the hematology analyzer and the flow cytometry analyzer. Thus, the controller is able to report a combined patient blood analysis to the operator. In addition absolute concentrations are reportable because of the precision and repeatability of automated dilution, cell preparation and analysis. Human error has all be been eliminated because the instrument system is the only thing to touch the sample once the operator has programmed the instrument and placed the sample on-board.

While specific embodiments of the invention will be discussed in detail to clarify understanding, it is to be remembered that other embodiments are also possible. Any desirable combination of elements of the described embodiments is also possible.

1. System Overview

FIG. 1 is a block diagram of a cell analysis system 60. The system 60 includes an analyzer module 64, a data station module 68, and a pneumatic unit 72. The analyzer module 64 is operatively connected to the data station module 68 by a serial data link 76 implementing a HDLC (high level data link) protocol. The pneumatic unit 72 is operatively connected to the analyzer module 64 by a serial data link 84 and a network of tubing 80.

The analyzer module 64 aspirates samples, diluent and reagents, dilutes samples, measures and collects data, transmits measured data to the data station module 68, manages reagents, and disposes of waste. An exemplary analyzer module 64 includes its own power supply, impedance transducer, HGB transducer, optical flowcell/transducer (light scattering and fluorescence), optical detectors, electronics, reagent reservoirs, fluidics system, integrated and fully automated sample processor for both hematology and fluorescent cytometry tests, and any necessary incubation and/or cooling systems. An exemplary analyzer module includes a Motorola 68302-type microcomputer that controls mechanical components of the analyzer 64 and executes the analyzer's flow sequences.

The pneumatic unit 72 houses pneumatic sources for moving fluids through the analyzer module 64. The pneumatic unit 72 receives instructions from the analyzer module 64 via that serial data link 84.

The data station module 68 provides general controls to the analyzer module 64, converts measured data into meaningful test results, stores measured data and test results, prints reports, and provides bi-directional communication with an off-line host computer (not shown). An exemplary data station module 68 includes an 80386 or 80486-type microcomputer, color display, 3½ inch disk drive, at least 540 megabyte hard disk, PC-style keyboard, a pointing device, and LAN connections. The data station 68 includes memory, such as a RAM, a ROM, an EPROM, a SRAM and the like, having sufficient software algorithms to manipulate measured data, calculate parameters, and display results in a variety of formats, including histograms, scattergrams, and other multidimensional plots.

2. Fast Lyse Multipurpose Reagent System

The cell analysis system 60 utilizes a multipurpose reagent system suitable for the rapid analysis of nucleated peripheral blood cells, including white blood cells ("WBC") and nucleated red blood cells ("NRBC"). The multipurpose reagent system can substantially completely and rapidly lyse red blood cells, while concurrently substantially preserving white cell morphology and the antigenicity of lymphocyte surface antigens.

The multipurpose reagent system is fully described in a U.S. patent application, Ser. No. 08/297,662, entitled "Multipurpose Reagent System For Rapid Lysis Of Whole Blood Samples", filed Aug. 29, 1994 and owned by the assignee of the present application. The entire disclosure of this application is incorporated herein by reference.

One embodiment of the multipurpose reagent system comprises from about 3 to about 7 grams per liter of a non-quaternary ammonium salt, from about 0.04 to about 0.1% by weight volume (i.e., grams per 100 ml) of an aliphatic aldehyde with one to four carbons, from about 10 to about 20 mM of a non-phosphate buffer which is substantially inert to the aliphatic aldehyde, and water. The pH of the reagent system is within a pH range of about 5.5 to about 7.5 and the osmolality of the reagent system is between about 160 to 310 (mOsm/L). The refractive index of the reagent system can be similar to that of saline and should preferably be within the range of about 1.333 to about 1.336. The non-phosphate buffer is inert to the aliphatic aldehyde in that the non-phosphate buffer will not react with the aliphatic aldehyde. Thus, generally, the non-phosphate buffer should not contain a primary amino group.

Another embodiment of the multipurpose reagent system comprises about 135 mm ammonium chloride, about 0.075% by volume of formaldehyde, about 20 mM acetate buffer, about 10 mM potassium bicarbonate, and about 0.01% by weight volume (i.e., grams per 100 ml) of saponin and the like. The pH of the reagent system is adjusted to about pH 6.2 and the osmolality of the reagent system is from about 267 to 270 mOsm/L.

The multipurpose reagent system is utilized in the automated determination of differential white cell patient counts, nucleated red blood cells, and lymphocyte immunophenotyping. A method for the rapid analysis of nucleated peripheral whole blood cells includes the following steps: mixing the described multipurpose reagent system with an anticoagulated whole blood sample (whereby the blood is diluted 10 to 100 fold), mixing the diluent-blood mixture at temperatures from about 25° C. to 46° C. for at least about 10 seconds, and analyzing the nucleated peripheral blood cells with the automated cell analysis system of the present invention.

A method of using the multipurpose reagent system in the differential analysis of peripheral white blood cells is a rapid, one-reagent method of concurrently lysing red blood cells and fixing white blood cells, wherein the white cells maintain their light scattering characteristics. In general, the cells flow through an optical view chamber where a photoelectric measuring process records the light absorbed or type of light scattered by each cell at selected angles.

A first ingredient of the multipurpose reagent system is a non-quaternary ammonium salt. Preferably, neither di- nor tri-ammonium salts should be used. A variety of monoammonium salts, particularly the halogenated salts, can be used from about three to about seven grams per liter, and preferably at about 5 grams per liter. Examples of such non-quaternary ammonium salts include $NH_4X$, where X is a halogen. Such a non-quaternary ammonium salt is $NH_4Cl$.

A second ingredient of the multipurpose reagent system is a short-chain aliphatic aldehyde. Preferably, such aliphatic aldehydes have from one to four carbons. Exemplary aldehydes include formaldehyde and the polymer paraformaldehyde. In proper ratios and concentrations, the aldehyde, in conjunction with the non-quaternary mono-ammonium salt, and the buffer, will rapidly and substantially completely lyse red blood cells. In addition, the aldehyde will fix white blood cells and substantially preserve their membrane integrity. Formaldehyde, or comparable aldehyde, is present in amounts from about 0.04% to about 0.10% by volume, and preferably from about 0.08% to about 0.1% by volume.

A third ingredient of the multipurpose reagent system is a non-phosphate buffer that is substantially inert to the aldehyde component of the reagent system. Thus, the buffer must not contain a primary amino group. The buffer should also have an effective buffering capacity between pH of about 6.0 to about 7.5, and an Osmolarity of about 230 to about 310 mOsm/L. Examples of effective organic buffers are acetate buffer, succinate buffer, maleate buffer, and citrate buffer. Examples of effective biologic buffers are 2-(N-morpholine) ethane sulfonic acid (MES) buffer, 3-(N-morpholine) propane sulfonic acid (MOPS) buffer, and N-(2-hydroxyethyl) piperazine-N'-(2-ethane sulfonic acid) HEPES buffer. An acetate, or other suitable buffer, will be present in amounts from about 10 mM to about 20 mM concentrations, and preferably at about 20 mM concentration.

An optional component of the multipurpose blood diluent is a surface active reagent. The preferred surface active agent is saponin, a plant extract that is available in a commercial grade powder isolated from quillaja tree bark as well as other sources. Although the chemical purity of commercial saponin varies from lot to lot, it is more selective towards red cells than are the quaternary ammonium salts. Saponin, or other surface active reagent, is present in amounts from about 10 to about 200 mg/L, and preferably at about 100 mg/L. Saponin, in concert with the other ingredients of the multipurpose reagent system, substantially completely lyses the red blood cells present in whole blood.

The erythrocyte fraction (i.e. red blood cells) of normal blood samples will normally be lysed within about 20 seconds at ambient temperatures. However, hard-to-lyse blood samples (such as blood samples from babies, kidney dialysis patients, multiple myloma patients, diabetics, or patients with uremia, for example) require incubating the blood with the reagent system at temperatures of about 38° C. to about 40° C. for up to about 20 seconds for complete erythrocyte lysis. Incubation of blood samples with the multipurpose reagent system, even at these slightly elevated temperatures, effectively preserves white cell membrane integrity and retains the antigenicity of lymphocyte surface antigens. In contrast, if saponin is used by itself to lyse the red cells, it should be used at a concentration about 10 to 20 times higher than those discussed above. Such concentrations may compromise the integrity of the white cells and require a rapid quenching of the lytic activity of the reagent to preserve white cell morphology. An advantage of the embodiments of this reagent system is that the combined constituents of the multipurpose reagent system serve to gently fix the white cells at the same time that the red cells are being lysed. Therefore, white cell integrity is substantially preserved even at relatively long incubation periods. In fact, even fragile white cells, such as those seen in chronic lymphocytic leukemia patients, are stabilized in the multipurpose reagent system for incubation periods of up to about 20 minutes.

An additional, optional ingredient of the multipurpose reagent system is an alkali salt, preferably a monovalent alkali salt of bicarbonate. Although a monovalent alkali salt of bicarbonate is not an essential component of the diluent, it may be added to the diluent to raise its osmolality without reducing the red cell lysability of the reagent system. Many other compounds, such as sodium chloride, potassium chloride or phosphate buffer, diminish the lysability of the reagent system when used to increase the osmolality of the reagent system. Exemplary monovalent alkali salts of bicarbonate are potassium bicarbonate, sodium bicarbonate, lithium bicarbonate and the like. Potassium bicarbonate, or other alkali bicarbonate salt, can be present in amounts from about 0.005% to about 0.015% by weight volume, and preferably at about 0.01% by weight volume.

Yet another optional ingredient of the multipurpose reagent system is a platelet anti-clumping agent. For example, an ethylenediaminetetraacetate (EDTA) salt can be added to the reagent system to reduce platelet aggregation in the sample/reagent mixture. Tetrasodium EDTA, or other EDTA salt, is present in amounts from about 20 to about 200 mgs per liter and preferably at about 100 mgs per liter.

A further embodiment of the multipurpose reagent system allows for the quantitative analysis of lymphocyte subpopulations. Lymphocyte subclassification is achieved by mixing fluorochrome-conjugated monoclonal antibodies (directed to specific lymphocyte surface antigens) with whole blood samples before adding the multipurpose reagent system, or blood diluent. The concentration of labeled antibody fractions added to a blood sample depends upon the individual antibody preparation, but is commonly about one-half to one-tenth of the volume of the blood for commercial antibody preparations. After the reagent system is added and the red cells are lysed, the lymphocyte-antibody reaction products can be analyzed on an automated flow cytometric system. There is no need to "separate" the lymphocytes from the lysed cells by centrifugation and washing as is common in the art.

The disclosed reagent system does not "quench" fluorescent markers, such as fluorescein isothiocyanate (FITC) or phycoerythrin (PE), which are used to fluorochrome-label antibodies. Lymphocyte subclassification is a diagnostic tool in the fight against many diseases, such as AIDS. The ability to identify surface markers on blood cell populations may be important when coupled with knowledge of surface components and characteristics of subpopulations of lymphocytes and other white cell fractions such as monocytes and neutrophils.

3. Nucleated Red Blood Cell Differentiation and Reagent

The cell analysis system 60 utilizes an automated method for simultaneous analysis of WBC/Diff and NRBC in a whole blood sample using a unique triple triggering method with lyse reagent, such as the rapid lyse reagent system described above. This method, claimed in U.S. Pat. application Ser. No. 08/356,932, entitled "Method For Rapid And Simultaneous Analysis Of Nucleated Red Blood Cells", and filed on Dec. 15, 1994 enables the accurate NRBC counts and WBC/Diff data, simultaneously from a whole blood sample containing NRBC. The entire contents of U.S. Ser. No. 08/356,932 is hereby incorporated by reference.

An important aspect of the NRBC method is that the signals from debris (both fluorescent and non-fluorescent) are blocked by the triple triggering method and the signals which fall below the ALL trigger but above the FL3 trigger can be identified and counted as NRBC. Therefore, accurate NRBC counts, which are essentially free of contamination from fluorescent nuclear debris, are obtained. Fragile blast cells and dead cells (non-viable) may also be detected utilizing the methods of this invention.

In the triple trigger method, it is possible to simultaneously count WBC/Diff and NRBC accurately by mixing the blood sample with a blood diluent which rapidly lyses RBC and preserves WBC, and to which has been added a suitable nuclear stain which will stain naked nuclei of the NRBC. Such a diluent is disclosed above. The diluent/sample mixture is then passed, essentially a cell at a time through an illuminated optical flow cell. This causes the cells to scatter the illuminating light and any stained nuclei present to fluoresce. The scattered and fluorescent light signals are detected by known means and, by using the triple triggering method in conjunction with the processing of the detected signals it is possible to identify and quantify WBC, WBC/Diff and NRBC.

The triple trigger method is unique in that the simultaneous analysis of WBC/Diff/NRBC can be carried out automatically, accurately, and rapidly without interference from other cellular debris such as RNA from lysed reticulocytes, Howell Jolly Bodies, reticulated platelets, giant platelets, DNA from WBC and megakaryocytic fragments, parasites, and RBC fragments.

The triple trigger method also permits accurate WBC/Diff analysis in a blood sample that contains NRBC by subtracting signals identified as NRBC from the total WBC signals before WBC/Diff analysis is performed. only one dye is needed for NRBC staining and the WBC/Diff analysis can be performed by the difference of light scattering characteristics of the WBC subclasses.

The NRBC method achieves all of the objectives described above by a unique triple triggering method in the three dimensional space of Axial Light Loss (ALL), Intermediate Angle Scatter (IAS) and Red Fluorescence (FL3).

To accomplish this, one or more detectors 380 (FIGS. 19, 20 and 21) are preferably placed in the forward light path for measuring forward intermediate angle scattering (IAS) 384 and either small angle forward scattering (SAS) or axial light loss (ALL, also known as forward extinction) 382.

ALL is generally the decrease in light energy due to a cell passing in front of a laser beam and being detected by a photodiode. The light loss is generally due to scattering and defined as the decrease in light energy reaching a detector in the path of a laser beam due to the passage of a cell through that beam (generally ALL is detected at an angle of from about 0° to about 1°.) Small angle forward scatter (SAS), in contrast, is light energy that reaches a detector outside (but within a narrow angle of about 1° to 3°) the incident laser beam due to scattering from a cell passing through the beam. A beam stop is generally provided to keep the laser beam from getting into the detector. ALL measuring systems collect light within the incident cone of laser illumination, while small angle scatter systems collect light outside this cone. In ALL measuring systems, the signal of interest is a negative signal subtracted from the steady state laser signal, whereas in small angle forward scatter measurement the signal is a small positive signal imposed on a very low background light level. Intermediate angle forward scattering (IAS) is similar to small angle forward scattering, except the light is scattered at a larger angle from the incident laser beam. More specifically, IAS relates to light scattered in a ring between about 3° and 10° away from the incident or center line of a laser beam. In a preferred embodiment, ALL is collected in the angles less than about 0.3° horizontally and less than about 1.2° vertically from the laser axis, and IAS is collected at angles between about 3° and 10° from the laser axis.

Another technical advantage of the disclosed system is that it requires much lower concentration of the dye to effectively and rapidly stain NRBC for accurate detection and counting because of complete lysis of the cytoplasm of NRBC making their nuclei more accessible to the stain. This condition permits high signal to noise (S/N) ratio, greater than 100, in NRBC detection. The concentration of a vital dye required this system to rapidly perform the simultaneous analysis of WBC/Diff/NRBC is only 1 to 2 $\mu$g/ml which is at least 50 fold less than that in the previous art.

Vital stains (nuclear stains which stain only dead or damaged cells) that can be used in the present invention can be any vital stain with relatively high extinction coefficient and low fluorescence intensity when they are not bound to nucleic acid. The spectral characteristics, i.e. Extinction (EX) max. (nm)/Emission (EM) max. (nm), of the vital dyes must be compatible with the laser light source used in the system.

The following characteristics are desired for the vital stains for the disclosed system:
High extinction coefficient
High quantum yield
High binding affinity to nucleic acid
Low fluorescence when it is not bound to nucleic acid
Light source compatibility of Spectral Characteristics. (e.g. EX max.~488 rim and EM max. ~630 nm with an Argon laser light source.)

There are a number of nuclear dyes qualified for use in the disclosed system with appropriate light source. Some of the commercially available dyes that can be used in the disclosed system are YOYO-1, YOYO-3, TOTO-1, TOTO-3, BO-PRO-1, YO-PRO-1, TO-PRO-1, and many more. It is known to those who are familiar in the art that the dyes with different EX max. can be excited with appropriate light source such as He-Ne, Xenon or Mercury lamps.

Qualified dyes which can be used with an Argon laser which are also commercially available are Propidium iodide (PI), ethidium bromide (EBr), ethidium homodimer-1 (EthD-1), ethidium homodimer-2 (EthD-2) or diethylene triamine (DTA).

In one application of the NRBC method, the vital stain used is PI.

A portion of a whole blood sample, about 25 microliters, is deposited by means of a sample aspiration probe into the WBC cup 138 which contains about 850 microliters of an isotonic lysing reagent. A lysing reagent described above is used to lyse the erythrocyte fraction of the blood sample and to lyse the cytoplasm of NRBC to expose the nuclei of any NRBC present. This reagent system is characterized in that it embodies a one reagent/one step process that achieves multipurpose goals. This reagent is gentle enough to preserve the morphology of all fragile white cells, and at the same time efficiently lyse all of the red cells. Both of these goals are accomplished even in hemaglobinophathic samples, which may require that the lysing time be extended.

No matter what the formulation of the lyse utilized with the triple trigger method, the reagent will additionally contain, or be combined with, a small concentration of a vital nuclear stain which effectively labels any NRBC which might be present in the peripheral blood. Preferably, for use with the herein referenced analyzer, the lysis chemistry will be configured such that the refractive index matches that of a sheath solution to substantially less than 0.1%.

The mixture of lyse reagent and sample will normally remain in the WBC cup 138 only for about 11 seconds. There it is lysed and mixed at 42° C.±3° C. At this point, the contents of the WBC cup are piped directly to an optical flowcell 170 for detection.

The measurement process begins as the cells stream passes through the flowcell 170, having been diluted with the addition of lyse so that the cells pass through the laser illuminated volume single file, in a laminar flowing sample stream surrounded by diluent/sheath solution.

Figure 2:
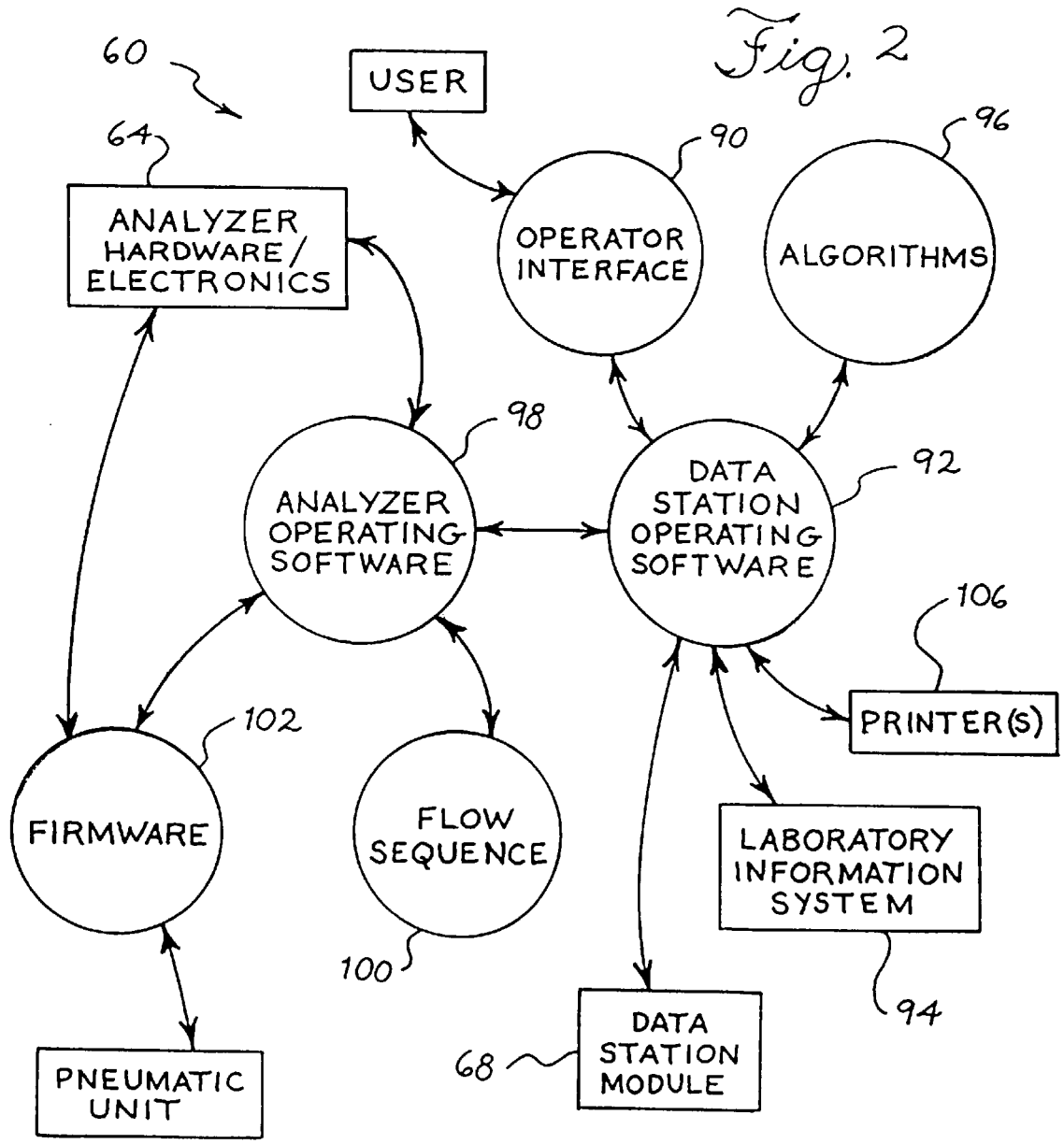
FIG. 2 is a block diagram of an embodiment of a software subsystem used with the cell analysis system shown in FIG. 1.

At this point the presence of a cell is detected by a compound photodiode 380 detecting axial light loss (ALL) and intermediate angle scatter (IAS), photomultiplier tube which detects red fluorescence, and a unique triple trigger circuit, shown in FIG. 2, in the three dimensional feature space of ALL, IAS, and FL3 (red fluorescence). The triple trigger circuit qualifies signals for digitization using AND/OR logic. A qualified signal must be greater than the IAS trigger, while at the same time it must be greater than either the ALL trigger or the FL3 trigger. The combination of this unique triggering circuit, and the lysing properties which include a balanced fixative, allow the exposed NRBC nuclei to be rapidly stained, and clearly and non ambiguously counted and excluded from the WBC differential cell count without the usual interference from background, both fluorescent and non-fluorescent, such as DNA fragments, RBC stroma, and platelets.

When cells, thus triggered, pass through the aforementioned illuminated volume, pulses are generated at detectors 380, 400, 401 and 404. The amplitudes of these pulses are then filtered, amplified, digitized, and stored in list mode in the corresponding five dimensional feature space of ALL, IAS, FL3, PSS (polarized side scatter), and DSS (depolarized side scatter). The normal counting time through flowcell 170 is 10 seconds. At the flow rate and dilution ratio described above, with a normal patient WBC count of 7000 cells per microliter of blood volume, the resulting event count rate would be 5000. In low count samples, this counting time can be automatically extended in order to improve the statistics of the measurement. At the conclusion of the measurement time, the sample stream is piped to waste, and probe is cleaned and dried and prepared to process a subsequent sample.

Algorithms are then applied to the list mode data of the aforementioned feature space of ALL, IAS, FL3, PSS, and DSS, and the following cell types are enumerated and/or flagged within less than 30 seconds of processing time:

| CELL TYPES ENUMERATED | PERCENTAGES | FLAGGED OR ENUMERATED |
|---|---|---|
| White Cell concentration | (WBC) | |
| Neutrophil concentration | % N of WBC | |
| Lymphocyte concentration | % LYMPH of WBC | |
| Monocyte concentration | % MONO of WBC | |
| Eosinophil concentration | % EOS of WBC | |
| Basophil concentration | % BASO of WBC | |
| NRBC | % NRBC of WBC | |
| Band concentration | | (BAND) |
| Blast concentration | | (BLST) |
| Immature gran. conc. | | (IG) |
| Variant-lymph conc. | | (VARL) |

ALL and IAS signals are detected and collected for the WBC/Diff analysis and FL3 signals from stained NRBC nuclei are collected for NRBC analysis, as will be described below. The triple trigger circuit, shown in FIG. 42, qualifies these signals for digitization using AND/OR logic. To be qualified a signal must be greater than the IAS trigger, while at the same time it must be greater than either the ALL trigger or the FL3 trigger.

Figure 42:
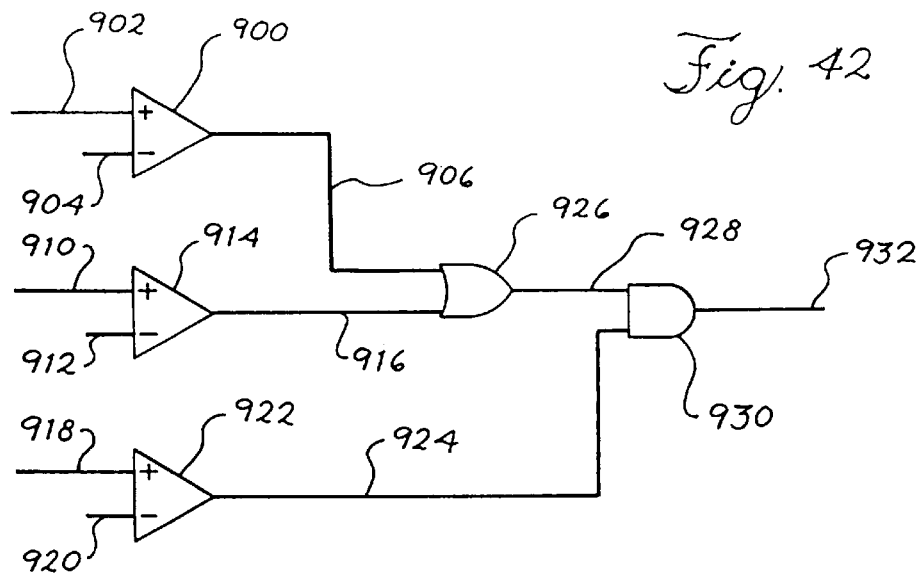
FIG. 42 is a block schematic diagram of the triple trigger circuit described in section 2., below.
Figure 48:
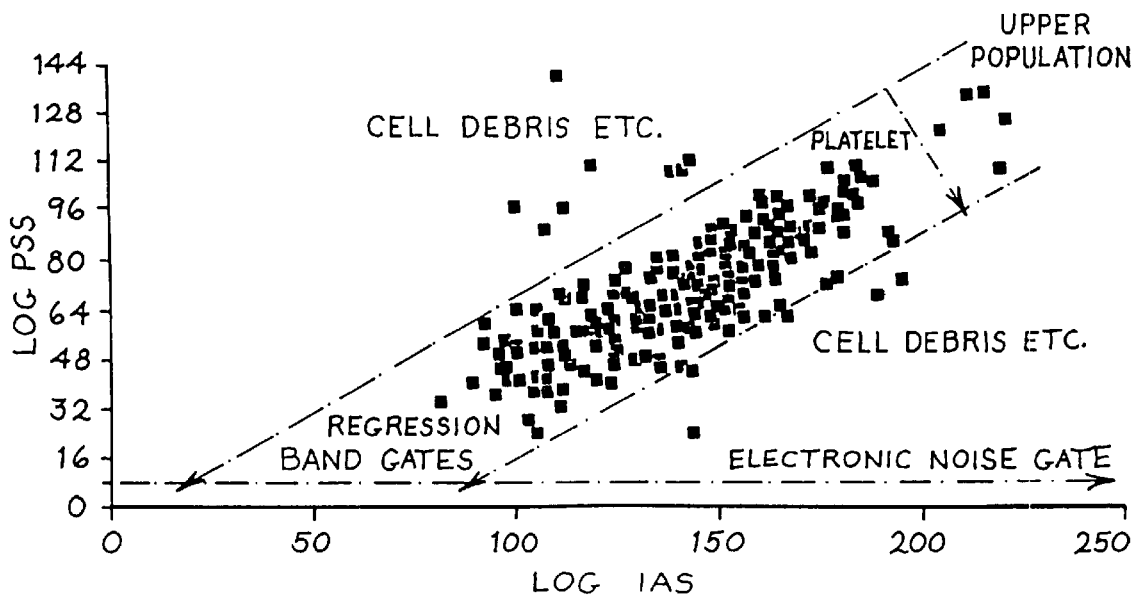
FIGS. 47 and 48 are illustrations of platelet scattergrams obtained with an embodiment of the cell analysis system.

The various components and generated or utilized signals identified in FIG. 42 correspond to the following labels:

900—ALL Voltage Comparator
902—ALL Signal
904—ALL Threshold Voltage (Vth1)
906—ALL Voltage Comparator Output
910—FL3 Signal
912—FL3 Threshold Voltage (Vth2)
914—FL3 Voltage Comparator
916—FL3 Voltage Comparator Output
918—IAS Signal
920—IAS Threshold Voltage (Vth3)
922—IAS Voltage Comparator
924—IAS Voltage Comparator Output
926—OR Gate
928—OR Gate Output
930—AND Gate
932—Valid Trigger Output Real time signals from their respective channels are present at the inputs of the voltage comparators. Voltage comparators 900, 914 and 922 function by comparing the "+ inputs" (902, 910 and 912) to the "− inputs" (904, 912 and 920) to resultant outputs (906, 916, 924). If the "+ input" is of a higher voltage than the "− input" the output will be high. If the "+ input" is of a lower voltage than the "− input" the output will be low.

The threshold voltages are independent voltages which are determined by system parameters.

The outputs of comparators 900 and 914 are inputs to OR gate 926 to give resultant OR gate output 928. The OR gate functions by comparing its inputs. The output will be high if either, or both, inputs are high.

The output of the OR gate 928 and the output of comparators 922 and 924 are inputs to AND gate 930. The AND gate functions by comparing its inputs to derive its output 932 which is also the valid trigger output. The output will be high only if both inputs are high.

The valid trigger output 932 will only be high if the IAS signal 918 is greater than its threshold voltage 920, and either or both, the ALL signal 902 is greater than its threshold voltage 904 or the FL3 signal 910 is greater than its threshold voltage 912.

Using the above triggering circuit, the NRBC's form a unique cluster in the aforementioned three dimensional space, see FIGS. 40A–C and 41A–B, which can be easily counted during the Optical WBC Differential analysis, and exclude non-ambiguously from the WBC count. Thus, a count of NRBC per 100 WBC, and an absolute NRBC per $\mu$l of patient blood is reported. Consequently, NRBC are subtracted from total WBC counts permitting accurate total WBC and Differential analysis in the presence of NRBC in a blood sample. Background noise, both fluorescent and non-fluorescent, from DNA fragments, RBC stroma, platelets, Howell-Jolly Bodies, Basophilic Stippling, RNA from lysed reticulocytes and DNA from WBC and Megakaryocytic fragments are substantially eliminated. Stained NRBC nuclei are separated from the various background noise signals via the disclosed triple-triggering process (on ALL, IAS and FL3) and only the FL3+ signals from NRBC nuclei above the FL3 trigger on the ALL vs. FL3 dot plot are counted as NRBC (FIGS. 40A–C and 41A–B).

4. Reticulocyte Method and Reagent

In one aspect of the cell analysis system 60 a stable, aqueous reagent composition is utilized for the detection and enumeration of reticulocytes. This reagent comprises: an unsymmetrical cyanine dye capable of staining reticulocytes, from about 20 mM to about 50 mM of a buffer selected from the group consisting of Imidazole buffer, 4-(2-Hydroxyethyl)-1-peperazineethane-sulfonic acid ("Hepes") buffer, Bis (2-Hydroxyethyl)-1-piperazineethane-sulfonic acid ("Bis-Tris") buffer and Tris Hydroxymethyl Aminomethane ("Tris") buffer; a pH from about 6.0 to about 8.0; an osmolarity adjusted to about 230 to about 340 mOsm/L with a mono, or di, valent alkali salt; and a non-ionic surfactant (from about 5 mg/dl to about 1.0 g/dl depending on the surfactant) which facilitates the membrane permeation and stabilizes the cyanine dyes in an aqueous isotonic solution. Preferably the dyes are cyclic substituted and exhibit enhanced fluorescence upon binding with DNA or RNA. Even more preferably, the reagent comprises from about 0.1 µg/ml to about 0.3 µg/ml of a cyclic substituted, unsymmetrical cyanine dye.

The methods for the rapid and continuous detection and enumeration of reticulocytes and CBC differentials, utilizing the present inventive reagent system. Such methods are distinct due to the particular absence of the need to provide for a separate incubation step. The minimal, 10 to 60 second incubation period is all that is necessary.

The disclosed method and reagent are the subject of U.S. patent application Ser. No. 08/426,408, entitled "Composition And Method For The Rapid Analysis Of Reticuiocytes", filed on Apr. 21, 1995. This application is owned by the assignee of the present invention and the entire contents of that application are herein incorporated by reference.

The method allows the enumeration of reticulocytes from a whole blood sample while simultaneously differentiating a separate aliquot of the sample to obtain a complete blood cell ("CBC") analysis. This method comprises, directing one or more aliquots of the sample to various positions within an automated analyzer for analysis and differentiation, while a reticulocyte aliquot of the sample is combined with a staining reagent.

The combined reagent/reticulocyte aliquot is then directed to an optical flow cell 170 of the automated analyzer 60. Thereafter the reagent/reticulocyte aliquot is passed through an illuminated sensing zone 300 essentially one cell at a time to cause fluorescence and scattered light events. These events are detected and the number of reticulocytes present in said sample are determined therefrom.

The unsymmetrical dyes usable with the reagent system generally have the following characteristics:

1. Absorption Maxima : 488+20 nm
2. High nucleic acid binding affinity
3. High quantum yield : >0.1
4. Molar Extinction Coefficient: >10,000
5. Fluorescence Enhancement upon binding to RNA or DNA: >20
6. Membrane Permeation Rate: <2 minutes Typically, the dyes utilized in the disclosed aqueous reagent and reticulocyte enumerating methods are highly unstable in aqueous environments. However the disclosed reagent formulation provides extended stability and shelf-life to the finished reagent.

A preferred embodiment of the reagent system comprises from about 0.05 µg/ml to about 0.5 µg/ml of Sybr 11, a proprietary dye sold by Molecular Probes, Inc. (Eugene, Oreg.), from about 20 mM to about 50 mM Imidazole buffer, and from about 5 mg/dl to about 20 mg/dl of N,N-bis[3-D-Glucon-amidopropyl]cholamide ("BIGCHAP"), from about 0.02% to about 0.05 5% Proclin® 300 (5-chloro-2-methyl-4-isothiazoline-3-one + 2-methyl-4-isothiazoline-3-one). The pH is adjusted to from about 6.8 to about 7.2 with iN HCl and the Osmolarity adjusted with NaCl from about 270 to about 310 mOsm/L.

A main ingredient of the reagent system is the dye. One such class of dyes are unsymmetrical cyanine dyes such as those disclosed in WO94/24213, "CYCLIC-SUBSTITUTED UNSYMMETRIC DYES", and herein incorporated by reference. Additionally, the dyes utilized in this invention exhibit enhanced fluorescence upon binding with DNA or RNA. Such useful dyes must also have high binding affinity to RNA and DNA and a high quantum yield. It is anticipated that a variety of unsymmetrical cyanine dyes which exhibit the characteristics described and claimed herein can be used. Some of the examples of such dyes include, but are not limited to Sybr 11, Sybr 14, Sybr 16, also obtained from Molecular Probes, Inc. (Eugene, Oreg.) ("MPI"). Other unsymmetrical cyanine dyes such as Syto 12, also sourced from MPI, are also useful in practicing the present invention. Syto 12 is believed to be a neutral, unsymmetrical cyanine dye comprising a substituted benzazolium ring system linked to a methine bridge to a pyridinic or quinoline ring system.

A further ingredient of the reagent system is a buffer whose pKa is from about 6.0 to about 8.0 and is capable of maintaining the required (for staining RNA or DNA) concentration of the cyanine dye in an aqueous solution in an extended period of time. Such buffers should not react with the cyanine dyes or the non-ionic surfactants used in the practice of this invention to stabilize the dye. Exemplary buffers include Imidazole, Hepes, Bis-Tris, and Tris.

Another ingredient of the reagent system is a non-ionic surfactant. Depending upon the surfactant, or combination of non-ionic surfactants, that are use, the concentration should be from about 5 mg/dl to about 1 g/dl. The surfactant (s) appear to enhance the rate of the cyanine dye permeation through the cell membrane (within 30 seconds). In addition, the solubility and the stability of the cyanine dyes in an isotonic aqueous solution are enhanced by the surfactant. Such surfactant(s) should not, however, precipitate or react with the cyanine dyes or lyse RBCS, even at the low concentrations. Examples of such surfactants are, but are not limited to, BIGcHAP, n-Dodecyl-D-Maltoside, Polyoxypropylene-polyoxyethylene block copolymer ("Pluronic® F127"), n-Tetradecyl-D-Maltoside, Decanoyl-N-methyl-glucamide, n-Dodecyl-D-glucopyranoside and n-Decyl-D-glucopyranoside.

Yet another ingredient of the reagent system is a mono-, or di-, valent alkali salt to adjust the osmolarity of the reagent from about 230 mOsm/L to about 340 mOsm/L to prevent the lysis of red cells, including the reticulocytes, or the white cells. Such salts should not react with the either the cyanine dyes or precipitate in solution. Examples of such salts include NaCl, KCl, LiCl, $CaCl_2$, $MgCl_2$, $ZnCl_2$ and others.

An optional ingredient, is a preservative to prevent microbial growth in the reagent. Such a preservative should not change the light scattering or fluorescent emission properties of the cells, or stained cells. Examples of such preservatives include Proclin® 300, Proclin® 150, sodium azide and others.

Generally, however, a method for practicing the present invention comprises the mixing of a whole blood sample with a reagent to stain the RNA of any reticulocytes present, flowing the mixture, essentially one cell at a time, through an illuminated optical flow cell, detecting the light scattered and fluorescence emitted therefrom and determining the amount of reticulocytes present in the sample without subjecting the sample/reagent mixture to a separate incubation step or period.

In order to analyze a whole blood sample for the percentage as well as the absolute counts of reticulocytes on the multi-parameter hematology analyzer described above, about 18.75 µl of a whole blood sample is deposited by means of a sample aspiration probe into the RBC cup 134 which contains about 7856 µl of a diluent/sheath solution (an isotonic saline) and the fluids are mixed. The diluted sample is then transported to a sheathed impedance aperture 174 to electronically determine the absolute RBC counts of the sample. In the mean time, about 200 µl of the diluted sample is transferred into Retic cup 136 which contains 600 µl of the disclosed reagent, where it is mixed. The prepared (mixed) sample is then transported to the sheathed optical flow cell 170 for detection. The measurement process begins as the cell stream passes through the flow cell essentially one cell at a time, in a laminar flowing sample stream surrounded by a diluent-sheath solution, disclosed hereinafter.

Figure 14A:
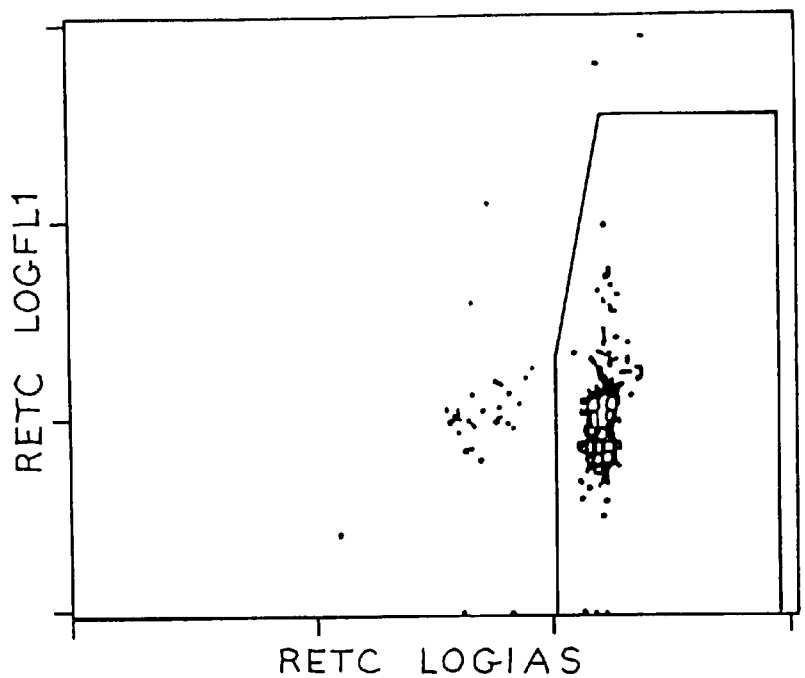
FIGS. 14A and 14B are illustrative displays isolating reticulocytes as described in section 4., below.

At this point, and as shown in the two dimensional feature space of IAS and FL1of the cytogram of FIGS. 14A and B, the presence of a cell is detected by an intermediate angle scatter photo-diode 380 which detects light in a 3° to 10° cone, and a photomultiplier tube ("PMT") 400 which detects green fluorescence, FL1. When cells pass through the aforementioned illuminated volume, pulses are generated and measured by these detectors. The amplitudes of these pulses are then filtered, amplified, digitized, and stored in list mode in the corresponding two dimensional feature space of IAS and FL1. The cells are counted for 8 seconds. At the flow rate and the dilution ratio described above, with a normal subject RBC counts of 5 millions per microliter of blood volume, the resulting event count rate would be 5950 per second. Algorithms are then applied to the list mode data of the aforementioned feature space of IAS and FL1 and the following parameters are measured within 20 seconds of computational time:

1. RBC gate: WBCs and platelets are excluded by gating the RBC population, including reticulocytes, but excluding WBCs and platelets.

2. The percent of reticulocytes: The gated RBC population is reanalyzed according to the size of their FL1 signals. A log fit is applied to the FL1 histogram to define the region which belongs to mature RBCS, and the cells whose FL1 signals fall above the region are labeled as reticulocytes. Reticulocyte % is computed by dividing the counts of reticulocytes by the total RBC counts.

3. The absolute reticulocyte counts: Obtained by multiplying the percent of reticulocytes by absolute RBC counts of the sample from the CBC mode.

4. Reticulocyte Maturity Index ("RMI"): RMI is expressed as the percent of reticulocytes whose FL1 signals are more than one (1) standard deviation ("S.D.") above the mean fluorescence of a normal reticulocyte population.

Such a description is merely for convenience and by no means is the expression of RMI of the present invention limited to only the algorithms discussed herein.

5. Alternate Reticulocyte Stain & Analysis

The disclosed alternate class of reticulocyte stains is stable to light at ambient temperature, possesses improved fluorescence enhancement of the bound stain over the unbound stain, exhibits RNA selectivity over DNA, enables improved gating of the reticulocyte cells, provides more rapid permeation of cell membranes, and possesses an optical absorption maximum closely aligned with the emission maximum of an argon laser (about 488 nm).

A preferred stain belongs to a class of molecules having the general structural formula:

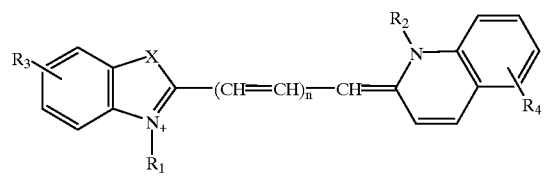

wherein:
x=O, S, Se, or $C(CH_3)_2$2
$R_1$=alkyl having from 1–6 carbons
$R_2$=alkyl having from 1–6 carbons
$R_3$=fused benzene, alkyl (having 1–6 carbons) methoxy or hydrogen
$R_4$=alkyl having 1–6 carbons, methoxy or hydrogen
n =zero or an integer from 1–6

This class of stains will be referred to herein as "2,2'-dyes."

The preferred embodiment of the reticulocyte stain shown above is where:
Preferably, x is sulphur (S)
Preferably, $R_3$ and $R_4$ are both hydrogen
Preferably, n=O and
Preferably, $R_1$ and $R_2$ are both ethyl.

This dye is listed in the Koch-light Biochemical Catalogue 1985, and 1988/89 at page 53 in the form of an iodide salt, and named 1,3'-diethyl-2,2'-quinolylthiacyanine iodide. It is also listed in the Nippon Kankoh-Shikiso Kenkyusho catalogue at page 7. For convenience hereinafter, we shall refer to this specific dye, the particularly preferred embodiment, as "DE22QTC", and to the general class of dyes, as defined above, as "2,2'-dyes".

Generally, these dyes are used in the form of their salts, iodides being particularly convenient. As used in this specification, all references to these dyes should be understood as including such dyes in salt form.

In one embodiment a reagent useful for staining RNA-containing material which is comprised of a 2,2'-dye which is capable of staining RNA-containing material.

Another embodiment a method for staining RNA-containing material wherein an aqueous staining solution of a 2,2'-dye which is capable of staining RNA-containing material is placed in contact with an RNA-containing material for a period of time adequate to enable the staining solution dye to penetrate the RNA-containing material.

Another embodiment provides a method for enumeration of reticulocytes in a whole blood sample using flow cytometry wherein an aqueous staining solution of a 2,2'-dye which is capable of staining RNA-containing material is placed in contact with an RNA-containing material for a period of time adequate to enable the staining solution dye equilibrate with the RNA-containing material. The stained sample is then directed through the optical sensing zone of a flow cytometry instrument and illuminated once within the optical sensing zone with an incident light beam. The fluorescence of the reticulocytes in sample solution are then measured as they pass through the optical sensing zone.

An important advantage of the 2,2'-dyes is that they appear to be more stable in aqueous solution than thiazole orange. This has been examined using samples of DE22QTC, thiazole orange (both at 0.1 µg/ml in isotonic diluent) and "Retic-COUNT" stored both at 4° C. in the dark and in room light at ambient temperature (about 25° C.) over a period of 5 days.

The 2,2'-dyes exhibit a significantly greater fluorescence when RNA rather than DNA is the binding substance, on a weight-for-weight basis DE22QTC allows easy gating of red blood cells away from platelets and white cells using a strategy not previously adopted for reticulocyte analysis. The dye, by its significant staining of platelets over the 30 minute period of a typical test and its expected staining of white cells in the same period, provides significant differentiation of both groups of cells from all the red cells in a plot of fluorescence versus forward scatter. The rapid staining is a property not shown by many other dyes; e.g. thiazole orange does not stain platelets significantly over the 30 minute time period although after several hours, staining does occur.

DE22QTC, when bound to RNA or DNA, has an absorption maximum of almost precisely 488 nm, and a Stokes shift of about 33 nm. This dye therefore can be used with maximum advantage with the standard argon ion laser. Moreover, the readily-available optical filters used for fluorescein-based assays can be used and the instrument need not be modified.

The 2,2'-dyes can be used in any conventional assay technique which requires the staining of reticulocytes with a fluorescent marker. In particular, these dyes can be used in any assay for which thiazole orange is currently recommended, such as reticulocyte detection and enumeration in an argon ion laser flow cytometer.

When these class of dyes are utilized to detect and differentiate reticulocytes an incubation site and associated temperature controls and sample handlers must be provided for within the instrument and operatively connected to the analyzer to maintain the automation of the inventive instrument system disclosed herein.

6. HGB Reagent

The hemoglobin ("HGB") reagent discussed herein is disclosed in U.S. patent application, Ser. No. 08/212,626, "CYANIDE-FREE REAGENT AND METHOD FOR THE DETERMINATION OF HEMOGLOBIN", filed on Mar. 11, 1994. This application is co-owned by the owner of the present application, and the complete disclosure thereof is incorporated herein by reference.

A cyanide-free reagent must be able to quickly lyse the erythrocytes and rapidly complex with the hemoglobin so that a detectable chromogenic structure is formed for detection and measurement. The disclosed reagent is stable for many weeks and is particularly advantageous because the resulting chromogen appears to be free of interference from other blood components and can be measured at wavelengths in the spectral range of automated hematology instruments already in the field. For comparison purposes, the cyan met hemoglobin method typically measures absorbance at 540 nm. A reddish brown chromogen can be formed according to the present invention which has an absorption maximum at about 544 nm.

A HGB reagent found to be useful in the present invention is an aqueous solution of a ligand-forming compound such as imidazole and imidazole derivatives. The ligand-forming compound is present at concentrations of 0.1M to 2.0M Imidazole, from the present reagent, ligates with the hemoglobin which is released from the erythrocytes in the sample. Other ligand-forming compounds useful in the present invention include N-hydroxyacetamide, N-hydroxyl amine, pyridine, oxazole, thiazole, pyrazole, pyrimidine, purine, quinoline, and isoquinoline. Anions which can bind the oxidized iron heme include cyanate, fluoride, azide, nitrite, hydroxide, acetate, and formate; acceptable salts of these anions include sodium, potassium, ammonium, and the like.

The reagent further contains a surfactant with a strong erythrolytic capability. Lauryl dimethylamine oxide (Ammonix L.O.) [Stepan Chemical Company, Northfield, Ill.], and octylphenoxy polyethoxyethanol (Triton X 100) or other strong detergents may be used as the surfactant component of the lysing reagent. The surfactant should be present at concentrations from about 0.1% to about 1.0% (w/v). The pH of the reagent should be adjusted to between 11 and 14, preferably 12.5. Monovalent bases such as sodium hydroxide and potassium hydroxide may be utilized for pH adjustment.

According to the method for determining HGB (described in more detail later in section 8 E. and Example 2 herein), the lysing reagent is mixed with a whole blood sample in the ratio of approximately 50–1000:1 reagent to blood. The sample and reagent can be rapidly mixed to achieve erythrolysis and conversion of hemoglobin to the chromogen. The sample and reagent mixture may then be presented to an absorbance spectrophotometer where the optical density of the chromogen formed is measured. When the ligand is imidazole the measurement can be made between 540 nm and 550 nm. The total hemoglobin concentration in the sample is related to the optical density of the converted chromogen.

7. Isotonic Diluent-Sheath Reagent

The cell analysis system 60 of the present invention utilizes a buffered isotonic solution with nonionic surfactant suitable for minimizing surface tension of the sheath stream and for the rapid analysis of red blood cells and platelets. The reagent system can substantially completely reduce bubble formation and enhance a smooth flow of the sheath stream for both impedance and optical flow cells. The diluent-sheath reagent disclosed below also improves the separation of microcytic red blood cells from platelets, while concurrently substantially preserving the morphology of both red blood cell and platelet populations for accurate and precise measurement of counts and volume.

In one embodiment from about 10 mM to about 50 mM of a buffered isotonic salt solution whose pKa is from about 6.0 to about 8.0, is capable of maintaining the pH of the reagent within a pH range of from about 7.0 to about 7.6, a monovalent salt of EDTA from about 0.1 gram per liter to about 0.4 gram per liter, to prevent platelet clumps is present, a monovalent salt sufficient to adjust Osmolarity of the reagent from about 270 mOsm/L to about 320 mOsm/L is also utilized, as is a nonionic surfactant which reduces surface tension, prevent bubble formation and enhance the separation of microcytic red blood cells from platelets, selected from the group n-Dodecyl -D-Maltoside, n-Tetradecyl -D-Maltoside, Decanoyl-N-methyl-glucamide, n-Dodecyl -D-glucopyranoside and n-Decyl -D-glucopyranoside, and finally a preservative is present to prevent microbial growth and deionized water.

In a preferred embodiment, the reagent comprises from about 2.45 grams per liter sodium phosphate, dibasic, about 0.40 grams per liter potassium phosphate, monobasic, about 0.20 grams of disodium EDTA per liter, about 8.05 grams of sodium chloride per liter, about 0.40 grams of potassium chloride per liter, about 0.012 grams per liter of n-Dodecyl-D-Maltoside and about 0.03 grams per liter of proclin 300, pH adjusted to 7.4 and osmolarity adjusted to 315 mOsm/L.

In the most preferred embodiment, 17.5 microliter of a blood sample is rapidly mixed with 7400 microliter of the diluent sheath reagent (1:420 dilution), and 0.5 microliters of the diluted sample is passed through a hydrodynamically focused (sheathed) impedance transducer for 12 seconds for red blood cell counts and volume measurement as well as platelet counts and 2.5 microliters of the diluted sample is passed through a sheathed optical flow cell for 6 seconds for accurate and precise platelet count determination. Noise signals from fragments of fragile abnormal cells are excluded from the optical platelet counts by bracketing the platelet population accurately by the platelet algorithm of the cell analysis system 60. Typical examples of red blood cell and platelet distribution of normal and abnormal blood samples of the cell analysis system 60 are presented in FIGS. 45A–F and 46–47.

8. Analyzer Module

A. Automated Sample Transport

The analyzer 64 may be provided with an autoloader (not shown) for automatically transporting sample tubes to the analyzer 64 for processing. Such an autoloader may include a holder which retains up to about 100 sample tubes of various sizes. A presenter which sequentially presents the sample tubes to the analyzer 64 for aspiration is operatively connected with the autoloader. A mixer which mixes the sample just before sample aspiration may also operatively associated with the autoloader. A bar code reader for reading the bar code label on each tube can also operatively be associated with the autoloader and operatively connected to the system controller to input sample information into the system controller.

B. Automated Sample Processing and Measurement

FIG. 3 illustrates a top view of one embodiment of an automated sample processing area 110 for use in the cell analysis system 60 shown in FIG. 1. The processing area 110 is part of the analyzer 64 portion of the cell analysis system 60. The processing area 110 includes a sample cup area 114 and an incubation area 118.

As shown in FIG. 3, the incubation area 118 includes a thermostated block 120 for housing reagent modules 122 and subset/phenotyping incubation trays 124. The thermostated block 120 includes a temperature controller (not shown) for heating and/or cooling the incubation trays 124 and reagent modules 122 disposed on the thermostated block 120.

The reagent modules 122 include wells 128 for holding a volume of antibody reagent. In the illustrated embodiment, each reagent module 122 has a housing with a reagent well 128, preferably six in number, packaged with a particular panel of reagents. The reagents in each panel are selected so that, for the tests associated with each panel, an approximately equal amount of reagent is used from each well 128. If less than six reagents are required for the test associated with the panel, the excess wells 128 are covered by a plug (not shown). Each reagent module 122 is also fitted with a memory, such as a non-volatile RAM and the like, to store module ID and usage information. The reagent modules 122 are preferably keyed so that they may be seated in an opening (not shown), located in the thermostated block 120, in a predefined orientation. This allows the central processing unit (CPU) of the analyzer 64 to store the location and, from the usage information, the volume of the contents of each well 128 in each reagent module 122.

The subset/phenotyping incubation trays 124 are, in the illustrated embodiment, substantially rectangular in shape, and have several rows of incubation sites 132 formed thereon. Each incubation site 132 is capable of holding a blood sample and antibody mixture that is incubated in preparation for immuno/phenotype testing. The subset/phenotyping trays 124 are removably seated in openings (not shown) in the thermostated block 120 such that their temperatures are controlled by the temperature controller of the thermostated block 120.

The sample cup area 114 includes a row of sample cups. In a preferred embodiment, these cups include an "RBC" cup 134, a "RETIC" cup 136, a "WBC" cup 138, a "transfer" cup 140, an "HGB" cup 142, and "wash" cup 144. Each sample cup is open at the top for accepting a fluid. The bottoms of the RBC cup 134, RETIC cup 136, WBC cup 138, and HGB cup 142 are connected to a tubing network 182 (shown in FIG. 5) for transporting samples to the measurement flowcells/transducers. It is also possible to deposit fluids, such as diluent, reagent, lyse, and the like, into the cups via the tubing network 182. This may be accomplished by connecting the tubing network 182 to ports (not shown) formed in the walls of the various cups. The positioning of these ports and their respective inside diameters allows mixing to take place as a result of the fluid motion caused by the delivery mechanism, which is preferably a dilution syringe coupled to the tubing network 182.

RBCs are lysed in the WBC cup 138 using, for example, the fast lyse, multipurpose reagent system discussed previously. Accordingly, the WBC cup 138 includes a temperature controller or heater for warming the fast lyse and-sample mixture, preferably to about 40° C. Additionally, the WBC cup 138 includes a vortexer 610 (FIG. 37) for providing motor-driven vortex mixing of the lyse and whole blood combination.

For the sake of clarity, an exemplary embodiment of the sample preparation is discussed with reference to FIGS. 37 through 39.

One embodiment illustrated in FIG. 37 provides an apparatus 610. The apparatus 10 generally includes a mixing apparatus 612, a fluid dispenser 614 and a mix controller 616. The mixing apparatus is further described and claimed in U.S. patent application, Ser. No. 08/356,412, filed on Dec. 15, 1994, the entire contains thereof hereby incorporated by reference.

The mixing apparatus 612 is operatively associated with the fluid dispenser 614 such that the fluid dispenser 614 introduces a first fluid, such as a whole blood sample, a cell suspension and the like, to the mixing apparatus 612. The fluid dispenser 614 is electrically connected with the mix controller 616 by conductor 618 so that the mix controller 616 monitors and coordinates operation of the fluid dispenser 614. The mix controller 616 is electrically connected with a source 620 of electrical energy by conduit 622 for supplying the mix controller 616 with electrical energy. In an exemplary embodiment, the fluid dispenser 614 is a pipettor operatively associated with a suitable source of fluid to be prepared by the apparatus 610. The mix controller 616 may be a computer having memory containing and running appropriate routines to control operation of the apparatus 610.

The illustrated embodiment of the mixing apparatus 612 comprises a first or inner housing 624, a second or outer housing 626 and a joining member 627. The inner housing 624 and the outer housing 626 are substantially cylindrical and include open ends to facilitate introduction of fluid from the fluid dispenser 614 into an interior 628 of the inner housing 624. The inner housing 624 and the outer housing 626 are disposed substantially coaxially with the inner housing 624 being disposed substantially within the outer housing 626.

The joining member 627, illustrated in FIGS. 37 and 39, substantially surrounds and operatively connects the open ends of the inner member 624 and the outer member 626. The joining member 627 includes a first substantially annular projection 630 which mates with a substantially annular notch 632 on the inner member 624 adjacent its open end and a second substantially annular projection 634 which mates with a substantially annular notch 636 on the outer member 626 adjacent its open end. To facilitate retention of the projection 630 within the notch 632, an O-ring 638 is provided that substantially surrounds an outer diameter surface of the substantially annular projection 630. The O-ring 638 performs essentially as a spring clamp for substantially securing the projection 630 within the notch 632. The O-ring 38 maintains the open end of the inner housing 624 substantially stationary with respect to the open end of the outer housing 626 during operation of the apparatus 610.

The inner housing 624 includes structures for introducing fluid into and removing fluid from the interior 628 of the inner housing 624. Specifically, the inner housing 624 includes a fluid inlet 642 and a fluid outlet 644. In one embodiment, the fluid inlet 642 and the fluid outlet 644 may be made from stainless steel tubing. In another embodiment, the fluid inlet 642 may comprise a conduit, such as a coil and the like, disposed adjacent the inner housing 624 such that thermal energy can be transferred from the inner housing 624 to the conduit thereby applying thermal energy to the fluid prior to introduction to the interior 628 of the inner housing 624. The fluid inlet 642, in an exemplary embodiment, is offset axially about 1.43 inches from a distal end of the inner housing 624. The fluid outlet 644 is disposed substantially centrally on a proximal end 646 of the inner housing 624. To facilitate movement of fluid from the interior 628 of the inner housing 624 into the fluid outlet 644, the proximal end 646 is inclined or sloped from an axial wall of the inner housing toward the fluid outlet 644.

The fluid inlet 642 is fluidly connected by a suitable conduit 648 to a source 650 of second fluid, such as a lysing solution, diluent or the like, to be introduced into the interior 628 of the inner housing 624. The source 650 may include a mechanism, such as a syringe pump and the like, to positively move fluid from the source 650 through the conduit 648 to the fluid inlet 642 and the interior 628 of the inner housing 624. The fluid outlet 644 is fluidly connected by a suitable conduit 652 to a tank 654. The tank 654 may be another portion of an analytical instrument with which the apparatus 610 is operatively associated. In other embodiments, the tank 654 may retain fluid from the interior 628 of the inner housing 624 until needed for further processing.

In some embodiments, it may be desirable to maintain fluid within the interior 628 of the inner housing 624 at a desired temperature. This fluid may be from the fluid dispenser 614, from the source 650 or a combination of fluids from the fluid dispenser 614 and the source 650. To do this, a heating element 656 is operatively associated with the inner housing 624. In the illustrated embodiment, the heating element 656 is an electrical heating element. The heating element 656, in the illustrated embodiment, substantially surrounds and contacts a portion of an outer diameter surface of the inner housing 624. In this way, thermal energy generated by the heating element 656 is transferred to the inner housing 624 and from there to the contents, i.e. fluid, disposed in the interior 628 of the inner housing 624.

The heating element 656 is electrically connected by conductor 658 to a heater controller 660. The heater controller 660 applies appropriate electrical energy to the heating element 656 such that the desired amount of thermal energy is generated by the heating element 656 and applied to the inner housing 624.

To monitor temperature associated with the heating element 656 and the inner housing 624, a sensor 664 is provided operatively thermally connected with the heating element 656 and the inner housing 624. In an exemplary embodiment, a recess is formed on the inner housing 624 to accept the sensor 664 such that an outer profile of the inner housing 624 is substantially constant and smooth. In one embodiment, the sensor 664 is a resistance temperature detector The heater controller 660 generally operates by comparing an electrical signal indicative of temperature associated with the inner housing 624 with a reference signal and using a result of the comparison to drive the heating element 656.

The inner housing 624 not only can maintain a fluid in the interior 628 at a desired thermal energy level, but also can combine or mix fluids, such as a first fluid from the fluid dispenser 614 and a second fluid from the source 650, if desired. To facilitate fluid combination, a proximal end of the inner housing 624 is operatively connected with a prime mover 686 such that the inner housing 624 moves responsive to action of the prime mover 686. A proximal end of the outer housing 626 is fixed to the prime mover 686 by fasteners 687. In an exemplary embodiment, the prime mover 686 is a direct current electric motor, such as model no. LC22-107 available from SKC Shinano Kenshi Corp. of Culver City, Calif. This embodiment of the prime mover 686 operates at about 3,000 rpm.

A linkage assembly 688 operatively or drivingly connects the prime mover 686 with the inner housing 624. The linkage assembly 688 comprises a drive member 690 (FIG. 38) and a bearing 692. A shaft 696 on the drive member 690 is coupled with the bearing 692 by appropriate means, such as a lock washer retained about a groove in the shaft 696. The bearing 692 is coupled with the proximal end of the inner housing 624 by an O-ring 694 which provides a relatively soft, elastomeric cushioned mechanical coupling of bearing 692 to the inner housing 624. The O-ring 694 also elastomerically compensates for angular centerline displacement caused by movement (e.g. eccentric) only at the proximal end of the inner housing 624. As shown in FIG. 38, the shaft 696 is offset from a midline of the drive member 690.

The drive member 690 includes a bore 698 for accepting a drive shaft, which is rotatable, associated with the prime mover 686 such that movement of the drive shaft of the prime mover 686 causes complementary movement of the drive member 690. Another bore 700, disposed substantially orthogonally to the bore 698, is provided in the drive member 690 for accepting a fastener which can bear against the drive shaft of the prime mover 686 such that the drive member 690 moves conjointly with the prime mover 686 drive shaft.

The inner housing 624 moves responsive to operation of the prime mover 686. The movement of the inner housing 624 is not identical to the rotary motion of the drive shaft of the prime mover 686. The motion of the inner housing 624 is defined, in part, by the offset disposition of the shaft 696 and the juncture between the open end of the inner housing 624 and the open end of the outer housing 626 provided by the joining member 627. Accordingly, the open ends of the inner housing 624 and the outer housing 626 remain substantially stationary with relative movement corresponding to flexibility provided by the elastomeric nature of the joining member 627. However, the proximal end of the inner housing 624 is free to move conjointly with the shaft 696 on the drive member, which moves responsive to movement of the drive shaft of the prime mover 686. Because the shaft 696 is disposed offset on the drive member 690, movement of the shaft 696 generally follows a substantially eccentric path. Thus, the inner housing 624 generally "vibrates" responsive to operation of the prime mover 686. It is to be noted that the inner housing 624 does not rotate freely with respect to the outer housing 626 responsive to the prime mover 686.

To control operation of the prime mover 686, and thereby to control motion of the inner housing 624, a controller 702 is provided. Specifically, the controller 702 is electrically connected with the prime mover 686 by conductor 704. A sensor 706 is operatively associated with the inner housing 624 and electrically connected with the controller 702 by conductor 708 to provide the controller 702 with feedback indicative of movement of the inner housing 624. The controller 702 is electrically connected with the mix controller 616 by conductor 701 and with source 620 by conductor 703. Thus, the controller 702 and the mix controller 616 are able to positively regulate operation of the prime mover 686 to cause intended movement of the inner housing 624.

To provide a magnetic field for interaction with the sensor 706 in this embodiment, a magnet 710 (FIG. 38) is provided with the drive member 690. In one embodiment, the magnet 710 is retained within a recess 712 in the drive member 690 by suitable means, such as an adhesive like an epoxy cement. The magnet 710 is oriented within the recess 712 such that a south pole of the magnet 710 faces the sensor 706. Thus, as the drive member 690 moves responsive to the operation of the prime mover 686, the magnet 710 generates a periodic electrical signal in the sensor 706. The electrical signal is substantially periodic with a frequency which is substantially equal to a rotational frequency of the drive shaft of the prime mover 686.

An example of operation of the apparatus 610 will now be given. It is to be noted that the following discussion is for illustrative purposes only.

It is assumed, for the sake of clarity, that the apparatus 610 is at rest (i.e. nothing is energized). An operator accesses the mix controller 616 to begin operation of the apparatus 610. A suitable first fluid, such as whole blood, a biological sample and the like, is made available to the fluid dispenser 614. A suitable second fluid, such as a blood diluent, a lyse and the like, is made available at the source 650.

The mix controller 616 issues an electrical signal to the heater controller 660 via conductor 662 such that the heater controller 660 electrically connects the source 620 of electrical energy to the heating element 656. The electrical energy from the source 620 passes along conductors 668 and 658 to the heating element 656. The electrical energy is converted into thermal energy by the heating element 656. The thermal energy in the heating element 656 is transferred to the inner housing 624. In one embodiment, the heating element 656 is supplied with electrical energy until the sensor 664 detects that the temperature associated with the inner housing 624 is about 43 degrees Celsius (±1.5 degrees Celsius). By using a temperature level of less than about 45 degrees Celsius, in the case where the first fluid is whole blood, some blood cell surface antigens do not substantially denature and some blood proteins do not substantially coagulate. If sufficient blood cell surface antigens were to denature or if sufficient blood proteins were to coagulate, then those substances could coat portions of the apparatus 610 and the associated instrument. The coatings could dislodge variably and compromise operation of the apparatus 610 and the associated instrument.

The heater controller 660 maintains the desired temperature associated with the inner housing 624 by regulating electrical energy flow from the source 620 of electrical energy to the heating element 656. Accordingly, the heater controller 660, and thus the heating element 656, may operate substantially continuously during operation of the apparatus 610 or the instrument with which the apparatus 610 is associated.

Once the inner housing 624 has the desired temperature associated with it, the mix controller 616 sends an electrical signal to the controller 702 along conductor 701. Responsive to this electrical signal, the controller 702 electrically connects the prime mover 686 with the source 620 of electrical energy thereby energizing the prime mover 686. The prime mover 686 moves or vibrates the inner housing 624.

A predetermined volume of the second fluid, such as about 1275 microliter ("$\mu l$") of lyse, is moved from the source 650 into the conduit 648 by a suitable mechanism, such as a syringe pump and the like. The second fluid flows through the fluid inlet 642 in the inner housing 624 toward the interior 628 of the inner housing 624. It is to be noted that, if desired, the prime mover 686 may be energized either before or after the predetermined volume of the second fluid is disposed within the interior 628 of the inner housing 624. The predetermined volume of second fluid moves conjointly with the inner housing 624 responsive to action of the prime mover 686 for a first predetermined time period, which may be on the order of about 5 seconds. After the first predetermined time period, the second fluid has substantially the same thermal energy as the inner housing 624.

The mix controller 616 sends an electrical signal to the fluid dispenser 614 along conductor 618. The fluid dispenser 614 acts to introduce a predetermined volume of first fluid, such as about 37.5 $\mu l$ of whole blood, into the interior 628 of the inner housing 624. In one embodiment, the fluid dispenser 614 may be a pipettor having a discharge nozzle which may be moved toward the opening 640 in the joining member 627. Once the discharge nozzle is in appropriate position with respect to the opening, the predetermined volume of first fluid is moved into the interior 628 of the inner housing 624.

Once the predetermined amount of first fluid is introduced into the interior 628 of the inner housing 624, the first fluid and the second fluid are moved within the inner housing 624 responsive to action of the prime mover 686 for a second predetermined time period which may be about 11 seconds. The prime mover 686 operates preferably at a frequency which is not equal to a resonant frequency associated with the apparatus 610.

In an exemplary embodiment, where the first fluid is whole blood and the second fluid is lyse, as described above, the first fluid and the second fluid substantially completely mix due to fluid movement within the inner housing 624 responsive to the prime mover 686. The ratio of first fluid to second fluid is about 1 to about 35. The red cells in the whole blood are relatively rapidly lysed and the white cells are relatively rapidly fixed, i.e. substantially preserving white cell morphology. Because the second fluid and the inner housing 624 are at substantially the same thermal energy level, the first fluid also reaches substantially the same thermal energy level after the second predetermined time period.

After the first and second fluids have been moved in the interior 628 of the inner housing 624 for the desired time period, operation of the prime mover 686 ceases. The mixture of the first fluid and the second fluid are moved through the fluid outlet 644 and conduit 652 toward the tank 654. The mixture is moved by an appropriate mechanism, such as a syringe pump, operatively associated with the fluid outlet 644. The mixture can be further processes or retained in the tank 654 until needed. The apparatus 610 is ready for further operation.

Figure 4A:
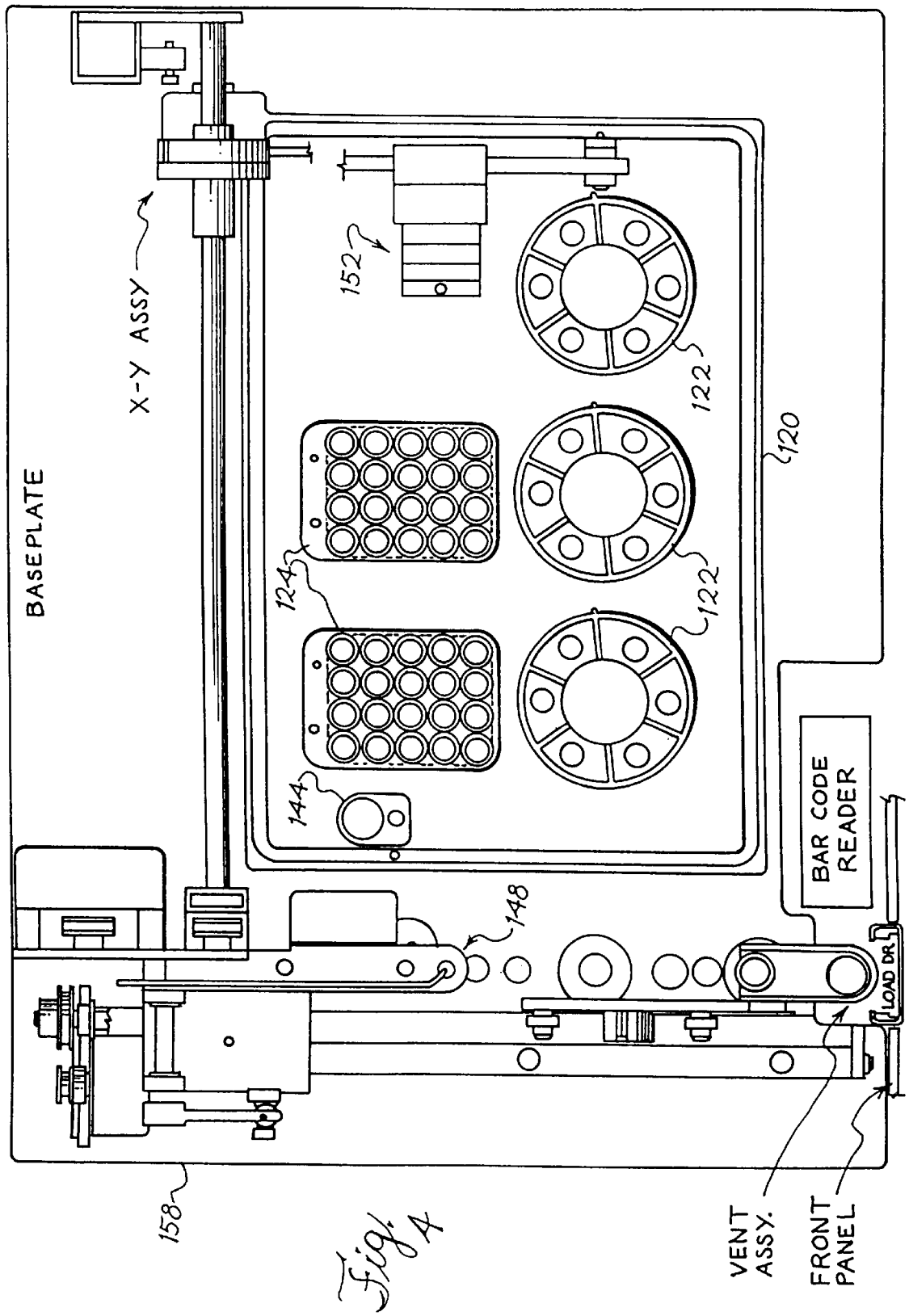
FIG. 4A is front elevational view of a vent/aspirate assembly of the system shown in FIG. 4.
Figure 4B:
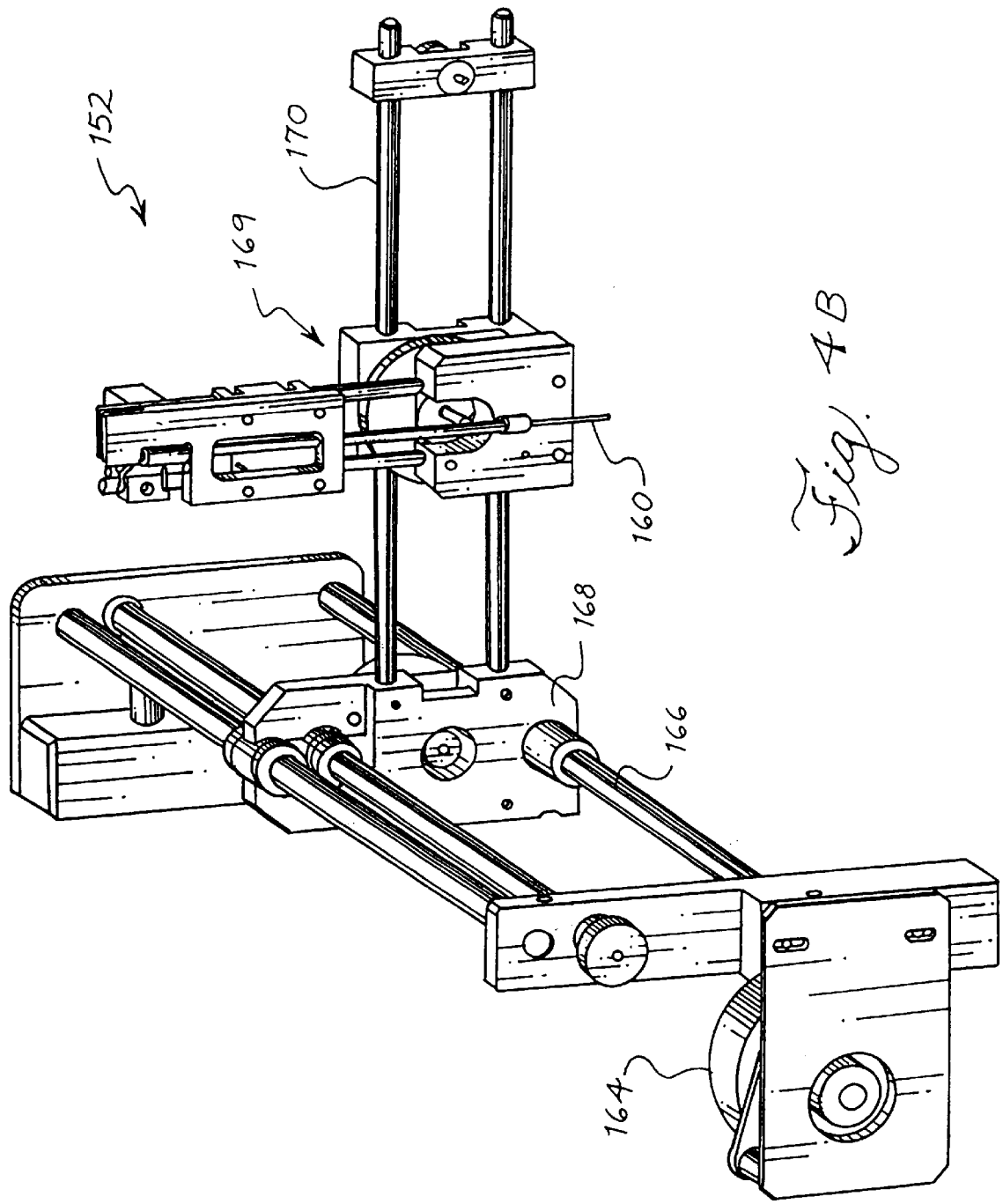
FIG. 4B is a perspective view of an incubation probe assembly used in the system of FIG. 4.

FIG. 4 is a more detailed illustration of the sample processing area 110 shown in FIG. 3. As shown in FIG. 4, the sample processing area 110 includes a vent/aspirate probe assembly 148 and an incubation probe assembly 152. The vent/aspirate probe assembly 148 (shown in FIG. 4A) includes a vent needle 154, an aspiration probe 156, a drive assembly 158 for moving the aspiration probe assembly 148 along a slide assembly 160, a drive assembly 159 for moving the vent needle 154 along the same slide assembly 160, and a vertical drive assembly 161. The slide assembly 160 is positioned above the sample cups so that the vent needle 154 and aspiration probe 156 can be positioned directly over the sample tube and sample cups.

The aspiration probe drive assembly 158 moves the aspiration probe 156 over the sample cups or sample tube so that the probe 156 can enter the sample tube or sample cups to aspirate or deposit fluid. When the aspiration probe 156 is making its approach to a pre-evacuated container or other sealed sample tube (not shown), the vent drive assembly 159 first moves the vent needle 154 over the sample tube. A piston assembly (not shown) moves the vent/aspirate probe assembly 148 downward so the vent needle 154 pierces the cap of the sample tube. While the vent needle 154 remains inserted in the cap, the vertical drive assembly 161 causes the aspiration probe 156 to slide through the vent needle 154 into the sample tube to aspirate the sample.

Preferably, the cell analysis system 60 has the flexibility to aspirate fluid from a variety of sample tube sizes and to adapt to varying tube closures. Accordingly, the vertical drive assembly 161 is provided with a switch that senses when the aspiration probe 156 reaches the bottom of the tube and stops further downward motion of the aspiration probe 156. The vertical drive assembly 161 then raises the aspiration probe 156 and begins blood aspiration.

The incubation probe assembly 152 (shown in FIG. 4B) can include an incubation probe 160, a first incubation probe drive assembly 164 for moving a second drive assembly 168 along a first slide assembly 166, and a second incubation probe drive assembly 168 for moving a vertical drive assembly 169 and the incubation probe 160 along a second slide assembly 170. This allows the incubation probe 160 to be moved in a diagonal direction and positioned directly above the required sample processing cups in the sample processing area 110. The incubation probe 160 can also be positioned above any of the incubation sites 132 on the subset/phenotyping trays 124, any of the six reagent wells 128 in each of the reagent modules 122, or the incubation wash cup 144.

The vertical drive assembly 169 moves the incubation probe 160 vertically so that the incubation probe 160 can enter the sample cups, the incubation sites 132, or the reagent wells 128 to aspirate or deliver fluids.

FIG. 5 further illustrates the analyzer's sample processing. As shown in FIG. 5, several of the sample processing cups 132, 134, 136, 138, 140 and 142 are connected to the flowcells/transducers 170, 174, 178 via a network of transport tubing 182. The RBC cup 134, RETIC cup 136, and WBC cup 138 are each in fluid communication with the impedance transducer 174 and the optical flowcell 170. The HGB cup 142 is in fluid communication with the HGB transducer 178.

FIGS. 6a, 6b, and 6c illustrate the incubation probe 160 during deposition, cleaning, and aspiration respectively. The probe 160 is constructed of a central tube 184 and an outer tube 186. The incubation probe 160 aspirates and deposits fluids through the central tube 184. The incubation probe 160 may be used to clean the sample cups and/or incubation sites by spraying cleaning fluid through an annular region formed between the central tube 184 and the outer tube 186 while aspirating through the central tube 184.

In the disclosed embodiment, the analyzer module 64 is supplied with diluent, monoclonal antibody (MAb) reagents if necessary, several lysing reagents, and reticulocyte stain. The diluent, lysing reagents, and reticulocyte stain are supplied through reservoirs 192 and 196 (shown in FIGS. 7, 8 and 9) coupled to the analyzer 64. The reservoirs 192 for diluent and lysing reagents are also coupled to bulk storage containers 193. When the flow script request the filling of a reservoir, the level sensing switch (not shown) in the reservoirs 192 checks for a full condition in the reservoir, and if the instrument controller determines that the reservoir can tolerate the filling sequence at this time, a pneumatic control line 189 switches from applying a positive pressure to applying a vacuum of about 15 inches of mercury. This vacuum causes fluid to flow from the bulk storage container 193 into the reservoir 192 until the level sensing switch senses that the reservoir 192 is full, at which time the pneumatic control line 189 returns to a positive pressure and fluid flow from the bulk storage container 193 to the reservoir 192 ceases. The Mab reagents can be supplied by disposable, pre-packaged reagent modules 122 (shown in FIGS. 3 and 4).

The analyzer 64 is provided with fluid sensors (not shown) for determining when one of the bulk containers is empty. These sensors detect air bubbles drawn into the tubing between the bulk storage containers 193 and the reservoirs 192. The analyzer 64 informs the data station module 68 which, in turn, signals the operator about the empty container. The operator can then replace the empty container with a full one and indicate via the user interface to the data station 68 that the container has been replaced. Until the container is replaced, the analyzer 64 will not aspirate additional samples from the sample tubes, although processing of samples already begun will continue with the sufficient reagent remaining in the reservoirs.

Figure 7:
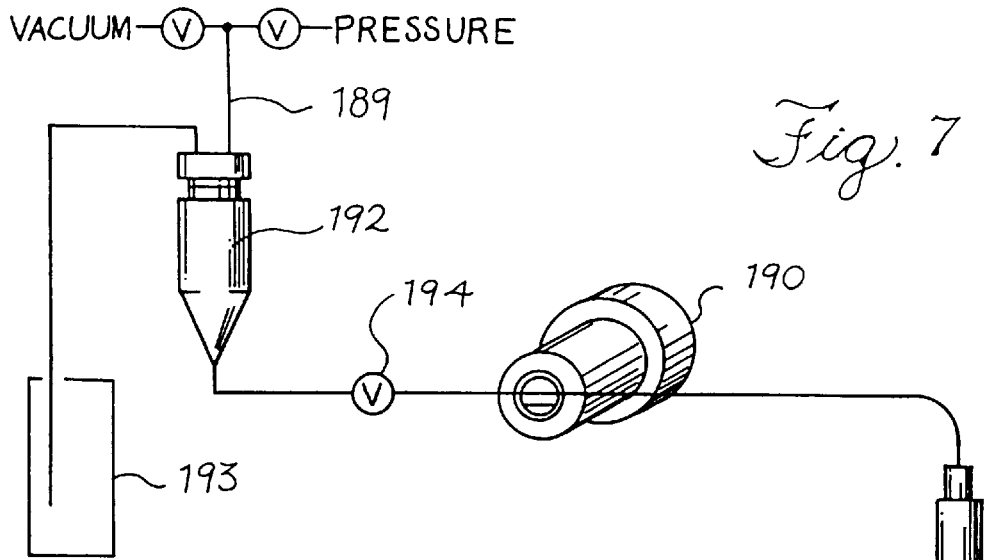
FIG. 7 is a diagram illustrating one embodiment of an aspiration and deposition system of the cell analysis system shown in FIG. 1.
Figure 8:
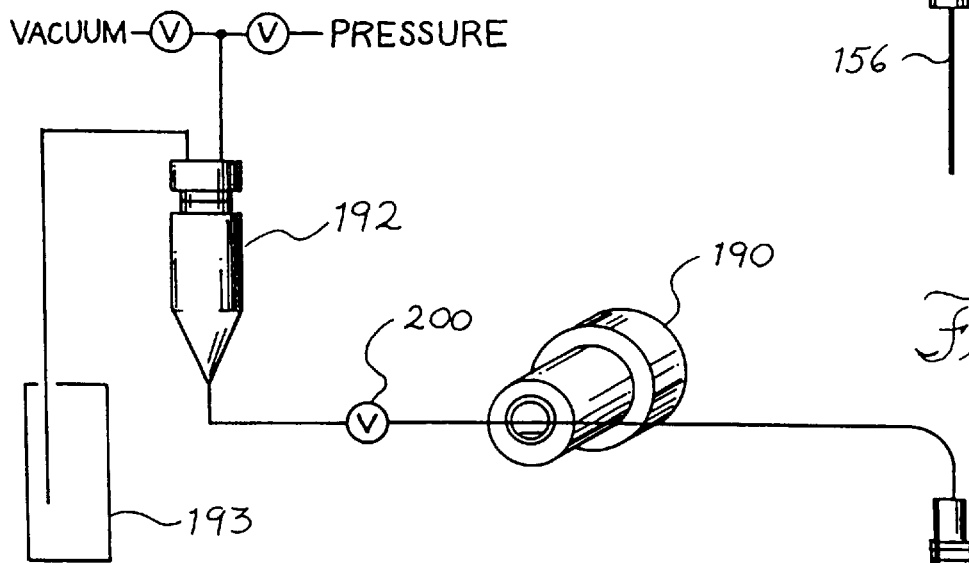
FIG. 8 is a diagram illustrating one embodiment of an incubation transfer system of the cell analysis system shown in FIG. 1.

The aspiration and dispensation by the aspiration probe 156 and the incubation probe 160 are effected by a series of piston pumps 190. FIGS. 7 and 8 illustrate how the aspiration probe 156 and incubation probe 160 are connected to piston pumps 190 and the reagent reservoirs 192. The volume and flow rate of these fluid transfers are controlled by the analyzer 64 and the data station 198.

As shown in FIG. 7, the aspiration probe 156 is coupled to a diluent reservoir 192 via a valve 194 and piston pump 190. FIG. 8 illustrates the incubation probe 160 coupled to a diluent reservoir 192 via a valve 200 and a piston pump 190.

Preferably, the piston pumps 190 are rotatable, reversible pumps capable of aspirating a predetermined volume of fluid for each piston rotation. Each piston pump 190 aspirates fluid as its piston is rotated in one direction, and deposits fluid when its piston is rotated in another direction. Suitable piston pumps are disclosed in U.S. Pat. Nos. 4,941,809; 5,015,157; 5,020,980; and 5,044,889. The entire disclosure of each of the above-identified patents is incorporated herein by reference.

Figure 9:
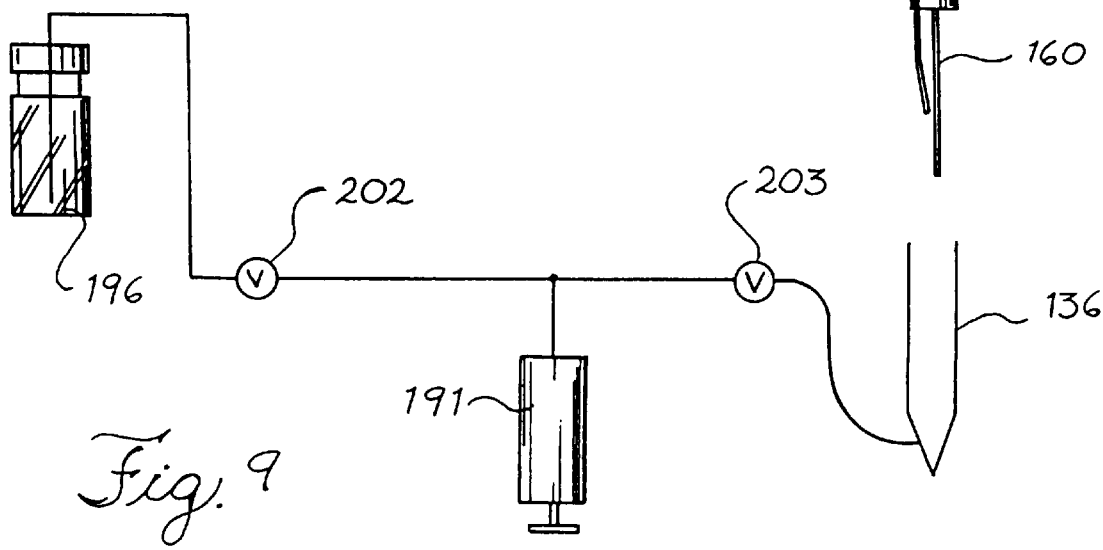
FIG. 9 is a diagram illustrating one embodiment of a reticulocyte stain delivery system of the cell analysis system shown in FIG. 1.

FIG. 9 illustrates how the reticulocyte stain reservoir 196 is connected to the reticulocyte cup 136 via valves 202 and 203 and a reticulocyte stain syringe 191.

Diluent may also be measured and delivered to the sample cups via diluent syringes (not shown) and the tubing network 182. The diluent syringes and the reticulocyte stain syringe 191 are substantially similar to the delivery syringes 204, 206, 208, shown in FIGS. 10a, 10b, 11a, 11b, and 12. The diluent syringes may be connected to the tubing network 182.

FIGS. 10a, 10b, 11a, 11b, and 12 illustrate how samples that are ready for measurement are delivered from the sample cups to the flowcells/transducers 170, 174, 178.

FIG. 10a illustrates bulk transfer of sample from a sample cup 216 to the proximity of impedance transducer 174 via pump 220. FIG. 10b illustrates metered delivery of the sample by the RBC delivery syringe 204 to the impedance transducer 174. The sample cup 216 is connected to the RBC syringe 204, the impedance transducer 174 and a peristaltic pump 220 by tubing 182. A first valve 210 is placed in the tubing 182 downstream of the sample cup 216, and a second valve 212 is placed in the tubing 182 upstream of the peristaltic pump 220. The flow rate and general operation of the RBC syringe 204 are controlled automatically by the analyzer's electronics and software.

Bulk transfer of sample from the sample cup 216 to the proximity of the impedance transducer 174 occurs when the first and second valves 210, 212 are open, as shown in FIG. 10a, and the peristaltic pump 220 is driven. Metered delivery of the sample from the RBC syringe 204 to the impedance transducer 174 occurs when the first and second valves 210, 212 are closed, as shown in FIG. 10b, and the plunger 224 of the RBC syringe 204 is moved a predetermined distance at a specified rate.

Figure 11A:
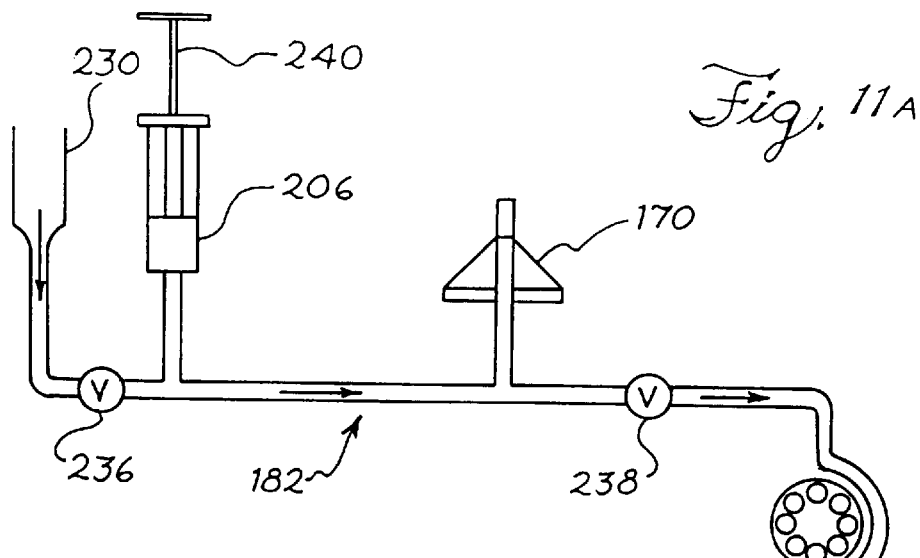
FIG. 11a is a diagram illustrating one embodiment of an optical sample delivery system of the cell analysis system shown in FIG. 1. In this view, the valves are open, and the sample is being transferred in bulk to the flow cell proximity via the pump 232.
Figure 11B:
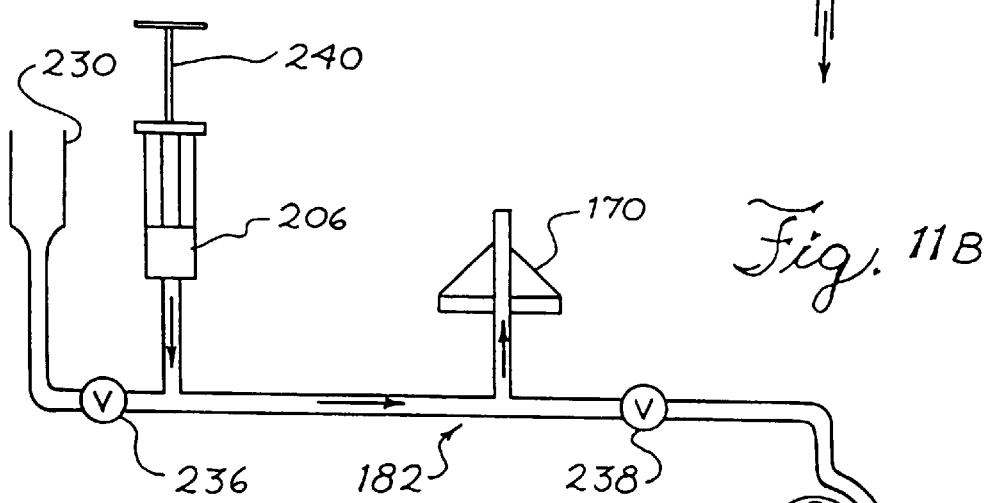
FIG. 11b is a diagram of the optical sample delivery system shown in FIG. 11a. In this view, the valves are closed, and a volume of the sample is being metered to the optical flowcell transducer.

FIG. 11a illustrates the bulk transfer of sample from a sample cup 230 to the proximity of the optical flowcell 170 via pump 232. Pump 232 may be substantially similar to pump 220. FIG. 11b illustrates the metered delivery of the sample by the WBC delivery syringe 206 to the optical flowcell 170. The sample cup 230 is connected to the WBC syringe 206, the optical flowcell 170 and a peristaltic pump 232 by tubing 182. A first valve 236 is placed in the tubing 182 downstream of the sample cup 230, and a second valve 238 is placed in the tubing 182 upstream of the peristaltic pump 232.

As shown in FIG. 11a, bulk transfer of sample from the sample cup 230 to the proximity of the optical transducer 170 occurs when the first and second valves 236, 238 are open and pump 232 is driven, thereby displacing a volume of sample to the proximity of the optical flowcell 170. Metered delivery of the sample by the WBC syringe 206 to the optical flowcell 170 occurs when the first and second valves 236, 238 are closed, as shown in FIG. 11b, and the plunger 240 of the WBC syringe 206 is moved a predetermined distance at a specified rate.

Figure 12:
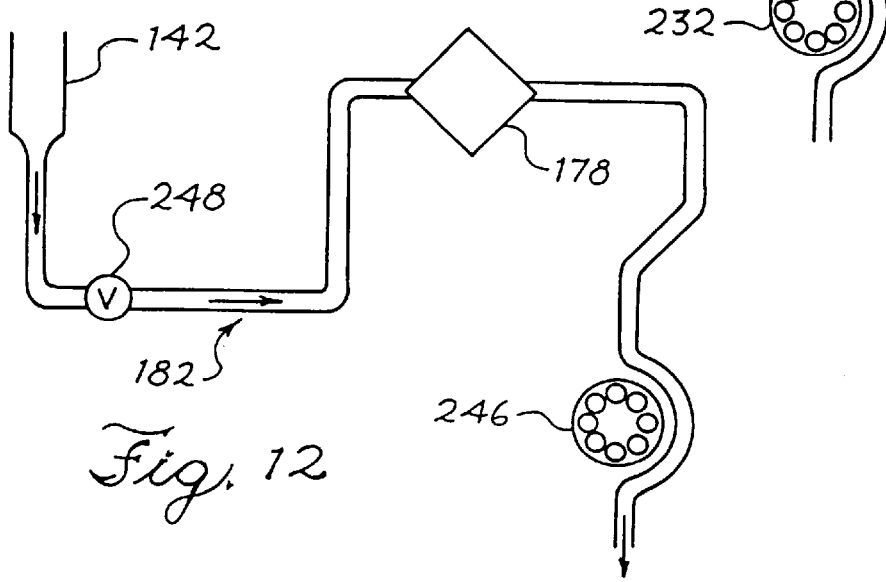
FIG. 12 is a diagram illustrating one embodiment of a HGB sample delivery system of the cell analysis system shown in FIG. 1.
Figure 13B:
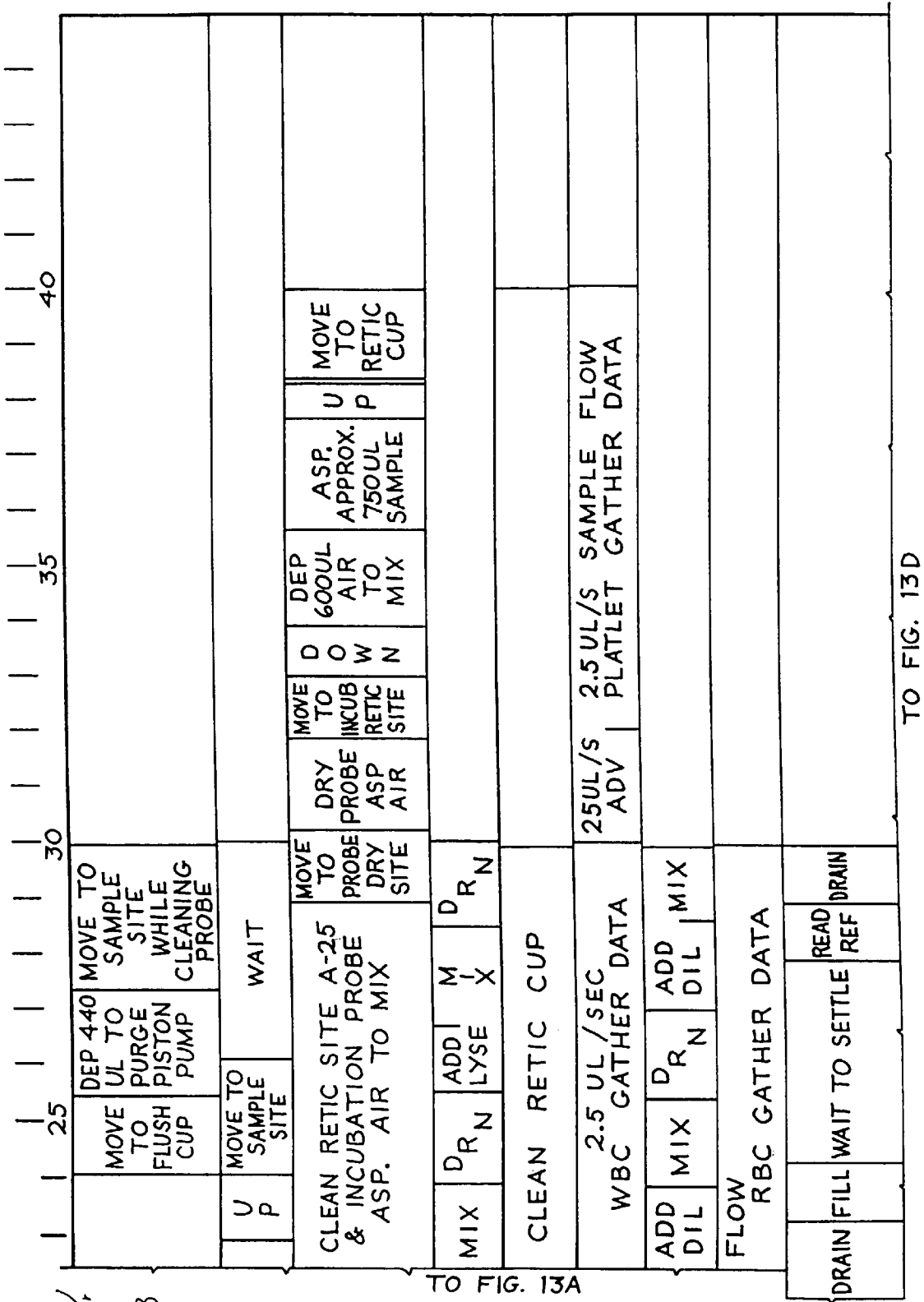
Figure 13C:
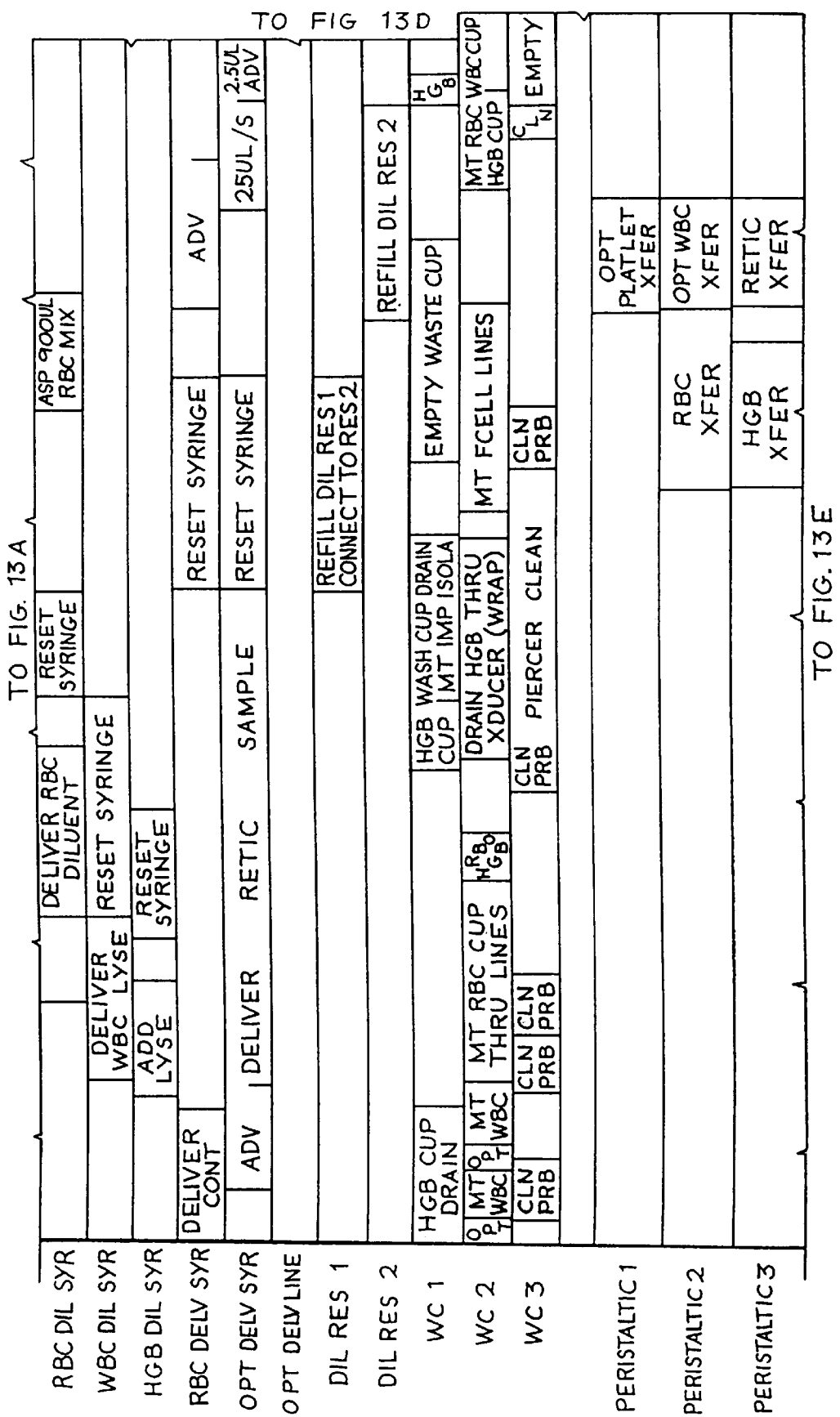
Figure 13D:
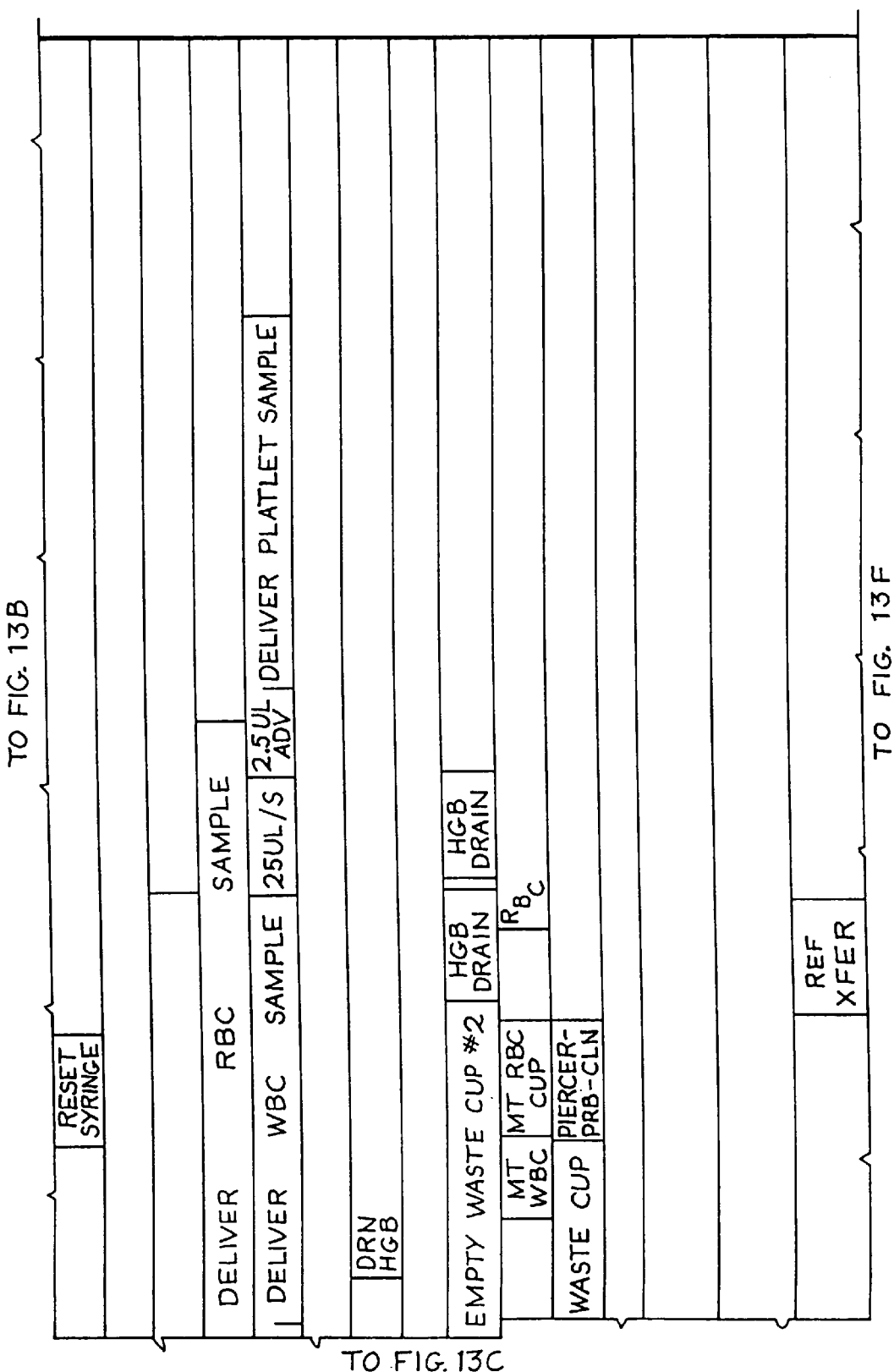
Figure 13F:
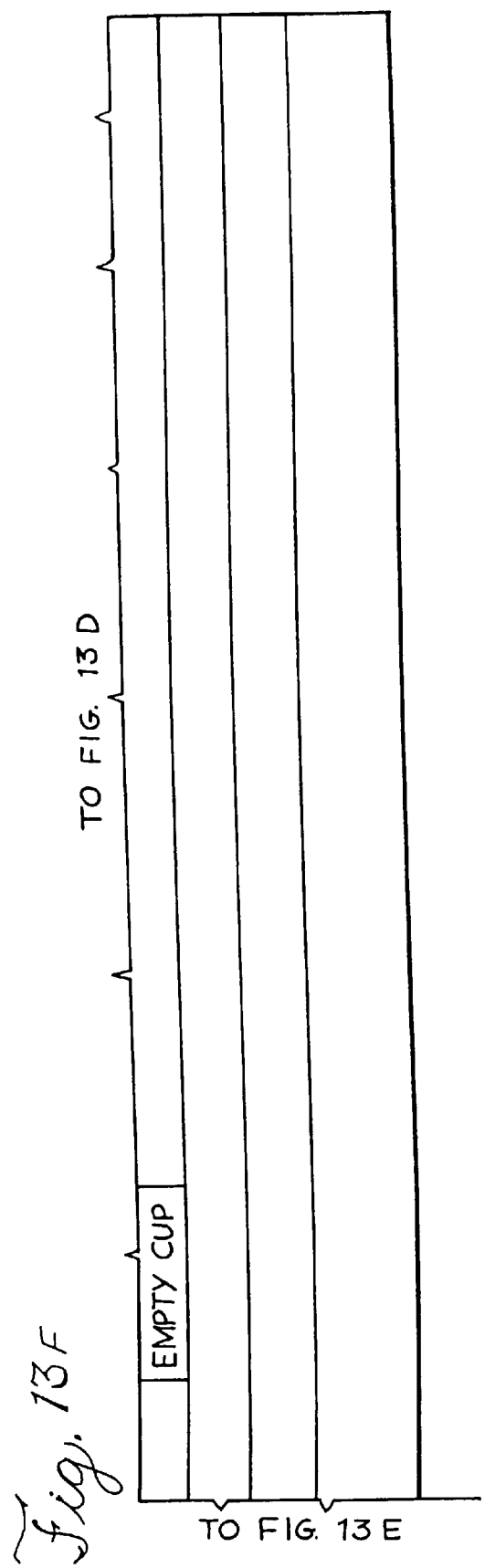

FIG. 12 illustrates the bulk transfer of a sample from a HGB sample cup 142 to the HGB transducer 178. The HGB sample cup 142 is connected to the HGB transducer 178 and a pump 246 by tubing 182. The pump 246 may be substantially similar to the pump 220. A valve 248 is placed in the tubing 182 downstream of the HGB sample cup 142. Bulk transfer of sample from the HGB sample cup 142 to the HGB transducer 178 occurs when the valve 248 is opened and the peristaltic pump 246 is activated.

C. Optical Flowcell/Transducer

Figure 16:
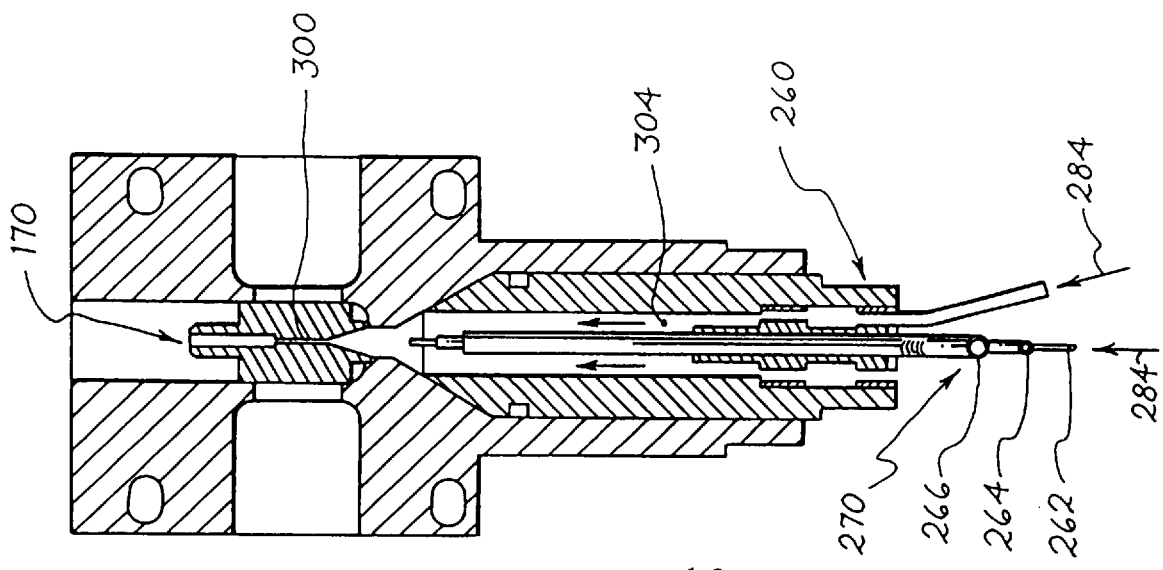
FIG. 16 is a sectional view of the optical flowcell shown in FIG. 15.
Figure 15:
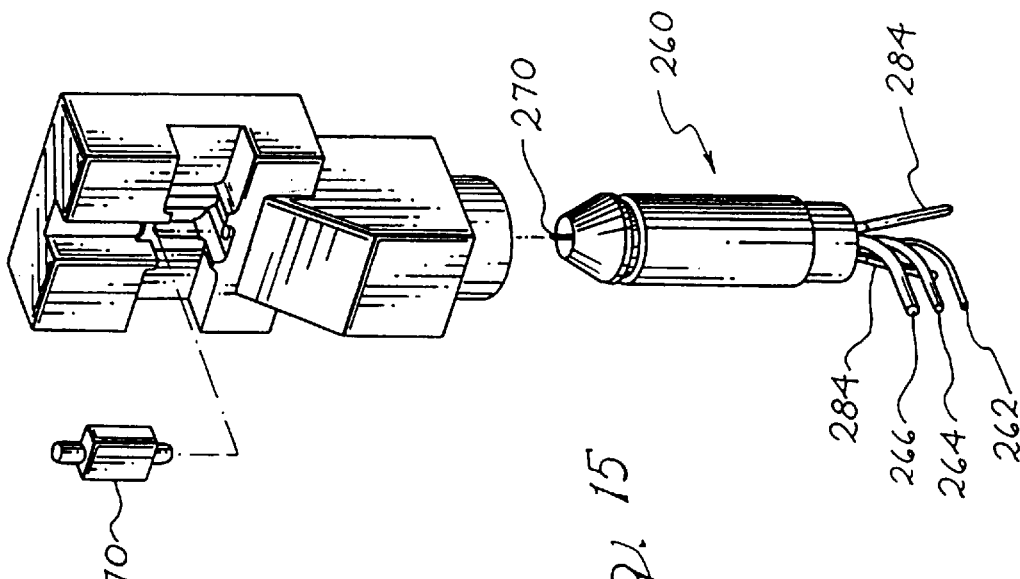
FIG. 15 is a diagram illustrating one embodiment of an optical flowcell transducer of the cell analysis system shown in FIG. 1.

Within the optical flowcell 170, individual cells are isolated within a flowing stream of fluid so that the optical properties of each cell may be detected and converted into meaningful information. FIGS. 15 and 16 illustrate a flowcell 170 for use with the cell analysis system 60.

Figure 43:
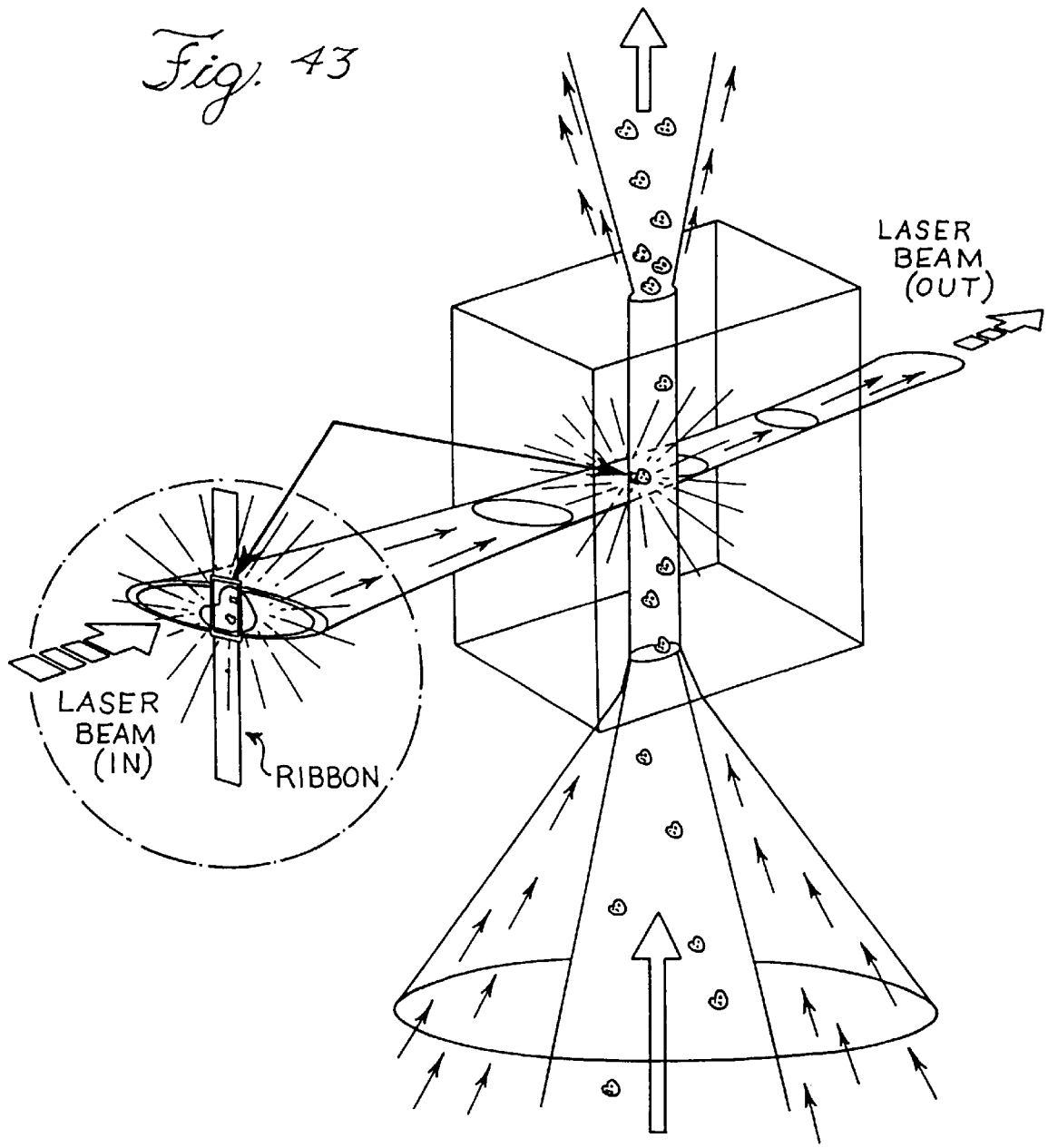
FIG. 43 is an illustration of the laser beam and flow stream configurations and interactions.
Figure 44B:
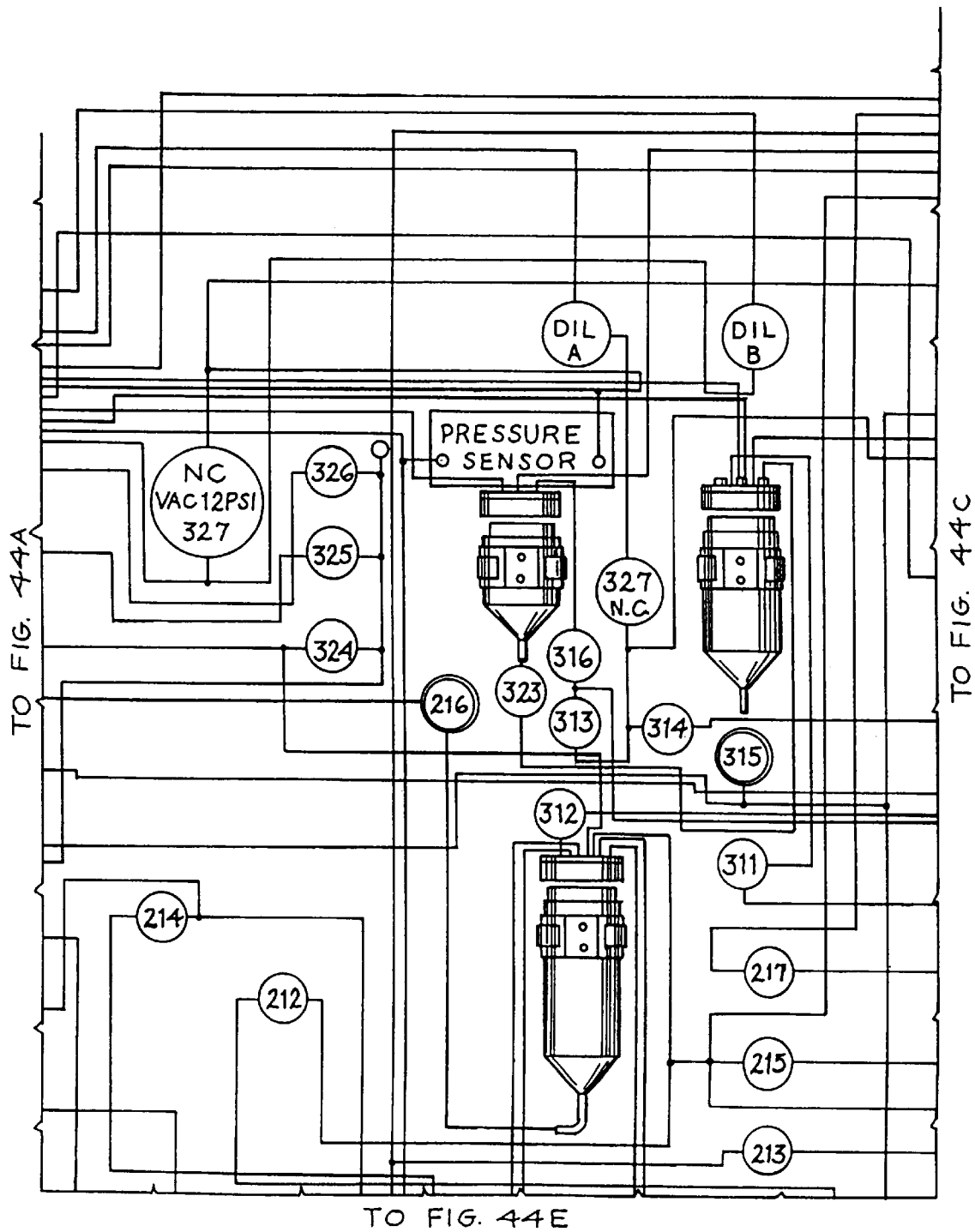
Figure 44C:
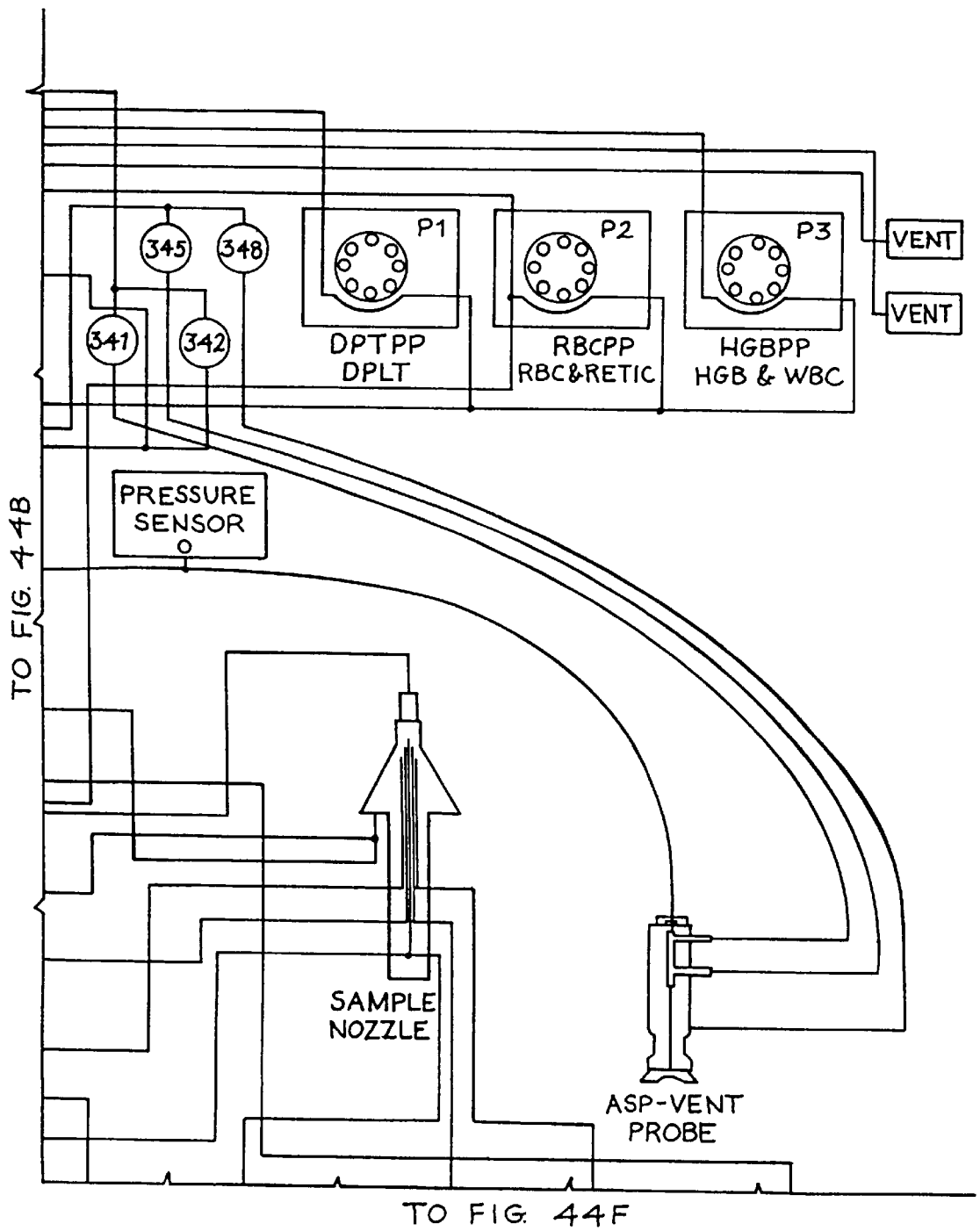

In one embodiment (as illustrated in FIG. 43, the optical flowcell 170 is a clear quartz block with a thin elongated, rectangular inner flow chamber 300 (FIG. 16) of cross sectional dimensions of about 160 $\mu$ by 400 $\mu$. A substantially conical channel at an angle of about 30 degrees converges into the flow chamber 300 at one end thereof. A diluted sample stream is injected from nozzle 270 positioned at the center of a moving sheath stream 304 into the flow chamber 300 in such a way that the sample portion of the stream is focused to a very small cross sectional dimension, approximately 5 $\mu \times 80\ \mu$, normal to the stream flow axis and confined to the center of flow chamber 300. This process is known as hydro-dynamic, or fluid focusing. At a predetermined position along the focused stream axis, a laser beam is directed into flow chamber 300 from a direction orthogonal to the flowing sample stream. In the region where the laser beam intersects the focused sample stream, the laser beam is also focused optically, as described below in section 8. F., to an approximately 17 $\mu$ dimension in a direction parallel to the stream flow axis. Thus, a sample illuminated volume is created in the center of the flow chamber 300 in the region where both the stream and the laser beam are focused, bounded in two dimensions by the stream extent, and on a third dimension by the laser beam extent. This illuminated volume, with the dimensions of approximately 5 $\mu \times 80\ \mu \times 17\ \mu$ is the sensing region of the flow cell 170. Each cell is detected as it passes through this region and the data collected and processed by the controller and the results are reported. See FIG. 43. Exemplary details of the nozzle 270 are discussed below with reference to FIGS. 31 through 36.

As shown in FIG. 32, embodiments disclosed herein relate to a fluid nozzle 270 and a method for introducing a fluid 812, the fluid 812 involved is the fluid used in the analytical instrument.

In one employment, Illustrated in FIG. 31, the fluid nozzle 270 is operatively associated with a conduit or a fluid 812 flow guide 814 and a flow cell 170 that detects an item of interest, such as a cell, a particle and the like, present in the fluid 812. In the illustrated embodiment, the flow guide 814 comprises a conduit formed from a suitable material, such as a polymer like acrylic, including a bore 818 for accepting the fluid nozzle 270. The fluid nozzle 270 is substantially centered with respect to the flow guide 814 to facilitate direction of fluid 812 from the fluid nozzle 270 to the bore 818. A conduit 820 is fluidly connected with the bore 818 such that a desired fluid 844 from a suitable source may be deposited in the bore 818 through the conduit 820. The flow cell 170, as described above may be an optical flow cell that measures the item of interest in the fluid 812 as the fluid 812 flows from the fluid nozzle 270 through the flow cell 170. The flow cell 170 may be used, in some embodiments, to perform a white blood cell differential analysis, platelet analysis and/or reticulocyte analysis. In these embodiments, preparatory steps for each analysis may be performed in processing paths, which may be separate, and the analysis may be performed in a single flow cell 170.

The construction of the fluid nozzle 270 is illustrated more clearly in FIGS. 32 and 33. The fluid nozzle 270 generally comprises a manifold 822 and a plurality of conduits fluidly connected with the manifold 822. The exact number of conduits may be chosen to facilitate a particular employment of the fluid nozzle 270. Specifically, in an exemplary embodiment, a first conduit 262, a second conduit 264 and a third conduit 266 are fluidly connected with one portion of the manifold 822. The conduits 262, 264 and 266 may be used as fluid 81L2 inputs. Thus, the conduits 262, 264 and 266 may be fluidly connected with suitable sources of desired fluid 812.

In a particular embodiment, the manifold 822 is made from a suitable polymer, such as acrylic and the like, and has an axial length of about 0.7 inches. The conduits 262, 264 and 266 are made from a suitable metal, such as 316 stainless steel and the like. The conduit 262 may have an axial length of about 1.14 inches, an inner diameter of about 0.023 inches and an outer diameter of about 0.0625 inches. The conduits 264 and 266 may have an axial length of about 0.5 inches, an inner diameter of about 0.019 inches and an outer diameter of about 0.0625 inches. The outer diameter surfaces of the conduits 262, 264 and 266 may be coated with an adhesive, such as an epoxy and the like, and inserted into complementary bores 830, 832 and 834, respectively, formed in the manifold 822. In the illustrated embodiment, the conduits 262, 264 and 266 are offset axially and circumferentially on the manifold 822. The conduit 266 is offset axially about 0.07 inches from an end 831 of the manifold 822. The conduit 264 is offset about 0.26 inches from the end 831 and the conduit 266 is offset about 0.45 inches axially from the end 831. Circumferentially, the conduit 262 is offset about 60 degrees from the conduit 264 and the conduit 266 is offset about 60 degrees from the conduit 264. Thus, the conduit 262 is offset about 120 degrees from the conduit 266.

The manifold 822 fluidly connects the conduits 262, 264 and 266 with conduits 272, 274 and 276, respectively, which are also operatively associated with the manifold 822. The manifold 822 can allow one of the conduits 272, 274 and 276 to be dedicated to a particular fluid or test run by the instrument with which the nozzle 270 is associated.

The conduits 272, 274 and 276 are disposed substantially coaxially and substantially centrally with respect to the flow guide 814. The disposition of the conduits 272, 274 and 276 with respect to the fluid guide 814 and the flow cell 170 may be chosen to provide intended positional accuracy of the flow of fluid 812 from the nozzle 270 to the flow cell 170. The manifold 822 includes a bore 42 for accepting the substantially coaxial disposition of the conduits 272, 274 and 276. The manifold 822 allows fluid 812 in conduits 262, 264 and 266 to flow through the manifold 822 and into conduits 272, 274 and 276, respectively. The conduits 272, 274 and 276 are substantially linear over their entire length. However, in some embodiments, to preserve the coaxial disposition of the conduits 272, 274 and 276, a spacer, not shown, may be provided radially between conduits 272 and 274 and between conduits 274 and 276. The spacer is configured, such as by providing outer diameter surface reliefs, channels and the like, so as not to interfere with fluid 812 movement in the conduits 272, 274 and 276. While the illustrated embodiment shows distal ends of the conduits 272, 274 and 276 being mutually axially offset, this is not necessary.

In an exemplary embodiment, the conduit 272 is made from a suitable metal, such as 304 stainless steel, #3 (full hard) temper hypodermic needle tubing and the like. The conduit 272 has an axial length of about 2.55 inches, an inner diameter of about 0.013 inches and an outer diameter of about 0.025 inches. The conduit 274 is also made from a suitable metal, such as 304 stainless steel, #3 (full hard) temper hypodermic needle tubing and the like. The conduit 274 has an inner diameter of about 0.038 inches, an outer diameter of about 0.050 inches and an axial length of about 2.26 inches. The conduit 276 is made from a suitable metal, such as 304 stainless steel hypodermic needle tubing and the like. The conduit 276 has an inner diameter of about 0.062 inches, an outer diameter of about 0.078 inches and an axial length of about 1.97 inches.

In one embodiment, the flow guide 814 includes a substantially tapered portion having an inner diameter of about 0.25 inches, at point "A", and an inner diameter of about 0.118 inches, at point "B". Both points A and B are labeled in FIG. 31. A relation between relevant conduit 272, 274 and 276 dimensions and corresponding dimensions of the flow guide 814 may be predetermined to provide desired fluid focusing of fluid 812, to reduce a probability of contact between the flow guide 814 and the fluid 812, to optimize flow cell 170, e.g. optics, operation, etc. In some embodiments, the dimensional relation may be related to the flow rate differential. Specifically, in an exemplary embodiment, a latitudinal cross section of relevant portions of the flow guide 814 is proportional to a related flow rate differential.

In an exemplary embodiment, the tapered portion defines a slope of about 60 degrees. A fluid-conveying portion of the flow cell 170 adjacent a distal end of the fluid nozzle 270 defines a slope of about 30 degrees with an inner diameter of about 0.118 inches. The dimensions may be chosen to produce intended positional accuracy of the flow of fluid 812 with respect to the flow cell 170.

With the construction of the fluid nozzle 270 being thusly disclosed in detail, a method of introducing fluid with the fluid nozzle 270 will now be discussed in detail.

A source of fluid 812, such as blood, a blood component and the like, to be processed by the flow cell 170 is fluidly connected with one of the conduits 262, 264 or 266 such that fluid 812 flows from the source to the selected conduit 262, 264 or 266. The other conduits 262, 264 or 266 which are not fluidly connected with source of fluid 812 are not supplied with fluid 812. The fluid 812 contains an item of interest, such as a particle, a cell and the like, detectable by the flow cell 170.

A source of another fluid 844, such as water, buffer solution, diluent or other fluid that does not adversely react with the fluid 812, and the like, is fluidly connected with the conduit 820 such that the another fluid 844 flows from the source to the conduit 820 and the flow guide 814. The fluid 844 flowing from the conduit 820 into the flow guide 814 surrounds a portion of the conduits 272, 274 and 276, as shown in FIGS. 34 through 36. The offset dispositions of the conduits 272, 274 and 276 permits reduction of fluid 844 flow discontinuities. A gradual reduction in latitudinal cross section of the fluid flow path through the flow guide 814 permits a reduction of the likelihood of fluid diffusion within the flow guide 814. If desired, as fluid 812 flows from one of the conduits 272, 274 or 276, the other two conduits 272, 274 or 276 may be cleaned or "back-flushed" with fluid 844 by applying an appropriate relatively reduced pressure source, for example, to the conduits 272, 274 or 276 being cleaned. Alternatively, after fluid 812 has been sequentially introduced through each of the conduits 272, 274 and 276, all of the conduits 272, 274 and 276 can be simultaneously cleaned by passing an appropriate fluid through the conduits. Thus, because all of the conduits 272, 274 and 276 can be cleaned substantially simultaneously, through put of the flow cell 170 can be increased by reducing down time needed to clean the nozzle 270 while also providing for rapid introduction of fluid 812. This also correspondingly can increase the through put of the analytical instrument with which the flow cell 170 is associated.

In an exemplary embodiment, the flow rate of fluid 844 is larger than the flow rate of fluid 812. For instance, in one embodiment, the flow rate of fluid 812 is about 2.5 $\mu l$ per second and the flow rate of the fluid 844 is about 300 $\mu l$ per second. This flow rate differential fluidly directs or focuses the flow of fluid 812 toward the flow cell 170. In general, the flow rate differential can be predetermined such that detection of the item of interest in the fluid 812 by the flow cell 170 is facilitated.

The fluid focusing provided by the flow rate differential is substantially similar irrespective of the conduit 272, 274 or 276 chosen to introduce the fluid 812 as fluid 812 introduced from either conduit 272, 274 or 276 is fluidly focused toward substantially the same position with respect to the flow cell 170. This allows fluids (312 from each of the conduits 272, 274 and 276, and tests performed by the instrument with which the fluid nozzle 270 is associated, to share the same flow cell 170. Accordingly, each of the conduits 272, 274 and 276 may be fluidly connected with a separate source of fluid 812 such that the likelihood that fluid 812 from one source might encounter fluid 812 from another source is reduced. Thus, the probability of fluid 812 cross over and/or fluid 812 contamination can be reduced. The fluids 812 from each of the conduits 272, 274 and 276 can be processed by the flow cell 170 in substantially parallel fashion, thereby improving throughput of the fluid nozzle 270 and the instrument with which the nozzle 270 is associated.

This ability of the fluid nozzle 270 has been verified empirically. In one experiment, illustrated in FIGS. 34 through 272, an exemplary embodiment of the fluid nozzle 270 was analyzed by a finite element method to reveal the fluid properties associated with the nozzle 270. In this, embodiment, the conduit 272 has an inner diameter of about 0.013 inches. The distal end of the conduit 274 is offset proximally about 0.29 inches from the distal end of the conduit 272. The conduits 272 and 274 define a substantially annular fluid flow path having an inner diameter oa about 0.025 inches and an outer diameter of about 0.037 inches. The distal end of the conduit 276 is offset proximally about 0.29 inches from a distal end of the conduit 274. The conduits 274 and 276 define a substantially annular fluid flow path having an inner diameter of about 0.049 inches and an outer diameter of about 0.061 inches.

The finite element analysis was performed using a FIDAP computer program, version 6.01, available from Fluid Dynamics International of Evanston, Ill. Steady-state axi-symmetric models of fluid flow through the conduits 272, 274 and 276 and steady-state three dimensional models of fluid flow through the flow cell 170 were analyzed to show that the position of the fluidly focused fluid 812 with respect to the flow cell 170 is independent of the conduit 272, 274 or 276 used to introduce fluid 812. In all cases, the fluid flow rate of the fluid 844 is about 300 $\mu$l per second and the fluid flow rate of the fluid 812 through the chosen conduit 272, 274 or 276 is substantially within the range of about 2.5 $\mu$l per second to about 2.0 $\mu$l per second. The analyses assumed Newtonian fluid properties with no slip boundary conditions on the solid surfaces.

In one example, to simulate white blood cell differential analysis, platelet analysis, and reticulocyte analysis, three separate fluid analyses were performed. The white blood differential analysis fluid 812 is introduced through the conduit 272, as shown in FIG. 34, at a fluid flow rate of about 2.5 $\mu$l per second. As shown in FIG. 35, the platelet analysis fluid 812 is introduced through the conduit 274 also at a fluid flow rate of about 2.5 $\mu$l per second. The reticulocyte analysis fluid 812 is directed through the conduit 276, as shown in FIG. 36, at a rate of about 2.0 $\mu$l per second. Upon comparison of FIGS. 34 through 272, the fluid flow pathlines from the respective conduits 272, 274 and 276 resulting from the fluid analyses demonstrate that no contamination of a flow of fluid 812 by a prior flow of fluid 812 occurs and that the position of the fluidly focused fluid 812 with respect to the flow cell 170 is independent of which conduit 272, 274 or 276 is selected.

The independence of the position of the fluidly focused fluid 812 with respect to the flow cell 170 with respect to the selection of the conduit 272, 274 or 276 is also verified experimentally by optically measuring flow of fluid 812 containing 7 $\mu$m diameter beads sequentially through each of the conduits 272, 274 and 276. The fluid 812 containing the beads is introduced at a fluid flow rate of about 2 $\mu$l per second.

| | % C.V., INDEX MATCHED | | |
|---|---|---|---|
| | ALL | IAS | DSS |
| Conduit 272 | 4.7 | 3.2 | 2.6 |
| | 4.3 | 3.1 | 2.2 |
| Conduit 274 | 5.0 | 3.6 | 2.0 |
| | 4.6 | 4.2 | 2.6 |
| Conduit 276 | 4.3 | 3.1 | 2.4 |
| | 5.1 | 2.8 | 2.7 |

As is evident from the above coefficients of variation, the coefficient of variation (CV) for three measured optical properties (ALL: axial light loss; IAS: intermediate angle scatter; and DSS: depolarized side scatter) are substantially similar for all of the conduits 272, 274 and 276. This similarity in optical response verifies that the fluid nozzle 270 can be used for multiple fluid 812 item of interest measurements prior to any cleaning step, thereby increasing the through put or analytical capacity of the flow cell 170 and any instrument associated with the flow cell 170. The number of fluid 812 measurements or fluid 812 introductions that may occur prior to cleaning corresponds to the number of conduits provided with the fluid nozzle 270. Irrespective of the number of conduits involved, the embodiments described herein allow for substantially simultaneous cleaning of substantially all of the conduits.

If the fluid 812 were to have sufficient propensity to interact with or stick to a portion of the conduits 272, 274 and 276, then remnants of a first fluid in the conduit 272, 274 or 276 may encounter (i.e. carry over) a second fluid passed through the same conduit 272, 274 or 276. Similar concerns are present with the conduits 262, 264 and 28. These concerns may compromise accuracy of the flow cell 170.

To address these concerns, it is possible to dedicate a specific conduit 272, 274 or 276 to a specific fluid 812 or test performed by the flow cell 170. The number of conduits 272, 274 and 276 so dedicated may be dependent upon the properties of the fluids 812 being introduced by the fluid nozzle 270. By substantially isolating at least one of the conduits 272, 274 and 276, carry over of one fluid 812 to another fluid 812 can be reduced. For instance, one conduit 272, 274 or 276 could be dedicated to a test that uses a fluid 812 containing a relatively bright fluorescent marker, such as auromine 0 and the like, and another conduit 272, 274 or 276 could be dedicated to a test that uses a fluid containing a relatively dim fluorescent marker. Once the fluids exit the conduits 272, 274 or 276, the volume and flow of fluid 844 through the fluid guide 814 is sufficient to reduce the probability of fluid 812 diffusion while fluidly focusing the fluid 812 toward a common flow cell 17C. Thus, the two tests can be performed substantially sequentially by the same flow cell 170 without substantially compromising accuracy or sensitivity of the flow cell 170.

Upon moving upward into the rectangular cross-section of flow cell 170, the velocity rapidly increases, which hydrodynamically focuses the sample stream to a central core measuring approximately 5 $\mu \times 80$ $\mu$ in cross-section. The small 5 $\mu$ dimension, which is in the direction of focus of the wide-angle condenser lens illustrated in FIG. 22, assures minimum defocusing and therefore equal brightness of fluorescent cells located at different positions within the stream. In addition, because the width of the flow chamber 300 is much larger than the sample stream, the flow chamber 300 should not clog readily, yet it still gives resolution comparable to that provided by a smaller sensing region.

A focusing lens (shown in FIG. 19) focuses a laser beam on the flow chamber 300, and detectors (shown in FIGS. 20 and 21) detect the light scattering and/or fluorescence properties of cells that pass through the flow chamber 300. These features are described in further detail in section 8.F. of this disclosure.

D. Impedance Transducer

The cell analysis system 60 may use an impedance transducer 174 to count red blood cells and platelets. FIG. 17 illustrates a preferred embodiment of an impedance transducer 174 that performs impedance-based cell counting and sizing, and makes use of hydrodynamic focusing. The impedance cell counting is based on the detection of changes in electrical resistance produced by a particle as it passes through a small orifice 314. Conduction is provided by an electrolyte fluid (such as buffered saline and the like) in two chambers 310, 312 of the impedance transducer 174.

A sample introduction nozzle 316 and hydrodynamic focusing direct cells to the orifice 314 of the impedance transducer 174. As each cell passes through the orifice 314, the electrical resistance of the path through the chambers 310, 312 and the orifice 314 increases. A current source 317 connected to two electrodes described below disposed in the chambers 310, 312 on either side of the orifice 314 causes this increase in resistance to be manifested as a electrical voltage pulse. The sample introduction nozzle 316 doubles as the upstream side electrode. The secondary electrode 318, is located downstream of the orifice 314. The number of pulses is indicative of cell count, while the amplitude of each pulse is related to cell volume. Volume histograms are created by plotting frequency distributions of pulse amplitudes. These histograms are used to obtain RBC and PLT parameters such as MCV (mean cell volume) and RDW (red cell distribution width).

The impedance transducer 174 is preferably made from a material that is non-conductive and transparent, such as acrylic, a similar polymer or the like. The secondary electrode 318 in the transducer 174 is preferably platinum because electrolysis at this polarity creates corrosive gasses which may dissolve some other electrode materials. other materials having similar corrosion resistance may be used for the electrode 318. The volume of the chamber 310 on the upstream side of the transducer 174 may be reduced without affecting the operation of the transducer 174 for the disclosed applications. The sample introduction nozzle 316 is preferably placed within about 1.5 mm from the orifice 314. The distance between the nozzle 316 and the orifice 314 should be maintained during operation, as well as a relatively high sheath velocity (about 10 m/sec through the orifice).

About 30% of the cells that flow through a non-hydrodynamically focused impedance transducer pass close to the edges of the flowcell's orifice rather than going through its center. This can clog the orifice and cause distorted measurements. Hydrodynamic focusing may be utilized in the impedance transducer 174 of the cell analysis system 60 to reduce clogging and improve measurement accuracy.

Hydrodynamic focusing is accomplished in the impedance transducer 174 by the following procedure. The RBC delivery syringe 204 (shown in FIGS. 10*a* and 10*b*) delivers the sample to the nozzle 316 of the impedance transducer 174 at a rate of about 0.333 μl/sec. As the flowing sample exits the impedance transducer nozzle 316, it is accelerated to a velocity of about 10 m/sec by an RBC sheath flow 315. Since the sample volumetric flow rate, which is preferably substantially constant at about 0.333 μl/sec, is the product of the velocity and the cross-sectional area, this area decreases as the sample accelerates. In a preferred embodiment, the acceleration to 10 m/sec causes the diameter of the sample stream to decrease to about 6.5 μm.

The impedance transducer 174 is provided with a waste tube 314*a* located immediately downstream of the orifice 314 to "catch" red cells as they leave the orifice. If the red cells are not disposed of after exiting the orifice 314, they may return to the vicinity of the orifice, and thereby generate signals which distort the platelet measurements and to a lesser degree distort the red cell measurement. To assist in capturing measured cells, a secondary flow (via port, E) is provided solely to propel cells down the waste tube 314*a*.

The impedance transducer 174 is also provided with several ports (A, B, C, D and E). Port A provides a vent for venting air (or other gases) from the upstream side of the orifice 314. Port B provides an inlet for injecting air into the chamber 310 in order to drain the upstream side of the transducer 174. Port D provides the drain for the upstream side of the transducer, along with a sheath inlet rport. Port C provides an inlet for injecting air into the chamber 312 in order to drain the downstream side of the transducer 174. Port C also provides a vent for venting gas from the downstream side of the transducer 174. Port E provides a drain and an inlet for the secondary flow. Port G provides an outlet for waste. Port H, although not used in the present embodiment, may be used to provide a tangential entry point for flowing additional fluids into the upstream side of the transducer 174.

E. HGB Transducer

The HGB transducer 178 measures the optical absorption of cells in a blood sample to determine the levels of HGB in the blood sample. A HGB transducer 178 is shown in FIG. 18, along with a block diagram of circuitry for detecting and analyzing signals from the HGB transducer 178. In one embodiment, HGB concentration is measured in grams per deciliter, and is proportional to the amount of lights absorbed by a sample in the green wavelength region (approximately 540 nm).

The HGB transducer 178 generates an electrical signal that is related to the light absorption of the liquid in the HGB transducer chamber 338. Light absorption is measured in the HGB transducer 178 for a prepared sample containing hemoglobin and for a clear reference solution. The difference in electrical signal generated by the transducer during these two measurements is approximately proportional to the hemoglobin content of the prepared sample.

The HGB transducer chamber 338, which may be transparent, is positioned between a light source 322, such as a light emitting diode and the like, and a detector 326, such as a photo diode, a phototransistor and the like (FIG. 18). An interference filter 326, preferably rated at about 540 nm, is placed between the HGB transducer chamber 338 and the detector 324. The detector 324 output current, which is approximately proportional to the light energy received, is amplified by a current-to-voltage amplifier 332. The analog signal processing of the HGB signals is discussed in section 8.F. of this disclosure in connection with the electronic systems.

Whole blood is mixed in the HGB cup 142 by the velocity of the incoming HGB lysing reagent to a dilution ratio of preferably about 190:1. A pump 246, which may be peristaltic, is used to draw a sample from the HGB cup 142, through a tubing network 182 connected to the HGB c(up 142, and into the HGB transducer chamber 338. The HGB cup 142 is rinsed by flushing HGB lysing reagent to reduce any carryover of a sample with subsequent samples. HGB reagent is placed directly into the HGB transducer to provide the HGB reference reading.

F. Optics Bench

A plan view of the optics bench 350 is shown in FIG. 19. The optics bench 350 is mounted on the analyzer module 64 and includes a laser light source 352, mirrors 354, 356, lenses 358, 360, a flowcell 170 (fused-silica in an exemplary embodiment), and several detectors 400, 402, 404. The laser beam 368 is directed by a rear mirror 354, a front mirror 356, a beam adjuster 370, shaped and focussed by a pair of cylindrical lenses 358 and a laser focusing lens 360.

The laser 352 is preferably a vertically polarized 488 nm air-cooled argon laser (Uniphase 2114B-125LAB, or equivalent) operating in the TEM. (transverse electromagnetic) mode with light feedback. In this mode, the light intensity has a gaussian distribution and is in phase. The laser beam 368 is held at about 10 mw by the light feedback system within the laser circuitry.

The optical elements between the laser 352 and the optical flowcell 170 are constructed so that the gaussian focal beam waist at the flow chamber 300 of the optical flowcell 170 is substantially elliptical and measures about 17 $\mu$ high by about 64 $\mu$ wide. The beam waist is defined as the position along the laser beam axis where the cross-sectional beam dimension, in a given direction normal to the axis, is minimum. In the preferred embodiment shown in FIG. 19, the optical system is characterized by two orthogonal planes of symmetry, a vertical plane and a horizontal plane, each of these planes containing the laser beam optical axis. Therefore, at any position along the beam axis, the beam extent is defined by two orthogonal dimensions, a vertical dimension, and a horizontal dimension. The vertical dimension is defined as the linear distance, in the vertical plane measured normal to the optical axis, between the points where the intensity is $1/e^2$ times the maximum intensity which occurs at the center of the beam. The corresponding horizontal dimension is defined identically except that it lies in the horizontal plane. This beam configuration is accomplished by a pair of cylindrical lenses 358 which act as a vertical beam expander. Preferably the upstream lens has a focal length of approximately −18.8 mm, and the downstream lens has a focal length of about +75.4 mm. The lenses 358 are positioned slightly off the confocal condition so that a coincident vertical and horizontal waist occurs at the flow chamber 300. Preferably, the focusing lens 360 is spherical with a focal length of about 79.5 mm.

A beam fine-adjust mechanism 370 is positioned between laser focusing lens 360 and flowcell 170. This mechanism consists of a pair of small 10° wedges with an adjustable air space which is used to produce a fine lateral displacement of the laser beam relative to the sample stream. These wedges are oriented with the entrance and exit surfaces normal to the laser beam axis. The air space can be adjusted by means of a 32 pitch screw in a direction parallel to the laser axis. The air space to lateral beam displacement ratio is 10.5/1 when using BK7 glass as the wedge material. One complete turn of the 32 pitch screw thus moves the incident laser beam laterally +75 $\mu$ relative to the sample stream, without producing any change in the incidence angle of illumination. The lateral beam displacement resolution is something less than ±1 $\mu$. This system, in conjunction with the design of the forward and side angle collection optics, allows easy control for optimally aligning the laser beam to the sample stream without affecting the alignment of the subsequent optics.

The flow chamber 300 of the flowcell 170 preferably has an aspect ratio of about 2.5x. Hydrodynamic focusing within the optical flowcell 170 creates a substantially elliptical sample core stream with an approximately 15x aspect ratio. When the sample flow rate is about 2.0 $\mu$l/sec, the resultant sample stream is a substantially elliptical cylinder. The length and width dimensions of the sample stream are approximately 80 $\mu$×5.0 $\mu$. The approximately 5 $\mu$ stream width corresponds to the approximately 80 $\mu$ horizontal focal waist. This results in a maximum intensity variation within the stream of about 1%.

The vertical focal waist of about 171 results in a pulse width of approximately 2.0 to 3.5 $\mu$sec, depending on cell size, whenever a cell passes through the laser beam 368 at the nominal stream velocity of about 8 meters/sec. The detectors 380, 400, 402, and 404 measure the effects of cells passing through the flowcell 170. Preferably, the detectors 380, 400, 402, and 404 are capable of measuring at least seven optical parameters. One or more detectors are preferably placed in the forward light path for measuring forward intermediate angle scattering and either small angle forward scattering or axial light loss (ALL, also known as forward extinction). ALL is generally the decrease in light energy due to a cell passing in front of a laser beam and being detected by a photodiode. The light loss is generally due to scattering. Preferably, one parameter measured is ALL, defined as the decrease in light energy reaching a detector in the path of a laser beam due to the passage of a cell through that beam. Small angle forward scatter, in contrast, is light energy that reaches a detector outside (but within a narrow angle of 1° to 3°) the incident laser beam due to scattering from a cell passing through the beam. A beam stop is generally provided to keep the laser beam from getting into the detector. ALL measuring systems collect light within the incident cone of laser illumination, while small angle scatter systems collect light outside this cone. In ALL measuring systems, the signal of interest is at negative signal subtracted from the steady state laser signal, whereas in small angle forward scatter measurement the signal is a small positive signal imposed on a very low background light level. Intermediate angle forward scattering (IAS) is similar to small angle forward scattering, except the light is scattered at a larger angle from the incident laser beam. More specifically, IAS relates to light scattered in a ring between about 3 and 10 degrees away from the incident or center line of a laser beam. In a preferred embodiment, ALL is collected in the angles less than about 0.3 degrees horizontally and less than about 1.2 degrees vertically from the laser axis, and IAS is collected at angles between about 3 degrees and 10 degrees from the laser axis.

The preferred forward path optical system shown in FIGS. 19 and 20 includes a spherical plano-convex lens 376 and a two-element photodiode 380 located in the back focal plane of the lens. In this preferred configuration, each point within the two-element photodiode 380 maps to a specific collection angle of light from cells moving through the flow chamber 300, independent of the position of the cells. Thus, the inner element 382 is preferably substantially rectangular, which accordingly maps to the asymmetry of the laser beam divergence, and measures ALL. The outer element 384 is preferably a substantially circular ring and accordingly maps to the range of collection angles of forward scatter desired for measurement of IAS.

This alignment of the forward path is independent of the optical flowcell 170 and laser beam fine-alignment. To provide the desired collection geometry, the two-element detector's lateral position is aligned with respect to the collecting lens 376. Changing the optical flowcell 170, or readjusting the incident laser beam 368 by means of element 370, which only repositions the beam without effecting any angular redistribution, has no effect on the angular acceptance of the detector 380, and therefore does not require any corresponding readjustment of the forward path optics.

Alternatively, the two-element, single unit detector 380 could be replaced with two separate detectors. In this case, a mirror with a center hole of proper diameter would be placed in the back plane of the lens 376. The mirror would reflect IAS to one of the detectors. A slit, coincident with the center hole of the mirror and shaped to pass only the laser beam, would transmit light for ALL measurement to the second detector located behind the mirror.

Either of the above-described schemes is a variation on small-angle collection systems. The described schemes do not require an obscuration bar and its related adjustments. In the preferred first case, both detectors can be incorporated onto one chip. No mirror is required. Incorporation of a neutral density filter 386, as shown in FIG. 20, is desirable in order to keep the All signal from saturating the inner ALL element 382. Preferably, the filter 386 is provided by coating the inner ALL element 382 with a Neutral Density 2.0 coating (a coating that transmits about 1% of the incident light). An anti-reflection coating can be coated over the outer IAS element 384.

Figure 21:
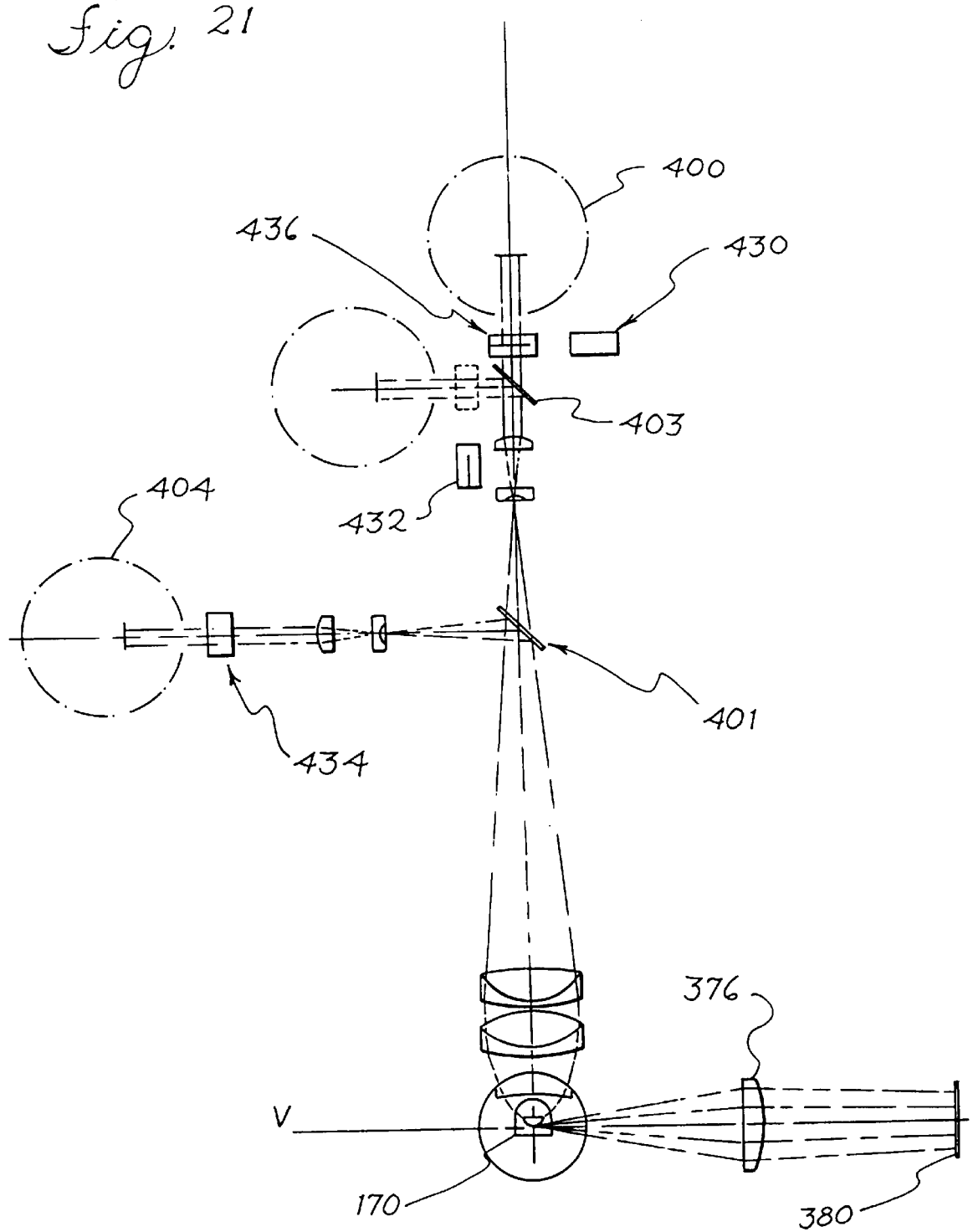
FIG. 21 is a diagram illustrating the side-scatter collection system of the optics bench shown in FIG. 19.

In an exemplary embodiment, as illustrated in FIGS. 19 and 21, the remaining detectors 400, 402 and 404, are three photomultiplier tubes (PMTs) which detect either side-scatter (light scattered in a cone whose axis is approximately perpendicular to the incident laser beam) or fluorescence (light emitted from the cells at a different wavelength from the incident laser beam). A movable polarizer, 436, placed in the light path of PMT 400 configures PMTs 400 and 401 to detect depolarized side-scatter (DSS) and polarized side scatter (PSS) respectively, while movable filters (430, 432, 434) enable detection of fluorescent emissions at specified wavelengths from the cells. FL1, green fluorescence, is detected between about 515 to 545 nm. FL2, yellow fluorescence, is detected between about 565 to 595 nm. FL3, red fluorescence, is detected between about 615 to 645 nm. Side-scatter and fluorescent emissions are directed to these PMTs by dichroic beam splitters 401 and 403 which transmit and reflect efficiently the required wavelengths to enable efficient detection.

Figure 22:
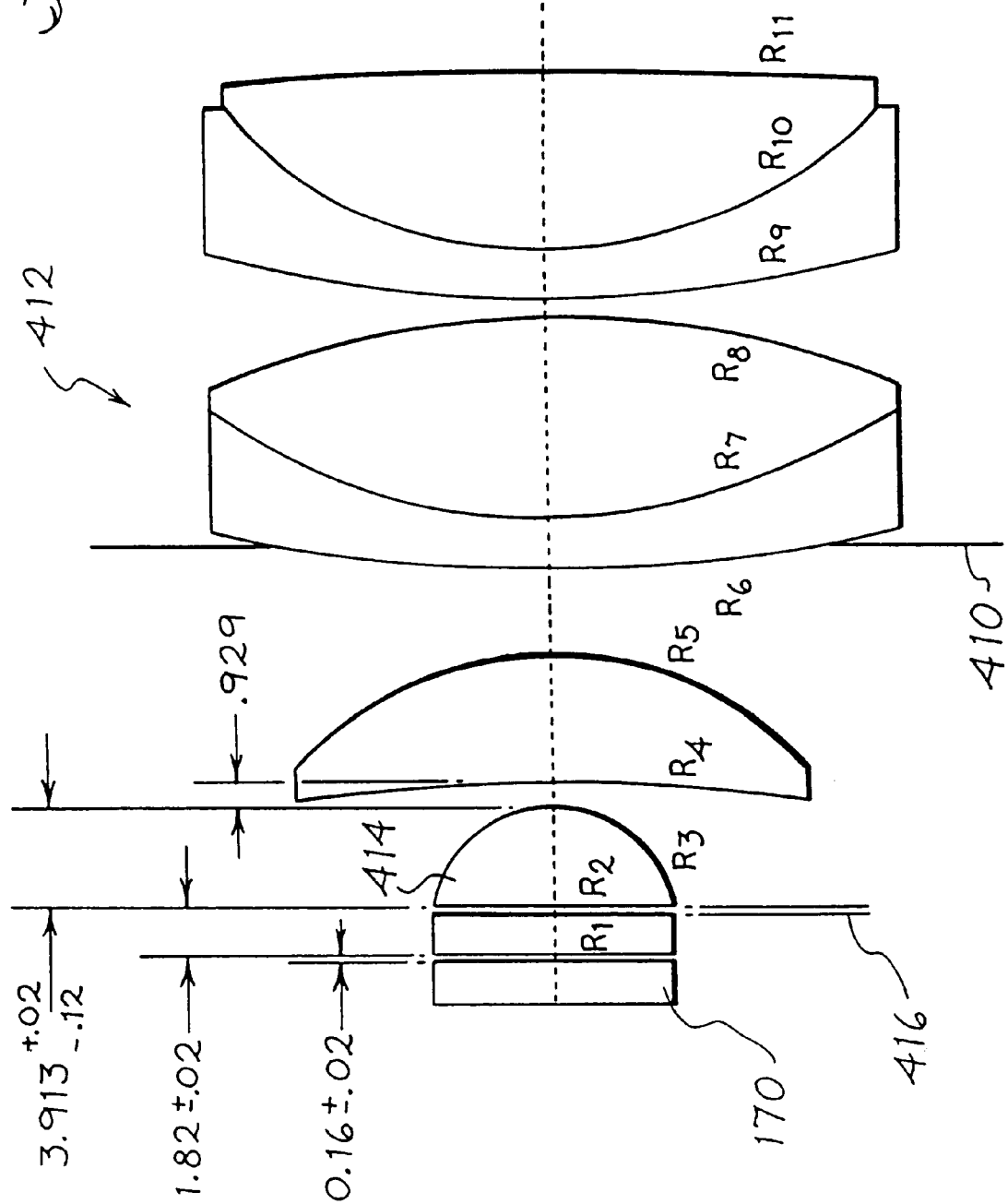
FIG. 22 is a diagram of the condenser of the optics bench shown in FIG. 19.

Sensitivity is enhanced at PMTs 400, 402, and 404, when measuring fluorescence, by utilizing an immersion collection system as illustrated in FIG. 22. In this instance, the immersion collection system is one that optically couples the first lens 414 to flow cell 170 by means of a refractive index matching layer 416, enabling collection of light over a wide angle. In a preferred embodiment this collection angle is about 130° at the sample stream, which compares to about 44° in a typical air-spaced condenser system with a Numeric Aperture of 0.5. It can be shown mathematically that the fluorescence energy collected from a fluorescing particle is proportional to (1-cosU), where U is defined as ½ the cone angle of collection. Thus the preferred 130° system collects almost 8 times more energy than the 44° system, a difference which enables fluorescence detection with smaller low-powered lasers and/or weaker fluorescence markers. The system is also color corrected so that a given optical path can be used at substantially different wavelengths without refocussing. This allows a single PMT to detect several wavelengths of light by interposing or removing optical filters 430, 432, 434.

Figure 24:
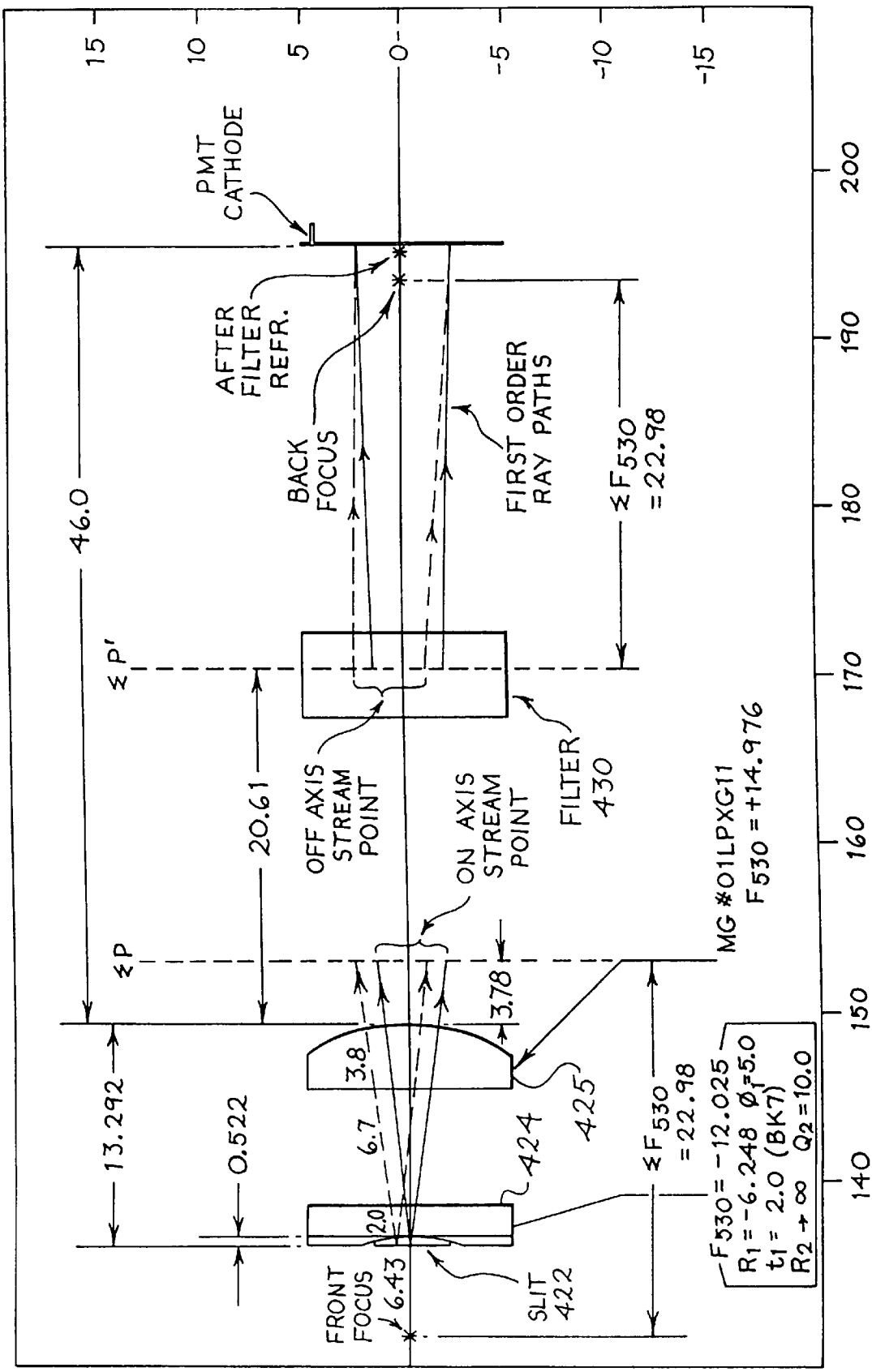
FIG. 24 is a diagram of the PMT lens set of the optics bench shown in FIG. 19.

As shown in FIGS. 21, 22 and 24, the illustrated immersion collection system is telocentric such that the cathode surface of a given PMT is conjugate with an objective aperture stop 410 (shown in FIG. 22) and located at infinity with respect to the flow chamber 300 of the flow cell 170. This construction reduces the need for precise alignment of the PMTs with respect to each other and the flow chamber 300.

As shown in FIG. 22, the condenser 412 preferably includes a plano-hemispherical first element 414 optically coupled to the quartz flowcell 170 by an index matching gel layer 416. Generally, the condenser 412 is an optical lens system with aberration correction sufficient for large angle light collection but not sufficient for diffraction limited imaging used in high resolution microscopy. A suitable gel is available front Dow Corning (identification number #02-3067). The specifications of a preferred embodiment of the condenser are listed in Table 1.

TABLE 1

$R_1 \to \infty$ $t_{12}=1.82$ ($SiO_2$ window)

$R_2 \to \infty$ $t_{23}=3.913$ (FK5- flint crown glass #487704)

$R_3=-3.913$ $d_{34}=0.929$ (Air space)

$R_4=-54.7$ $t_{45}=5.14$ (FK5)

$R_5=-9.753$ $d_{56}=3.343$ (Air space)

$R_6=45.7$ $t_{67}=2.0$ (SF5- dense flint glass #673322)

$R_7=16.853$ $t_{78}=7.9$ (BK7)

$R_8=-24.028$ $d_{89}=0.635$ (Air space)

$R_9=35.649$ $t_{910}=2.0$ (SF5)

$R_{10}=13.014$ $t_{1011}=6.95$ (BK7)

$R_{11}=-120.59$

Figure 23:
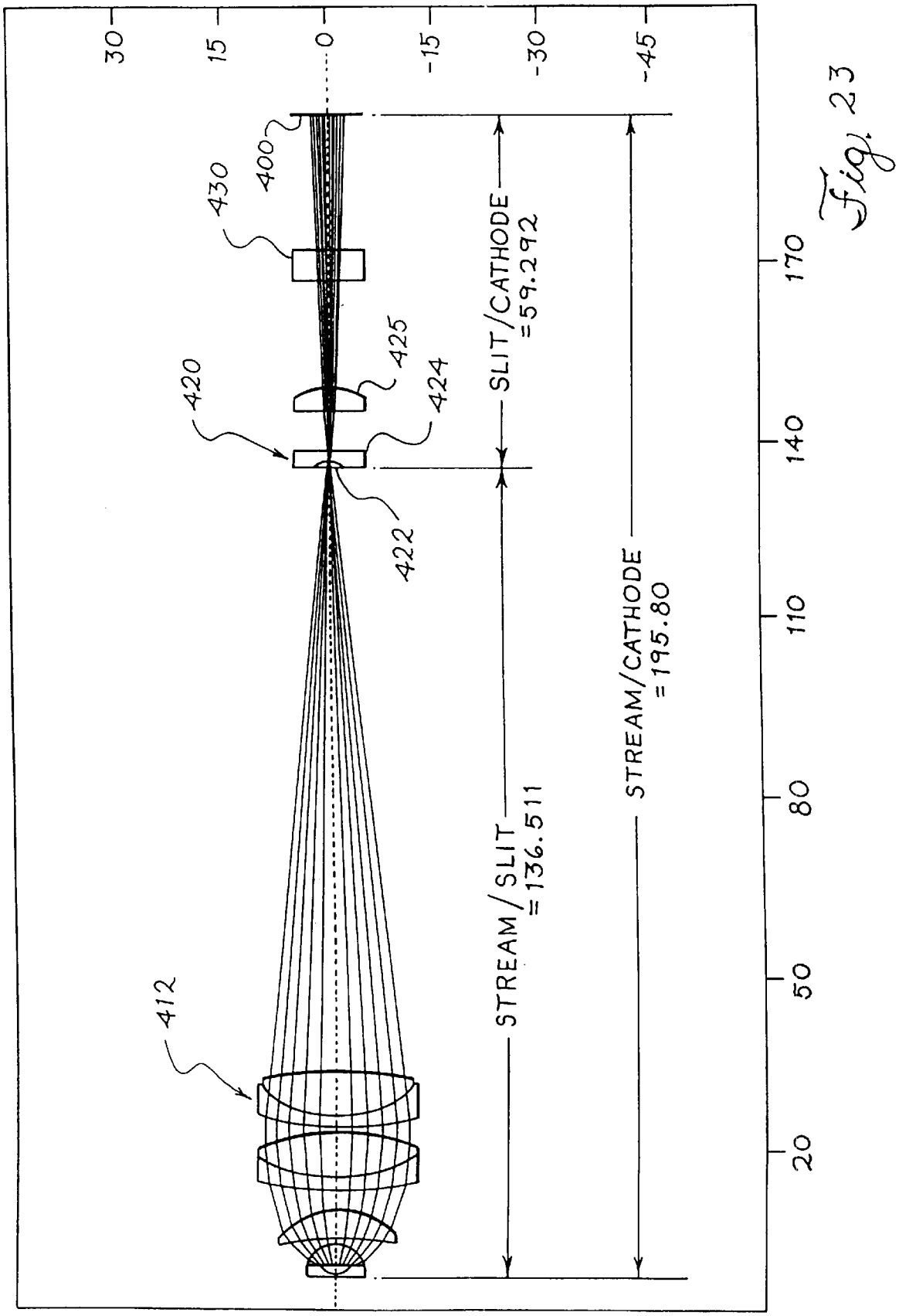
FIG. 23 is a diagram of the ray fan from the flowcell to the cathode of the optics bench shown in FIG. 19.

The PMT optical system is preferably modular and is illustrated in FIGS. 23 and 24. Each PMT module includes either 1 or 2 PMT's and a slit/field lens assembly 420, which includes a slit 422 and field lenses 424 and 425 (FIGS. 23 and 24). The slit 422, which is conjugate with the flow chamber 300, minimizes background light at the cathode of the PMT 400. The field lenses 424 (preferably with focal length of about -12.0 mm) and 425 (preferably with focal length of about 15.0 mm) effect the telocentric configuration discussed above. Optical filters 430, 432, 434 and polarizer 436 are inserted into the light paths of the PMTs to change the wavelength and/or the polarization of the detected light. It should be mentioned that the system is designed so that a third PMT module can easily be added, which, with the addition of appropriate dichroic mirrors and bandpass, filters, would enable as many as 6 PMTs to be incorporated into the system. For example, one could imagine a sophisticated analysis requiring simultaneous measurements of four fluorescence detectors along with polarized (PSS) and depolarized (DSS) side scatter.

In an exemplary embodiment, ALL is measured by a substantially rectangular photodiode and a N.D. 2.0 filter (See: FIG. 20). IAS is measured by an outer ring photodiode with no filter. PSS is measured by a Harrmamatzu R928

PMT (402) with no filter. DSS is measured by an R928 PMT (400) and a horizontal polarizer (436). FL1 is measured by an R928 (400) PMT and a 530/30 filter (a bandpass filter centered at about 530 nm with a passband of about 30 nm, 430). FL2 is measured by an R928 PMT 402 and a 580/30 bandpass filter (432). FL3 is measured by an R928 PMT (404) and a 630/30 bandpass filter (434).

9. Pneumatic Unit

In a preferred embodiment of the cell analysis system 60, the pneumatic unit 72 is a separate unit having a dedicated power supply. This construction reduces weight, size and power consumption of the analyzer module 64 and data station module 68.

The pneumatic unit 72 includes a pressure pump and a vacuum pump. It provides a regulated pressure of approximately 8 ½ psi, another pressure from about 12–15 psi, a higher pressure of about 40 psi, and a vacuura of about 15 inches of mercury.

The vacuum pressures are controlled by the analyzer software present in a suitable memory, such as a RAM, a ROM, an EPROM, a SRAM and the like.

10. Data Station/Computer

The data station module 68 is preferably a 80386 or 80486-based PC compatible computer including a display terminal, disk drive, hard-disk, keyboard, pointing device, and LAN connection. In an exemplary embodiment, the display terminal is color, the disk drive is 3.5 inch, the hard disk has at least 540 megabytes of memory and the keyboard is PC-style. The data station 68 may be provided with memories, such as RAM's, ROM's, SRAM's, EPROM's and the like, containing sufficient software algorithms to manipulate measured data, calculate parameters, and display results in a variety of formats, including histograms, scattergrams, and other multidimensional plots.

The data station 68 of the cell analysis system 60 has memories and other devices which apply algorithms for various cellular analyses. These algorithms are used to analyze clusters of data points generated by the analysis module 64 to yield information of clinical relevance. The disclosed integrated hematology/immunology instrument provides a single platform on which such software may be implemented, thereby providing an instrument that not only automates hematology and immunology sample processing and measurement, but also automates data analysis.

The data station 68 also provides data repositories which are collections of related sample records. FIG. 283 illustrates a preferred set of data repositories, including data logs, patient histories, quality control (QC) files, standard reference particle files, paired duplicates files, Bull's algorithm (X-B) batches, moving average files, and calibration files.

11. Electronic Systems

Electronic systems are found in the analyzer module 64, data station module 68, and pneumatic unit 72. The analyzer 64 provides the hardware platform for data acquisition and fluidics and motion control. In an exemplary embodiment, the data station 68 is a general purpose computer that serves as a user interface and processes, displays and stores the acquired data. The pneumatic unit 72 controls the vacuum and pressure sources.

In a preferred embodiment, the three modules are physically separate, and each unit is powered from a separate AC outlet. The data station 68 and the pneumatic unit 72 communicate with the analyzer 64 through independent serial communication channels 76, 84.

Figure 25:
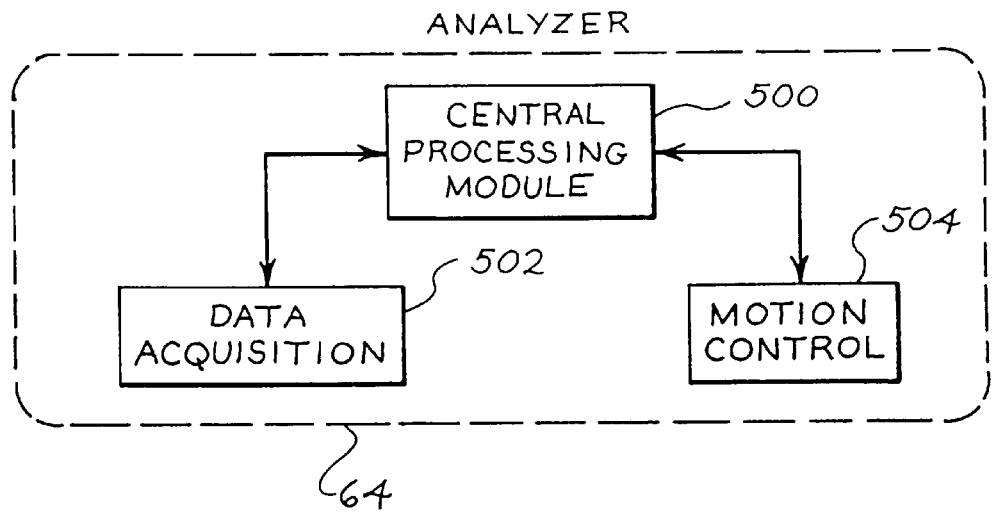
FIG. 25 is a block diagram illustrating one embodiment of the analyzer module of the cell analysis system shown in FIG. 1.

FIG. 25 is a block diagram illustrating some electronic hardware components of the analyzer 64. These components include a central processing module 500 (CPM), a data acquisition subsystem 502, and a motion control subsystem 504. The CPM 500 controls the data acquisition subsystem 502, the motion control subsystem 504, and communication functions.

A preferred embodiment of the CPM 500 includes the following features:

Motorola 68302 Integral Multiprotocol Processor clocked at 20 MHz

1 MB Dynamic FAM expandable in steps of 1 MB up to 4 MB

128 KB EPROM

2 KB Non-Volatile RAM

Figure 26:
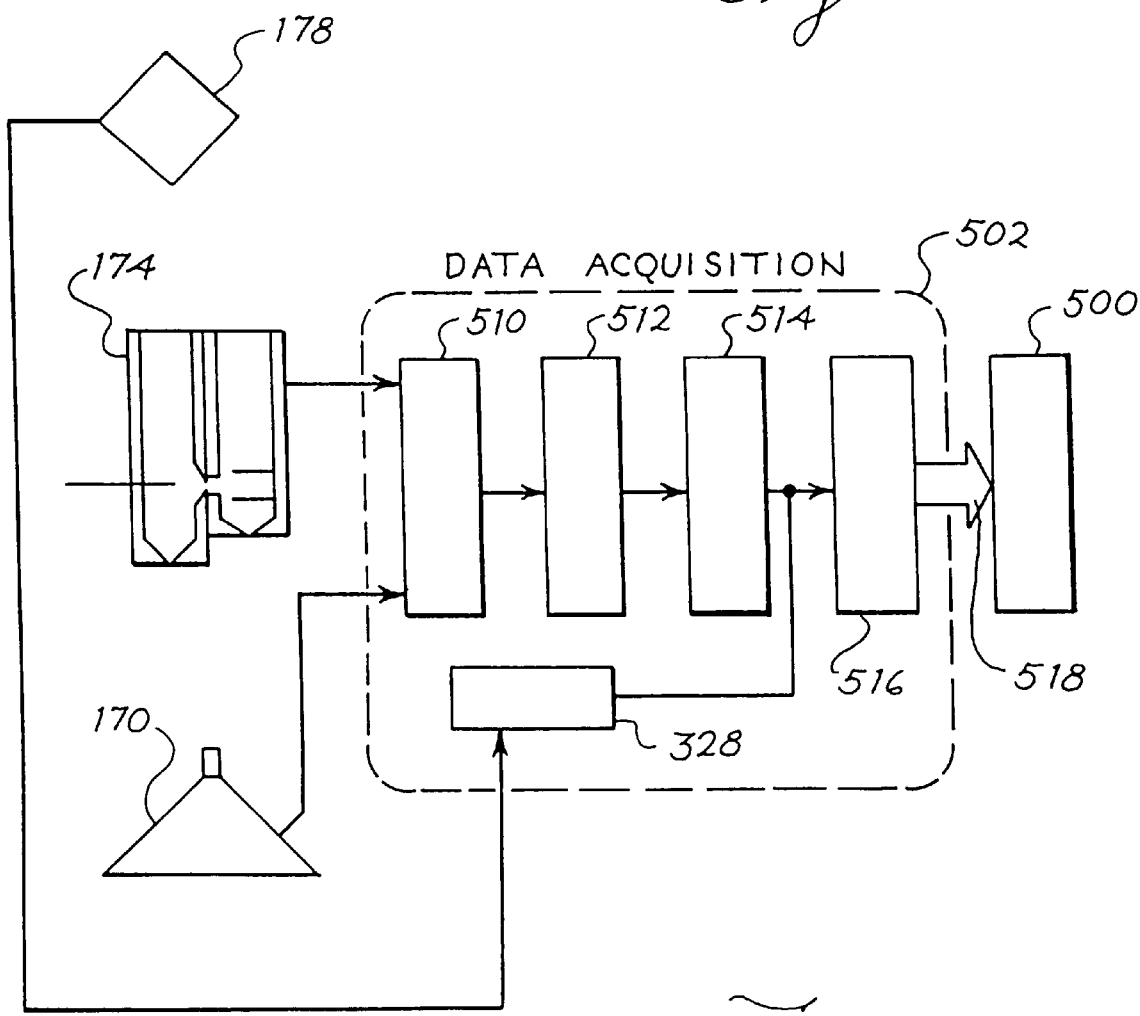
FIG. 26 is a block diagram illustrating one embodiment of the data acquisition module shown in FIG. 25.

DMA Controller for fast 16-Bit transfers of acquired pulse data from A/D Converters to CPM RAM Buffered 8-Bit bus for data acquisition control and diagnostics functions Two Motor Processing Module (MPM) Serial Links One peripheral serial link One Pneumatic Unit Serial Link One HDLC serial link Direct Memory Access (DMA) channel dedicated to HDLC serial link One RS-232 port for bar code reader One RS-232 port for diagnostics terminal FIG. 26 is a block diagram illustrating details of the data acquisition subsystem 502 shown in FIG. 25. Cell or sample characteristics are converted to electrical signals at the HGB transducer 178, the impedance transducer 174, and the optical flowcell 170. The impedance transducer 174 and the optical flowcell 170 generally produce electrical pulses as their output signals, and the HGB transducer 176 outputs a low frequency signal. The output of each flowcell/transducer is processed separately by the data acquisition subsystem 502.

The output signals from the impedance transducer 174 and the optical flowcell 170 are generated by several detectors 510. These detectors consist of the PMTs and photodiodes of the optical bench 350 or the electrical circuitry of the impedance transducer 174. Each detector output is fed through a preamplifier module 512 and a signal processing module 514 to an analog to digital converter (ADC) module 516. The signal processing modules 514 include circuitry for the measurement of pulse attributes such as pulse height and the like. The ADC converter 516 is a multiplexed converter that changes analog outputs from the signal processing module 514 to digital values that represent these pulse attributes. The digital values are then transferred to the CPM 500 via direct memory access (DPIA) 518. The CPM 500 process;es the information and then sends the data to the data station 68 through the high level data link control (HDLC, a communications protocol) data link 76. The data acquisition subsystem 502 also generates the analog voltages required for various parameter settings, such as trigger levels, gating levels, laser output poster, and others.

The outputs from the HGB transducer 178 are fed through a HGB-detector/analog-multiplexer board 328 directly to the ADC module 516. In general, the HGB board 328 includes a transresistance amplifier 332 and a current source 3434 (FIG. 18). The HGB board 328 and its components are discussed in more detail under section 8.F. of this disclosure.

A. ADC Module

The ADC module 516 contains an analog-to-digital converter. The ADC module 516 is multiplexed to measure analog voltages from the signal processing modules 514 and auxiliary voltages within the ADC module 516 itself.

The digital representation of each voltage measurement has an associated identifying tag. In a stream of data, the tag indicates the specific measured value which follows. All tags are 7 bits long, allowing for a maximum of 128 different parameters.

The signal processing modules 514 contain one peak-hold circuit assigned to each output signal from the preamplifiers 512. A peak-hold circuit. receives an electrical pulse as its input signal and generates a steady voltage equal to the maximum voltage detected during the pulse. A programmable tag sequencer in the ADC module 516 points to one of these peak-hold circuits at a time, routing the value to be measured (the steady output voltage) to the ADC module, which performs the conversion of that particular signal from its analog form (voltage) to a digital value. After sufficient time has been allowed for this conversion, the tag sequencer points to the next peak-hold circuit holding a value to be measured. When each conversion is finished, the corresponding tag identifying the measured signal is attached to the data. In this way, the tag sequencer time-shares the ADC module by assigning a time slot to each input. The results of these conversions are transferred to the main memory on the CPM 500 via the DMA 518. DMA is utilized to transfer data at high rates without CPU intervention.

B. Impedance Transducer Preamplifier

The preamplifier 512 contains a low-noise programmable constant current source. This constant current is divided between two paths. One current path flows through the electrodes in the impedance transducer; the other flows into the preamplifier 512. Since the sum of both currents is constant, a change in the current through the electrodes (caused by cell passage through the impedance transducer 174) is reflected as a change in the output voltage of the preamplifier 512.

C. Impedance Transducer Signal Processing

The output from the impedance transducer preamplifier is routed to two independent paths, each having a 12-bit programmable gain, baseline restorer, pulse detector, and peak hold circuit. One path is for RBC pulse detection, and the other path is for PLT pulse detection. The same pulse is thus screened simultaneously in the following two different criteria.

A pulse is detected as valid if its peak value exceeds a given threshold. The data acquisition subsystem 502 recognizes level thresholds and slope thresholds. The slope threshold improves the hardware counter dead time by allowing the counting of two pulses that arrive very close in time.

Each type of cell requires its own qualification criteria. RBC pulses should exceed a certain level and slope. A certain negative slope should be exceeded in order to reset the detector for the next pulse.

PLT pulses occur in the same sequence with RBC pulses. However, PLTs are distinguishable from RBCs because PLTs are smaller. A pulse is classified as a detected PLT if it exceeds a lower level threshold but does not go above an upper threshold. Additionally, the pulse must exceed a predetermined positive slope in order to be considered a valid PLT. A certain negative slope should be exceeded in order to reset the detector for the next pulse.

If a pulse satisfies the qualification criteria, a trigger signal is sent to the peak-hold circuit, and subsequent ADC conversion is initiated. Trigger pulses from the impedance transducer 174 are counted in two dedicated 16-bit counters. One counter is for RBCs, and the other counter is for PLTs.

Each output path from the impedance transducer preamplifiers includes a baseline restoration circuit to subtract the background DC component from the amplified signals. The offset voltage created by these circuits is monitored, thus providing a tool for diagnostics.

D. Optical Preamplifiers

Light emitted from the optical flowcell 170 is collected at different angles by the detectors 510, which incLude photodiodes (PD1 and PD2) and photomultipliers (PMT1, PMT2, and PMT3). These signals have a wide dynamic range, and accordingly a wide range of gain adjustment is provided. For the PMTS, gain adjustment is preferably accomplished by controlling a dynode voltage on the PMT itself (about 200 V to about 1100 V). This procedure can adjust the gain over an approximate 105 range. The optical preamplifiers of the PMTs convert the current output from the PMTs to a voltage with fixed gain.

The gain of each photodiode (PD) is programmable at its preamplifier in power-of-2 steps. The PD preamplifiers convert the PD output current to voltage.

E. Optical Signal Processing

The optical preamplifier outputs are routed to five independent paths or channels. Each channel include its own baseline restorer, pulse detector, peak hold circuit, and 12-bit programmable gain (post peak-capture).

An "optical" pulse is detected as valid if its peak value exceeds a predetermined programmable threshold. A valid pulse generates a digital trigger pulse. The trigger pulse can be programmed to be one of several selected logical combinations of channels (PD1, PD2, PMT1, PMT2, PMT3). Each channel has its own programmable lower threshold.

The trigger pulse initiates the peak-capture and subsequent ADC conversion of the captured peak values for the five channels. The trigger may be qualified by requiring a gating criteria. For example, the trigger may be invalidated if the signal on PD1, PD2, or PMT2 exceeds a predetermined gate threshold.

A baseline restorer circuit is provided for subtracting the DC component from the pulse signals, thereby reducing any DC background offsets. The response time of these circuits is slower than the width of the average pulse. The offset voltage created by these circuits is monitored, providing a tool for diagnostics.

Trigger pulses from the optical flowcell 170 are counted in two dedicated 16-bit counters. One counter is for the gated cells (those that have not been rejected by the gating criteria), and the other counter is for the total number of cells that meet the lower threshold requirement.

F. HGB Signal Processing

FIG. 18 is a block diagram of a simplified hemoglobin (HGB) measuring system. The concentration of hemoglobin contained in the prepared sample is measured, for example, in grams per deciliter. This concentration is proportional to the absorbance of the light by the sample in the green (about 540 nanometers) wavelength region.

The light path consists of a current controlled light emitting diode 322, a transducer chamber 338, a filter 326 (about 540 nm), and a photodiode 324.

The output current from the photodiode, which is proportional to the light energy received, is amplified by the transresistance amplifier 332. The output of the transresistance amplifier 332 is sent to the ADC module 516.

The difference between voltages developed when measuring a clear reference solution in the transducer chamber 338 and when measuring the prepared sample containing hemoglobin is representative of hemoglobin concentration.

G. Time Stamp

The signal processing module 514 uses a 16-bit counter (not shown) to generate a time stamp with an approximately 0.5 ms resolution. The time stamp value is stored with the data from each automatic sequence iteration which resulted in valid data acquired in the ADC module 516.

H. Motion Control

Figure 27:
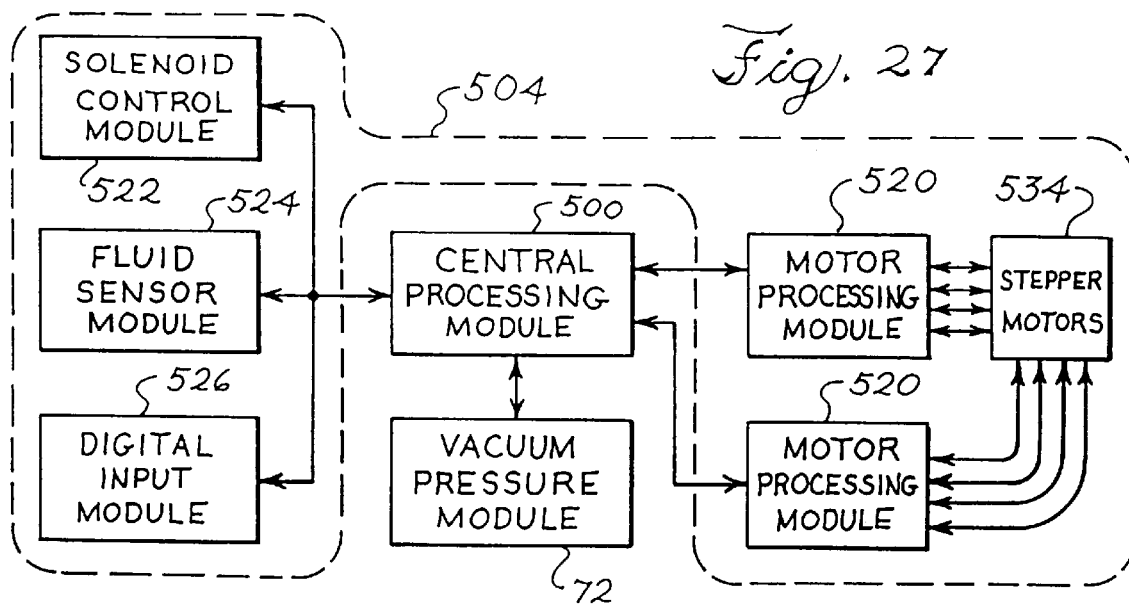
FIG. 27 is a block diagram illustrating further details of the analyzer module shown in FIG. 25.
Figure 28:
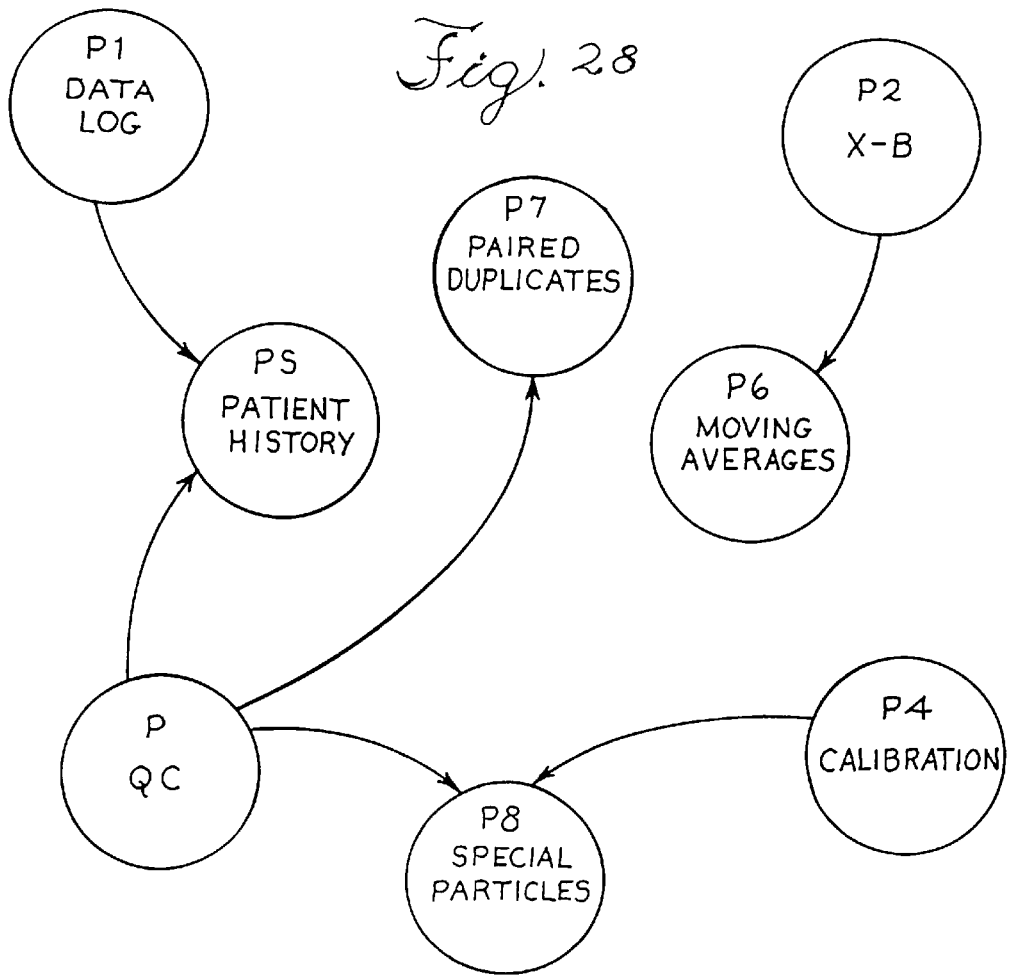
FIG. 28 is a diagram illustrating the data repositories of the cell analysis system shown in FIG. 1.

FIG. 27 is a block diagram illustrating an exemplary embodiment of the motion control subsystem 504. The flow sequences and automated sample processing operations of the analyzer 64 are controlled through the motion control subsystem 504.

As illustrated, the motion control subsystem 504 includes a motor processing module 520 (MPM), a valve control module 522 (VCM), a fluid sensor module 524 (FSM), and a digital input module 526 (DIM). The MPMs 520 communicate with the CPM 500 through two independent serial links 530, 532 (500 KB), and each MPM 520 preferably controls up to 12 stepper motors 534. The VCMs 522 control all valves in the analyzer 64. The DIMs 526 monitor all digital inputs (switches, optical sensors, and magnetic sensors). The FSM 524 monitors all fluid sensors.

The VCMs 522, DIMs 526, and the FSM 524 are intelligent modules that preferably communicate with the CPM 500 through a half-duplex, differential serial peripheral bus. Additional peripheral modules can be added to this bus.

12. Software

Software controls the major operations of the cell analysis system 60, including the analyzer flow sequences, the timing and sequence of events, gathering data, and converting measured data into meaningful results. The software is resident on suitable memories, such as RAM's, ROM's, EPROM's, SRAM's and the like, found in the system 60. The software components are preferably partitioned into the six domains (represented by circles) shown in FIG. 2.

The operator interface domain 90 regulates user interaction with the data station 68 including all operator controlled input devices attached to the data station, definition and generation of all data station displays, and definition of all printed output.

The data station operating software 92 controls sample processing, data management, security, communications with the analyzer module and laboratory information systems (LIS), and generation of printed outputs.

The algorithm software 96 may include any desired combination of applied mathematics. The algorithms are applied in the analysis of sample data, the conversion of list mode data into graphic and numeric results, and the statistical analysis of groupings of numeric results. These algorithms preferably include clustering techniques for identifying discrete cell types or conditions.

The analyzer operating software (AOS) 98 controls the analyzer module's electronics (hardware), data collection, and communications to the data station module. The timing and scheduling of all analyzer activities, including the analyzer flow sequences, is also controlled by the ACS 98.

The flow sequence (FSQ) software 100 controls the mechanical components responsible for moving fluids through the analyzer module 64, including the execution of automated sample processing protocols and integrated hematology and immunology testing.

The firmware 102 includes a network of EPROM resident device controllers for various hardware modules of the analyzer 64 and pneumatic unit 72.

The operator interface (OI), data station operating software (DSOS), and algorithms use the data station module 68 as their platform. The AOS 98, FSQ software 100, and firmware 102 reside in and use the analyzer module 64, as their platform. The preferred software is a multitasking, multithreaded application.

Figure 29:
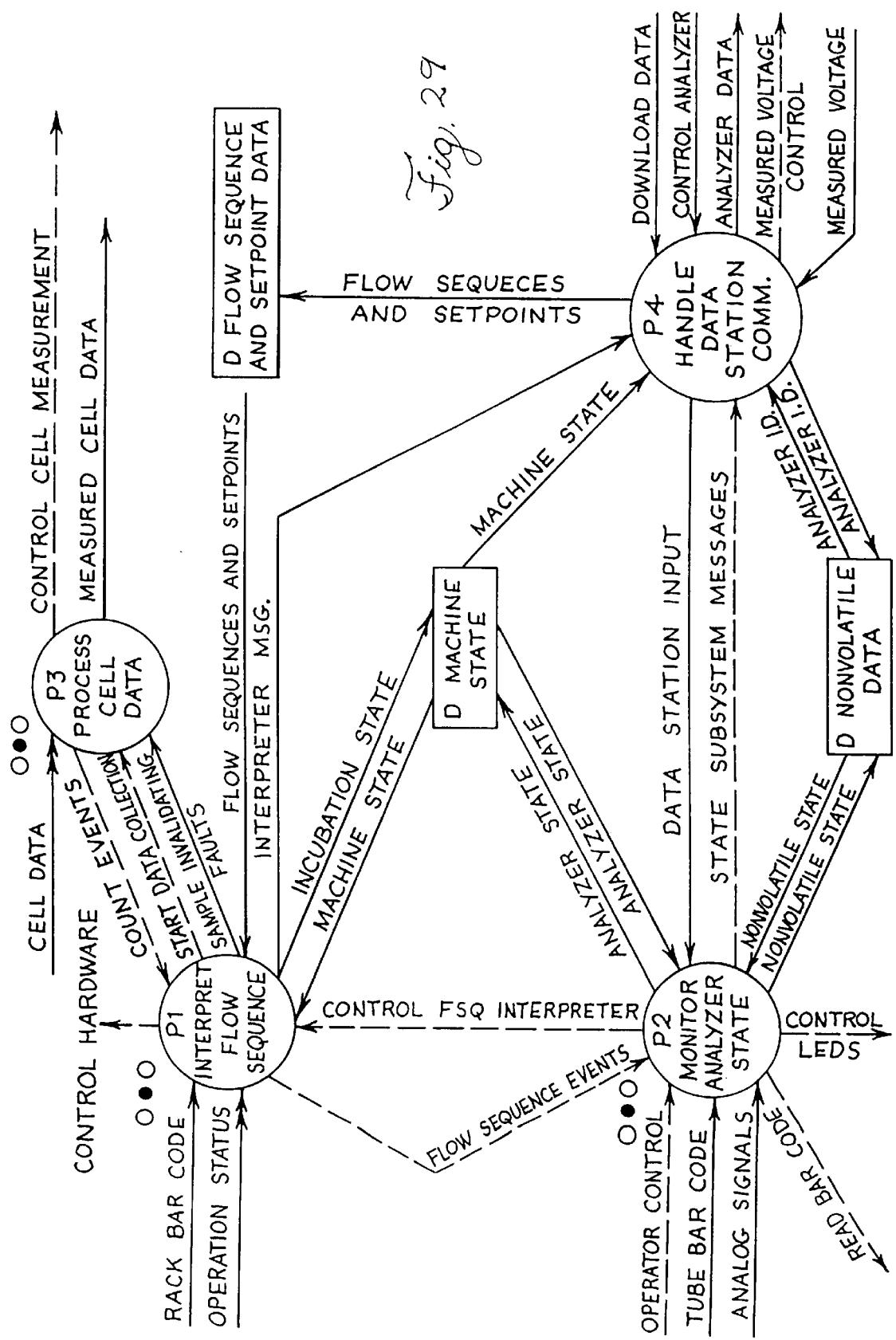
FIGS. 29 and 30 are state diagrams illustrating one embodiment of the software architecture shown in FIG. 28.
Figure 30:
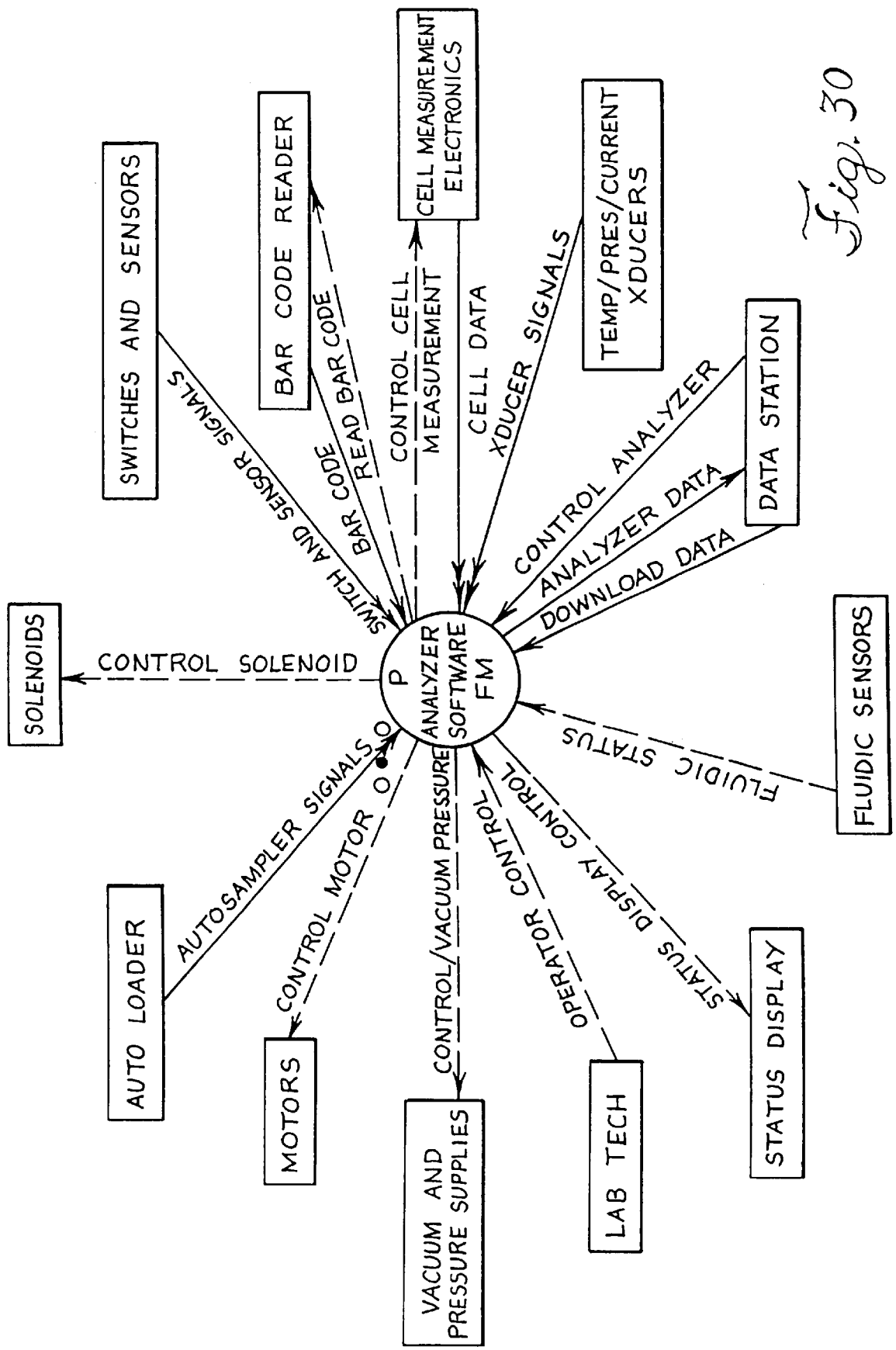
Figure 40A:
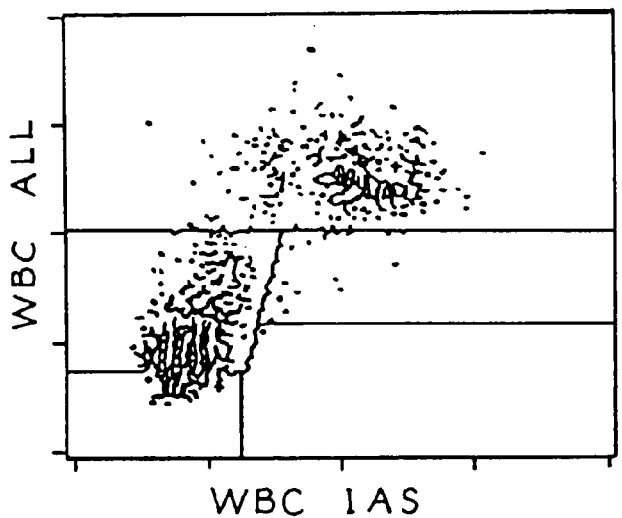
FIGS. 40A–C illustrate displayed data for NRBC obtained by an embodiment of the cell analysis system.
Figure 40B:
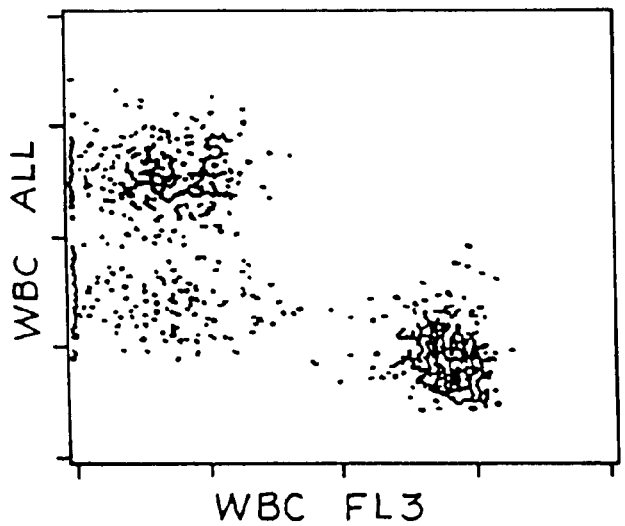
Figure 40C:
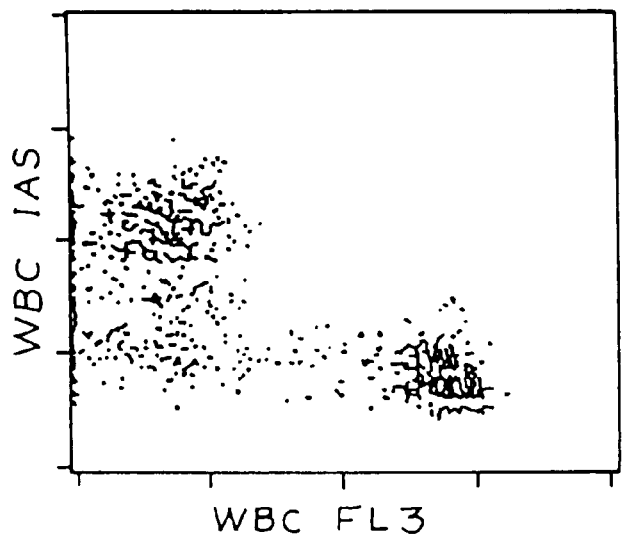
Figure 41A:
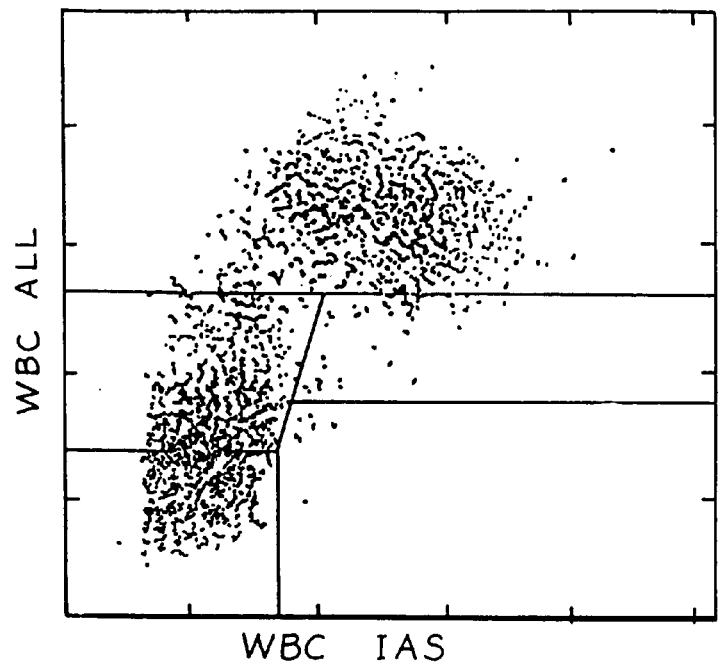
FIGS. 41A and 41B illustrate displayed data for NRBC obtained by an embodiment of the cell analysis system.
Figure 41B:
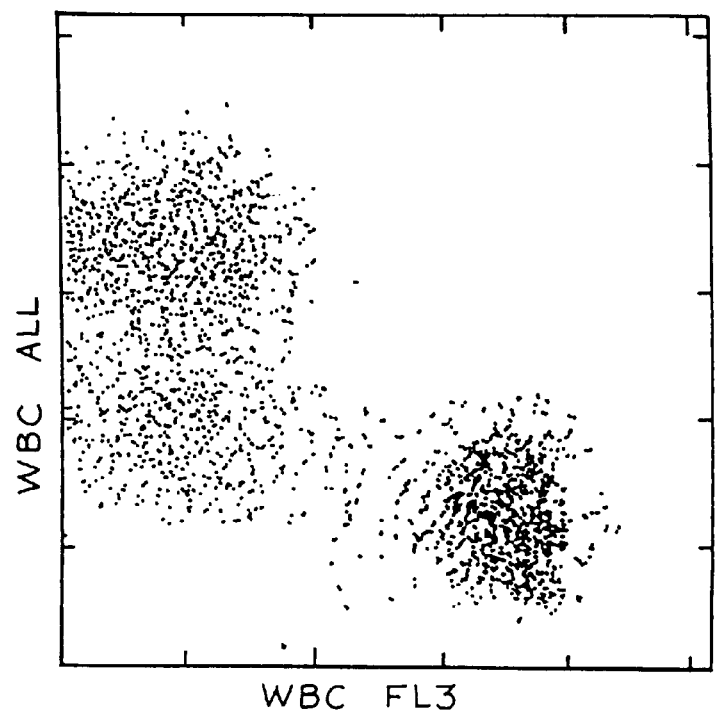

The AOS 98 resides in the CPM 500 and is the main controller of the detailed operation of the analyzer 64. It communicates with several slave microcontrollers responsible for stepper motor timing, analog-digital conversion, vacuum/pressure closed loop monitor/control, valve control, and digital sensor inputs. In addition, it is responsible for data, status and control communication with the data station 68 to which it is connected. The AOS 98 is preferably executed on a Motorola 68302 CPU chip. Its firmware is stored in external EPROM(s), and the downloaded AOS and flow sequences are stored in on-board RAM. An embodiment of AOS operation is shown in FIGS. 29 and 30.

The AOS 98 includes multitasking features for implementing the flow sequences. The AOS downloads flow sequences from the data station, storing them in its memory. The AOS executes the flow sequences required for the desired sample tests upon direction from the data station 68.

Each flow sequence requires tasks of multiple analyzer components in accordance with a schedule. FIGS. 13A–F comprise is a timing diagram of an exemplary flow sequence for integrating and automating hematology and immunology sample preparation and measurement on a single unit. The upper-most horizontal axis, as viewed, represents time in seconds, and the left-most vertical axis lists sample processing and measurement components of the analyzer 64. The grids of the diagram describe the activities of the analyzer components. Each of the components listed along the left vertical axis in FIGS. 13A–F performs a specific set of tasks in the flow sequence. When a component has completed its task, it begins to look for its next instruction without waiting for downstream components to finish work on the current sample.

The AOS maintains a collection of count-related hardware set points and parameters. One set is provided for each count type (CBC WBC, CBC OPLT, etc.). In addition, one set is provided for diagnostic purposes. The AOS accommodates the download of any of these sets from the data station 68. In addition, any set may be activated (i.e. used to configure the hardware) under command from either the data station 68 or flow sequence software.

In addition to the count-related hardware set points and parameters, the AOS maintains a collection of event count-independent parameters. The AOS accommodates the modification of any of these parameters from the data station 68. In contrast to the count-related parameters, the AOS loads these values directly.

To commence a flow sequence, the AOS 98 determines that a sample is available for aspiration. This is based either on operator activation of a pushbutton or a command from an autoloader mechanism. All the information known by the analyzer 64 about the sample is sent to the data station 68. The data station 68 responds with information about. the required measurements to be performed on the sample. Based upon this response, and in conjunction with the state of the analyzer 64 (i.e. reagents, incubations, flow sequence aspiration enable/disable flags), the AOS determines whether or not to proceed with sample aspiration. Whether or not an aspiration occurs, the AOS informs the data station 68 of the status of the sample.

When a flow sequence requires incubation, the AOS provides the flow sequence with the ability to "allocate" an unused site 132 in the sample processing area 110 for an incubation. The sample type (and therefore the appropriate flow sequence to run at the completion of incubation) is specified as part of the allocation process. When the incubation is started, the AOS starts an incubation timer associated with a particular incubation site 132. A sample identifier, sample type, and incubation time are also associated with each incubation site 132. The AOS updates the active incubation timers periodically and recognizes the completion of incubation intervals. When complete, the AOS continues the execution of the flow sequence for that test. The AOS reports the total incubation time of each incubated sample and the incubation site number (position) as part of the data accumulated for each test on each sample. After the incubated sample has been processed and the incubation site has been cleaned and dried, the flow sequence notifies the AOS that the site is again available for allocation. The AOS 98 inhibits aspiration of samples to the incubation area 118 when the appropriate incubation trays 124 are not present. Any changes in the incubation trays 124 or reagent modules 122 are relayed to the data station 68. Whenever an aspiration is disallowed, the AOS sends an advisory message to the data station 68.

Upon data station request, the AOS supplies the current incubation status of all sites in the analyzer 64. This information includes incubation time, site status (clean/dirty) and site usage counts.

The flow sequence interpreter 100 is capable of running multiple flow sequences simultaneously. The flow sequence interpreter allows flow sequences to coordinate their activities through the setting and testing of various "flags." Flow sequence logic makes decisions based upon the state of flags which are set and cleared by other flow sequences running concurrently.

The flow sequence interpreter supports fixed or variable sample event count times. Variable event count times may be set through either software or hardware set points. Variable event count times are preferably provided with an upper limit as defined by the flow sequences.

The flow sequence interpreter allows flow sequences to initiate event count and data collection intervals. Data generated during the data collection interval is automatically sent to the data station 68 by the AOS. The data sent to the data station 68 preferably includes at least the sample identifier, hardware counters, list mode data, and incubation time (if any). Count types preferably include:

CBC: complete blood count including all hematology measurements except those related to reticulocytes.

RETICS

SUBSET/PHENOTYPE

The AOS allows the analyzer 64 to overlap counting activity on the flowcells/transducers 170, 174, 1783. Thus, multiplexing and piplining the analyzer activity maximizes instrument throughput.

The analyzer 64 may be connected to external containers for waste (not shown) or bulk reagent storage (193). AOS monitors sensors that detect when the waste container becomes full or a bulk reagent storage container 193 becomes empty. Further aspiration of samples is inhibited by the AOS 98 until the condition is remedied.

The AOS reads and modifies the non-volatile serial access memory in each antibody reagent module 122. At least the following information is stored in each antibody reagent module memory:

lot number expiration date test type (panel number)

module number number of wells used in module usages of module initialized flag redundancy/error control The antibody reagent modules 122 are read as part of normal analyzer initialization. Thereafter, any operation that affects the status of the module 122 is recorded in the module's memory.

The AOS 98 communicates with the motor processor modules 520 which are responsible for controlling the analyzer stepper motors 534. The AOS resets the motor processor modules 520 at initialization. The AOS keeps track of the position of each motor in the analyzer 64 and verifies this information with the controlling motor processor module 520. Position discrepancies are reported to the data station 68.

Upon successful completion of power-on self tests, the analyzer 64 accepts AOS operating software downloaded from the data station 68. At the completion of the software download, a start address is supplied from the data station 68 specifying the address at which to begin execution.

13. Sample Processing Examples

A. General Sample Processing

The following paragraphs discuss in detail exemplary operation of the cell analysis system 60. Further understanding of details of the system 60 may be gained by reference to this discussion. While specific examples are discussed for the sake of clarity of understanding, it is to be remembered that the system 60 may perform other method steps without departing from the intended scope of the claims.

The automated sample processing protocol of the cell analysis system 60 can be considered in three phases—sample preparation, sample measurement, and sample analysis. The particular protocol for each of these phases is test dependent. For example, the preparation, measurement, and analysis for the WBC differential is different from that for platelets, reticulocytes, lymphocyte subsets, etc. General steps, however, are common to each phase.

In the first phase, automated sample preparation, the analyzer 64 aspirates a volume of the sample, transports the sample to designated cups, and mixes the sample with diluent and/or reagent as required to prepare the sample for measurement. The preparation may only involve diluting the sample, and the diluting means may also be the lysis for removing RBCs. Sometimes, as in the reticulocyte test, the preparation phase involves two steps, a first step predilution with a diluent/sheath reagent, and a second step dilution adding a known volume of fluorescent stain.

In other tests, such as the lymphocyte subset test, the preparation phase may involve many steps and require an extended incubation with a reagent. when this occurs, aspiration probe assembly 148 places a volume of the sample into transfer cup 140 and returns to a position ready to aspirate a subsequent patient sample. The remaining steps in the preparation process are executed by the incubation probe assembly 152. These steps may include further dividing the sample into one or more portions in incubation sites 132, adding a specific Mab reagent to each portion, and incubating. Most of these steps, performed by incubation probe 152 may occur while the vent/aspiration probe assembly 148 is occupied with the processing of subsequent samples.

After incubation is complete, incubation probe assembly 152 completes the preparation phase by mixing the incubated sample portion with a lysis reagent to remove the red cells so that the sample portion is ready to be pipelined to the optical flowcell for measurement.

The second phase, the measurement phase, begins when the sample cups contain a sample that is ready for measurement. The sample is then routed through a tubing network 182 connected from the bottom of the sample cups to the desired measurement transducer 170, 174, 178. After leaving the transducer, the samples are sent to waste containers (not shown). The signals are sensed by the appropriate detectors for each test, then amplified, processed, digitized, and stored in a list mode file corresponding to the particular test.

The third, the analysis phase begins with the list mode data. Algorithms are applied to the data which map the various particles or cell types into the feature space with axes corresponding to the detectors appropriate for each test, thereby identifying unique population clusters, and enumerating the cells within each cluster. The final output may be graphic and/or numeric, and may be a measure or function of cell volume, hemoglobin content, population type, or some other cellular characteristic. The output is usually quantified in both absolute terms and in percentages. For example populations of cell subtypes are given as percentages of parent cells and also enumerated as events per microliter of patient blood. Whenever incubated samples are analyzed, the analysis of the conventional hematology tests is done first. When the incubated sample measurement is complete, the incubated sample analysis takes place and the combined patient analysis is completed.

The testing protocol for the sample preparation and measurement phases of sample processing are implemented automatically by means of flow sequences, which vary in complexity. In tests involving extended incubation, the flow sequence integrates the incubation and non-incubation testing so that whenever a sample is incubating, the analyzer 64 is allowed to proceed with subsequent tests. When the incubating sample is ready for measurement, processing of further samples is interrupted and the incubated sample undergoes measurement and analysis.

B. Hemoglobin Sample Processing

A greater understanding of this discussion may be had with reference to FIGS. 5 and 12. For example, a portion of patient sample 166, about 18.75 microliters in volume, is deposited into the HGB cup 142 by means of the aspiration probe 156, where it is mixed with a large volume of HGB lyse reagent with a resulting dilution of about 200:1. After about 20 seconds of lysing time, the cup contains only diluted hemoglobin, which is transferred for measurement through line 182 to the hemoglobin transducer 178 by means of peristaltic pump 246. The optical transmittance of the hemoglobin sample in the transducer chamber 338 is measured by means of the LED source 122 and photodiode 324. The transmittance, represented by T, is amplified, progressed, digitized, and stored. It is then converted to absorption in the analysis phase by means of an algorithm A=log(1/T), which is further converted to hemoglobin concentration, HGB, in grams per deciliter of patient sample, by means of a previously determined calibrator. The hemoglobin lest, in combination with the RBC impedance test results, enables determination of the following measured and calculated parameters:

HGB=(hemoglobin concentration)
MCH=HGB×10/RBC (mean cell hemoglobin)
MCHC=HGB×100/HCT (mean cell hemoglobin concentration)

where RBC is the red blood cell count (RBCs per $\mu$l) and HCT is the hematocrit (volume fraction, in percent, of the blood sample that consists of red blood cells), both of which are measured in the impedance transducer 174.

C. RBC and Platelet Sample Processing

The reader should refer to FIGS. 4 and 5. A portion of patient sample 166, about 18.75 microliters in volume, is deposited into cup 134 by means of aspiration probe 156, where it is mixed with a volume of diluent/sheath reagent with a resulting dilution of about 420:1. The diluent/sheath reagent is appropriate both as a sheath carrier in the laminar flow systems in impedance flowcell 174 and optical flowcell 170 and as a sample diluent so that the RBCs and Platelets travel in single file in each transducer. The formulation includes a surfactant which enables unambiguous distinction of small red cells from large platelets. After mixing in the RBC cup 134 is complete, the diluted sample is transferred to impedance transducer 174 (FIGS. 10*a* and *b*) by pump 220, valves 210 and 212, and syringe assembly 204, 224. Platelets are sized and counted in impedance transducer 174 (FIG. 17). Platelets are also transferred to and counted in the optical transducer 170 (FIG. 16). Because of the smaller illuminated volume and lower noise in the optical transducer, the optical platelet count has superior performance. The platelet count from the optical transducer 170 is reported as patient data, with the impedance count being used as a diagnostic tool for monitoring instrument performance.

The impedance transducer 174 is used for reporting the platelet size parameters. A lower threshold is set which distinguishes platelets from noise, and an upper threshold is set which distinguishes platelets from RBCs. Pulse amplitudes are filtered, amplified, digitized and stored as list mode events. From this data algorithms are applied for calculating the following platelet size parameters, and displaying the platelet histogram:

Platelet count (PLT)
Mean platelet volume (MPV)
Platelet distribution width (PDW)
Plateletcrit (PCT=MPV×PLT)
Platelet concentration (Used for instrument diagnostic purposes)

The diluted sample from the RBC cup 134 is also transferred to the optical transducer by valves 236 and 238, pump 232, and syringe 240, 206. The platelets are determined in two dimensional feature space using the PSS (polarized side scatter) and,IAS (intermediate angle scatter) optical parameters. The pulses from detectors 384 and 402 are processed, digitized, and stored in list mode files for processing by algorithms. The sample flow rate for measuring platelets is about 2.5 microliters per second, and the counting time through the flowcell is about 6 seconds for normal patients. This counting time is extended automatically for low count samples to improve the count statistics. The count reported from the optical transducer is platelet concentration (PLT).

The impedance transducer 174 is also used for determining RBC size and count parameters. The upper threshold used for detecting platelets in the impedance transducer 174 is also the lower threshold for the RBC count. The pulses above this threshold are processed, digitized, and stored in the RBC list mode file. Algorithms are applied for calculating the following RBC parameters and displaying the RBC histogram:

Red cell concentration (RBC)
Mean cell volume (MCV)
Red cell distribution width (RDW)
Hematocrit (HCT)

D. WBC Differential Sample Processing

Referring to FIGS. 4 and 5, a portion of patient sample 166, about 37.5 microliters, is deposited by means of sample aspiration probe 156 into WBC cup 138 which contains about 850 microliters of WBC lyse.

The lyse is a one reagent/one step process that achieves multipurpose goals. It is gentle enough to preserve the morphology of fragile white cells and at the same tire efficiently lyse substantially all of the red cells. Both of these goals are accomplished even in hemaglobinophathic samples, which may require that the lysing time be extended beyond 11 seconds. Additionally, in the preferred embodiment, the lyse contains a small concentration of a vital nuclear stain which effectively labels any nucleated red blood cells (NRBCs) which might be present in the peripheral blood. The lysis chemistry has been predetermined such that the refractive index matches that of the sheath to substantially less than about 0.1%.

The mixture of lyse and sample normally remains ir cup 138 for about 11 seconds, where it is lysed and agitated at an elevated temperature. In a preferred embodiment, the lysing temperature is controlled at 42° C. ±3°. At this point, the contents of cup 138 are piped directly to optical flowcell 170.

Referring to FIGS. 19 and 20, the measurement process begins as the cell stream passes through the optical transducer 170, having been diluted with the addition of lyse so that the cells pass through the laser illumination in single file, in a laminar flowing sample stream surrounded by diluent/sheath 304 (illustrated in FIG. 16). The illuminated volume is bounded in the two dimensions normal to the flow axis by the hydrodynamically focused cell stream, and in a dimension parallel to the flow axis by the vertical beam waist of the laser beam which is about 17 microns. The sample flow rate during this test is about 2.5 microliters per second, and the corresponding illuminated sensing volume of the WBC and NRBC cells approximates an elliptical cylinder with dimensions of about 80 $\mu \times 5$ $\mu \times 17$ $\mu$. The approximately 17 $\mu$ dimension is measured along the axis of the cylinder.

The presence of a cell in the illuminated region is detected by photodiodes 382 and 384, photomultiplier tube 404, and a unique triple threshold trigger circuit that operates in three feature space dimensions. That is, it processes the three parameters of ALL (axial light loss), IAS (intermediate scatter), and FL3 (red fluorescence) and qualifies signals for digitization using AND/OR logic. A qualified signal must be greater than the IAS threshold, while at the same time it must be greater than either the ALL threshold or the FL3 threshold. The combination of this unique triggering circuit and the lysing properties (which include a balanced fixative, allowing the NRBC nuclei to be rapidly stained) clearly and non ambiguously counts and excludes NRBCs from the WBC differential cell count. This test counts WBC populations and NRBCs without the usual interference from background signals, both fluorescent and non-fluorescent, such as that emitted from DNA fragments, RBC stroma, and platelets.

When cells that meet the triple threshold criteria pass through the illuminated volume, pulses are generated at detectors 382, 384, 400, 402, and 404. The amplitudes of these pulses are filtered, amplified, digitized, and stored in list mode in the corresponding five dimensional feature space of ALL, IAS, FL3, PSS (polarized side scatter), and DSS (depolarized side scatter). The normal counting time through flowcell 170 is about 10 seconds. At the flow rate and dilution ratio described, and with a normal patient NBC count of about 7000 cells per microliter of blood volume, the resulting event count rate would be about 5000. In low count samples, this counting time can be automatically extended in order to improve the statistical accuracy of the measurement. At the conclusion of the measurement time, the sample stream is piped to waste, and probe 156 is cleaned and dried and prepared to process a subsequent sample.

Algorithms are applied to the five parameters quantified in the list mode data (ALL, IAS, FL3, PSS, and DSS), and the following cell types are quantitated and/or flagged within less than about 30 seconds of processing time: White Cell concentration (WBC), Neutrophil concentration (NEU) and percentage(% N), Lymphocyte concentration (LYMPH) and percentage (% L), Monocyte concentration (MONO) and percentage (% M), Eosinophil concentration (EOS) and percentage (% E), Basophil concentration (BASO) and percentage (% B), Nucleated Red Blood Cell (NRBC) and percentage of WBC (% NRBC), Blast concentration (BLST), Immature Granulocyte concentration (IG), Variant-lymph concentration (VARL), and Band concentration (BAND).

E. Lymphocyte Subset Sample Processing

In a preferred embodiment, sample processing for lymphocyte subset tests Involves the following steps as illustrated in FIGS. 3, 4, and 5. Aspiration probe 156 first aspirates a quantity of whole blood sufficient for the subset test and deposits the quantity into transfer cup 140.

The volume of blood required is about 50N microliters, where N is the number of Mab (monoclonal antibody) pairs required for the test. In the standard panel, N is expected to be 5, and thus the required volume for deposition in cup 140 is about 250 microliters. At this point the aspiration probe 156 is cleaned and then returns to sample station 166 to process subsequent samples while the incubation probe assembly 152 continues the subset sample processing.

The incubation probe 160 aspirates the blood from the transfer cup 140 and deposits about 40 microliters in each of 5 sequential cups 132 in incubation trays 124. Then incubation probe 160 is cleaned before moving to the reagent module 122, removing about 20 microliters of the first mab pair 128, and depositing it into the first corresponding incubation cup 132. After probe 160 is again cleaned, it returns to the reagent module 122 and transfers from the 2nd mab pair 128 another about 20 microliters of reagent into the 2nd corresponding incubation cup 132. This process continues until each of the required incubation cups contains a mixture of blood and Mab for incubation.

At this point incubation probe 160 is cleaned and dried and waits for the first Mab/blood sample incubation to complete. All activity of the sample aspiration assembly 148 is then suspended until the incubated subset samples are processed as follows. Incubation probe 160 deposits about 30 microliters of the first incubated subset 132 into the WBC cup 138 which contains about 670 microliters of WBC lysing reagent. After the incubated sample is lysed and vortexed at approximately 42° C. +3° for about 11 seconds, the first incubated mab/blood pair is ready for measurement, whereupon the contents of cup 138 are piped directly to optical flowcell 170.

The measurement process begins as the cell stream intersects the laser illuminated volume at flowcell 170. Data is acquired from optical detectors 382, 384, 400, and 402, via the system electronics and analyzer software and stored in list mode for each Mab/blood reagent mixture. The sample has been diluted so that the cells within the stream pass through the illumination zone of the laser in single file. Each cell is detected by the presence of pulses indicative of four features—ALL(axial light loss), IAS (intermediate angle scatter), FL1(green fluorescence), and FL2(orange fluorescence). The amplitude of each pulse is amplified, digitized, and stored in list mode on the appropriate feature space axis.

Analysis begins with the application of algorithms to the stored four dimensional data, from which subset percentages are calculated. After the counting time for the first subset measurement is completed, probe 160 is cleaned and cried before returning to the next incubated subset 132 and repeating the process until all subsets have been measured and analyzed. The final analysis, with results in both percentages and absolute counts per microliter of patient blood volume, is a composite of all of the above described subset measurements and the WBC differential hematology measurement.

The normal counting time through flowcell 170 is about 10 seconds. In certain low count samples, this counting time will be automatically extended in order to improve the counting statistics of the measurement.

After the sample measurement process is completed, sample aspiration assembly 148 is reactivated and ready to continue processing of any subsequent samples.

The disclosed automated sample preparation features accommodate numerous antibody panels for use in a variety of immunology and phenotyping tests. For lymphocyte subsets, each panel preferably includes five 2-color antibody sets. Preferably, each antibody set includes one antibody Mab) marked with FITC (fluorescein isothyocyanate) and the like, and a second Mab marked with PE (Phycoerithrin) and the like. The antibodies are distinguished by cluster desigration (CD) numbers. Illustrating by means of example, at least the following lymphocyte subset Mabs may be included in a panel.

| Mab Combination | Cell Type Enumerated | Cell Percentages |
|---|---|---|
| CD45/CD14 + CD13 | lymphocytes | % of WBC |
| CD3/CD4 | T-helper subset | % of Ts, lymphs & WBCs |
| CD3/CD8 | T-suppressor subset | % of Ts, lymphs & WBCs |
| CD3/CD16 | Tot. T/Tot. NK cells | % of lymphs & WBCs |
| CD5/CD19 | Tot. T/Tot. B cells | % of lymphs & WBCs |

A reduced panel is also proposed which could be used for monitoring CD4 positive cells in HIV patients. At least the following Mabs may be included in this panel:

| Mab Combination | Cell Type Enumerated |
|---|---|
| CD45/CD14 + CD13 | lymphocytes |
| CD3/CD4 | T-helper subset |

In certain other phenotyping Mab tests, the number of Mab pairs, N, might be 1, and hence the required sample volume would be about 50 microliters. Any combination of Mab's may be used. For some tests, the volume of Mab reagent required might be based on an estimate of the WBC patient count obtained from the hematology measurements made on the sample. As for example, in extreme cases of leukocytosis or leukopenia, it may be necessary to adjust the ratio of Mab antibody to patient blood to assure adequate antibody binding or to prevent excess free-antibody background. Because the hematology measurements do not require incubation, they proceed through the flowcell transducer well before the lymphocyte subset sample preparations are completed. The data station can therefore calculate an estimated patient count of the hematology results for that sample to enable the analyzer 64 to adjust as necessary the Mab to blood ratios in order to carry out these tests.

F Reticulocyte Sample Processing

Referring to FIGS. 4a and 5 for processing reticulocyte tests, after aspiration probe 156 has completed mixing the RBC and Platelet dilutions in the RBC cup 134, the aspiration probe 156 removes about 200 microliters of blood diluted to about 420:1 and places it into the retic cup 136. The retic cup 136 contains about 600 microliters of retic reagent, making the resulting dilution ratio about 1680:1.

The reagent of the preferred embodiment contains a fluorescent dye with an excitation maximum near the 488 nm argon laser wavelength and a high quantum yield. The preferred reagent stains both DNA and RNA quickly, and in such a way that a single dimension fluorescence histogram avoids the normal WBC confusion. It is so sensitive that the analyzer 64 will detect two fragments of RNA in a cell. The method is linear to up to about 90% reticulocyte count.

After an appropriate incubation period (about 25 seconds with the preferred reagent described previously) or immediately upon mixing, the mixture of diluted blood and retic reagent is transported to optical flowcell 170. This transportation process can be timed to provide sufficient incubation time for the staining of the reticulocytes, i.e., 25 seconds, if separate Incubation processes are not necessary.

As the population which includes mature red blood cells and reticulocytes passes through the laser illuminated volume at flowcell 170, the scatter and fluorescence properties of the sample are measured by using photodiode 384 and photomultiplier tube 400, which is configured for FL1 with a green fluorescence filter 430. The amplitudes of the pulses are filtered, amplified, digitized, and stored as list mode data in the two dimensional feature space of IAS and FL1. The measurement time through the flowcell is about 8 seconds with a sample flow rate of about 2 microliters per second. At a patient RBC of about 5,000,000 per microliter of blood, a preferred embodiment measures approximately 50,000 events, which corresponds to 500 reticulocyte events in a patient with a 1% reticulocyte concentration.

An algorithm is applied which excludes WBCs and platelets and counts reticulocytes by means of fluorescence positive events superimposed on the negative RBC histogram. This method also characterizes a reticulocyte maturity index, RMI, by means of fluorescence intensity. The time to process a sample which includes both the standard hematology tests and reticulocytes in the preferred embodiment is about 45 seconds. The following parameters are reported for the reticulocyte test: Reticulocyte concentration (RETC), Reticulocyte percent (% R of RBC) and Reticulocyte maturity index (RMI).

Another method which uses extended incubation of the nuclear stain can also be used to measure reticulocytes by using both incubation probe 160 and aspiration probe 156 in a method similar to that used in lymphocyte subset processing, as discussed above.

For the sake of illustration, a number of uses of an embodiment discussed herein are presented. The following discussion is provided for exemplary purposes only and this discussion is not exhaustive. Specifically discussed below are ways of using a disclosed embodiment to perform an integrated blood cell analysis, a hemoglobin analysis, a red blood cell and platelet analysis, a white blood cell differential analysis, a reticulocyte analysis, lymphocyte immunophenotyping analysis, measurement of a T helper set, measurement of a T suppressor subset and measurement of T and B lymphocytes. Appropriate references are made to software, which may be present on a RAM, a ROM, an EPROM, a SRAM or other suitable memory device, used in performing the described steps. FIGS. A–F and A–F.

EXAMPLE 1

Integrated Blood Cell Analysis

An embodiment of the invention may be used to perform cellular analyses of whole blood samples. One example of such an analysis procedure follows.

1—A sample tube containing a whole blood sample is placed by the operator in the sample tube holder.
2—The vent assembly lowers and pierces the sample tube cap (Step A1).
3—The aspiration probe is lowered into the sample tube (Step A2).
4—75 µl of blood is aspirated into the aspiration probe (Step A3).
5—The aspiration probe is raised out of the tube, being cleaned while it rises (Step A4).
6—A check is performed to ensure the aspiration probe is completely raised (Step A5).
7—The aspiration probe moves to a point directly over the HGB cup (Step A6).
8—The vent assembly rises to withdraw from the sample tube cap (completion of step A7).
9—The aspiration probe is lowered slightly toward the HGB cup (Step A8).
10—18.75 µl of blood is deposited into the HGB cup for HGB analysis (Step A9).
11—The aspiration probe moves to a position directly over the WBC cup (Step A10).
12—18.75 µl of blood is deposited into the WBC cup for WBC analysis (Step A11).
13—The aspiration probe moves to a position directly over the RBC cup (Step A12).
14—The aspiration probe is lowered into the RBC cup (Step A13).
15—A valve supplying diluent to the aspiration probe is opened (Step A14)
16—2000 µl of diluent is dispensed through the aspiration probe, along with the remaining 18.75 µl of blood, into the RBC cup for RBC and platelet analysis (Step A15).
17—1000 µl of the blood/diluent mixture is aspirated into the aspiration probe from the RBC cup (Step A16)
18—The aspiration probe is raised and cleaned (Step A17).
19—The aspiration probe is moved to a position directly over the RETIC cup (Step A18).
20—The aspiration probe is lowered slightly toward the RETIC cup (Step A19).
21—200 µl of the blood/diluent mixture is dispensed from the aspiration probe into the RETIC cup for reticulocyte analysis (Step A20). While 600 µl of retic reagent is simultaneously deposited into the RETIC cup from a fixed port.
18—The vent assembly is returned to its home position (Step A21).
19—The aspiration probe is moved to the wash cup (Step A22).
20—The aspiration probe is lowered into the wash cup (Step A23).
21—The aspiration probe is flushed (Step A24).
22—The aspiration probe is raised (Step A25).
23—The aspiration probe is returned to its home position (Step A26).
24—The instrument executes the sample processing and data analysis for HGB, WBC, RBC, platelet, and reticulocyte analyses, as described in detail in following examples (top level algorithm file mcCBCAlgorithm.cc).
25—The results of the analyses are stored and displayed, such as that illustrated in FIGS. 45A through 45F.

EXAMPLE 2

Hemoglobin (HGB) Analysis

An embodiment of the invention may be used to perform hemoglobin analyses of whole blood samples. One example of such an analysis procedure follows.

1—1590 µl of HGB lyse is dispensed into the HGB cup (step H1)
2—18.75 µl of whole blood is deposited into the HGB cup from the aspiration probe, as part of the sequence of Example 1 (step A9).
3—4273 µl of HGB lyse is dispensed into the HGB cup in a manner that causes fluid mixing (step H2).
4—About 7 seconds are allowed to lapse to allow cell lysing.
5—The lysed HGB sample is moved though the instrument tubing to facilitate transfer to the HGB transducer (step H3).
6—The lysed HGB sample is pumped into the HGB transducer (step H4).
7—The HGB cup is drained and rinsed (step H5).
8—The HGB cup is filled with HGB lyse to form the reference sample (step H6).
9—The light transmission in the HGB transducer is read (step H7). The transducer contains the lysed HGB sample, and this step occurs about 15–20 seconds after the mixing of the blood sample and lyse.
10—The reference sample is moved though the instrument tubing to facilitate transfer to the HGB transducer (step H8).
11—The reference sample is forced into the HGB transducer (step H9).
12—The syringe pump used to dispense HGB lyse is reset (step H10).
13—The HGB cup is drained (step H11).
14—Backlash is removed from the HGB lyse syringe pump (step H12).
15—The optical transmission of the reference sample in the HGB transducer is read (step H13).
16—The data from the sample and reference sample are stored in a file for subsequent analysis, described in steps 17–22 and executed by the algorithm file mcRBCAlgorithm.cc.
17—Analysis variables and flags are initialized (subroutines ParamDefaults and ClassFlagDefaults).
18—The HGB data is transferred from a data file to local storage (subroutine GetHGBData).
19—Hemoglobin concentration is calculated as HGB=log (ref measurement/sample measurement)*0.64* (calibration factors) (subroutine DoHGBAnalysis).
20—Calculate cellular HGB parameters (subroutine DoHGBAnalysis), using parameters RBC (red blood cell concentration) and HCT (hematocrit) determined by RBC analysis described later:
Mean Cell Hemoglobin
MCH=HGB/RBC*(unit conversion factor)
Mean Cell Hemoglobin Concentration
MCHC=HGB*(unit conversion factor)/HCT
21—Set HGB flags if any results are abnormal or suspect (subroutine SetHgbFlags).
22—Return analysis results and flags for storage (subroutines SendNumResults and SendAlertResults) an(d display on display device.

EXAMPLE 3

Red Blood Cell (RBC) and Platelet (PLT) Analysis 17.5 microliter of a blood sample is rapidly mixed with 7400 microliter of the reagent of the present invention (1:420 dilution), and 0.5 microliters of the diluted sample is passed through a hyrodynamically focused (sheathed) impedance transducer 174 for 12 seconds for red blood cell counts and volume measurement as well as platelet counts. Additionally, 2.5 microliters of the diluted sample is passed through a sheathed optical flow cell 170 for 6 seconds for accurate and precise platelet counts. Noise signals from fragments of fragile abnormal cells are excluded from the optical platelet counts by bracketing the platelet population aaccurately by a platelet algorithm.

An embodiment of the present invention was used to perform red blood cell (RBC) and platelet (PLT) analyses of whole blood samples as described above. One example of such an analysis procedure follows.

1—The RBC cup is drained (step RBC1).

2—2.2 µl of RBC diluent is dispensed into the RBC cup with the RBC diluent syringe (step RBC2).

3—18.75 µl of whole blood and 2000 µl of RBC diluent is dispensed via the aspiration probe into the RBC cup, as described in Example 1 (step A15).

4—3.2 µl of diluent is dispensed into the RBC cup with the RBC diluent syringe (step RBC3).

5—The blood and diluent mixture is moved to the vicinity of the impedance transducer with the RBC peristaltic pump (step RBC4).

6—The RBC delivery syringe is filled (step RBC5).

7—Diluent flow is initiated through the optical transducer (step RBC6).

8—The blood and diluent mixture is moved to the vicinity of the optical transducer with the optical peristaltic pump (step RBC7).

9—The blood and diluent mixture is advanced toward the impedance transducer with the RBC delivery syringe (step RBC8).

10—The blood and diluent mixture is sent through the optical transducer at about 52 µl/sec with the optical delivery syringe (step RBC9).

11—Flow through the optical transducer is reduced to about 2.5 µl/second (step RBC10).

12—The blood and diluent mixture is sent through the impedance transducer at about 0.5 µl/second with the RBC delivery syringe (step RBC11).

13—Data is collected from the optical transducer (step RBC12). A hardware gate is applied to collect only data corresponding to platelets.

14—Data is collected from the impedance transducer (step RBC13). A hardware gate is used to collect and separate data relating to platelets (<35 fL) and data relating to red blood cells (>30 fL), based on the magnitude of the impedance spikes.

15—The RBC cup is drained (step RBC14).

16—The RBC diluent syringe is reset (step RBC15).

17—The RBC cup is filled with diluent (step RBC16).

18—The RBC cup is drained (step RBC17).

19—Backlash is removed from the RBC diluent syringe (step RBC18).

20—RBC lines to the optical transducer are rinsed (step RBC19).

21—The impedance transducer is back flushed (step RBC20).

22—Other RBC lines are flushed (step RBC21).

23—The RBC delivery syringe is reset (step RBC22).

24—Backlash is removed from the RBC delivery syringe.

25—Data from the impedance transducer and optical transducer are saved in a file for use in subsequent RBC analysis (steps 26–34, executed by the algorithm file mcRBCAlgorithm.cc) and platelet analysis (steps 35–50, executed by the algorithm file mcPLTAlgorithm.cc).

26—Flags and parameters are initialized (subroutines ParamDefaults and ClassFlagDefaults).

27—RBC impedance data are retrieved from a file and stored locally (subroutine GetRBCData).

28—A 256 bin histogram of RBC impedance values is generated (subroutine mmHist256).

29—Bin thresholds are set for the histogram as follows (subroutine BinCut):
  a. The histogram mode is determined.
  b. On either side of the mode, the first bin with a population less than 0.04 times the population of the mode is identified. These limits are termed the discriminants, and only values between them are used for calculating distribution parameters FDW (RBC Distribution Width) and MCV (Mean Cell Volume).
  c. To the left (i.e., for lower values of RBC volume) of the lower bin threshold, the first valley or zero count bin, if present, is identified and set as the Mount threshold. Values greater than this threshold are considered to be due to RBCs.

30—RBC (red blood cell concentration) is calculated (subroutine CalcRedConc):
  RBC=(number of events)*(proportion that are RBCs) *(dilution ratio)*(coincidence correction factor)* (calibration factors)/(flow rate*measurement time);
  where number of events is the number of cells detected by the hardware gate in step 14;
  proportion that are RBCs is the histogram count to the right of the count threshold divided by the total histogram count.
  Coincidence correction factor accounts for double cell counting and equals 2- exp(uncorrected RBC concentration* transducer volume/dilution ratio)

31—Calculate MCV and RDW (subroutine CalcRedDist):
  MCV=(mean of histogram between discriminants)* (0.8 fL per bin)*(calibration factor)
  RDW=standard deviation of RBC volume/mean cell volume (within discriminants)

32—Set RBC associated flags to indicate abnormal analysis results (subroutine SetRbcFlags).

33—Numerical and flag RBC results are returned to the system for storage and display (subroutines SendNumResults and SendAlertResults). Examples of RBC numerical results are shown in FIGS. 45A–F.

34—A histogram is generated for storage and display of RBC volume values (subroutine MakeDisplayHist). Examples of RBC volume histograms are shown in FIGS. 45A–F and 46.

35—Flags and parameters are initialized (subroutines ParamDefaults and ClassFlagDefaults).

36—Optical and impedance platelet data are retrieved from a file and stored locally (subroutines GetPLTiData and GetPLToData). Impedance data consists of impedance values representing platelet volumes. Optical data consists of polarized side scatter (PSS) and intermediate angle scatter (IAS) optical values.

37—A 265 bin histogram of impedance platelet delta is generated (subroutine mmHist256). This represents volume values ranging from 0 to 35 fL.

38—Bin thresholds are set on either side of the histogram mode (subroutine BinCut), as follows:
  a. The first bins on either side of the mode whose count is less than 0.04 times the count of the mode are identified.
  b. A second peak beyond the original threshold is identified, if it exists, along with the valley between such a peak and the mode.
  c. If a second peak exists and the count in the valley is less than 0.02 times the count of the mode, the threshold is moved to the valley.

39—PLTi, the platelet concentration based on impedance values (subroutine CalcPLTiConc):
  PLTi=(number of events)*(proportion that are platelets)*(dilution ratio)*(calibration factors)/(flow rate*measurement time);
where number of events is the number of cells detected by the hardware gate in step 14;
proportion that are platelets is the histogram count to the right of the left threshold divided by the total histogram count.

40—Platelet distribution parameters MPV (mean platelet volume) and PDW (platelet distribution width) are calculated (subroutine CalcPLTDist):
  MPV=(bin number of mean of histogram values between thresholds)*(0.137 fL per bin)*(calibration factors)
  PDW=(standard deviation of platelet volume values between thresholds)/(mean platelet volume)

41—Impedance associated platelet flags are set to abnormal analysis results (subroutine SetPLTiFlags).

42—A noise gate is applied to the optical platelet data at log(PSS)=8.0 (subroutine PLToNoiseGate).

43—Regression band gates are applied to the remaining optical platelet data as follows (subroutine PLToRegressBandGate):
  a. A linear regression is calculated for the optical platelet data above the noise gate in the analysis plane log(IAS) vs. log(PSS), along with a standard error estimate for this regression.
  b. The upper regression band gate is drawn parallel to and at a distance of 2.0 standard errors above the regression line.
  c. The lower regression band gate is drawn parallel to and at a distance of 2.5 standard errors below the regression line.

44—The optical platelet data above the noise gate and between the regression band gates is checked for an upper population (subroutine PLToFindUpperPopulation):
  a. The remaining points are projected on the regression line of step 43.
  b. A 256 bin histogram is generated, reduced to 64 bins by averaging, filtered with a 7 pin boxcar filter, and expended to 256 bins by interpolating.
  c. A mode is identified in the lower ⅔ of the histogram.
  d. The upper ¼ of the histogram is searched for a second peak.
  e. If a second peak in the upper ¼ exists, the upper population gate is set at the valley between the mode and the second peak. Otherwise, the upper population gate is set at the right edge of the histogram. Cells not previously excluded that are above this gate are the "upper population." Cells not previously excluded that are below this gate are the "lower population."
  f. The upper population is compared to a set of criteria to determine if it includes microcytic RBCs. If so, a warning flag is set.

45—The optically determined platelet concentration (PLTO) is calculated (subroutine CalcPLToParams):
  PLTo=(number of events)*(proportion that are platelets)*(dilution ratio)/(flow rate*measurement time) where number of events is the number of optical events counted by hardware that fall within the square hardware gate in log(IAS) vs. log(PSS) space;
  proportion that are platelets is the count of the upper population divided by the sum of the counts of the upper and lower populations.

46—The plateletcrit (PCT, or fraction of whole blood comprised of platelets) is calculated (subroutine CalcPCT):
  PCT=PLTo*MPV*(unit conversion factor)

47—Flags associated with optically determined platelet parameters are set to indicate abnormal results (subroutine SetPLToFlgs).

48—Numerical results and flags associated with optically determined platelet parameters are returned to the system for storage and display (subroutine SendNumResults and SendAlertResuls). Examples of platelet numerical results are shown in FIGS. 45A—F, 47 and 48.

Figure 47:
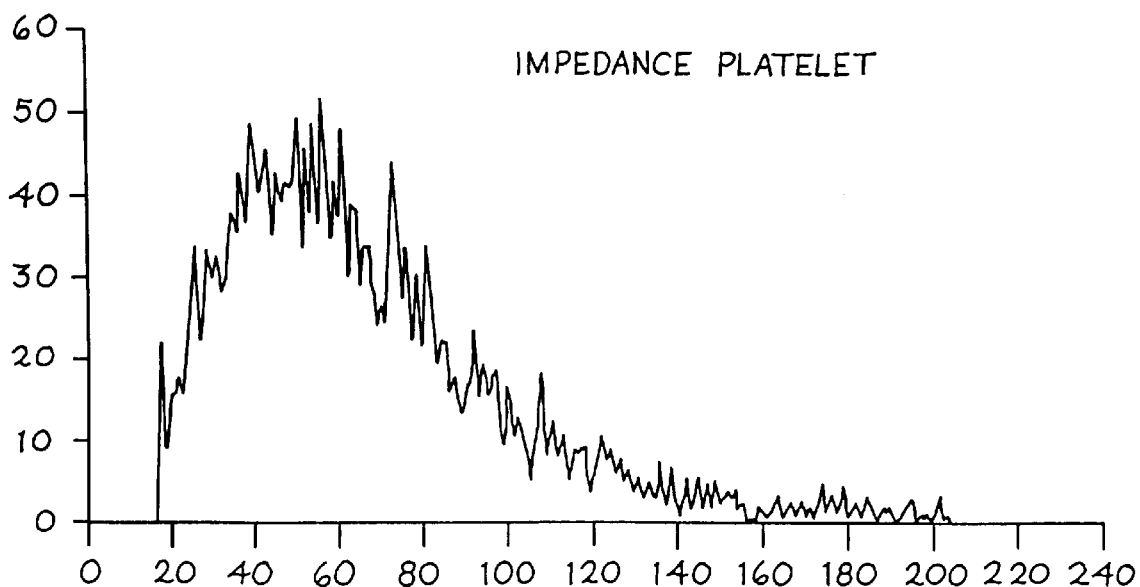

49—A histogram of platelet impedance values is generated for storage and display (subroutine MakeDisplayHist). Example of platelet impedance histogram is shown in FIG. 47.

50—A scattergram of platelet optical values and gates is generated for storage and display (subroutine SendScatResults). Examples of platelet scattergrams are shown in FIGS. 45A–F, 47 and 48.

EXAMPLE 4

White Blood Cell (WBC) Differential Analysis

An embodiment of the invention may be used to perform white blood cell (WBC) differential analysis of whole blood samples. One example of such an analysis procedure follows.

1—The WBC cup motor begins the mixing motion of the cup (step W1).

2—1275 μl of WBC lyse is dispensed into the WBC cup with the WBC diluent syringe (step W2).

3—37.5 μl of whole blood is deposited into the WBC cup by the aspiration probe (step A9 of Example 1).

4—The WBC diluent syringe is reset (step W3).

5—The WBC diluent syringe is moved to remove backlash (step W4).

6—About 9.4 seconds is allowed to elapse after the mixing of the blood sample and WBC lyse.

7—Sheath flow is initiated in the optical transducer (step RBC6 of Example 3).

8—The blood and lyse mixture is moved to the optical transducer line using the HGB peristaltic pump (step W5).

9—The WBC cup is drained and rinsed (step W6).

10—A valve realignment allows the WBC sample flow through the optical transducer (step W7).

11—WBC sample flow begins through the optical transducer at about 27.6 μl/sec with the optical delivery syringe (step W8).

12—The WEC sample flow rate is reduced to about 2.5 μl/second (step W9).

13—Optical WBC data is collected by the optical transducer (step W10).

14—The optical delivery syringe is reset (step W11).

15—Backlash is removed from the optical delivery syringe (step W12).

16—Data from the optical transducer are saved in a file for use in subsequent WBC differential analysis (steps 17—XX, executed by the algorithm file mcWBCAlgorithm.cc).

17—WBC data is retrieved from a file and stored locally (subroutine GetWBCData). This data consists of axial light loss (ALL), intermediate angle scatter (IAS), polarized side scatter (PSS), depolarized side scatter (DSS), and red fluorescence (FL3) values for each detected event.

Steps 18–22 identify nucleated red blood cells (NRBCs).

18—A 256 bin histogram of FL3 values is generated (subroutine mmHist256).

Figure 49A:
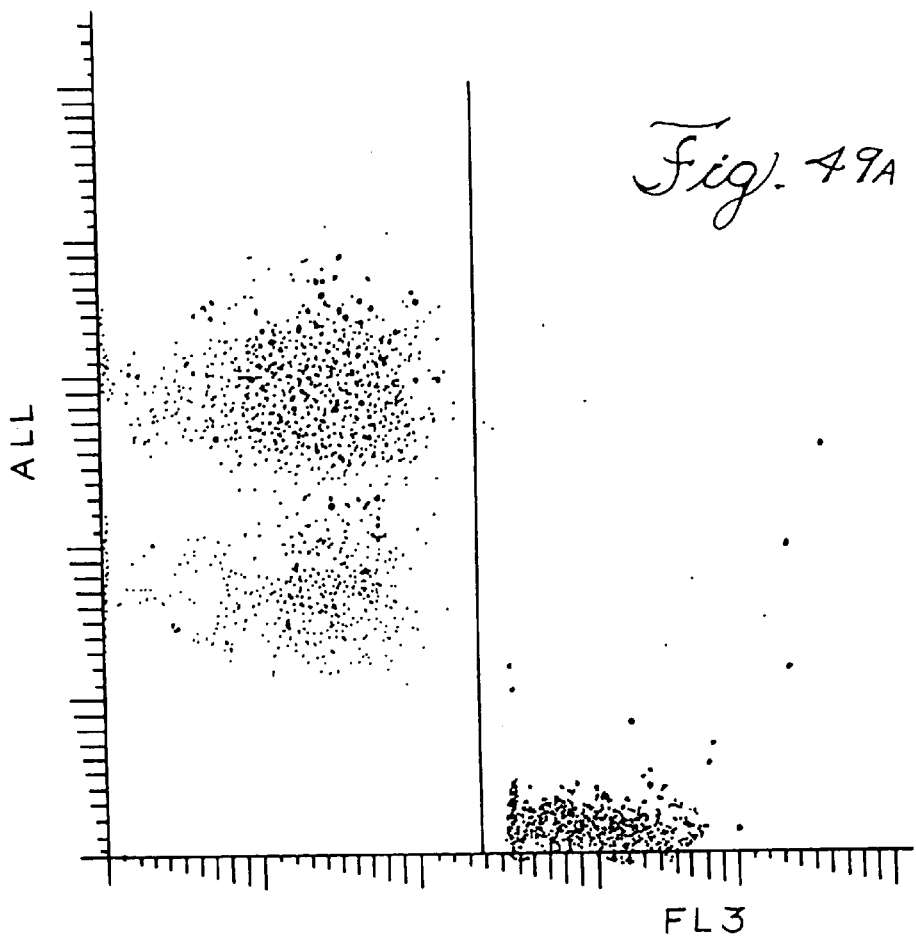
FIGS. 49A and 49B illustrate event divisions detected by an embodiment of the cell analysis system.
Figure 49B:
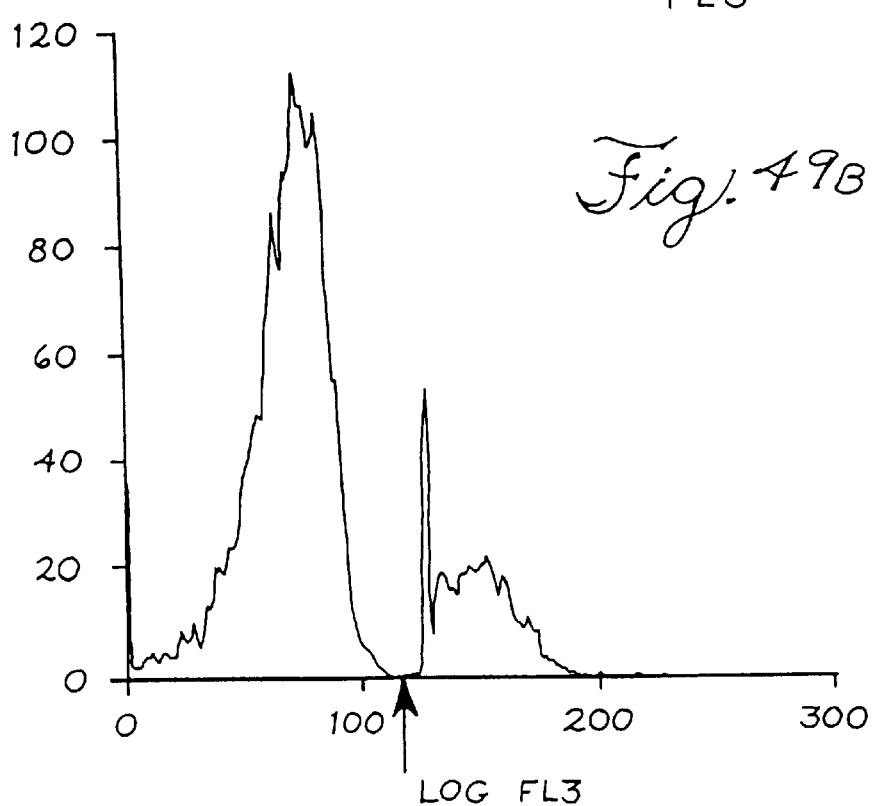

19—The events are divided into "high FL3" or "low FL3" by identifying a valley in the vicinity of log(FL3)=100 (subroutine FindF13Cells). An example of this division is illustrated in FIGS. 49A and 49B.

Figure 50A:
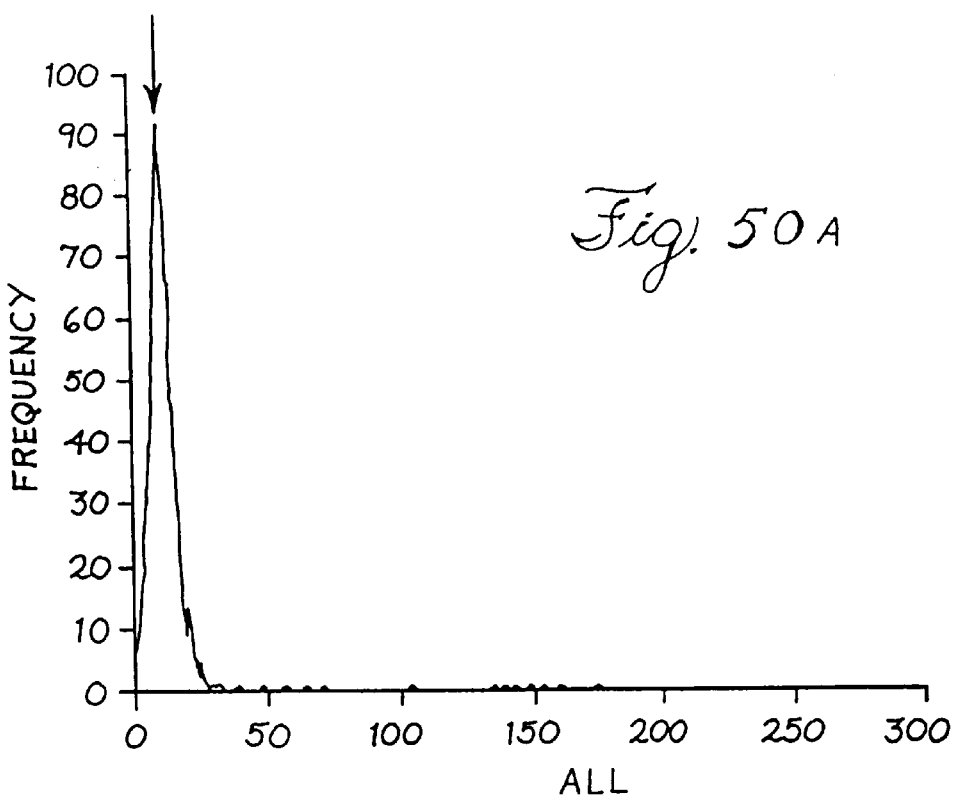
FIGS. 50A and 50B show ALL values of high FL3 cells detected by an embodiment of the cell analysis system.
Figure 50B:
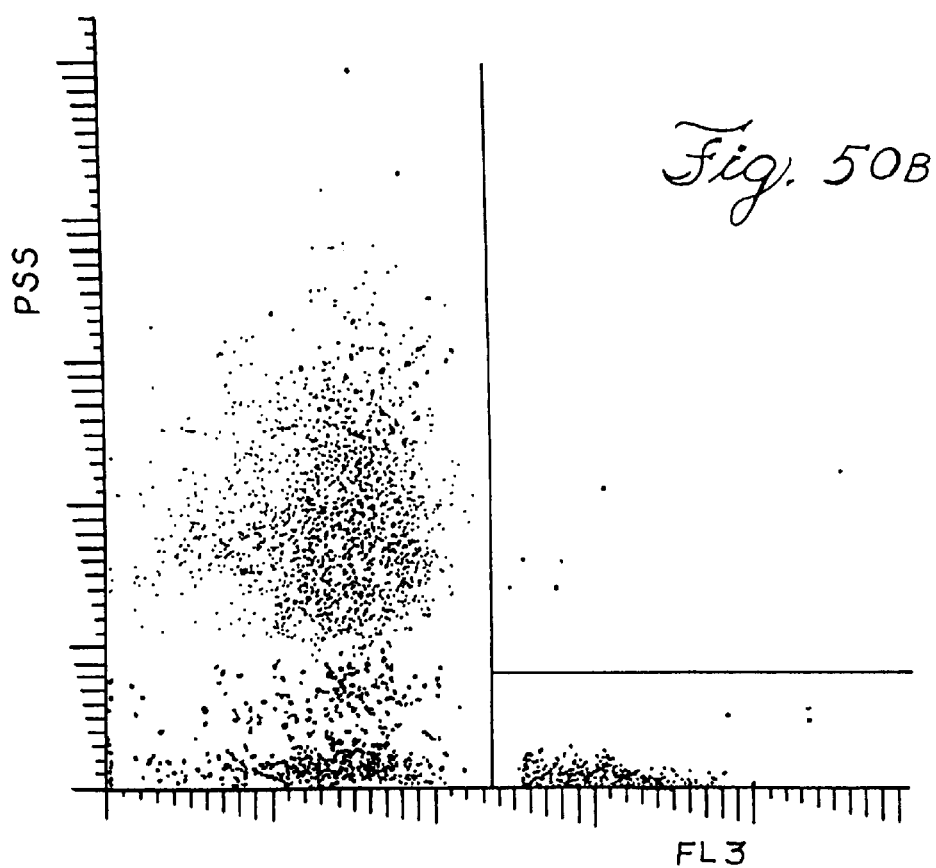

20—A histogram of the ALL values of the high FL3 cells is generated (subroutine mmHist256). An example of this histogram is illustrated in FIGS. 50A and 50B.

21—A peak is identified at a value of less than ALL=75, if it exists (subroutine AnalyzeF13Cells). If it does not exist, no NRBCs are reported.

22—If a peak at ALL<75 exists, the events with a PSS value greater than the PSS threshold (about 45) are classified as NRBCs and undergo no further analysis.

Steps 23–26 identify neutrophils and eosinophils.

23—A plot of all events on the plane PSS vs. ALL is used to identify the two largest peaks, which are the neutrophil peak and the monocyte peak (subroutine FindMGLine).

Figure 51A:
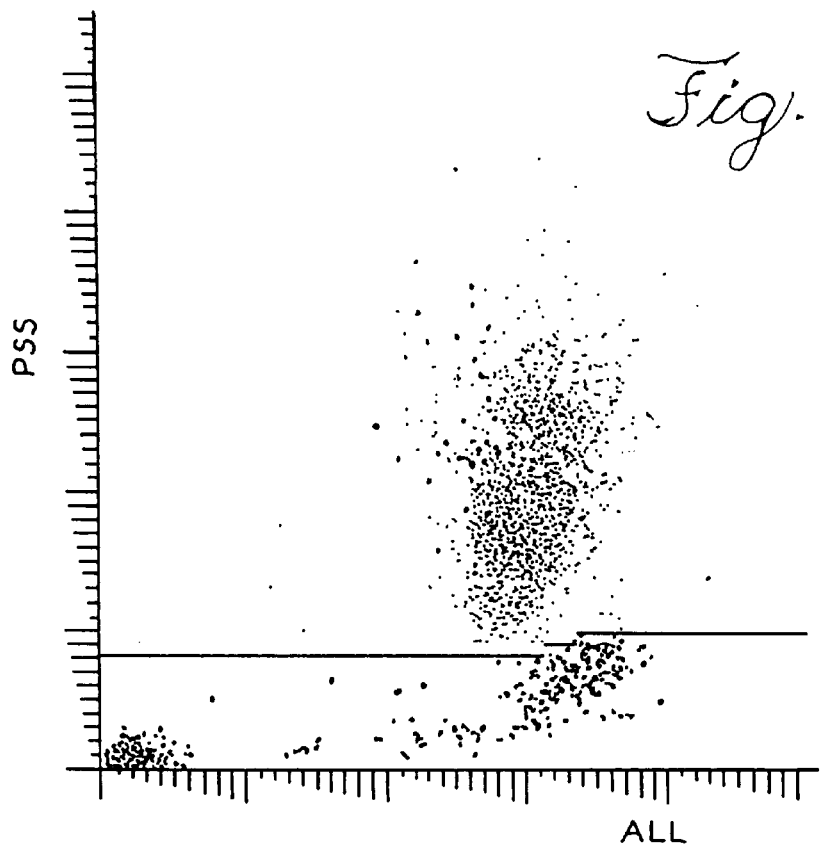
FIGS. 51A and 51B are examples of a dividing line drawn with an embodiment of the cell analysis system between granulocytes and mononuclear cells.
Figure 51B:
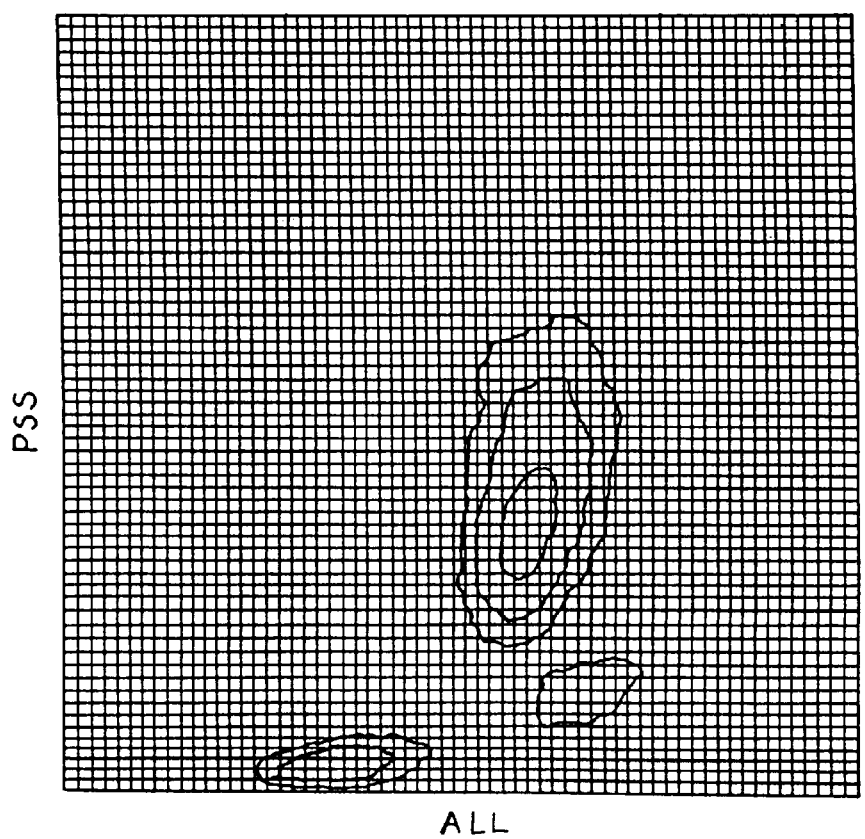

24—A line is drawn between the two peaks. Starting at the minimum value along this line, a dividing line is drawn between the granulocytes (above the line) and mononuclear cells (below the line) (subroutine FindMGLine, continued). An example of the dividing line is illustrated in FIGS. 51A and 51B.

25—For the granulocytes (above the line), a histogram of the values of arctan(DSS/PSS) is generated (subroutine FindNELine).

Figure 52A:
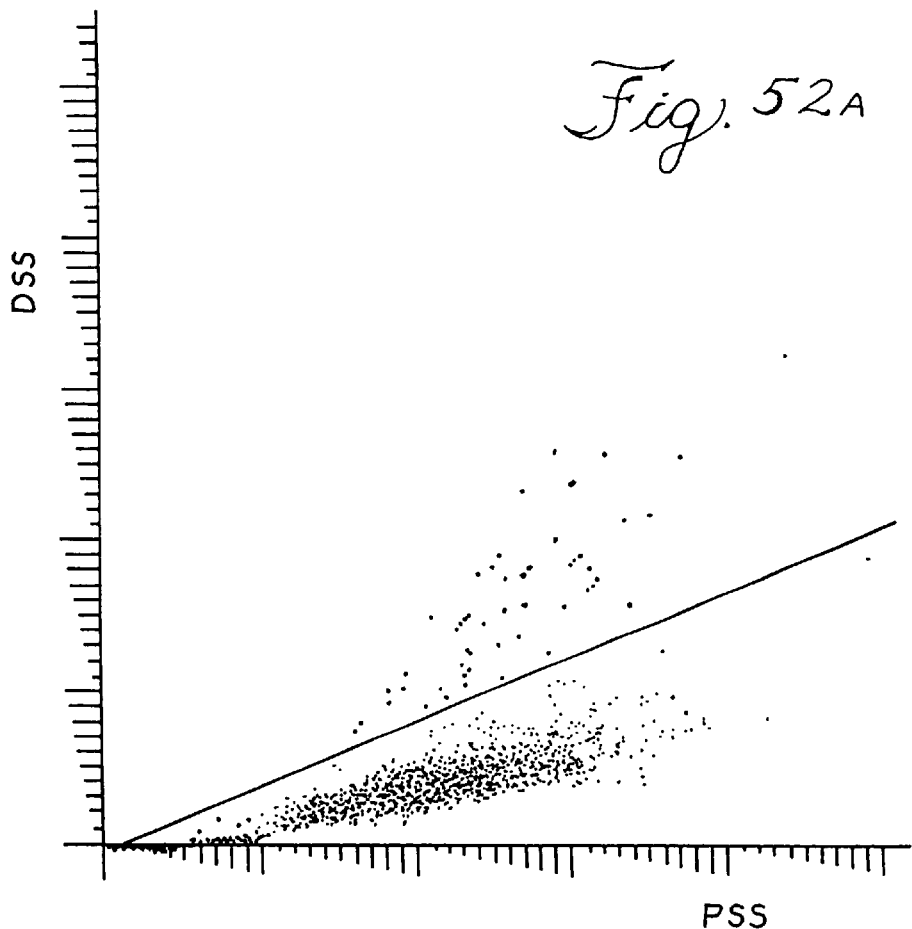
FIGS. 52A and 52B show examples of a histogram and angular dividing line formed by an embodiment of the cell analysis system.
Figure 52B:
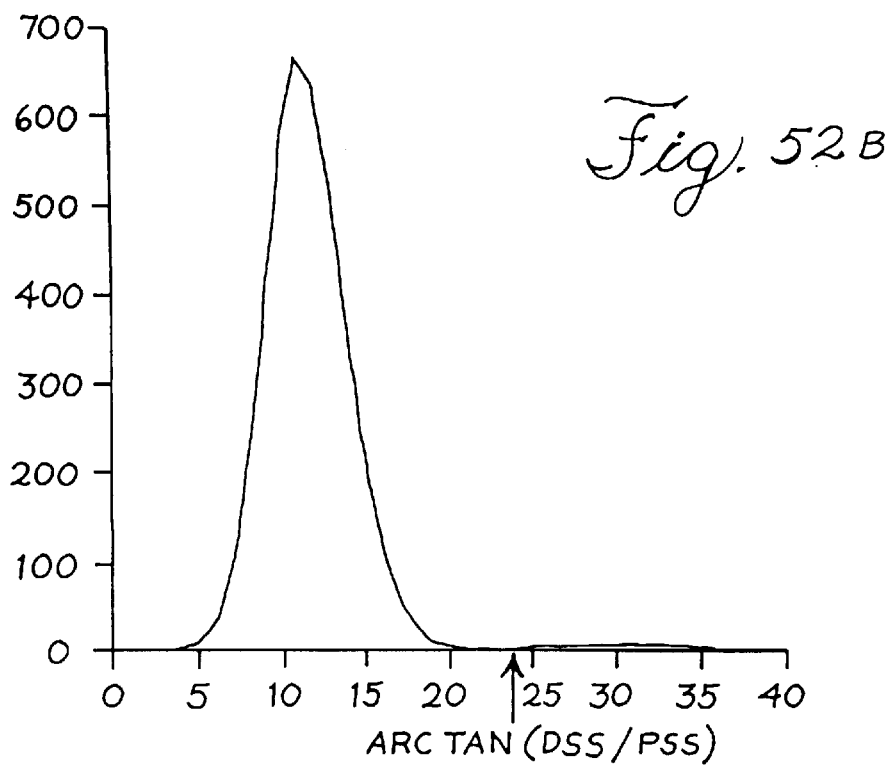

26—The histogram of step 25 is searched for a valley between the angular values of 102 and 311 (subroutine FindNELine continued). Cells with an angular value of arctan(DSS/PSS) greater than this valley are classified as eosinophils, and the cells with angular values less than this valley are classified as neutrophils. An example of this histogram and angular dividing line is illustrated in FIGS. 52A and 52B.

Steps 27–28 identify monocytes and stroma.

27—From the remaining cells, a 256 bin histogram of ALL values is generated (subroutine mmHist256).

Figure 53:
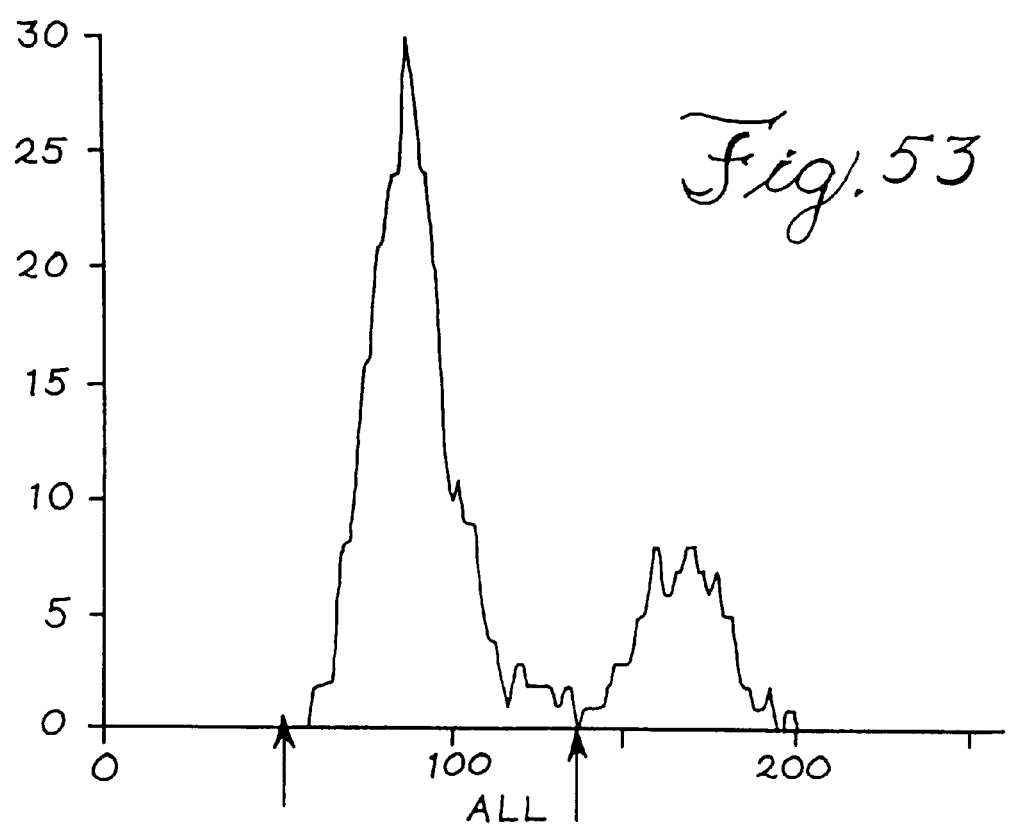
FIG. 53 illustrates an example of an ALL histogram and dividing lines obtained with an embodiment of the cell analysis system.

28—The ALL histogram is searched for two valleys, in the high region (bins 100–160) and in the low region (bins 45–75). Cells above the upper valley are classified as monocytes. Cells below the lower valley are classified as stroma (subroutine FindLymphLines). An example of the ALL histogram and dividing lines is illustrated in FIG. 53.

Steps 29–30 are used to identify lymphocytes.

29—From the remaining cells, a 256 bin histogram is generated of IAS values (subroutine mmHist256).

Figure 54:
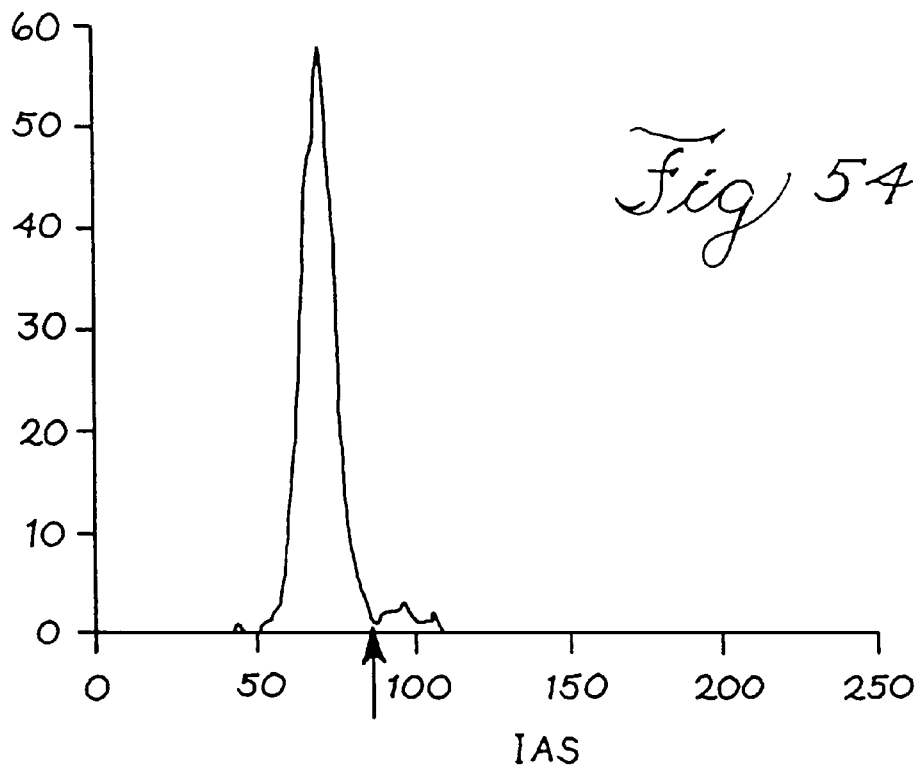
FIG. 54 illustrates a division drawn at a value equal to the mean of IAS values plus 2.5 times a standard deviation of the IAS values by an embodiment of the cell analysis system.

30—A valley is identified, if it exists, between bins 70 and 110. If such a valley does not exist, a dividing line is drawn at a value equal to the mean of the IAS values plus 2.5 times the standard deviation of the IAS values. Cells to the left of this valley or line are classified as lymphocytes. An example of this division is illustrated in FIG. 54.

Steps 31–32 are used to identify basophils.

31—From the remaining cells, a 256 bin histogram of ALL values is generated (subroutine mmHist256).

Figure 55:
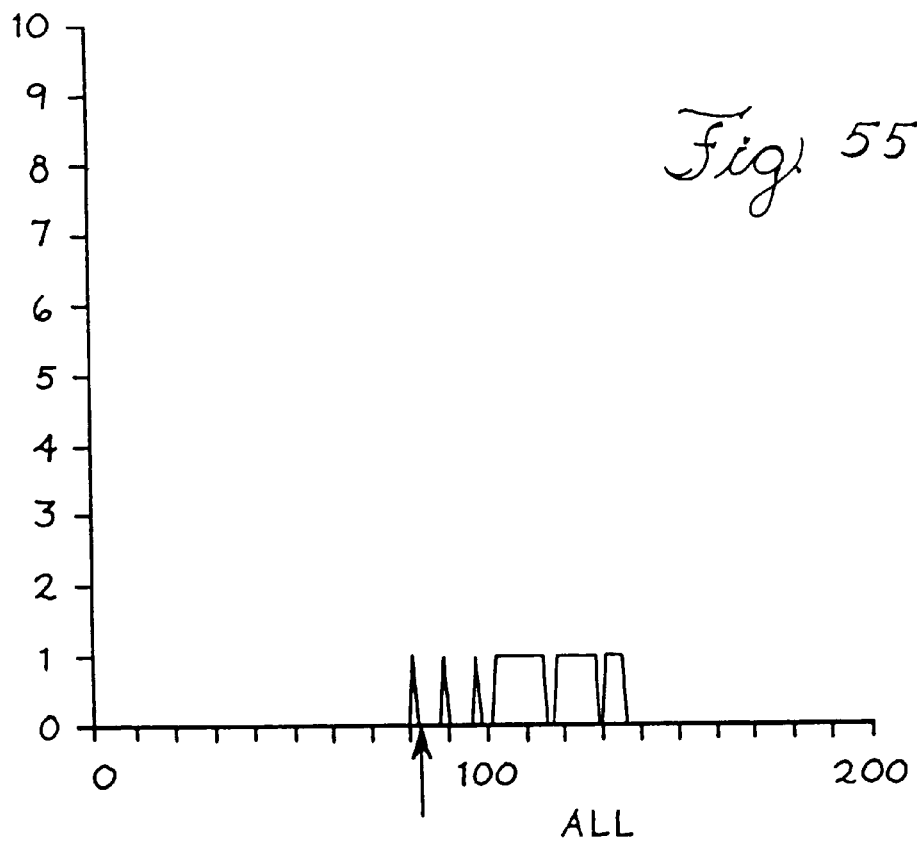
FIG. 55 shows a division drawn between ¼ and ¾ of the distance from lymphocyte-stroma and lymphocyte-monocyte separation lines formed by an embodiment of the cell analysis system.

32—A valley in the ALL histogram is identified, if it exists, between ¼ and ¾ of the distance from the lymphocyte-stroma and lymphocyte-monocyte separation lines determined in step 28. If no such valley exists, a default dividing line is drawn at half of this distance. Cells with ALL values above this line are classified as basophils. Events with ALL values below this line are classified as noise (subroutine FindBasoLines). An example of this division is illustrated in FIG. 55.

33—Histograms and statistics are generated for each classified population (subroutine DoPopStats).

34—Alert flags are set for any abnormal analysis results (subroutine SetFlags). In particular, this step includes performing a statistical check for the presence of lyse-resistant RBCs and for blasts. A blast alert flag is set if a weighted combination of the following statistics is above a threshold value (about 3.874):

| Population Statistic | Weighting Factor |
| --- | --- |
| Monocyte percentage | 0.030352 |
| Mean of lymphocyte ALL | 0.013182 |
| Mean of monocyte ALL | 0.016766 |
| Coefficient of variation of monocyte ALL | 0.152739 |
| Coefficient of variation of monocyte IAS | −0.041058 |
| Mean of monocyte PSS | −0.051015 |
| Coefficient of variation of monocyte PSS | 0.028661 |
| Coefficient of variation of lymphocyte and monocyte PSS | −0.02960 |
| Mean of all WBC FL3 | 0.024813 |

35—All numerical results and alert flags are returned to the system for storage and display (subroutines SendNumResults and SendFlagResults).

36—A scattergram set is generated and sent to the system for storage and display (subroutine SendScatResults) A typical display will present ALL vs. IAS, DSS vs. PSS, and ALL vs. FL3, as illustrated in FIGS. 45A–F.

EXAMPLE 5

Reticulocyte Analysis

An embodiment of the invention may be used to perform reticulocyte analyses of whole blood samples. One example of such an analysis procedure follows. The scatterplots generated by this analysis is exemplified in FIGS. 14A and 14B.

1—Analysis begins with an empty RBC cup.

2—2200 μl of RBC diluent is dispensed into the RBC cup with the RBC diluent syringe (step RBC2).

3—18.75 μl of whole blood and 2000 μl of RBC diluent is dispensed via the aspiration probe into the RBC cup, as described in Example 1 (step A15).

4—3656 μl of diluent is dispensed into the RBC cup with the RBC diluent syringe (step RBC3). A dilution ratio of about 420:1 is produced.

5—500 μl of the blood/diluent mixture is aspirated into the aspiration probe from the RBC cup (Step A16)

6—The aspiration probe is raised and cleaned (Step A17).

7—The aspiration probe is moved to a position directly over the RETIC cup (Step A18).

8—The aspiration probe is lowered slightly toward the RETIC cup (Step A19).

9—200 μl of the blood/diluent mixture is dispensed from the aspiration probe into the RETIC cup for reticulocyte analysis (Step A20).

10—600 μl of reticulocyte stain is dispensed through a fixed port into the RETIC cup with the reticulocyte diluent syringe (step R1). A dilution ratio of about 1680:1 is produced.

11—The reticulocyte diluent syringe is reset (step R2).

12—The reticulocyte sample is transferred to near the optical flowcell with the RBC peristaltic pump (step R3).

13—Brief backflow in the WBC sample line to the optical flowcell is initiated to prevent carryover (step R4).

14—The RETIC cup is drained (step R5).

15—Reticulocyte sample flow is initiated through the optical flowcell at 78 μl/sec using the optical delivery syringe (step R6) in order to displace fluid line dead volume.

16—Reticulocyte sample flow through the optical flowcell is reduced to about 2.0 μl/sec (step R7).

17—The RETIC cup is filled with diluent to rinse (step R8).

18—Reticulocyte data is collected in the optical transducer (step R9). A hardware gate collects data for each optical event with an intermediate angle scatter (IAS) value greater than a certain threshold value.

19—The RETIC cup is drained, rinsed, and drained (step R10).

20—The optical delivery syringe is reset (step R11).

21—Reticulocyte sample delivery lines are rinsed (step R12).

22—Backlash is removed from the optical delivery syringe (step R13).

23—Reticulocyte optical data is stored in a file for subsequent analysis. The analysis of steps 24–33 is controlled by the algorithm file mrRETCAlgorithm.cc.

24—Data is retrieved from a file and stored locally (subroutine GetRETCData). This data consists of intermediate angle scatter (IAS) and green fluorescence (FL1) values.

25—A 256 bin histogram of log(IAS) values is generated (subroutine mmHist256).

Figure 56:
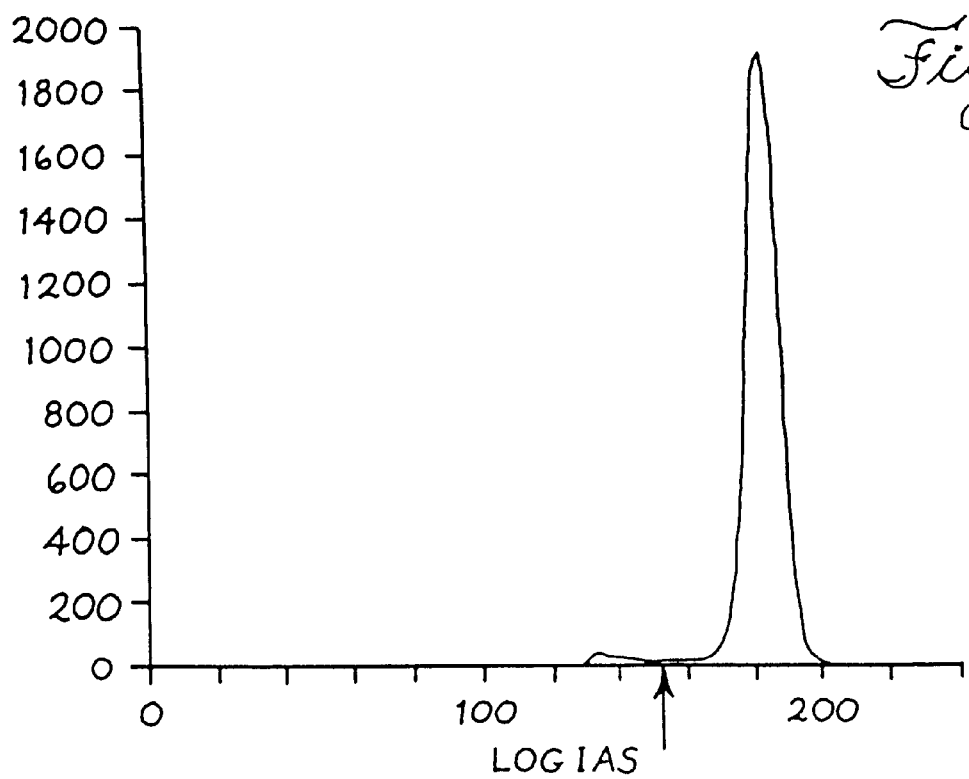
FIG. 56 displays a histogram and a dividing line generated by an embodiment of the cell analysis system.

26—A valley is identified between channels 150 and 190, if it exists. Cells with log(IAS) values lower than this valley (or 170, if no valley exists) are considered platelets and removed from further analysis (subroutine FindPLTs). An example of this histogram and dividing line is illustrated in FIG. 56.

27—From the remaining cells, a 256 bin histogram of log(FL1) values is generated (subroutine mmHist256).

28—A valley is identified, if it exists, in the upper region of this histogram (between bins 175 and 225). Cells with log(FL1) values greater than this valley (or 200, if no valley exists) are considered WBCs and removed from the analysis (subroutine FindWBCs).

Figure 45A:
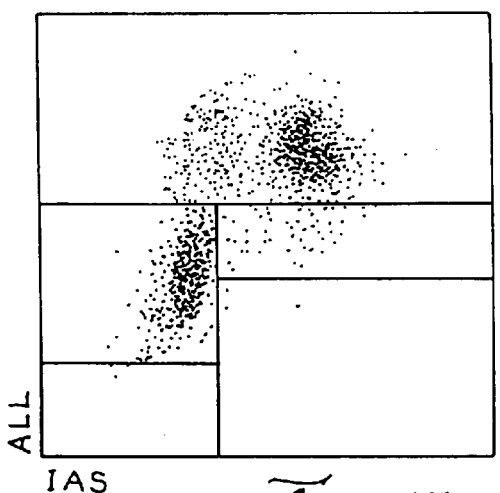
FIGS. 45A–F illustrate displayed data obtained by an embodiment of the cell analysis system.
Figure 45B:
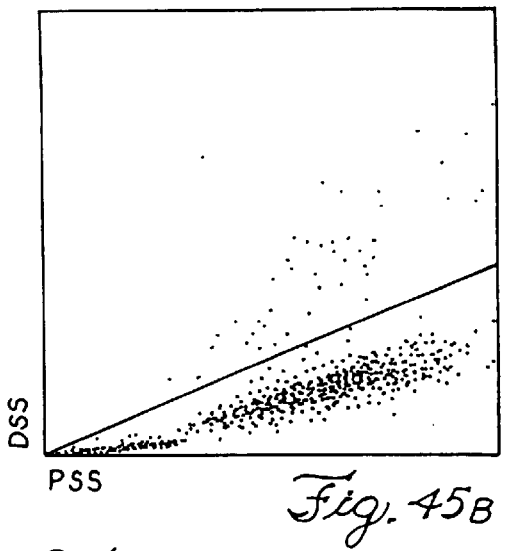
Figure 45C:
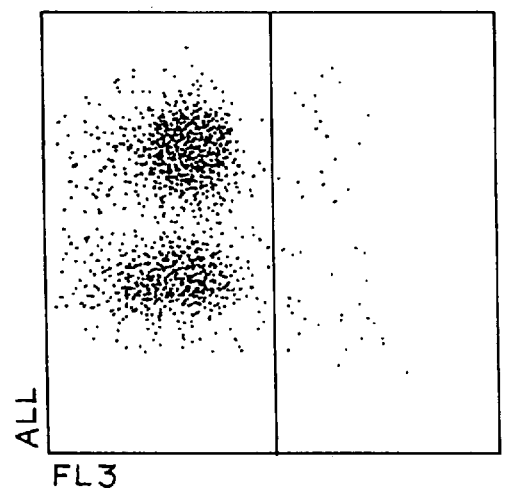
Figure 45D:
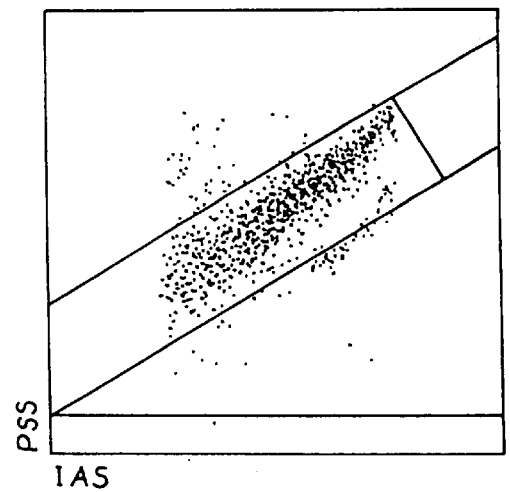
Figure 45E:
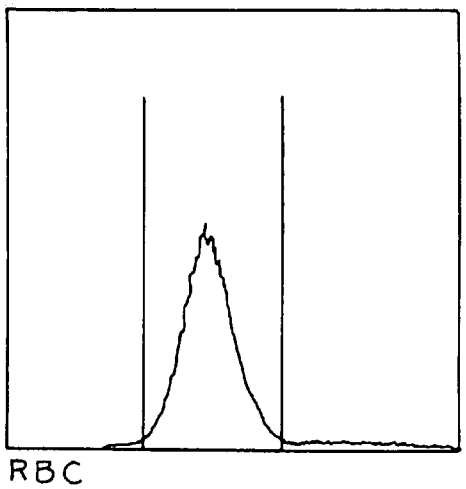
Figure 45F:
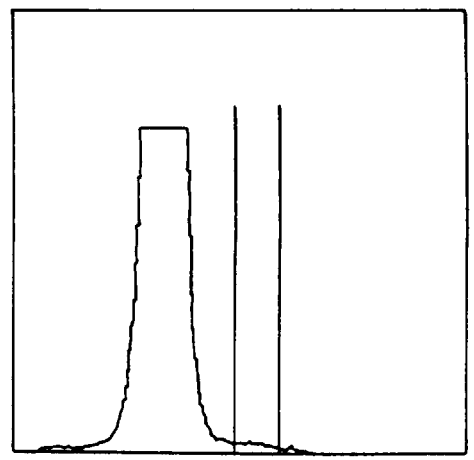
Figure 46:
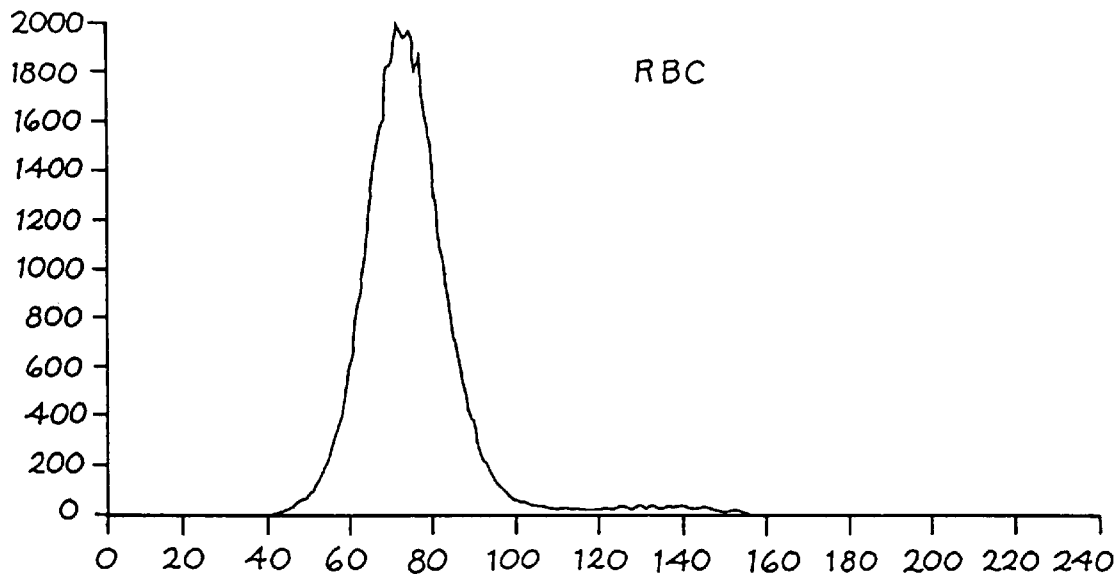
FIG. 46 shows an RBC volume histogram obtained with an embodiment of the cell analysis system.
Figure 57:
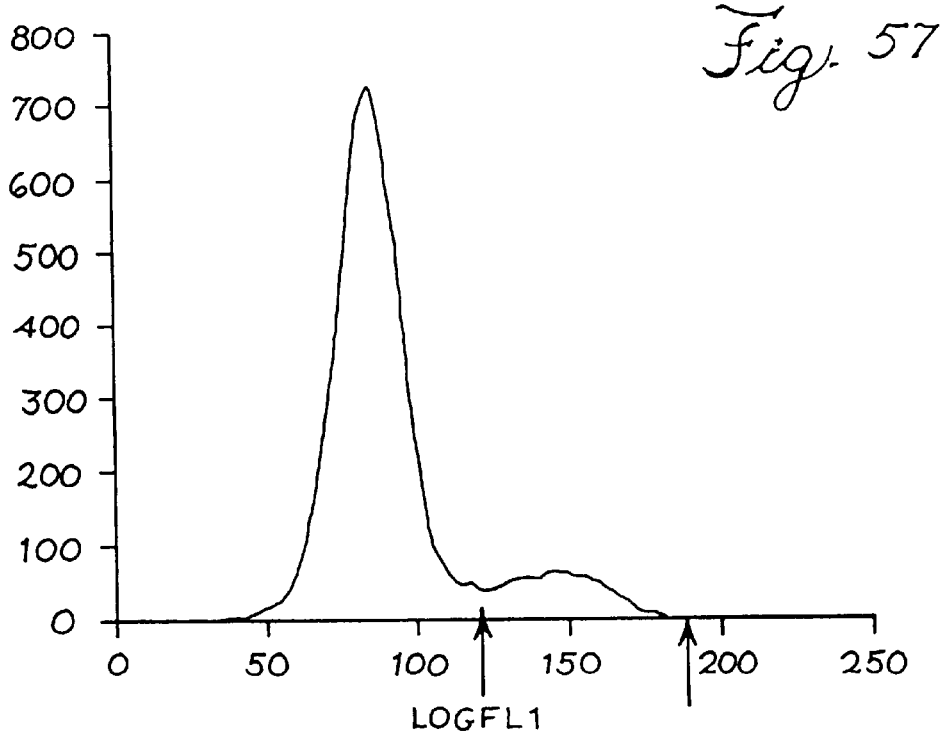
FIG. 57 displays another histogram and a dividing line generated by an embodiment of the cell analysis system.

29—The log(FL1) histogram is searched for a valley to the right of the major (RBC) peak. If such a valley exists, cells to the right of it are classified as reticulocytes. If no valley exists, a dividing line is put at channel 120 (default reticulocyte cursor) Cells to the right of this dividing line are classified as reticulocytes (subroutine FindRETCs). Examples of this histogram and the dividing lines are illustrated in FIGS. 45F and 57.

30—The reticulocyte maturity index (RMI) is calculated. This value is equal to the percentage of reticulocytes that fall in a "high FL1" region, defined as having log(FL1) histogram bins higher than the lower reticulocyte boundary (as established in step 29) plus a fixed value (about 24) (subroutine GetFionalCounts).

31—Numerical results are returned to the system for storage and display (subroutine SendNumResults).

Figure 58:
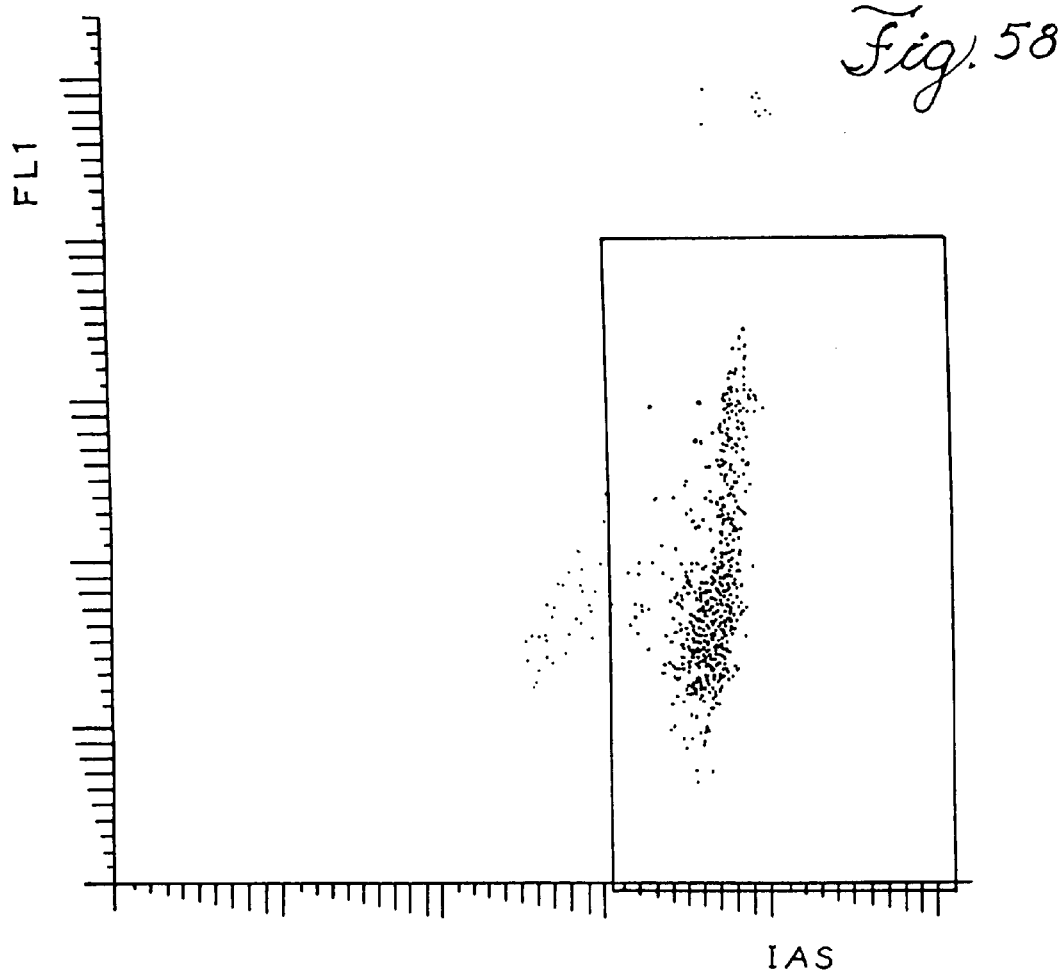
FIG. 58 illustrates an example of a reticulocyte scattergram drawn by an embodiment of the cell analysis system.

32—A scattergram is generated for storage and display (subroutine SendScatResults). An example of a reticulocyte scattergram is illustrated in FIGS. 14A and 58.

Figure 14B:
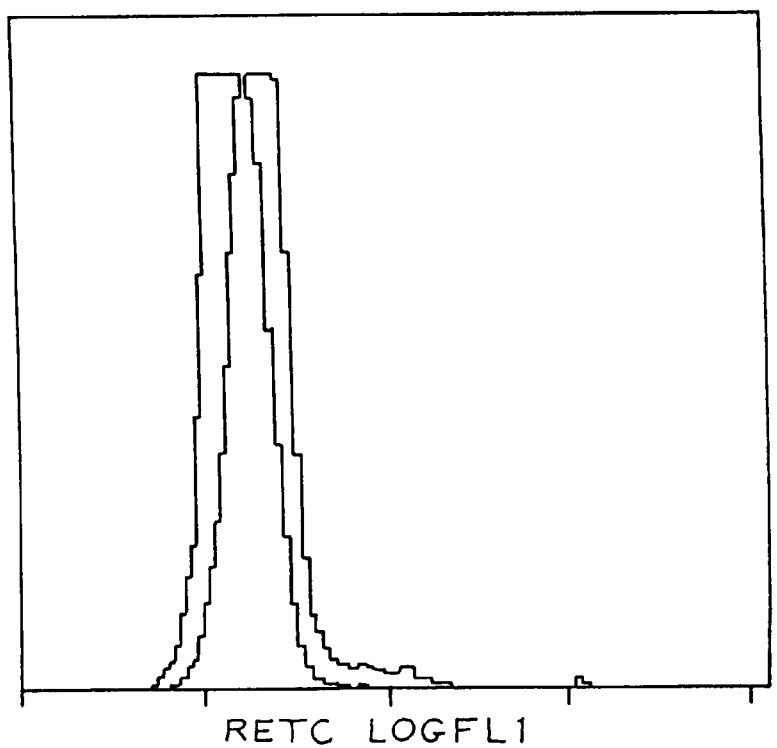
Figure 59:
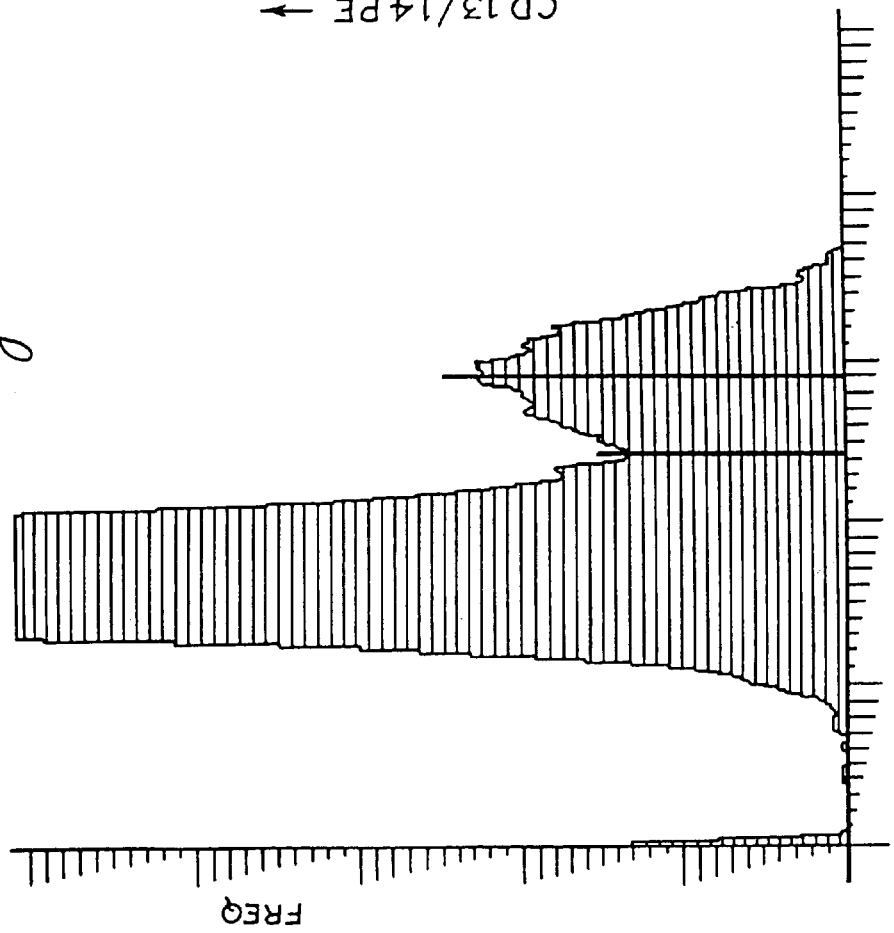
FIG. 59 shows an example of reticulocyte histogram drawn by an embodiment of the cell analysis system.

33—A histogram of log(FL1) values is generated for display and storage (subroutine SendHistResults). Examples of reticulocyte histograms are illustrated in FIGS. 14B, 45F and 59.

EXAMPLE 6

Lymphocyte Immunophenotyping Analysis

An embodiment of the invention may be used to perform lymphocyte immunophenotyping analysis of whole blood samples. One example of such an analysis procedure follows.

1. 100 μl of whole blood is aspirated by the aspiration probe and deposited into the transfer cup (subroutine subasp.f). This volume may be adjusted if necessary to provide enough blood to execute all of the desired immunophenotyping assays for that sample.

2. The incubation probe aspirates about 70 μl from the transfer cup and deposits in the appropriate number of incubation cups (subroutine subprep.f).

3. Reagents such as antibody reagents for immunophenotyping are aspirated by the incubation probe and deposited in the appropriate incubation cups (subroutine subinc.f).

4. An appropriate time delay occurs for incubation.

5. About 670 μl of wbc diluent is added to the WBC cup. This and the following sample processing steps (5 through 8) are controlled by software such as that in subroutine subvu.f.

6. Following incubation, about 30 μl of the sample is aspirated by the incubation probe and deposited in the WBC cup.

7. The sample and diluent mixture is mixed by the WBC cup for about 5 seconds

8. The mixture is sent through the optical transducer for measurement of optical properties. The properties measured may include axial light loss (ALL), intermediate angle scatter (IAS), and two fluorescence values (FL1 and FL2).

9. The data is stored for subsequent analysis. General analysis steps may include those listed here.

10. A plot of ALL vs. IAS values is created divided into polar bivariate regions. Such regions are bounded by radii and arcs stemming from an origin. The origin may be varied, but is usually positioned at the maximum ALL limit and the zero IAS point. See FIG. 60A.

11. A second plot of log(FL2) vs. log(FL1) is created and divided into polar bivariate regions. The origin for this division is usually at (0,0). An illustration of an example of both the ALL vs. IAS plot and the log(FL2) vs. log(FL1) plot is presented in FIGS. 60A and 60D.

12. Both plots are searched counterclockwise and then radially outward for lymphocyte peaks. Thresholds are set at 1/10 the peak heights. Cells whose associated data points lie within the thresholds are considered lymphocytes.

13. The number of lymphocyte events in each plot is counted and compared to each other and to the hematological lymphocyte count to detect possible errors. See FIGS. 60B, 60C, 60E and 60F.

14. Statistical analysis may further refine the limits of IAS and ALL values that most specifically identifies lymphocytes. This delineation may form ellipsoids, polygons, or other geometric areas within the ALL vs. IAS analysis space.

15. Analysis of the same sample treated with different antibody reagents may proceed. Cells are considered for analysis only if their IAS and ALL values fall within the limits determined by the lymphocyte identification (steps 10 through 14).

EXAMPLE 6A

Measurement of T Helper Subset

An embodiment of the invention may be used to measure the traction of lymphocytes that are T Helper cells, by following a procedure similar to the following:

1. A portion of a whole blood sample is incubated with a reagent mixture including fluorescently labelled antibodies that will bind to CD45 receptors on WBCs and emit fluorescence detectable by one of the two fluorescence detectors (FL1 or FL2) and fluorescently labelled antibodies that will bind to both CD13 and CD14 receptors on WBCs and emit fluorescence detectable by the other of the two fluorescence detectors. In this Example, the CD45 antibody is bound to fluorescein isothiocynate (FITC) and the CD13 and CD14 antibodies are bound to phycoerythrin (PE). Typical incubation occurs for about 15 minutes at ambient temperature.

2. A second portion of the same whole blood sample is incubated with a reagent mixture including fluorescently labelled antibodies that will bind to CD3 receptors on WBCs and emit fluorescence detectable by one of the two fluorescence detectors (FL1 or FL2) and fluorescently labelled antibodies that will bind to CD4 receptors on WBCs and emit fluorescence detectable by the other of the two fluorescence detectors. In this Example, the CD3 antibodies are bound to FITC and the CD4 antibodies are bound to PE.

Figure 61A:
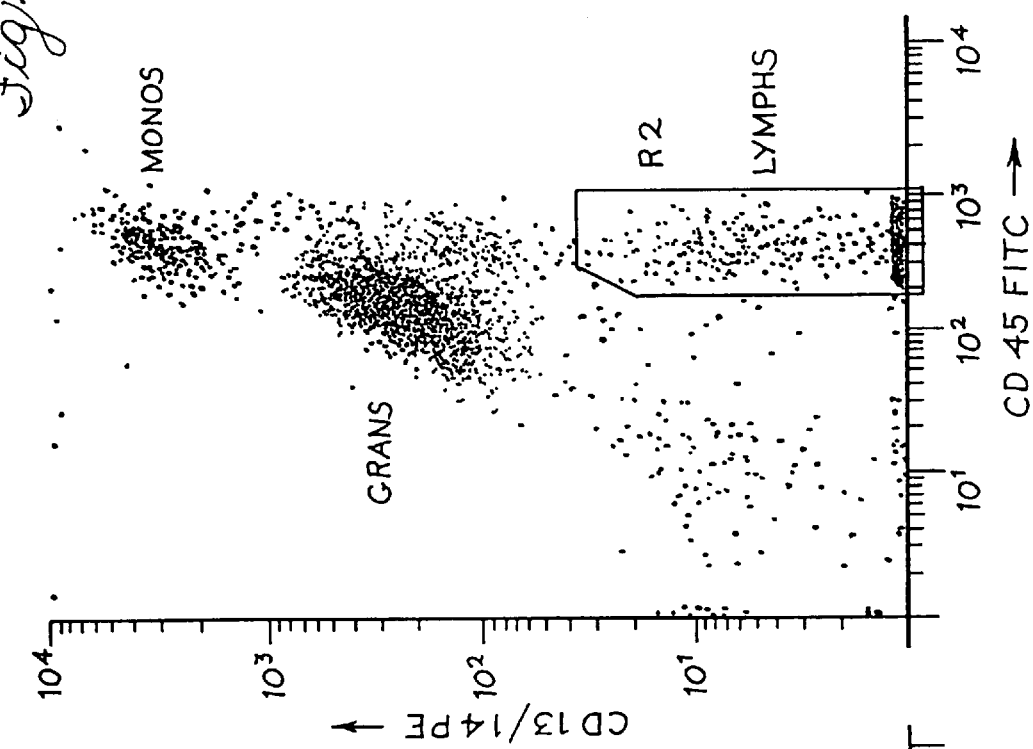
FIGS. 61A–G depict illustrations of data accumulated by an embodiment of the cell analysis system.

3. The first incubated blood sample is analyzed in a manner similar to that described in Example 6. This analysis yields a region of IAS and ALL values (the lymphocyte gate) that corresponds to lymphocytes, which are characterized by the presence of CD45 receptors and the absence of CD13 and CD14 receptors. A plot of fluorescence levels corresponding to CD13/CD14 activity and CD45 activity and the resulting designation of lymphocytes is presented in FIG. 61A. A plot of the IAS and ALL values for the same cells and the resulting lymphocyte gate is presented in 61B.

Figure 61C:
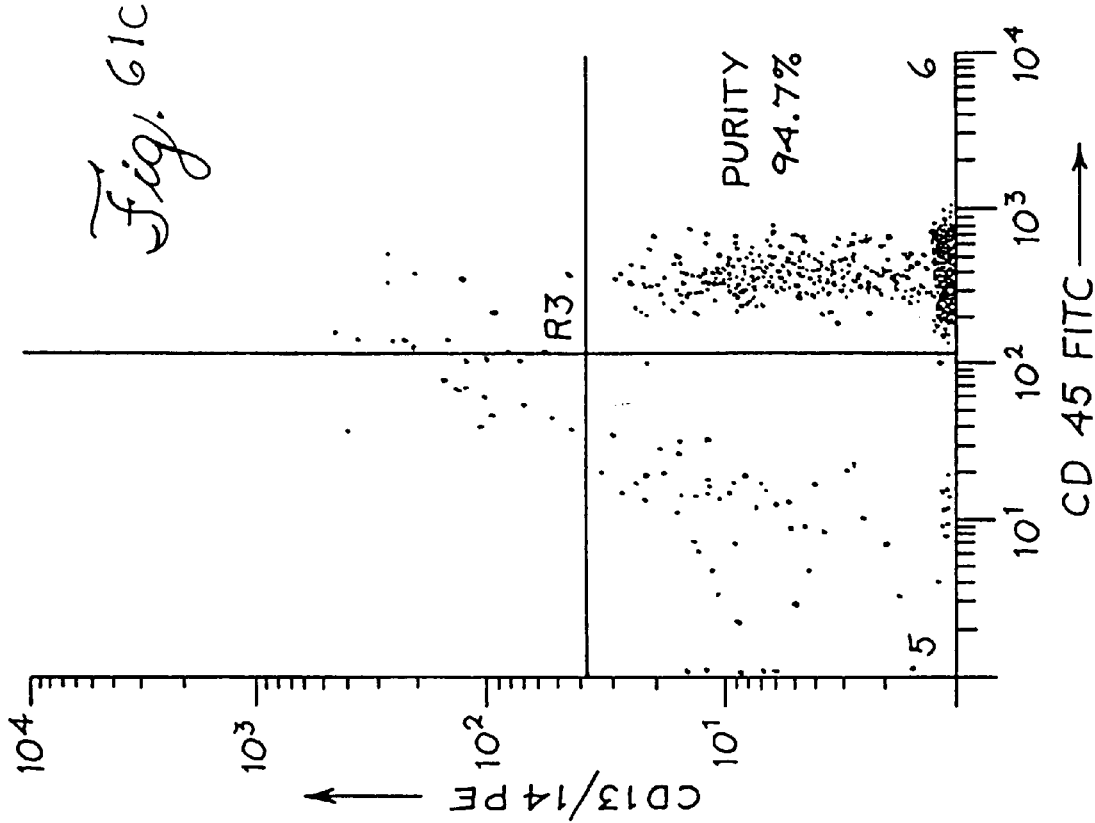
Figure 61B:
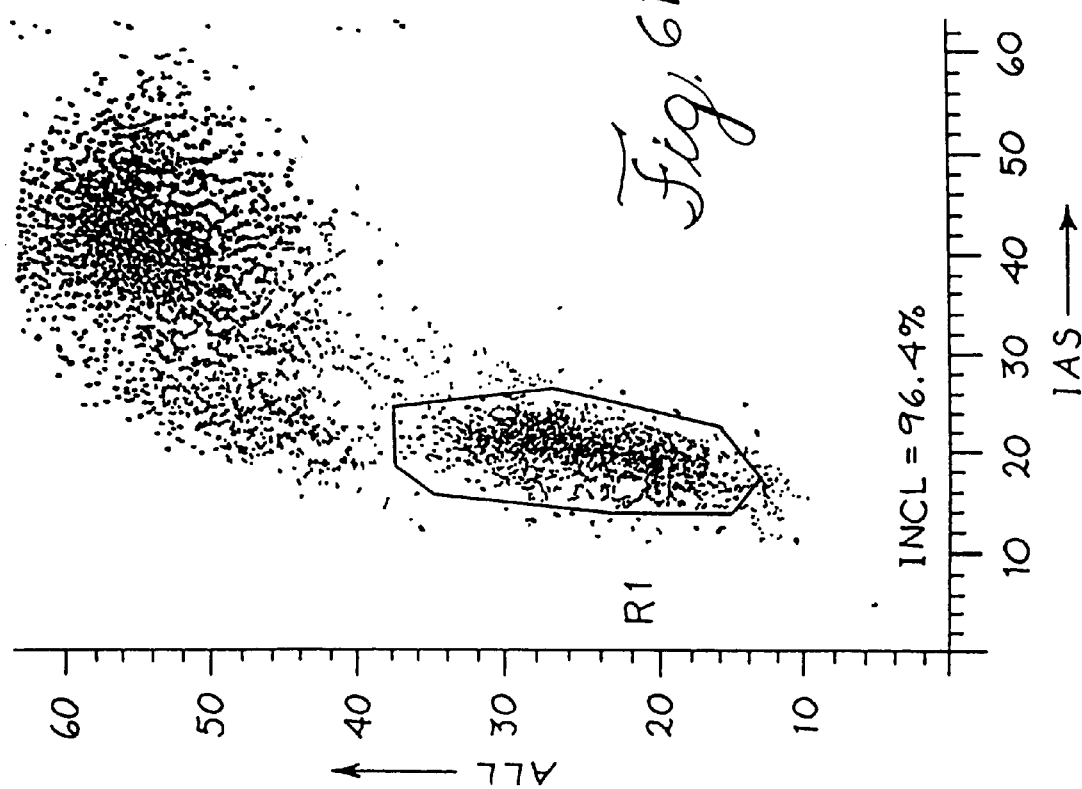

4. The purity of the lymphocyte gate procedure may be determined by calculating the fraction of all cells within the lymphocyte gate that demonstrate the presence of CD45 receptors and the absence of CD13 and CD14 receptors, as indicated by the levels of fluorescence detected by the FL1 and FL2 detectors. A plot of the fluorescence levels corresponding to CD13/CD14 activity and CD45 activity for cells within the lymphocyte gate is presented in FIG. 61C.

Figure 61E:
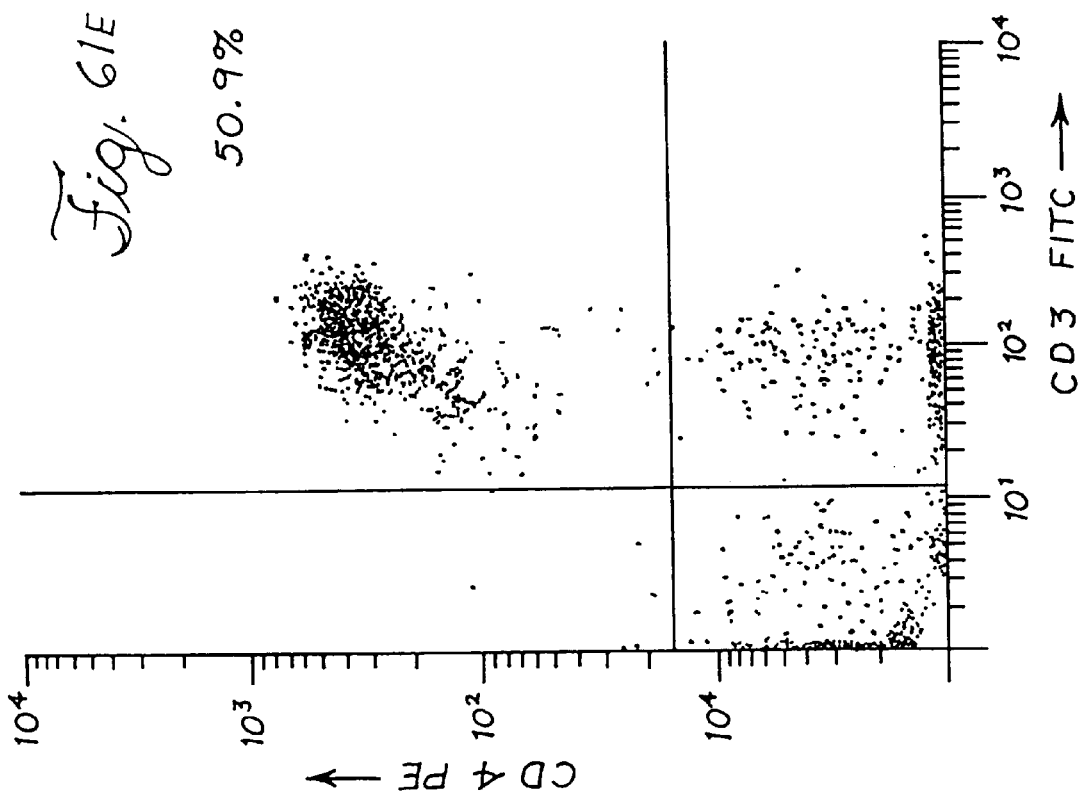
Figure 61D:
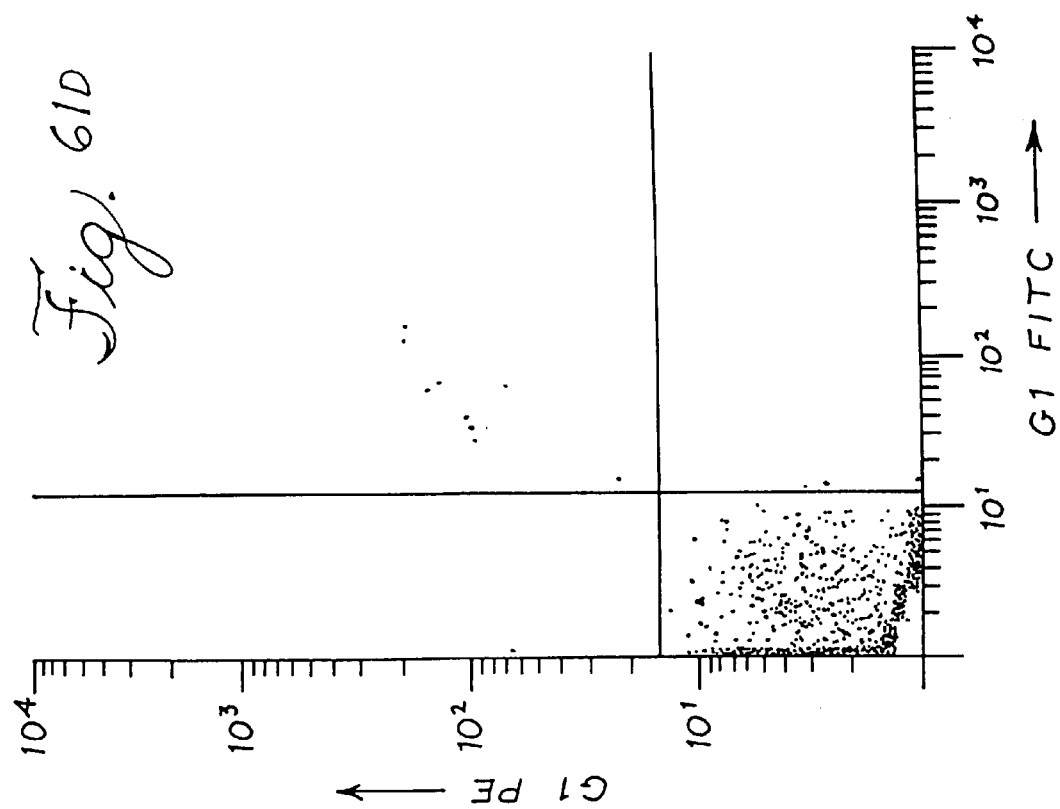

5. The second incubated blood sample is analyzed in a manner similar to that described in steps 1 through 2 of Example 6. Each cell whose values of IAS and ALL fall within the lymphocyte gate is characterized as positive or negative for each of the two antibodies within the reagent mixture (CD3 and CD4), based on a comparison of the detected levels of FL1 and FL2 to fluorescence levels of control cells incubated with an antibody mixture considered to be non-binding and labelled with PE and FITC. The fluorescence levels of the control cells (representing negative reactions) are illustrated in FIG. 61D.

6. The fraction of Lymphocytes that are T Helper cells is determined as the fraction of cells within the lymphocyte gate that are positive for CD3 and positive for CD4. A plot of the fluorescence levels corresponding to CD3 activity and CD4 activity for cells within the lymphocyte gate, showing the fraction that are positive for both, is presented in FIG. 61E.

7. The concentration of T Helper cells may be determined as the fraction of lymphocytes that are positive for CD3 and positive for CD4 (determined in step 6) times the lymphocyte count determined in the WBC differential analysis described in Example 4.

EXAMPLE 6B

Measurement of T Suppressor Subset

A similar procedure may be used to quantify the lymphocyte subset of T Suppressor cells, characterized by being positive for both CD3 and CD8.

1. A portion of a whole blood sample is incubated with a reagent mixture including fluorescently labelled antibodies that will bind to CD45 receptors on WBCs and fluorescently labelled antibodies that will bind to both CD13 and CD14 receptors on WBCs, as in step 1 of Example 6A. Analysis of this incubated sample is executed as described in steps 3 and 4 of Example 6A, yielding a lymphocyte gate. Typical incubation occurs for about 15 minutes at ambient temperature.

2. A second portion of the same whole blood sample is incubated with a reagent mixture including fluorescently labelled antibodies that will bind to CD3 receptors on WBCs and emit fluorescence detectable by one of the two fluorescence detectors (FL1 or FL2) and fluorescently labelled antibodies that will bind to CD8 receptors on WBCs and emit fluorescence detectable by the other of the two fluorescence detectors. In this Example, the CD3 antibodies are bound to FITC and the CD8 antibodies are bound to PE.

3. The second incubated blood sample is analyzed in a manner similar to that described in steps 1 through 8 of Example 6. Each cell whose values of IAS and ALL fall within the lymphocyte gate is characterized as positive or negative for each of the two antibodies within the reagent mixture (CD3 and CD8), based on a comparison of the detected levels of FL1 and FL2 to control fluorescence levels.

Figure 61G:
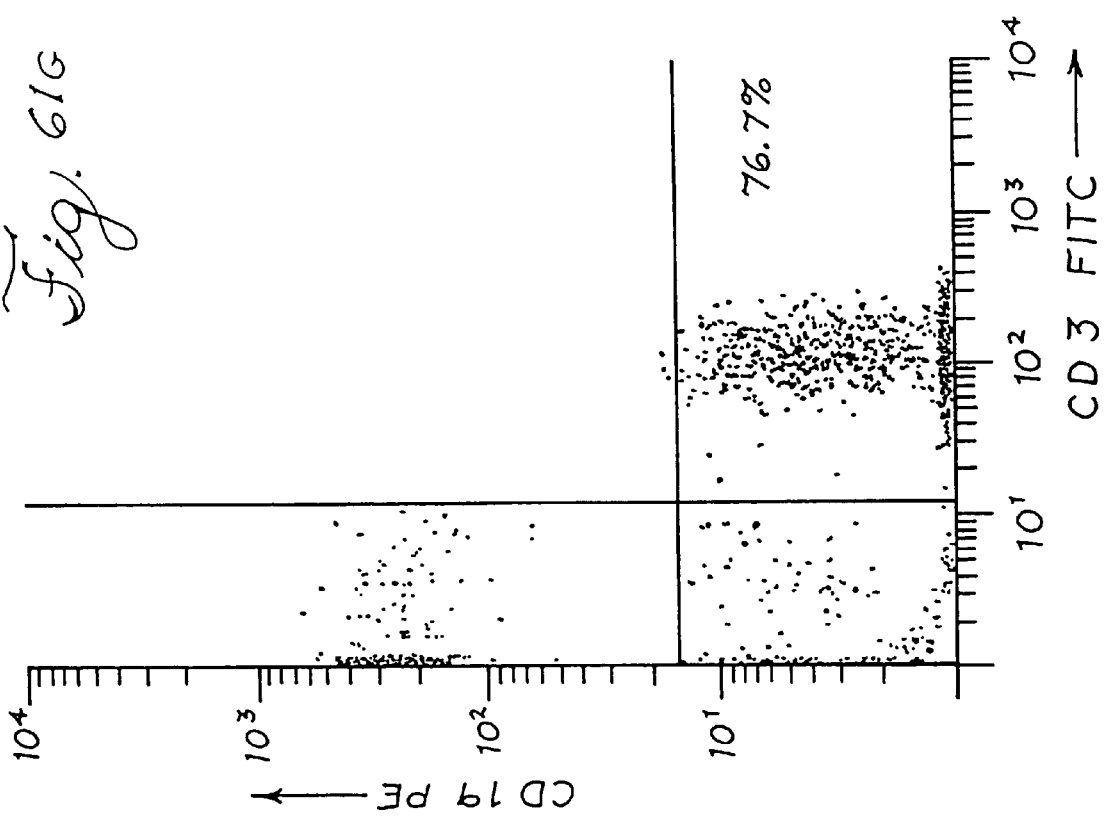
Figure 61F:
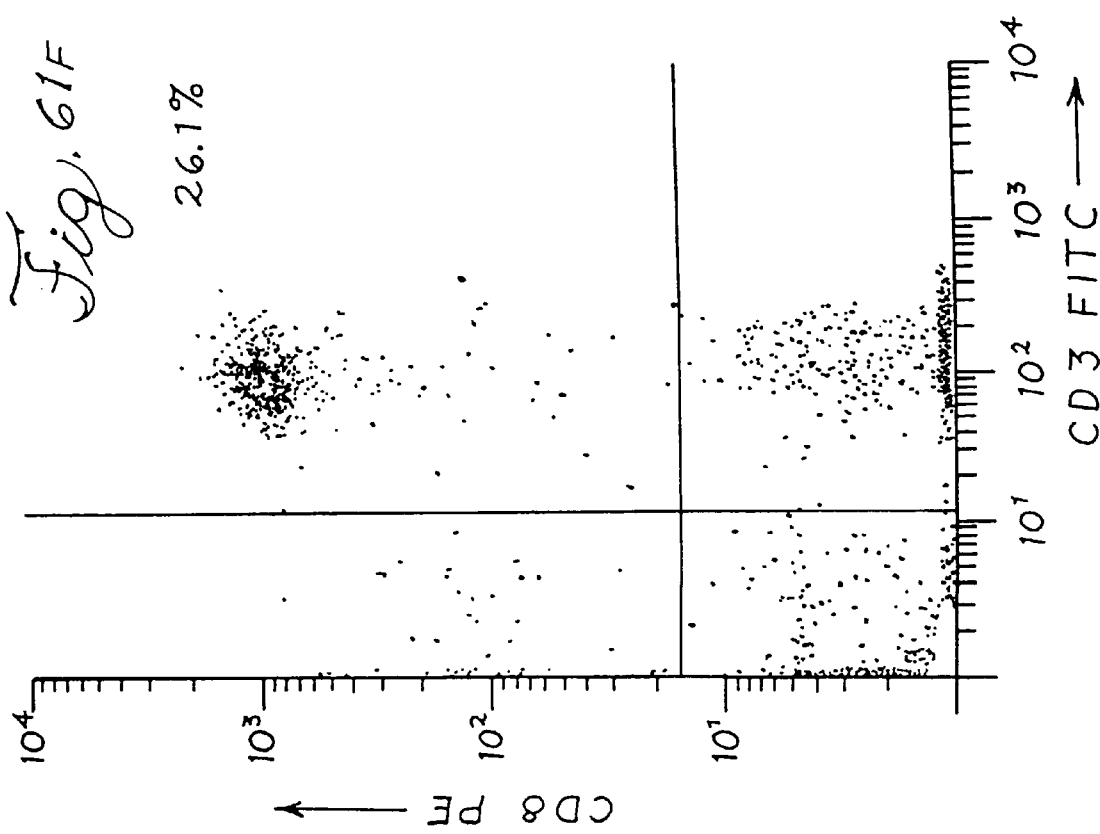

4. The fraction of lymphocytes that are T Suppressor cells is determined as the fraction of cells within the lymphocyte gate that are positive for CD3 and positive for CD8. A plot of the fluorescence levels corresponding to CD3 activity and CD8 activity for cells within the lymphocyte gate, showing the fraction that are positive for both, is presented in FIG. 61F.

5. The concentration of T Suppressor cells may be determined as the fraction of lymphocytes that are positive for CD3 and positive for CD8 (determined in step 5) times the lymphocyte count determined in the WBC differential analysis described in Example 4.

EXAMPLE 6C

Measurement of T and B Lymphocytes

The number of T and B lymphocytes may be measured using a procedure similar to that described in Examples 6A and 6B. The first incubated sample, used to establish the lymphocyte gate, is the same mixture of CD45 and CD13/CD14 labelled antibodies as in Examples 6A and 6B. The second portion of the blood sample is incubated with a mixture of CD3 antibodies (labelled with FITC) and CD19 antibodies (labelled with PE). The fractions of T cells and B cells are determined from the fraction of cells that are CD3 positive and CD19 negative (T cells) and the fraction that are CD3 negative and CD19 positive (B cells). A plot of the fluorescence levels corresponding to CD3 activity and CD19 activity, indicating the fractions of T cells and B ce(lls, is presented in FIG. 61G.

The validity of the lymphocyte subset measurements described in these Examples is demonstrated by comparing the analysis results using an embodiment of this invention with results of conventional manual flow cytometry assays. The results of such a comparison, between an embodiment of the current invention (termed BB3) and conventional analyses on a FACScan system by Becton Dickinson Immunocytometry Systems, are presented in FIGS. 62A–D.

Figure 62A:
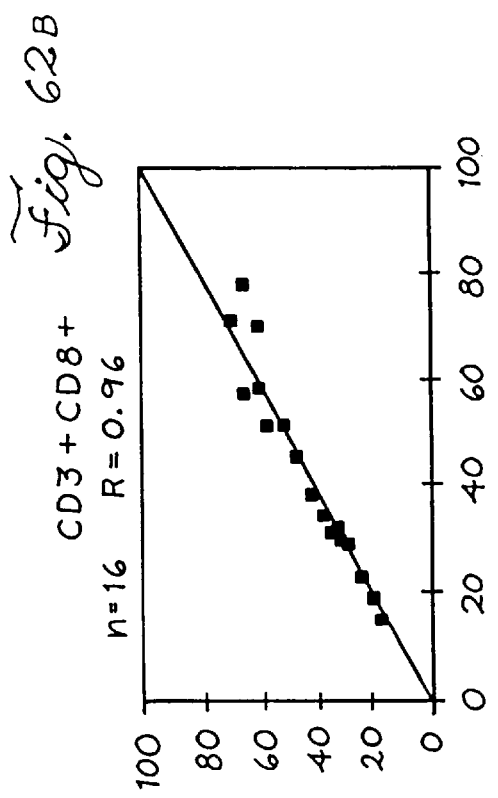
FIGS. 62A–D illustrate a correlation between fractions of lymphocytes that are positive for both CD3 and CD4, positive for both CD3 and CD8, positive for CD19, and positive for CD3 alone.
Figure 62B:
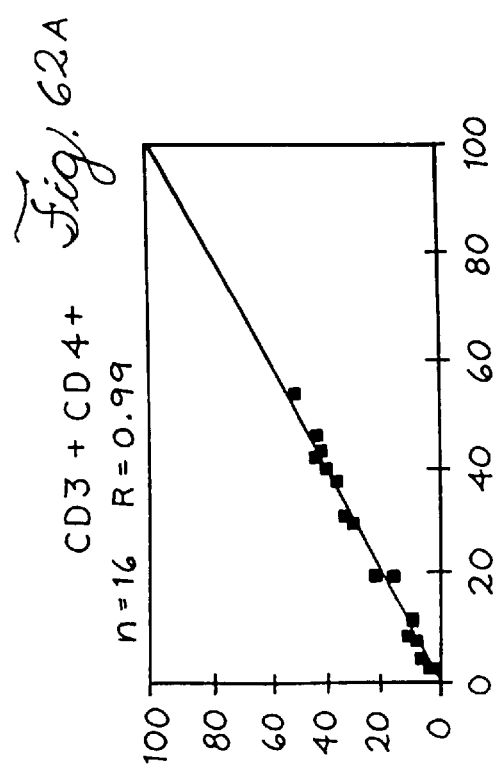
Figure 62C:
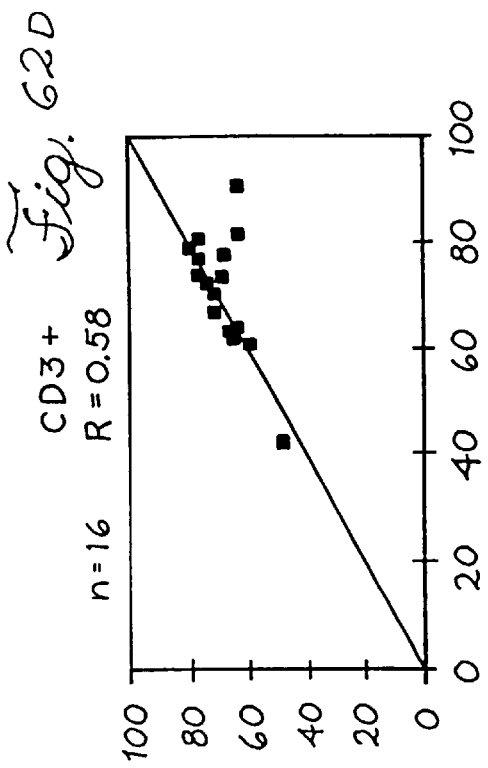
Figure 62D:
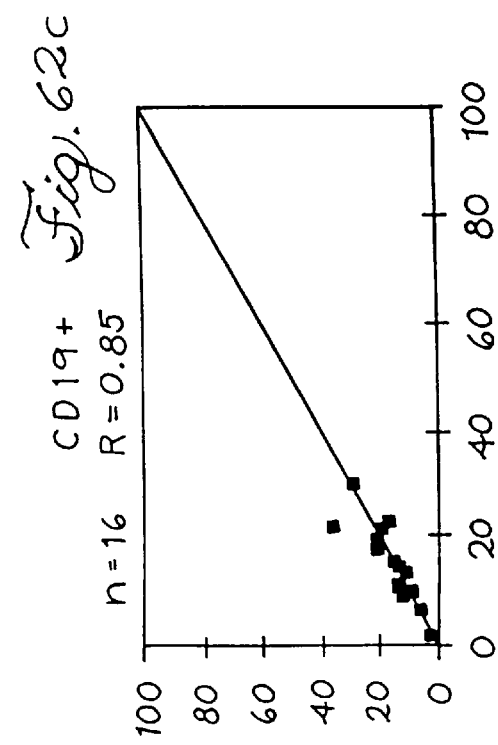

The plots in FIGS. 62A–D illustrate the correlation between fractions of lymphocytes that are positive for both CD3 and CD4 (FIG. 62A), positive for both CD3 and CD8 (FIG. 62B), positive for CD19 (FIG. 62C), and positive for CD3 alone (FIG. 62D).

EXAMPLE 7

NRBC Analysis

Twenty five (25) μl of a whole blood clinical sample, are mixed on-line in the cell analysis instrument system disclosed above, with 675 μl of the multipurpose reagent, pre-warmed at 42° C. in the WBC cup 138. The sample/reagent are mixed and incubated for 11 seconds. This mixture is then transported to the flow cell 170 which takes approximately 8 and ½ seconds for a WBC/Diff/NRBC analysis. FIGS. 40A–C and 41A–B show the result of this analysis on sample containing 56NRBC/100WBC and 140 NRBC/100 WBC, respectively.

What is claimed is:

1. An automated method for distinguishing and differentiating cells in a whole blood sample with an automated instrument system capable of performing both hematology analysis and fluorescent cytometry analysis to which a whole blood sample is provided, the automated method comprising the steps of:

(a) selecting a series of one or more tests to be performed on the whole blood sample by the automated instrument system;

(b) correlating the one or more tests to be performed on the whole blood sample by the automated instrument system;

(c) aspirating a volume of the whole blood sample;

(d) dispensing an aliquot of the whole blood sample into at least two sample receiving vessels;

(e) diluting a first aliquot of the whole blood sample with a diluent reagent thereby producing a diluted sample in one of the at least two sample receiving vessels;

(f) lysing a second aliquot of the whole blood sample with a lysing reagent thereby producing a lysed sample in another one of the at least two sample receiving vessels;

(g) transporting an aliquot of the diluted sample through a flow transducer of the automated instrument system;

(h) detecting and counting red blood cells in the aliquot of the diluted sample with the flow transducer;

(i) transporting an aliquot of the lysed sample through the flow transducer;

(j) detecting multi-angle light scatter from the aliquot of lysed sample and counting and differentiating white blood cells ("WBC") therein with the flow transducer;

(k) detecting multi-angle light scatter and fluorescence from the lysed sample or the diluted sample and counting and differentiating nucleated red blood cells or reticulocytes or both therein with the flow transducer;

(l) storing flow transducer detecting and differentiating data for the tests performed on the whole blood sample; and (m) reporting results of each test performed on the whole blood sample, wherein the automated instrument system automatedly performs method steps (b) through (m) without physically separating cells from the whole blood sample or an aliquot thereof and results of hematology analysis are utilized in at least reporting of the results of the fluorescent cytometry analysis.

2. The method of claim 1 further comprising the steps of:

(n) staining an aliquot of the diluted sample thereby producing a stained aliquot in one of the at least two sample receiving vessels;

(o) transporting the stained aliquot through the flow transducer, wherein reticulocytes in the stained aliquot are counted and differentiated.

3. The method of claim 1 wherein an aliquot of the diluted sample is transported by the automated instrument system through the flow transducer and multi-angle light scatter is detected to count and to differentiate platelets in the diluted sample.

4. The method of claim 1 wherein nucleated red blood cells and white blood cells are counted and are differentiated from the lysed sample.

5. The method of claim 1 wherein a third aliquot of whole blood sample is placed in at least one of the at least two sample receiving vessels by the automated instrument system and the method further comprising the steps of:

(n) combining the third aliquot with fluorescent-labelled monoclonal antibodies for a sufficient time to allow the fluorescent-labelled monoclonal antibodies to become attached to cell surface antigen on cells in the third aliquot, thereby producing a labelled sample in the at least one of the at least two sample receiving vessels;

(o) lysing the labelled sample with a lysing reagent without thereafter separating the unlysed cells in the third aliquot, thereby producing a lysed and labelled sample in the at least one of the at least two sample receiving vessels;

(p) transporting the lysed and labelled sample through the flow transducer; and (q) detecting multi-angle light scatter and fluorescence and counting and differentiating sub-populations of lymphocytes in the lysed and labelled sample.

6. The automated method of claim 1 wherein a reported quantitative white blood cell result is obtained from multi-angle light scatter and fluorescent detected data.

7. The automated method of claim 6 wherein the white blood cell result comprises a five-part differential.

8. The automated method of claim 7 wherein the five part differential further comprises a percentage of nucleated red blood cells.

* * * * *